United States Patent
Johnson et al.

(10) Patent No.: US 8,853,408 B2
(45) Date of Patent: Oct. 7, 2014

(54) CYCLOPROPYLAMINES AS LSD1 INHIBITORS

(75) Inventors: Neil W. Johnson, Collegeville, PA (US); Jiri Kasparec, Collegeville, PA (US)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 0 days.

(21) Appl. No.: 14/007,035

(22) PCT Filed: Mar. 26, 2012

(86) PCT No.: PCT/US2012/030552
§ 371 (c)(1),
(2), (4) Date: Sep. 24, 2013

(87) PCT Pub. No.: WO2012/135113
PCT Pub. Date: Oct. 4, 2012

(65) Prior Publication Data
US 2014/0018393 A1    Jan. 16, 2014

Related U.S. Application Data

(60) Provisional application No. 61/467,524, filed on Mar. 25, 2011, provisional application No. 61/514,140, filed on Aug. 2, 2011, provisional application No. 61/594,012, filed on Feb. 2, 2012.

(51) Int. Cl.
| | | |
|---|---|---|
| C07D 211/32 | (2006.01) |
| A01N 43/40 | (2006.01) |
| A61K 31/445 | (2006.01) |
| C07D 401/04 | (2006.01) |
| C07D 223/04 | (2006.01) |
| C07D 265/30 | (2006.01) |
| C07D 211/96 | (2006.01) |
| C07C 271/24 | (2006.01) |
| C07D 413/06 | (2006.01) |
| C07D 211/26 | (2006.01) |
| C07D 401/06 | (2006.01) |
| C07D 401/10 | (2006.01) |
| C07C 211/35 | (2006.01) |
| C07D 211/62 | (2006.01) |
| C07F 9/59 | (2006.01) |
| C07D 207/09 | (2006.01) |
| C07F 5/02 | (2006.01) |
| C07C 211/36 | (2006.01) |

(52) U.S. Cl.
CPC .......... *C07D 211/26* (2013.01); *C07C 2101/02* (2013.01); *C07D 401/04* (2013.01); *C07D 223/04* (2013.01); *C07D 265/30* (2013.01); *C07D 211/96* (2013.01); *C07C 271/24* (2013.01); *C07D 413/06* (2013.01); *C07D 401/06* (2013.01); *C07D 401/10* (2013.01); *C07C 211/35* (2013.01); *C07D 211/62* (2013.01); *C07C 2101/14* (2013.01); *C07F 9/591* (2013.01); *C07D 207/09* (2013.01); *C07F 5/025* (2013.01); *C07C 211/36* (2013.01)
USPC .......................................... 546/235; 514/331

(58) Field of Classification Search
None
See application file for complete search history.

(56) References Cited

FOREIGN PATENT DOCUMENTS

| WO | WO 2010/043721 A1 | 4/2010 |
|---|---|---|
| WO | WO 2010/084160 A1 | 7/2010 |
| WO | WO 2011/035941 A1 | 3/2011 |
| WO | WO 2011/042217 A1 | 4/2011 |
| WO | WO 2011/131697 A1 | 10/2011 |
| WO | WO 2012/013727 A1 | 2/2012 |
| WO | WO 2012/013728 A1 | 2/2012 |
| WO | WO 2012/107498 A1 | 8/2012 |
| WO | WO 2012/107499 A1 | 8/2012 |

OTHER PUBLICATIONS

Chen, et al. PNAS, 103: 13956-14961 (2006).
Suzuki, et al. J. Med. Chem., 54: 8236-8250 (2011).
Yang, et al. Biochem., 46: 8058-8065 (2007).

*Primary Examiner* — James D Anderson
*Assistant Examiner* — William Lee
(74) *Attorney, Agent, or Firm* — Duke M. Fitch; John Lemanowicz; William Majarian

(57) ABSTRACT

This invention relates to the use of cyclopropylamine derivatives for the modulation, notably the inhibition of the activity of Lysine-specific demethylase 1 (LSD1). Suitably, the present invention relates to the use of cyclopropylamines in the treatment of cancer.

4 Claims, No Drawings

CYCLOPROPYLAMINES AS LSD1 INHIBITORS

This application is a 371 of International Application No. PCT/US2012/030552, filed 26 Mar. 2012, which claims the benefit of U.S. Provisional Application Nos. 61/594,012, filed 2 Feb. 2012, 61/514,140, filed 2 Aug. 2011, and 61/467,524, filed 25 Mar. 2011, which are incorporated herein in their entireties.

FIELD OF THE INVENTION

This invention relates to novel cyclopropylamines which are inhibitors of Lysine-specific demethylase 1 (LSD1; also known as BHC110), to pharmaceutical compositions containing them, and to their use in therapy for the treatment of cancers.

BACKGROUND OF THE INVENTION

Chromatin modification plays an essential role in transcriptional regulation (T. Kouzarides, 2007, Cell 128: 693-705). These modifications, which include DNA methylation, histone acetylation and histone methylation, are disregulated in tumors. This epigenetic disregulation plays an important role in the silencing of tumor suppressors and overexpression of oncogenes in cancer (M. Esteller, 2008, N Engl J Med 358:1148-59. P. Chi et al, 2010, Nat Rev Canc 10:457-469.). The enzymes that regulate histone methylation are the histone methyl transferases and the histone demethylases.

Lysine-specific demethylase 1 (LSD1; also known as BHC110) is a histone lysine demethylase reported to demethylate H3K4me1/2 (Y. Shi et al., 2004, Cell 119: 941-953) and H3K9me1/2 (R. Schüe et al., 2005, Nature 437: 436-439). LSD1 is overexpressed in multiple human cancers, including prostate where it is associated with more frequent relapse (P. Kahl et al., 2006, Canc. Res. 66: 11341-11347), breast (J. Kirfel et al., 2010, Carcinogenesis 31: 512-520) neuroblastoma (J. Kirfel et al., 2009, Canc. Res. 69: 2065-2071. G. Sun et al., 2010, Mol. Cell. Biol. 28: 1997-2000). LSD1 is essential for transcriptional regulation mediated by a number of nuclear hormone receptors, including androgen receptor in prostate cancer (R. Schuele et al, 2005, Nature 437: 436-439. R. Schuele et al, 2007, Nat. Cell Biol. 9: 347-353. R. Schuele et al, 2010, Nature 464: 792-796), estrogen receptor in breast carcinomas (M. G. Rosenfeld et al., 2007, Cell 128: 505-518), and TLX receptor in neuorblastoma (S. Kato et al., 2008, Mol. Cell. Biol. 28: 3995-4003). These studies have shown that knockdown of LSD1 expression results in decreased cancer cell proliferation. Additionally, LSD 1 is overexpressed in multiple cancer types that are nuclear hormone receptor-independent. Those tumors include ER-negative breast (J. Kirfel et al., 2010, Carcinogenesis 31: 512-520), small-cell lung, bladder, head & neck, colon, serous ovary, and kidney Wilm's tumor. Therefore, potent selective small molecule inhibitors of LSD1 may be useful for treatment of cancers that are nuclear hormone receptor-dependent and/or nuclear hormone receptor-independent.

The compositions and methods provided herein can potentially be useful for the treatment of cancer including tumors such as skin, breast, brain, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can potentially be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of or related to the above identified conditions.

SUMMARY OF THE INVENTION

The present invention relates to a compound of Formula (I)

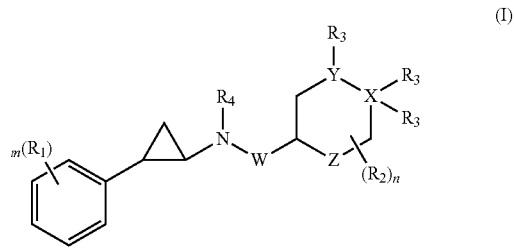

wherein
R₁ is selected from the group consisting of: $C_1$-$C_6$alkyl, —NSO₂Me, —NSO₂Ph, arylalkoxy, $C_3$-$C_7$cycloalkyl, —NC(O)R$_a$, 1-methyl-1H-pyrazol-4-yl, hydroxyl, $C_1$-$C_4$alkoxy, halogen, amide, amino, substituted amino, and —C(O)OR$_a$;

R₂ is hydrogen or COOH;

each R₃ is independently selected from the group consisting of: aryl, heteoaryl, hydrogen, $C_1$-$C_6$alkyl, —SO₂R$_a$, —NC(O)R$_a$, —CH₂C(O)OR$_a$, —C(O)OR$_a$, —C(O)R$_a$, —C(O)NR$_a$R$_b$, substituted amino, amino, urea, amide, sulfonamide, arylalkyl, and heteroarylalkyl;

R$_a$ is hydrogen, phenyl, phenylmethyl, 3,5-dimethylisoxazol-4-yl, 1,2-dimethyl-1H-imidazol-4-yl, $C_3$-$C_7$cycloalkyl, $C_1$-$C_6$alkyl, $C_1$-$C_4$alkoxy, $C_1$-$C_3$alkylamino or —NHPh;

R$_b$ is hydrogen or $C_1$-$C_3$alkyl, or when attached to the same atom; or

R$_a$ and R$_b$ together form a 5- or 6-membered heterocycloalkyl ring;

R₄ is $C_1$-$C_4$alkyl, acyl, —C(O)CF₃ or hydrogen;

W is —(CH₂)$_{1-4}$, or —CH(R$_c$)(CH₂)$_{0-3}$, in which R$_c$ is CN or $C_1$-$C_4$alkyl;

Y is N or C;

X is N or C;

Z is O or (CH₂)$_q$, wherein q is 0-2, when q is 0, Z represents a bond;

m is 0-3, n is 0-3;

provided that when Z is O, Y is N and X is C;

also provided that when X is C, at least one of the R₃ groups attached to X is not hydrogen;

or a pharmaceutically acceptable salt thereof.

This invention also relates to pharmaceutical compositions, which comprise compounds of Formula (I) and pharmaceutically acceptable carriers.

This invention also relates to methods of treating cancer which comprise administering an effective amount of a compound of Formula (I) to a human in need thereof.

This invention also relates to methods of treating cancer which comprise co-administering a compound of Formula (I) and a second compound, suitably an antineoplastic agent, to a human in need thereof.

This invention also relates to methods of inhibiting Lysine-specific demethylase 1 in a human in need thereof, which comprise administering an effective amount of a compound of Formula (I).

DETAILED DESCRIPTION OF THE INVENTION

The present invention also relates to a compound of Formula (II)

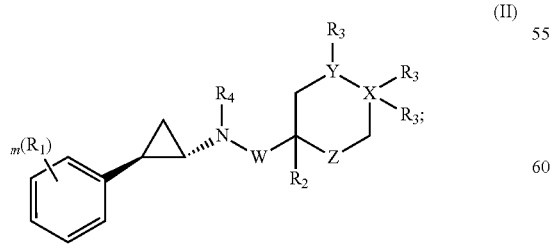

(II)

wherein, R₁-R₄, m, W, X, Y and Z are defined according to Formula (I);
or a pharmaceutically acceptable salt thereof.

The present invention also relates to a compound of Formula (III)

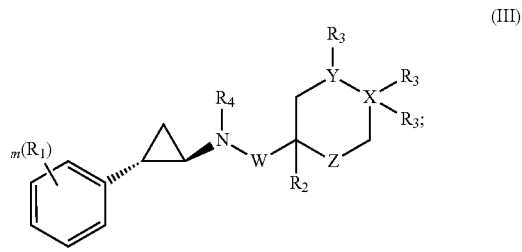

(III)

wherein, R₁-R₄, m, W, X, Y and Z are defined according to Formula (I);
or a pharmaceutically acceptable salt thereof.

The present invention also relates to a compound according to any one of Formula (I), (II) or (III), wherein Z is CH; or a pharmaceutically acceptable salt thereof.

The present invention also relates to a compound according to any one of Formulas (I), (II) or (III), wherein X is C, Y is N and Z is O; or a pharmaceutically acceptable salt thereof.

The present invention also relates to a compound represented by formula (IV)

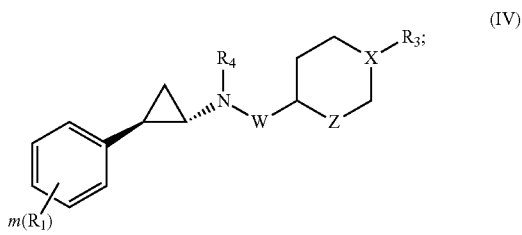

(IV)

wherein
Z is (CH₂)$_q$, wherein q is 0-2, when q is 0, Z represents a bond;
m is 0-3, preferably 0-1;
X is C or N;
W, R₁, R₃ and R₄ are defined according to Formula (I); or a pharmaceutically acceptable salt thereof.

The present invention also relates to a compound represented by Formula (V)

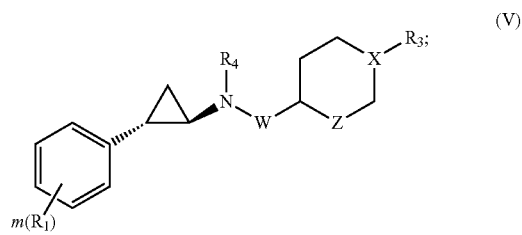

(V)

wherein
Z is O or (CH₂)$_q$, wherein q is 0-2, when q is 0, Z represents a bond;
m is 0-3, preferably 0-1;
X is C or N;
W, R₁, R₃ and R₄ are defined according to Formula (I); or a pharmaceutically acceptable salt thereof.

The present invention also relates to a compound of Formula (I), wherein one and only one of the two $R_3$ groups attached to X is hydrogen.

The present invention also relates to a compound according to any one of the above formulas, wherein $R_4$ is H and X is N; or a pharmaceutically acceptable salt thereof.

The present invention also relates to a compound according to any one of the above formulas, wherein $R_1$ is F, Cl, $C_1$-$C_4$alkoxy, or $C_1$-$C_4$alkyl; or a pharmaceutically acceptable salt thereof.

The present invention also relates to a compound according to any one of the above formulas, wherein m is 0; or a pharmaceutically acceptable salt thereof.

The present invention also relates to a compound according to any one of the above formulas, wherein each $R_3$ is independently selected from the group consisting of: aryl, arylalkyl, heteoaryl, heteroarylalkyl, wherein said aryl and heteroaryl are each optionally substituted with 1-3 groups selected from the group consisting of: —COOH, $C_1$-$C_4$alkoxy, —C(O)O$C_1$-$C_4$alkyl, $C_1$-$C_4$alkyl, halogen, CN, tetrazolyl, —NSO$_2$Me, —SO$_2$Me, —C(O)N(CH$_2$)OH, —C(O)NSO$_2$Me, —OCH$_2$COOH; or a pharmaceutically acceptable salt thereof.

The present invention also relates to a compound according to any one of above formulas, wherein each $R_3$ is independently selected from the group consisting of: hydrogen, $C_1$-$C_6$alkyl, —SO$_2$R$_a$, —NC(O)R$_a$, —CH$_2$C(O)OR$_a$, —C(O)OR$_a$—C(O)R$_a$, —C(O)NR$_a$R$_b$, substituted amino, amino, urea, amide, sulfonamide, arylalkyl, and heteroarylalkyl, wherein R$_a$ is phenyl, phenylmethyl, $C_3$-$C_7$cycloalkyl, $C_1$-$C_6$alkyl, $C_1$-$C_4$alkoxy, $C_1$-$C_3$alkylamino or —NHPh; R$_b$ is hydrogen or $C_1$-$C_4$alkyl, or when attached to the same atom, R$_a$ and R$_b$ together form a 5- or 6-membered heterocycloalkyl ring, wherein said phenyl may be substituted with one to three groups selected from the group consisting of: $C_1$-$C_4$alkyl, halogen, and COOH; or a pharmaceutically acceptable salt thereof.

The present invention also relates to a compound according to Formula (I), (II), or (III), wherein each $R_3$ is independently selected from the group consisting of: hydrogen, $C_1$-$C_6$alkyl, —SO$_2$R$_a$, —NC(O)R$_a$, —C(O)OR$_a$—C(O)R$_a$, —C(O)NR$_a$R$_b$, substituted amino, amino, urea, amide, sulfonamide, arylalkyl, and heteroarylalkyl, wherein R$_a$ is phenyl, phenylmethyl, $C_3$-$C_7$cycloalkyl, $C_1$-$C_6$alkyl, $C_1$-$C_4$alkoxy, $C_1$-$C_3$alkylamino or —NHPh; R$_b$ is hydrogen or $C_1$-$C_4$alkyl; or a pharmaceutically acceptable salt thereof.

This invention also relates to a compound of Formula (VI):

(VI)

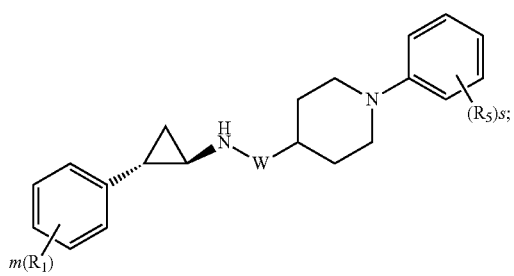

wherein
$R_1$ and W are defined as in Formula (I);
s is 1-2; m is 0-1;
each $R_5$ is independently selected from the group consisting of: —COOH, $C_1$-$C_4$alkoxy, —C(O)O$C_1$-$C_4$alkyl, $C_1$-$C_4$alkyl, halogen, CN, tetrazolyl, —NSO$_2$Me, —SO$_2$Me, —C(O)N(CH$_2$)OH, —C(O)NSO$_2$Me, —OCH$_2$COOH; or a pharmaceutically acceptable salt thereof.

This invention also relates to a compound according to any one of Formula (I), (II) or (III), which is represented by formula (VII):

(VII)

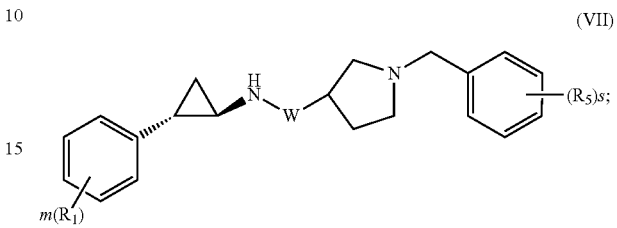

wherein
$R_1$ and W are defined as in formula (I);
s is 1-2; m is 0-1;
each $R_5$ is independently selected from the group consisting of: —COOH, alkoxy, —C(O)O$C_1$-$C_4$alkyl, $C_1$-$C_4$alkyl, halogen, CN, tetrazolyl, —NSO$_2$Me, —SO$_2$Me, —C(O)N(CH$_2$)OH, —C(O)NSO$_2$Me, —OCH$_2$COOH; or a pharmaceutically acceptable salt thereof.

This invention also relates to a compound of Formula (VI) or (VII), wherein $R_5$ is —COOH.

This invention also relates to any one or any subgroup of the following compounds:
1,1-Dimethylethyl 4-({[trans-2-phenylcyclopropyl]amino}methyl)-1-piperidinecarboxylate;
1,1-Dimethylethyl 4-({[(1R,2S)-2-phenylcyclopropyl]amino}methyl)-1-piperidinecarboxylate;
1,1-Dimethylethyl 4-({[(1S,2R)-2-phenylcyclopropyl]amino}methyl)-1-piperidinecarboxylate;
[trans-2-Phenylcyclopropyl](4-piperidinylmethyl)amine;
[(1S,2R)-2-Phenylcyclopropyl](4-piperidinylmethyl)amine;
[(1R,2S)-2-Phenylcyclopropyl](4-piperidinylmethyl)amine;
trans-N-(Cyclohexylmethyl)-2-phenylcyclopropanamine;
[trans-2-Phenylcyclopropyl]{[1-(phenylmethyl)-4-piperidinyl]methyl}amine;
1,1-Dimethylethyl[trans-4-({[trans-2-phenylcyclopropyl]amino}methyl)cyclohexyl]carbamate;
trans-4-({[trans-2-Phenylcyclopropyl]amino}methyl)cyclohexanamine;
2-(4-(((trans-2-Phenylcyclopropyl)amino)methyl)piperidin-1-yl)ethanol;
N-Phenyl-4-(((trans-2-phenylcyclopropyl)amino)methyl)piperidine-1-carboxamide;
Phenyl(4-(((trans-2-phenylcyclopropyl)amino)methyl)piperidin-1-yl)methanone;
1-(4-(((trans-2-Phenylcyclopropyl)amino)methyl)piperidin-1-yl)ethanone;
[trans-2-Phenylcyclopropyl](3-piperidinylmethyl)amine;
N-(trans-2-Phenylcyclopropyl)-N-(piperidin-4-ylmethyl)acetamide;
Benzyl 4-(((trans-2-phenylcyclopropyl)amino)methyl)piperidine-1-carboxylate;
4-(((trans-2-Phenylcyclopropyl)amino)methyl)piperidine;
[(1-Methyl-4-piperidinyl)methyl][trans-2-phenylcyclopropyl]amine;
1,1-Dimethylethyl 4-({[trans-2-phenylcyclopropyl]amino}methyl)hexahydro-1H-azepine-1-carboxylate; or a pharmaceutically acceptable salt thereof;

N-(Hexahydro-1H-azepin-4-ylmethyl)-trans-2-phenylcyclopropanamine;
[trans-2-Phenylcyclopropyl][2-(4-piperidinyl)ethyl]amine;
[trans-2-Phenylcyclopropyl][1-(4-piperidinyl)ethyl]amine;
N-(2-Morpholinylmethyl)-trans-2-phenylcyclopropanamine;
4-((4-(((trans-2-phenylcyclopropyl)amino)methyl)piperidin-1-yl)methyl)benzoic acid;
2-(4-(((trans-2-phenylcyclopropyl)amino)methyl)piperidin-1-yl)acetic acid;
4-{[(3R)-3-({[(1R,2S)-2-Phenylcyclopropyl]amino}methyl)-1-pyrrolidinyl]methyl}benzoic acid;
4-{[(3S)-3-({[(1R,2S)-2-Phenylcyclopropyl]amino}methyl)-1-pyrrolidinyl]methyl}benzoic acid;
4-((4-((((1R,2S)-2-phenylcyclopropyl)amino)methyl)piperidin-1-yl)methyl)benzoic acid;
4-{3-[4-({[(1R,2S)-2-Phenylcyclopropyl]amino}methyl)-1-piperidinyl]propyl}benzoic acid;
trans-N-((1-Isopropylpiperidin-4-yl)methyl)-2-phenylcyclopropanamine;
trans-N-((1-(2-Methoxyethyl)piperidin-4-yl)methyl)-2-phenylcyclopropanamine;
trans-2-Phenyl-N-((1-(pyridin-4-ylmethyl)piperidin-4-yl)methyl)cyclopropanamine;
trans-N-((1-(2-Fluorobenzyl)piperidin-4-yl)methyl)-2-phenylcyclopropanamine;
1,1-Bis(2-fluorobenzyl)-4-(((trans-2-phenylcyclopropyl)amino)methyl)piperidin-1-ium chloride;
trans-N-((1-(3-Fluorobenzyl)piperidin-4-yl)methyl)-2-phenylcyclopropanamine;
1,1-Bis(3-fluorobenzyl)-4-(((trans-2-phenylcyclopropyl)amino)methyl)piperidin-1-ium chloride;
trans-N-((1-(4-Fluorobenzyl)piperidin-4-yl)methyl)-2-phenylcyclopropanamine;
1,1-bis(4-Fluorobenzyl)-4-(((trans-2-phenylcyclopropyl)amino)methyl)piperidin-1-ium chloride;
trans-N-((1-(2,4-Difluorobenzyl)piperidin-4-yl)methyl)-2-phenylcyclopropanamine;
1,1-Bis(2,4-difluorobenzyl)-4-(((trans-2-phenylcyclopropyl)amino)methyl)piperidin-1-ium bromide;
Ethyl 4-((4-(((trans-2-phenylcyclopropyl)amino)methyl)piperidin-1-yl)methyl)benzoate;
trans-N-((1-(4-(Methylsulfonyl)benzyl)piperidin-4-yl)methyl)-2-phenylcyclopropanamine;
1-(4-(((trans-2-Phenylcyclopropyl)amino)methyl)piperidin-1-yl)butan-2-ol;
2-((4-(((trans-2-Phenylcyclopropyl)amino)methyl)piperidin-1-yl)methyl)benzonitrile;
trans-2-Phenyl-N-((1-(2-(trifluoromethyl)benzyl)piperidin-4-yl)methyl)cyclopropanamine;
trans-N-((1-((5-Methylisoxazol-3-yl)methyl)piperidin-4-yl)methyl)-2-phenylcyclopropanamine;
trans-N-((1-((1H-Pyrazol-4-yl)methyl)piperidin-4-yl)methyl)-2-phenylcyclopropanamine
trans-N-((1-Ethylpiperidin-4-yl)methyl)-2-phenylcyclopropanamine;
Diethyl (3-(4-(((trans-2-phenylcyclopropyl)amino)methyl)piperidin-1-yl)propyl)phosphonate;
Diethyl ((4-(((trans-2-phenylcyclopropyl)amino)methyl)piperidin-1-yl)methyl)phosphonate;
3-(4-(((trans-2-Phenylcyclopropyl)amino)methyl)piperidin-1-yl)propanoic acid;
4-(((trans-2-Phenylcyclopropyl)amino)methyl)piperidin-1-yl)butanoic acid;
N-(4-(4-(((trans-2-Phenylcyclopropyl)amino)methyl)piperidin-1-yl)methyl)phenyl)acetamide;
4-((4-(((trans-2-Phenylcyclopropyl)amino)methyl)piperidin-1-yl)methyl)benzo[c][1,2]oxaborol-1(3H)-ol;
5-((4-(((trans-2-Phenylcyclopropyl)amino)methyl)piperidin-1-yl)methyl)benzo[c][1,2]oxaborol-1(3H)-ol;
(4-((4-(((trans-2-phenylcyclopropyl)amino)methyl)piperidin-1-yl)methyl)phenyl)boronic acid;
2-((4-(((trans-2-Phenylcyclopropyl)amino)methyl)piperidin-1-yl)methyl)benzoic acid;
3-((4-(((trans-2-Phenylcyclopropyl)amino)methyl)piperidin-1-yl)methyl)benzoic acid;
4-((4-(((trans-2-(4-Bromophenyl)cyclopropyl)amino)methyl)piperidin-1-yl)methyl)benzoic acid;
4-((4-(((trans-2-(4-Chlorophenyl)cyclopropyl)amino)methyl)piperidin-1-yl)methyl)benzoic acid;
4-((4-(((trans-2-(3,4-Dichlorophenyl)cyclopropyl)amino)methyl)piperidin-1-yl)methyl)benzoic acid;
4-((4-(((trans-2-(4-(Trifluoromethyl)phenyl)cyclopropyl)amino)methyl)piperidin-1-yl)methyl)benzoic acid;
4-((4-(((trans-2-(3,4-Dimethoxyphenyl)cyclopropyl)amino)methyl)piperidin-1-yl)methyl)benzoic acid;
4-((4-(((trans-2-(4-Acetamidophenyl)cyclopropyl)amino)methyl)piperidin-1-yl)methyl)benzoic acid;
4-((4-(((trans-2-(4-Benzamidophenyl)cyclopropyl)amino)methyl)piperidin-1-yl)methyl)benzoic acid;
1,1-Dimethyl-4-(((trans-2-phenylcyclopropyl)amino)methyl)piperidin-1-ium Iodide trans-2-Phenyl-N-((1-phenylpiperidin-4-yl)methyl)cyclopropanamine;
Ethyl 4-(((trans-2-phenylcyclopropyl)amino)methyl)piperidine-1-carboxylate;
trans-4-((4-(((trans-2-Phenylcyclopropyl)amino)methyl)piperidin-1-yl)methyl)cyclohexanecarboxylic acid;
3-(4-((((1R,2S)-2-Phenylcyclopropyl)amino)methyl)piperidin-1-yl)propanoic acid;
trans-N,N-Dimethyl-4-(((trans-2-phenylcyclopropyl)amino)methyl)cyclohexanamine;
N-(trans-4-(((trans-2-Phenylcyclopropyl)amino)methyl)cyclohexyl)acetamide;
N-(trans-4-(((trans-2-Phenylcyclopropyl)amino)methyl)cyclohexyl)benzamide;
4-(((trans-4-(((trans-2-Phenylcyclopropyl)amino)methyl)cyclohexyl)amino)methyl)benzoic acid;
4-(((trans-2-Phenylcyclopropyl)amino)methyl)piperidine;
trans-N-Methyl-2-phenyl-N-(2-(piperidin-4-yl)ethyl)cyclopropanamine;
trans-N-Methyl-N-((1-methylpiperidin-4-yl)methyl)-2-phenylcyclopropanamine;
trans-N-(1-Cyclohexylethyl)-2-phenylcyclopropanamine;
trans-Methyl 4-(((trans-2-phenylcyclopropyl)amino)methyl)cyclohexanecarboxylate;
trans-4-(((trans-2-Phenylcyclopropyl)amino)methyl)cyclohexanecarboxylic acid;
trans-4-((((1R,2S)-2-Phenylcyclopropyl)amino)methyl)cyclohexanecarboxylic acid;
4-(((trans-2-(4-Benzamidophenyl)cyclopropyl)amino)methyl)cyclohexanecarboxylic acid;
4-(((trans-2-(4-Acetamidophenyl)cyclopropyl)amino)methyl)cyclohexanecarboxylic acid;
trans-2-(3-Fluoro-2-methoxyphenyl)-N-(piperidin-4-ylmethyl)cyclopropanamine;
trans-2-(2-(benzyloxy)-3-fluorophenyl)-N-(piperidin-4-ylmethyl)cyclopropanamine;
trans-2-(3,5-difluorophenyl)-N-(piperidin-4-ylmethyl)cyclopropanamine;
trans-2-(2,5-difluorophenyl)-N-(piperidin-4-ylmethyl)cyclopropanamine;
N-(4-((trans)-2-((Piperidin-4-ylmethyl)amino)cyclopropyl)phenyl)acetamide;

N-(4-((trans)-2-((piperidin-4-ylmethyl)amino)cyclopropyl)phenyl)methanesulfonamide;
N-(4-((trans)-2-((piperidin-4-ylmethyl)amino)cyclopropyl)phenyl)benzenesulfonamide;
N-(4-((trans)-2-((piperidin-4-ylmethyl)amino)cyclopropyl)phenyl)benzamide;
(trans)-N-((1-(Methylsulfonyl)piperidin-4-yl)methyl)-2-phenylcyclopropanamine;
N-ethyl-4-(((((trans)-2-phenylcyclopropyl)amino)methyl)piperidine-1-carboxamide;
N-cyclopropyl-4-(((((trans)-2-phenylcyclopropyl)amino)methyl)piperidine-1-carboxamide;
N,N-dimethyl-4-(((((trans)-2-phenylcyclopropyl)amino)methyl)piperidine-1-carboxamide;
(4-(((((trans)-2-phenylcyclopropyl)amino)methyl)piperidin-1-yl)(pyrrolidin-1-yl)methanone;
trans-N-((1-(cyclopropylsulfonyl)piperidin-4-yl)methyl)-2-phenylcyclopropanamine;
trans-N-((1-(isopropylsulfonyl)piperidin-4-yl)methyl)-2-phenylcyclopropanamine;
trans-N-((1-((3,5-dimethylisoxazol-4-yl)sulfonyl)piperidin-4-yl)methyl)-2-phenylcyclopropanamine;
trans-N-((1-((1,2-dimethyl-1H-imidazol-4-yl)sulfonyl)piperidin-4-yl)methyl)-2-phenylcyclopropanamine;
(trans)-N-(2-(1-Methylpiperidin-4-yl)ethyl)-2-phenylcyclopropanamine;
(trans)-2-Phenyl-N-(2-(1-(pyridin-2-yl)piperidin-4-yl)ethyl)cyclopropanamine;
6-(4-(2-(((trans)-2-Phenylcyclopropyl)amino)ethyl)piperidin-1-yl)nicotinic acid;
trans-2-phenyl-N-(2-(1-(pyridin-4-yl)piperidin-4-yl)ethyl)cyclopropanamine;
trans-2-phenyl-N-(2-(1-(pyrimidin-4-yl)piperidin-4-yl)ethyl)cyclopropanamine;
trans-2-phenyl-N-(2-(1-phenylpiperidin-4-yl)ethyl)cyclopropanamine;
trans-2-phenyl-N-(2-(1-(pyridin-3-yl)piperidin-4-yl)ethyl)cyclopropanamine;
trans-2-phenyl-N-(2-(1-(pyrimidin-2-yl)piperidin-4-yl)ethyl)cyclopropanamine;
trans-N-(2-(1-(2-methoxyethyl)piperidin-4-yl)ethyl)-2-phenylcyclopropanamine;
trans-N-(2-(1-isopropylpiperidin-4-yl)ethyl)-2-phenylcyclopropanamine;
3-Cyano-4-((4-(((((trans)-2-phenylcyclopropyl)amino)methyl)piperidin-1-yl)methyl)benzoic acid;
2-fluoro-4-((4-(((((trans)-2-phenylcyclopropyl)amino)methyl)piperidin-1-yl)methyl)benzoic acid;
3-fluoro-4-((4-(((((trans)-2-phenylcyclopropyl)amino)methyl)piperidin-1-yl)methyl)benzoic acid;
3-chloro-4-((4-(((((trans)-2-phenylcyclopropyl)amino)methyl)piperidin-1-yl)methyl)benzoic acid;
3-methoxy-4-((4-(((((trans)-2-phenylcyclopropyl)amino)methyl)piperidin-1-yl)methyl)benzoic acid;
2-chloro-4-((4-(((((trans)-2-phenylcyclopropyl)amino)methyl)piperidin-1-yl)methyl)benzoic acid;
4-(3-(4-(Cyano(((1R,2S)-2-phenylcyclopropyl)amino)methyl)piperidin-1-yl)propyl)benzoic acid;
4-{3-[4-({[(trans))-2-phenylcyclopropyl]amino}methyl)-1-piperidinyl]propyl}benzoic acid;
4-(4-(4-(((((1R,2S)-2-Phenylcyclopropyl)amino)methyl)piperidin-1-yl)butyl)benzoic acid;
4-(4-(4-(Cyano(((1R,2S)-2-phenylcyclopropyl)amino)methyl)piperidin-1-yl)butyl)benzoic acid;
4-(2(4-(((((trans)-2-Phenylcyclopropyl)amino)methyl)piperidin-1-yl)ethyl)benzoic acid;
4-(2-(4-(((((1R,2S)-2-phenylcyclopropyl)amino)methyl)piperidin-1-yl)ethyl)benzoic acid;
6-((4-(((((trans)-2-Phenylcyclopropyl)amino)methyl)piperidin-1-yl)methyl)-2-naphthoic acid;
6-((4-(((((1R,2S)-2-Phenylcyclopropyl)amino)methyl)piperidin-1-yl)methyl)-2-naphthoic acid;
(trans)-N-((1-(4-(1H-Tetrazol-5-yl)benzyl)piperidin-4-yl)methyl)-2-phenylcyclopropanamine;
2-(4-((4-(((((trans)-2-Phenylcyclopropyl)amino)methyl)piperidin-1-yl)methyl)benzamido)acetic acid;
N-(4-((4-(((((trans)-2-Phenylcyclopropyl)amino)methyl)piperidin-1-yl)methyl)phenyl)methanesulfonamide;
(trans)-N-((1-(3-(1H-Tetrazol-5-yl)propyl)piperidin-4-yl)methyl)-2-phenylcyclopropanamine;
4-((4-(2-(((trans)-2-Phenylcyclopropyl)amino)ethyl)piperidin-1-yl)methyl)benzoic acid;
2,2-Dimethyl-3-(4-(((((trans)-2-phenylcyclopropyl)amino)methyl)piperidin-1-yl)propanoic acid;
6-((4-(((((trans)-2-Phenylcyclopropyl)amino)methyl)piperidin-1-yl)methyl)nicotinic acid;
2-(4-((4-(((((trans)-2-Phenylcyclopropyl)amino)methyl)piperidin-1-yl)methyl)phenyl)acetic acid;
2-((4-(((((trans)-2-Phenylcyclopropyl)amino)methyl)piperidin-1-yl)methyl)oxazole-4-carboxylic acid;
2-(4-((4-(((((trans)-2-phenylcyclopropyl)amino)methyl)piperidin-1-yl)methyl)phenoxy)acetic acid;
N-(Methylsulfonyl)-4-((4-(((((trans)-2-phenylcyclopropyl)amino)methyl)piperidin-1-yl)methyl)benzamide;
4-((4-(((((trans)-2-(4-Iodophenyl)cyclopropyl)amino)methyl)piperidin-1-yl)methyl)benzoic acid;
4-((trans)-2-(((1-Benzylpiperidin-4-yl)methyl)amino)cyclopropyl)benzoic acid;
4-((4-(((((trans)-2-(4-(1-Methyl-1H-pyrazol-4-yl)phenyl)cyclopropyl)amino)methyl)piperidin-1-yl)methyl)benzoic acid;
4-((4-(((((trans)-2-(4-Cyclopropylphenyl)cyclopropyl)amino)methyl)piperidin-1-yl)methyl)benzoic acid;
1-Methyl-4-(((((trans)-2-phenylcyclopropyl)amino)methyl)piperidine-4-carboxylic acid
4-(((((trans)-2-Phenylcyclopropyl)amino)methyl)piperidine-4-carboxylic acid;
1-Benzyl-4-(((((trans)-2-phenylcyclopropyl)amino)methyl)piperidine-4-carboxylic acid;
2-Chloro-4-((4-(((((1R,2S)-2-phenylcyclopropyl)amino)methyl)piperidin-1-yl)methyl)benzoic acid;
3-(3-(4-(((((trans)-2-Phenylcyclopropyl)amino)methyl)piperidin-1-yl)propyl)benzoic acid;
4-(3-(2-(((((1R,2S)-2-Phenylcyclopropyl)amino)methyl)morpholino)propyl)benzoic acid;
4-((2-(((((1R,2S)-2-phenylcyclopropyl)amino)methyl)morpholino)methyl)benzoic acid;
3-(3-(((((1R,2S)-2-Phenylcyclopropyl)amino)methyl)pyrrolidin-1-yl)propanoic acid;
2-(4-((4-(((((1R,2S)-2-Phenylcyclopropyl)amino)methyl)piperidin-1-yl)methyl)phenyl)acetic acid; and
3-((R)-3-(((((1R,2S)-2-Phenylcyclopropyl)amino)methyl)pyrrolidin-1-yl)propanoic acid; or a pharmaceutically acceptable salt thereof.

This invention also relates to compounds exemplified in the Experimental section.

Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. In general, the salts are formed from pharmaceutically acceptable inorganic and organic acids.

More specific examples of suitable acid salts include maleic, hydrochloric, hydrobromic, sulphuric, phosphoric, nitric, perchloric, fumic, acetic, propionic, succinic, glycolic, formic, lactic, aleic, tartaric, citric, palmoic, malonic, hydroxymaleic, phenylacetic, glutamic, benzoic, salicylic, fumaric, toluenesulfonic, methansulfonic (mesylate), naphthalene-2-sulfonic, benzenesulfonic, hydroxynaphthoic, hydroiodic, malic, teroic, tannic, and the like.

Other representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, oxalate, pamoate (embonate), palmitate, pantothenate, phosphate/diphosphate, polygalacturonate, salicylate, stearate, subacetate, succinate, sulfate, tannate, tartrate, teoclate, tosylate, triethiodide, and valerate salts.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. The invention also covers the individual isomers of the compound or salt represented by Formula (I) as mixtures with isomers thereof in which one or more chiral centers are inverted. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. Also included within the scope of the invention are individual isomers of the compound represented by Formula (I), as well as any wholly or partially equilibrated mixtures thereof. The present invention also includes the individual isomers of the compound or salt represented by the Formula (I) as well as mixtures with isomers thereof in which one or more chiral centers are inverted. It is to be understood that the present invention includes all combinations and subsets of the particular groups defined hereinabove.

DEFINITIONS

Terms are used within their accepted meanings. The following definitions are meant to clarify, but not limit, the terms defined.

As used herein, the term "alkyl" (or "alkylene") refers to a straight or branched chain alkyl, preferably having from one to twelve carbon atoms, which may be unsubstituted or substituted, saturated or unsaturated with multiple degrees of substitution, preferably 1 to 3. Suitable substituents are selected from the group consisting of: halogen, amino, substituted amino, urea, cyano, hydroxyl, methoxy, ethoxy, methylthio, ethylthio, methylsulfonyl, ethylsulfonyl, phosphonate, amidosulfonyl, carboxylic acid, carboxylic ester, carboxamide, tetrazolyl and aminocarbonyl. Examples of "alkyl" as used herein include methyl, ethyl, propyl, isopropyl, isobutyl, n-butyl, t-butyl, isopentyl, n-pentyl, and the like, as well as substituted versions thereof.

As used herein, the term "cycloalkyl" refers to an unsubstituted or substituted mono- or polycyclic non-aromatic saturated ring, which optionally includes an alkylene linker through which the cycloalkyl may be attached. Exemplary "cycloalkyl" groups include, but are not limited to, cyclopropyl, cyclobutyl, cyclopentyl, cyclohexyl, cycloheptyl, and the like, as well as substituted versions thereof.

As used herein, the term "alkoxy" refers to the group —ORa, where Ra is unsubstituted $C_1$-$C_4$alkyl or unsubstituted $C_3$-$C_7$cycloalkyl as defined above.

As used herein, the term "substituted amino" is meant —NR'R" wherein each R' and R" is independently selected from a group including hydrogen, unsubstituted $C_1$-$C_6$alkyl, acyl, unsubstituted $C_3$-$C_7$cycloalkyl, wherein at least one of R' and R" is not hydrogen. Examples of substituted amino includes, but are not limited to alkylamino, dialkylaminio, acylamino, and cycloalkylamino.

As used herein, the term "heterocycle" or "heterocyclyl" or "heterocycloalkyl" refers to unsubstituted and substituted mono- or polycyclic non-aromatic ring system containing one or more heteroatoms. Preferred heteroatoms include N, O, and S, including N-oxides, sulfur oxides, and dioxides. Preferably the ring is three to eight-membered and is either fully saturated or has one or more degrees of unsaturation. Multiple degrees of substitution are included within the present definition. Examples of "heterocyclic" groups include, but are not limited to tetrahydrofuranyl, pyranyl, 1,4-dioxanyl, 1,3-dioxanyl, piperidinyl, pyrrolidinyl, morpholinyl, azetidinyl, piperazinyl, pyrrolidinonyl, piperazinonyl, pyrazolidinyl, and their various tautomers, as well as substituted versions thereof.

As used herein, the term "aryl", unless otherwise defined, is meant aromatic, hydrocarbon, ring system. The ring system may be monocyclic or fused polycyclic (e.g., bicyclic, tricyclic, etc.), substituted or unsubstituted. In various embodiments, the monocyclic aryl ring is C5-C10, or C5-C7, or C5-C6, where these carbon numbers refer to the number of carbon atoms that form the ring system. A C6 ring system, i.e. a phenyl ring, is a suitable aryl group. In various embodiments, the polycyclic ring is a bicyclic aryl group, where suitable bicyclic aryl groups are C8-C12, or C9-C10. A naphthyl ring, which has 10 carbon atoms, is a suitable polycyclic aryl group. Suitable substituents for aryl are described in the definition of "optionally substituted".

As used herein, the term "heteroaryl", unless otherwise defined, is meant an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include: benzofuran, benzothiophene, furan, imidazole, indole, isothiazole, oxazole, pyrazine, pyrazole, pyridazine, pyridine, pyrimidine, pyrrole, quinoline, quinazoline, quinoxaline, thiazole, hydroxy-1,3-dihydrobenzo[c][1,2]oxaborole, and thiophene. Suitable substituents for heteroaryl are described in the definition of "optionally substituted".

As used herein, the term "cyano" refers to the group —CN.

As used herein, the term "acyl" refers to the group —C(O)Rb, where Rb is unsubstituted $C_1$-$C_6$alkyl, unsubstituted $C_3$-$C_7$cycloalkyl, or unsubstituted $C_3$-$C_6$heterocyclyl, as each is defined herein.

As used herein, the term "aryloxy" refers to the group —$OC_1$-$C_6$alkylaryl, wherein the $C_1$-$C_6$alkyl is normally unsubstituted, for example, phenylmethoxy, naphthylmethoxy.

As used herein, the term "arylalkyl" refers to the group —$C_1$-$C_6$alkylaryl, wherein the $C_1$-$C_6$alkyl is normally unsubstituted, for example, phenylmethyl, naphthylmethyl.

As used herein, the term "heteroarylalkyl" refers to the group —$C_1$-$C_6$alkylheteroaryl, wherein the $C_1$-$C_6$alkyl is suitably unsubstituted; for example, pyridinylmethyl.

As used herein, the term "optionally" means that the subsequently described event(s) may or may not occur, and includes both event(s) that occur and event(s) that do not occur.

As used herein, unless otherwise defined, the phrase "optionally substituted", "substituted" or variations thereof denote an optional substitution, including multiple degrees of substitution, with one or more substitutents, preferably one to three, more preferably one to two. The phrase should not be interpreted as duplicative of the substitutions herein described and depicted. Exemplary optional substituent groups include acyl, $C_1$-$C_6$alkyl, carboxylic acid, boronic acid, $C_1$-$C_3$alkylsulfonyl, $C_1$-$C_4$alkoxy, $C_1$-$C_4$alkoxycarbonyl, cyano, halogen, $C_1$-$C_6$haloalkyl, hydroxyl, oxo, amide, sulfamide, urea, amino, substituted amino, acylamino, phenylcarbonyl, dialkylaminosulfonamide, morpholino, sulfonamide, thiourea, tetrazolyl, and nitro.

The invention further provides a pharmaceutical composition (also referred to as pharmaceutical formulation) comprising a compound of Formula (I) or pharmaceutically acceptable salt, thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

In accordance with another aspect of the invention there is provided a process for the preparation of a pharmaceutical composition comprising mixing (or admixing) a compound of Formula (I) or salt thereof with at least one excipient.

The compounds of Formula I or salts, including pharmaceutically acceptable salts, thereof may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates wherein water is the solvent that is incorporated into the crystalline lattice are typically referred to as "hydrates." Hydrates include stoichiometric hydrates as well as compositions containing viable amounts of water. The invention includes all such solvates.

Pharmaceutical Compositions

Pharmaceutical compositions may be in unit dose form containing a predetermined amount of active ingredient per unit dose. Such a unit may contain a therapeutically effective dose of the compound of Formula (I) or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

As used herein, the term "treatment" includes prophylaxis and refers to alleviating the specified condition, eliminating or reducing one or more symptoms of the condition, slowing or eliminating the progression of the condition, and preventing or delaying the reoccurrence of the condition in a previously afflicted or diagnosed patient or subject. Prophylaxis (or prevention or delay of disease onset) is typically accomplished by administering a drug in the same or similar manner as one would to a patient with the developed disease or condition.

The present invention provides a potential treatment in a mammal, especially a human, suffering from disease conditions targeted by the present compounds. Such treatment comprises the step of administering a therapeutically effective amount of a compound of Formula (I) or salt thereof to said mammal, particularly a human. Treatment can also comprise the step of administering a therapeutically effective amount of a pharmaceutical composition containing a compound of Formula (I) or salt thereof to said mammal, particularly a human.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I), as well as salts thereof, may be administered as the raw chemical. Additionally, the active ingredient may be presented as a pharmaceutical composition.

While it is possible that, for use in therapy, a therapeutically effective amount of a compound of Formula (I) or salt thereof may be administered as the raw chemical, it is typically presented as the active ingredient of a pharmaceutical composition or formulation.

The precise therapeutically effective amount of a compound or salt thereof of the invention will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a compound of Formula (I) or salt thereof will be given for the treatment in the range of about 0.01 to 100 mg/kg body weight of recipient (patient, mammal) per day and more usually in the range of 0.1 to 10 mg/kg body weight per day. Acceptable daily dosages may be from about 1 to about 1000 mg/day, and preferably from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the compound of Formula (I) per se. Similar dosages should be appropriate for treatment (including prophylaxis) of the other conditions referred herein for treatment. In general, determination of appropriate dosing can be readily arrived at by one skilled in medicine or the pharmacy art.

Combinations

When a compound of Formula (I) is administered for the treatment of cancer, the term "co-administering" and derivatives thereof as used herein is meant either simultaneous administration or any manner of separate sequential administration of a LSD1 inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice f Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients for use in combination or co-administered with the present LSD1 inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects Occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino)carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

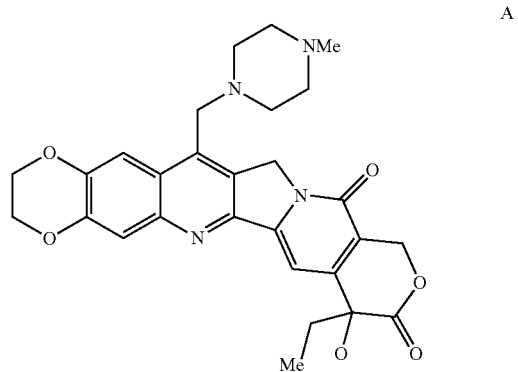 [SMILES: CCC1(O)C(=O)OCc2c1cc1n(c2=O)Cc2c-1nc1cc3c(cc1c2CN1CCN(C)CC1)OCCO3]

A known by the chemical name "7-(4-methylpiperazino-methylene)-10,11-ethylenedioxy-20(R,S) camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor –I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, *London*.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta) IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), *Biochemical Pharmacology*, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myo-inositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed erb family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230. Further, p21WAF1/CIP1 has been described as a potent and universal inhibitor of cyclin-dependent kinases (Cdks) (Ball et al., *Progress in Cell Cycle Res.*, 3: 125 (1997)). Compounds that are known to induce expression of p21WAF1/CIP1 have been implicated in the suppression of cell proliferation and as having tumor suppressing activity (Richon et al., *Proc. Nat. Acad. Sci. U.S.A.* 97(18): 10014-10019 (2000)), and are included as cell cycle signaling inhibitors.

Modulators of the Retinoid Acid Receptor have been used to treat leukemias. The pathology of the leukemia is associated with the abnormal accumulation of immature progenitor cells that are sensitive to retinoc acid therapy. The majority of cases of acute promyelocytic leukemia (APL), also called acute myeloid leukemia subtype M3, involve a chromosomal translocation of chromosomes 15 and 17 that causes genetic fusion of the retinoic acid receptor (RAR) gene to the promyelocytic leukemia (PML) gene. This fusion PML-RAR protein is responsible for preventing immature myeloid cells from differentiating into more mature cells. This block in differentiation is and subsequent accumulation of less differentiated cells is thought to cause leukemia. ATRA, Tretinoin, acts on PML-RAR to lift this block, causing the immature promyelocytes to differentiate to normal mature blood cells thus decreasing promyelocytes and promoting a population of terminally differentiated cells with a restricted lifespan. Talazorole is an experimental drug in the same class as Tretinoin.

Epigenetic alterations have been implicated in virtually all types of human cancers. Cancer specific changes are often associated with silencing of tumor suppressor genes via histone modifications and modifications to DNA including DNA hypermethylation. Epigenetic pharmaceuticals control regulatory regions associated with tumor suppressor genes by causing conformational changes in histones and removing repressive modifications to DNA. These changes directly affect the formation and progression of cancer. Examples of epigenetic agents include histone deacetylase inhibitors and DNA methylation inhibitors.

Histone deacetylase inhibitors (HDAC inhibitors, HDI) are a class of compounds that interfere with the function of histone deacetylases Inhibitors of histone deacetylases have been shown to be useful in the treatment of cutaneous T-cell lymphoma. They are being investigated in the clinic for multiple other tumor types. Examples of HDAC inhibitors approved for use are Vorinostat and Romidepsin. These compounds are thought to inhibit the activity of HDACs and result in the accumulation of acetylation to histones promoting gene expression.

Azacitidine (INN) or 5-azacytidine, sold under the trade name Vidaza, is a chemical analogue of cytidine, a nucleoside present in DNA and RNA. Azacitidine and its deoxy derivative, decitabine (also known as 5-aza-2' deoxycytidine), are used in the treatment of myelodysplastic syndrome and are currently under study for other tumor indications. Azacitidine acts as a false substrate and potent inhibitor of DNA methyltransferases leading to reduction of DNA methylation. DNA methyltransferases incorporate azacitidine into DNA during replication and into RNA during transcription in the cell. Inhibition of DNA methylation occurs through the formation of stable complexes between the molecule and DNA methyltransferases, thereby saturating cell methylation machinery. This results in a loss of DNA methylation and can affect the way cell regulation proteins, such as transcriptional machinery, are able to associate with the DNA.

Examples of such HDAC inhibitors include:
1. Vorinostat, including pharmaceutically acceptable salts thereof. Marks et al., *Nature Biotechnology* 25, 84 to 90 (2007); Stenger, Community Oncology 4, 384-386 (2007). Vorinostat has the following chemical structure and name:

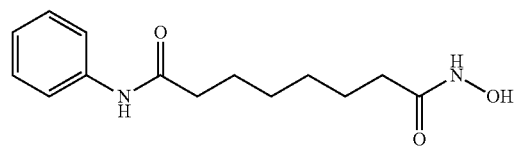 [SMILES: O=C(CCCCCCC(=O)Nc1ccccc1)NO]

N-hydroxy-N'-phenyl-octanediamide

2. Romidepsin, including pharmaceutically acceptable salts thereof. Vinodhkumar et al., *Biomedicine & Pharmaco-*

*therapy* 62 (2008) 85-93. Romidepsin, has the following chemical structure and name:

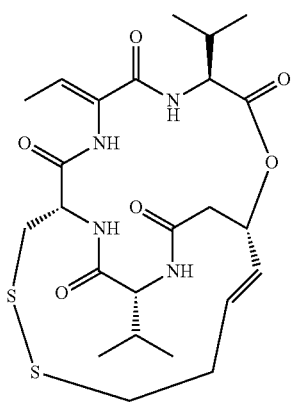 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

(1S,4S,7Z,10S,16E,21R)-7-ethylidene-4,21-di(propan-2-yl)-2-oxa-12,13-dithia-5,8,20,23-tetrazabicyclo[8.7.6]tricos-16-ene-3,6,9,19,22-pentone 3. Panobinostat, including pharmaceutically acceptable salts thereof. *Drugs of the Future* 32(4): 315-322 (2007).

Panobinostat, has the following chemical structure and name:

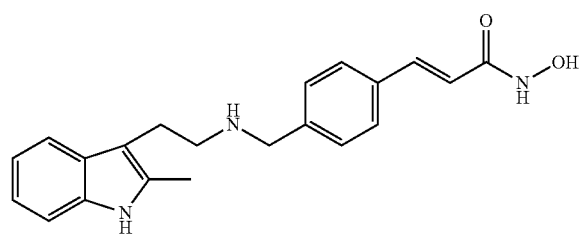 [SMILES: Cc1[nH]c2ccccc2c1CCNCc1ccc(/C=C/C(=O)NO)cc1]

(2E)-N-hydroxy-3-[4-({[2-(2-methyl-1H-indol-3-yl)ethyl]amino}methyl)phenyl]acrylamide 4. Valproic acid, including pharmaceutically acceptable salts thereof. Gottlicher, et al., EMBO J. 20(24): 6969-6978 (2001).

Valproic acid, has the following chemical structure and name:

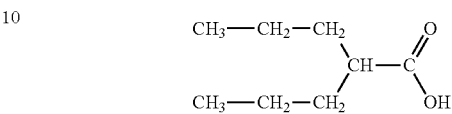

2-propylpentanoic acid

5. Mocetinostat (MGCD0103), including pharmaceutically acceptable salts thereof. Balasubramanian et al., Cancer Letters 280: 211-221 (2009).

Mocetinostat, has the following chemical structure and name:

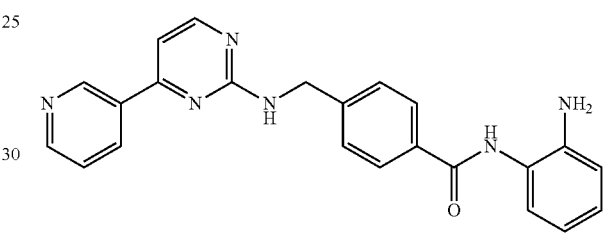

N-(2-Aminophenyl)-4-[[(4-pyridin-3-ylpyrimidin-2-yl)amino]methyl]benzamide

Further examples of such HDAC inhibitors are included in Bertrand European Journal of Medicinal Chemistry 45, (2010) 2095-2116, particularly the compounds of table 3 therein as indicated below.

| Hydroxamic acids | |
|---|---|
| 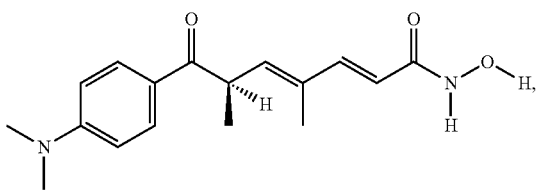<br>Trichostatine A (TSA) | 1 |
| 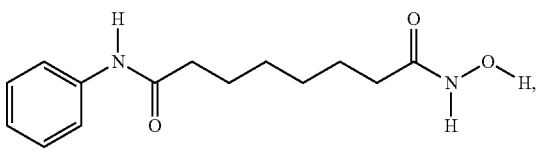<br>SAHA | 2 |

-continued
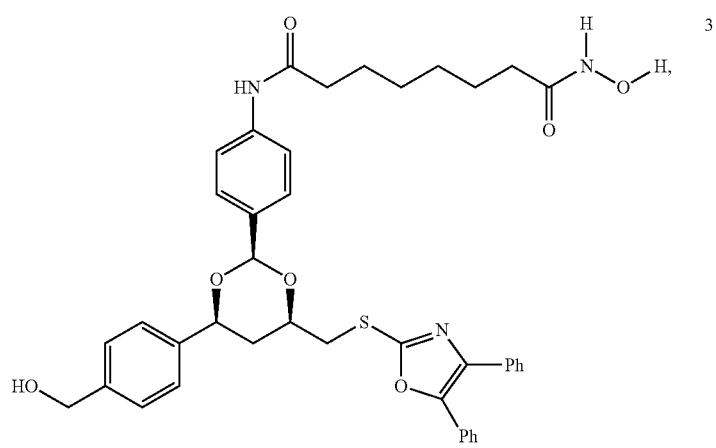
Tubacin
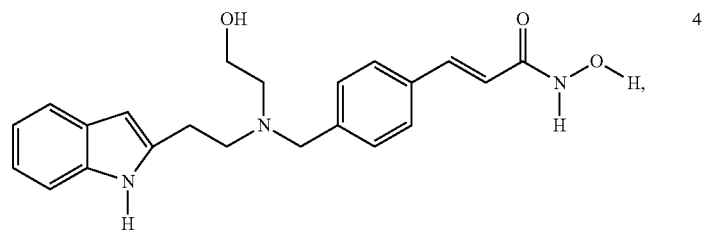
LAQ824
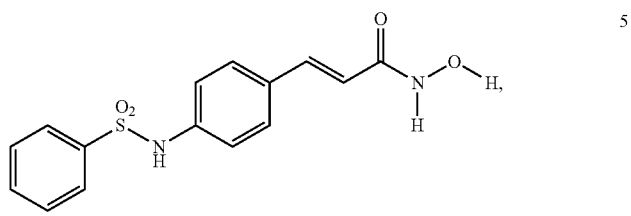
Sulfonamide
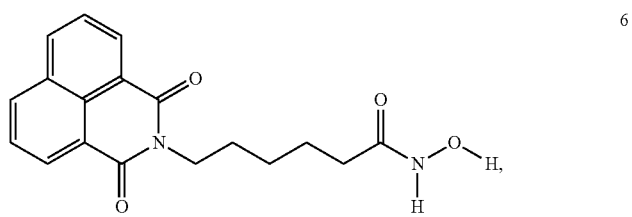
Scriptaid
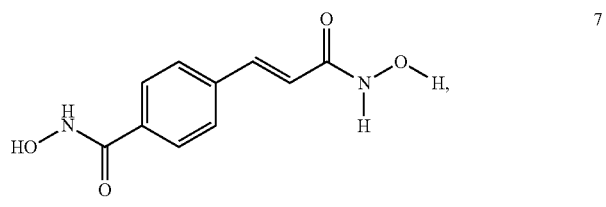
CBHA -continued
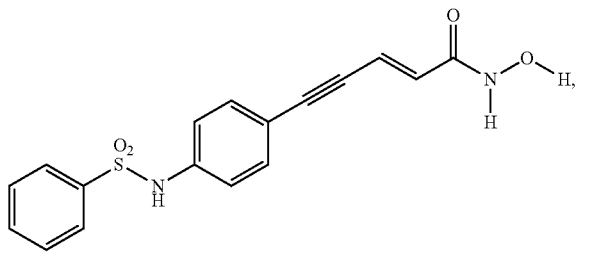
Oxamflatin
Cyclic tetrapeptides
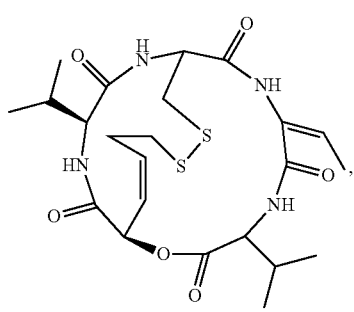
FK228
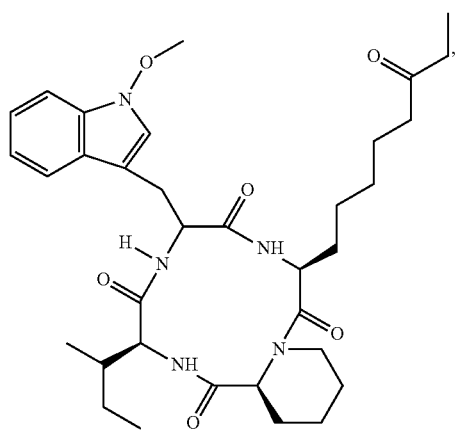
Apicidin
Short chain carboxylic acids
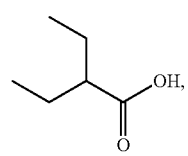
Valproic acid
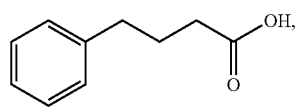
Phenylbutyric acid -continued Benzamides

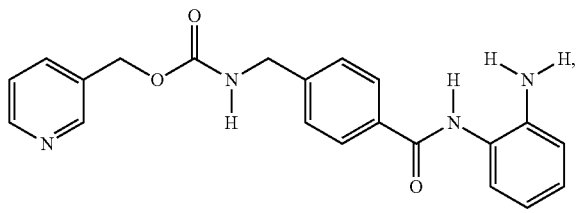

MS-275

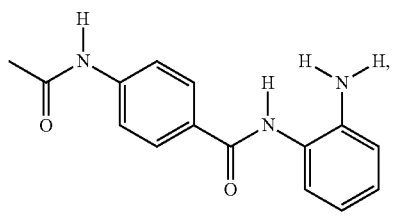

Cl-994

Keto derivatives

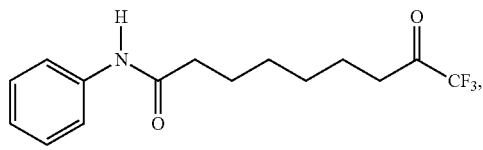

Trifluoromethyl cétone

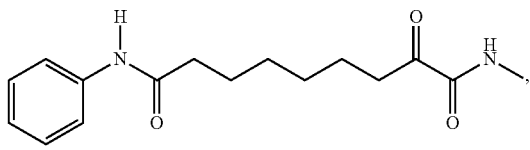

alpha-cétoamide

Proteasome inhibitors are drugs that block the action of proteasomes, cellular complexes that break down proteins, like the p53 protein. Several proteasome inhibitors are marketed or are being studied in the treatment of cancer. Suitable proteasome inhibitors for use in combination herein include:

1. Bortezomib (Velcade®), including pharmaceutically acceptable salts thereof. Adams J, Kauffman M (2004), *Cancer Invest* 22 (2): 304-11.

Bortezomib has the following chemical structure and name.

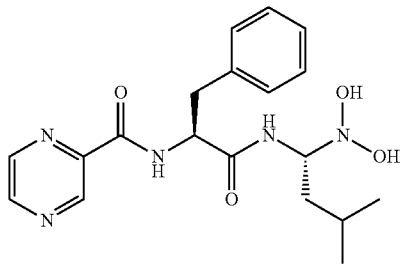 [SMILES: CC(C)C[C@H](NC(=O)[C@H](Cc1ccccc1)NC(=O)c1cnccn1)N(O)O]

[(1R)-3-methyl-1-({(2S)-3-phenyl-2-[(pyrazin-2-ylcarbonyl)amino]propanoyl}amino)butyl]boronic acid 2. Disulfuram, including pharmaceutically acceptable salts thereof. Bouma et al. (1998). *J. Antimicrob. Chemother.* 42 (6): 817-20.

Disulfuram has the following chemical structure and name.

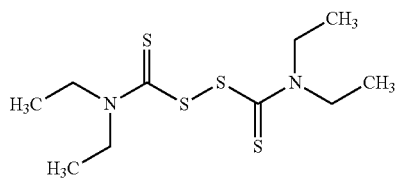 [SMILES: CCN(CC)C(=S)SSC(=S)N(CC)CC]

1,1',1'',1'''-[disulfanediylbis(carbonothioylnitrilo)]tetraethane

3. Epigallocatechin gallate (EGCG), including pharmaceutically acceptable salts thereof. Williamson et al., (December 2006), *The Journal of Allergy and Clinical Immunology* 118 (6): 1369-74.

Epigallocatechin gallate has the following chemical structure and name.

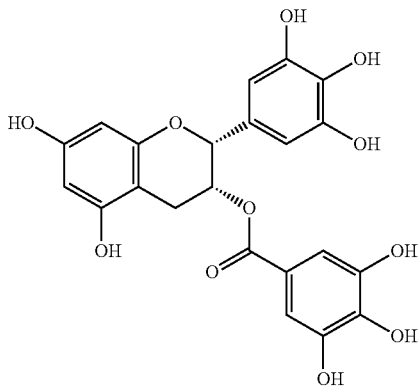 [SMILES: O=C(O[C@@H]1Cc2c(O)cc(O)cc2O[C@@H]1c1cc(O)c(O)c(O)c1)c1cc(O)c(O)c(O)c1]

[(2R,3R)-5,7-dihydroxy-2-(3,4,5-trihydroxyphenyl)chroman-3-yl]3,4,5-trihydroxybenzoate 4. Salinosporamide A, including pharmaceutically acceptable salts thereof. Feling et at., (2003), *Angew. Chem. Int. Ed. Engl.* 42 (3): 355-7.

Salinosporamide A has the following chemical structure and name.

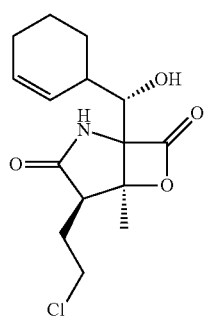 [SMILES: C[C@@]12OC(=O)C1([C@@H](O)C1C=CCCC1)NC(=O)[C@@H]2CCCl]

(4R,5S)-4-(2-chloroethyl)-1-((1S)-cyclohex-2-enyl(hydroxy)methyl)-5-methyl-6-oxa-2-azabicyclo3.2.0heptane-3,7-dione 5. Carfilzomib, including pharmaceutically acceptable salts thereof. Kuhn D J, et al, Blood, 2007, 110:3281-3290.

Carfilzomib has the following chemical structure and name.

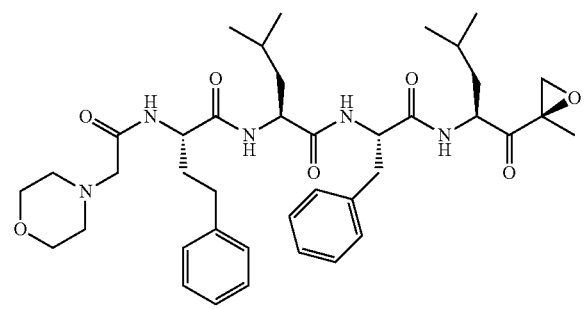 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1]

(S)-4-methyl-N—((S)-1-4(S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide The 70 kilodalton heat shock proteins (Hsp70s) and 90 kilodalton heat shock proteins (Hsp90s) are a families of ubiquitously expressed heat shock proteins. Hsp70s and Hsp90s are over expressed certain cancer types. Several Hsp70s and Hsp90s inhibitors are being studied in the treatment of cancer. Suitable Hsp70s and Hsp90s inhibitors for use in combination herein include:

1. 17-AAG(Geldanamycin), including pharmaceutically acceptable salts thereof. Jia W et al. Blood. 2003 Sep. 1; 102(5):1824-32.

17-AAG(Geldanamycin) has the following chemical structure and name.

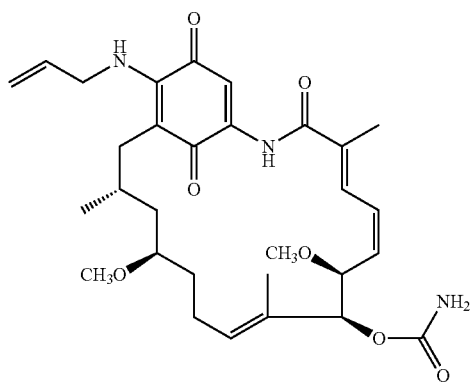

17-(Allylamino)-17-demethoxygeldanamycin

2. Radicicol, including pharmaceutically acceptable salts thereof (Lee et al., Mol Cell Endocrinol. 2002, 188, 47-54)

Radicicol has the following chemical structure and name.

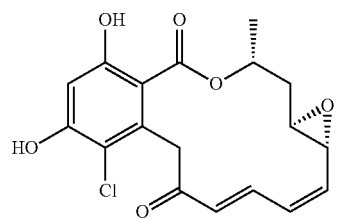

(1aR,2Z,4E,14R,15aR)-8-chloro-9,11-dihydroxy-14-methyl-15,15a-dihydro-1aH-benzo[c]oxireno[2,3-k][1]oxacyclotetradecine-6,12(7H,14H)-dione Inhibitors of cancer metabolism—Many tumor cells show a markedly different metabolism from that of normal tissues. For example, the rate of glycolysis, the metabolic process that converts glucose to pyruvate, is increased, and the pyruvate generated is reduced to lactate, rather than being further oxidized in the mitochondria via the tricarboxylic acid (TCA) cycle. This effect is often seen even under aerobic conditions and is known as the Warburg Effect.

Lactate dehydrogenase A (LDH-A), an isoform of lactate dehydrogenase expressed in muscle cells, plays a pivotal role in tumor cell metabolism by performing the reduction of pyruvate to lactate, which can then be exported out of the cell.

The enzyme has been shown to be upregulated in many tumor types. The alteration of glucose metabolism described in the Warburg effect is critical for growth and proliferation of cancer cells and knocking down LDH-A using RNA-i has been shown to lead to a reduction in cell proliferation and tumor growth in xenograft models.

D. A. Tennant et. al., Nature Reviews, 2010, 267.

P. Leder, et. al., Cancer Cell, 2006, 9, 425.

High levels of fatty acid synthase (FAS) have been found in cancer precursor lesions. Pharmacological inhibition of FAS affects the expression of key oncogenes involved in both cancer development and maintenance.

Alli et al. *Oncogene* (2005) 24, 39-46. doi:10.1038

Inhibitors of cancer metabolism, including inhibitors of LDH-A and inhibitors of fatty acid biosynthesis (or FAS inhibitors), are suitable for use in combination with the compounds of this invention.

In one embodiment, the cancer treatment method of the claimed invention includes the co-administration a compound of Formula (I) and/or a pharmaceutically acceptable salt thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, cell cycle signaling inhibitors; proteasome inhibitors; and inhibitors of cancer metabolism.

EXPERIMENTALS

Schemes

Compounds of Formula (I) may be prepared by the methods outlined in Scheme 1 below.

Formulas and R group designations used in the schemes below are meant to be used for this section only. Compounds of formula (II) and (III) are commercially available or may be synthesized using techniques conventional in the art. A person skilled in the art understands that the exemplified compounds below may exist in the form of hydrochloride salt if HCl is used in the last step of the preparation.

The compounds of formula (II) and (III) may be reacted under traditional reductive amination conditions to give compounds of formula (I). The addition reaction is typically done using a polar, aprotic solvent such as dichloroethane or tetrahydrofuran in the presence of an acid such as acetic acid. The acid is typically present in an amount of 50-100 mol % with respect to the compound of formula (I). The reducing agent is typically a borohydride such as NaBH(OAc)$_3$ but can also be performed under catalytic hydrogenation conditions with a platinum, palladium or nickel catalyst.

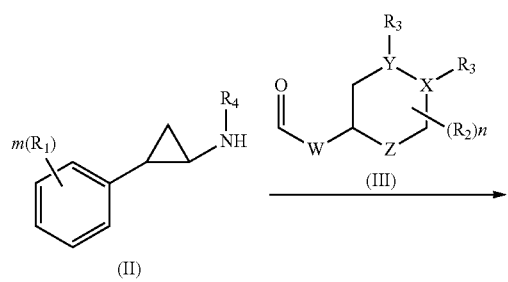

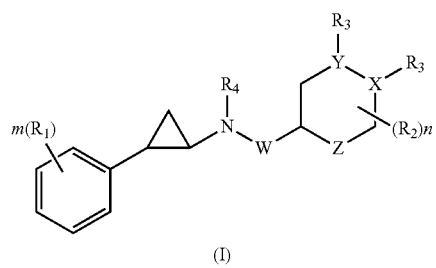

Compounds of formula (I) may be conveniently prepared by the methods outlined in Scheme 2, starting with an appropriate phenyl cyclopropylamine (II) and appropriately protected aldehyde (V). Reductive amination of amine (II) with aldehyde (V) gives intermediate (VI). The amine can then be protected. The X or Y group can then be deprotected to allow for functionalization with the appropriate R$_3$ substituent to give compounds of formula (VIII). The amine can then be deprotected and functionalized with an R$_4$ group.

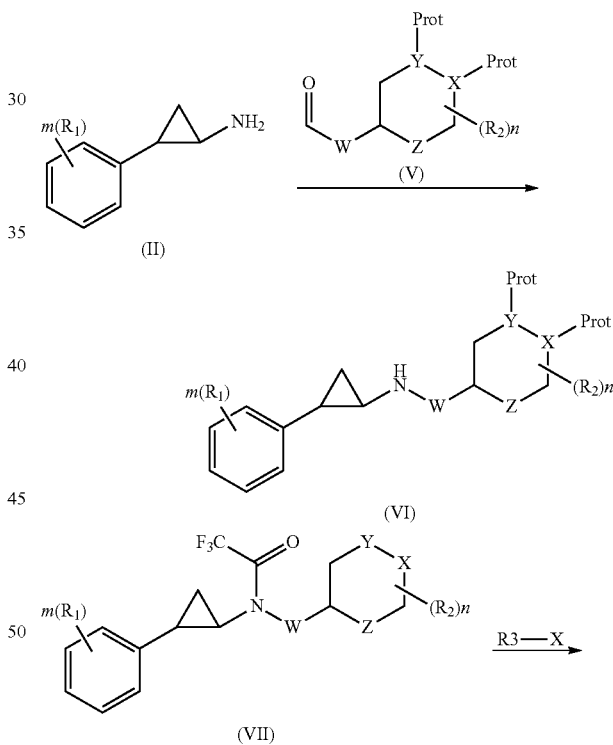

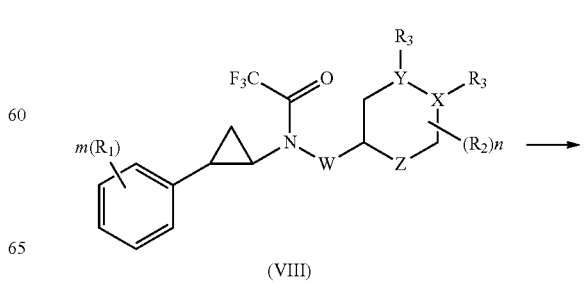

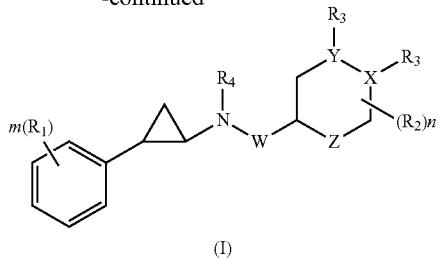

(I)

Compounds of formula (II) and (IV) may be synthesized as outlined in Scheme 3. Starting from a cinnamate, a cyclopropanation can be performed under standard conditions such as the reaction of diazomethane with $Pd(OAc)_2$ to give compounds of formula (X). This ester is then saponified to give acids of formula (XI) that are then reacted with under standard Curtius rearrangement conditions to give the desired compounds of formula (IV). The compounds of formula (IV) can be converted to compounds of formula (II) under standard conditions.

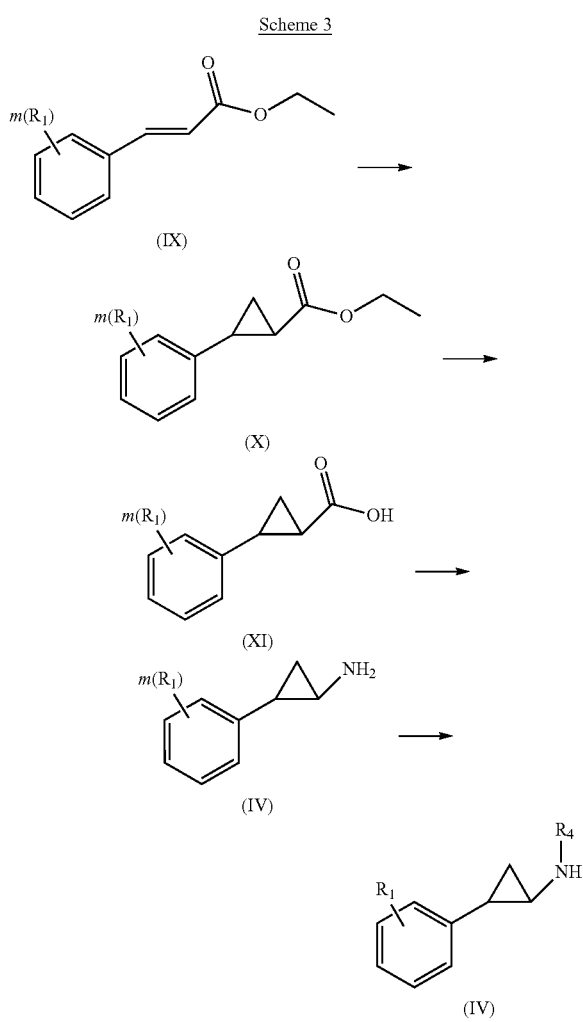

Alternatively, compounds of formula (II) and (IV) may be synthesized as outlined in Scheme 4. Starting from a styrene, a cyclopropanation can be performed under standard conditions such as the reaction of diazomethane with $Pd(OAc)_2$ to give compounds of formula (IX). These can then be modified as in Scheme 3.

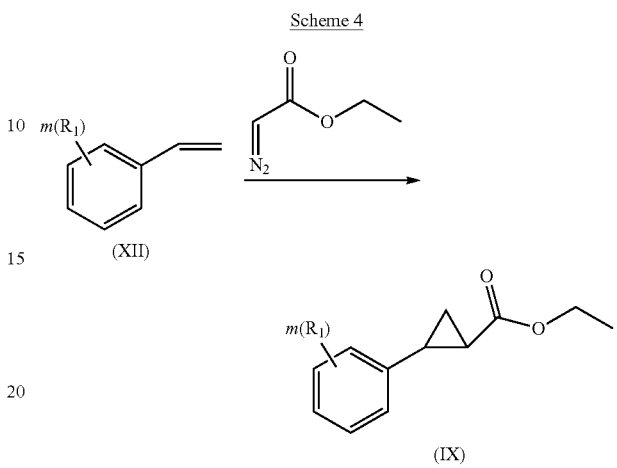

The following chemistry examples are for illustrative purposes only and are not intended to limit the scope of the present invention. The compounds were named using ACD Name software (Advanced Chemistry Development, www.acdlabs.com). All compounds have $PIC_{50}$ of greater than 4.7 for the above-described biochemical assay.

A PE Sciex API 150 single quadrupole mass spectrometer (PE Sciex, Thornhill, Ontario, Canada) was operated using electrospray ionization in the positive ion detection mode. The nebulizing gas was generated from a zero air generator (Balston Inc., Haverhill, Mass.; www.parker.com) and delivered at 65 psi and the curtain gas was high purity nitrogen delivered from a Dewar liquid nitrogen vessel at 50 psi. The voltage applied to the electrospray needle was 4.8 kV. The orifice was set at 25 V and mass spectrometer was scanned at a rate of 0.5 scan/sec using a step mass of 0.2 amu and collecting profile data.

Method A, LCMS. Samples are introduced into the mass spectrometer using a CTC PAL autosampler (LEAP Technologies, Carrboro, N.C.) equipped with a Hamilton 10 uL syringe which performed the injection into a Valco 10-port injection valve. The HPLC pump was a Shimadzu LC-10ADvp (Shimadzu Scientific Instruments, Columbia, Md.) operated at 0.3 mL/min and a linear gradient 4.5% A to 90% B in 3.2 min. with a 0.4 min. hold. The mobile phase was composed of 100% ($H_2O$ 0.02% TFA) in vessel A and 100% ($CH_3CN$ 0.018% TFA) in vessel B. The stationary phase is Aquasil (C18) and the column dimensions are 1 mm×40 mm. Detection was by UV at 214 nm, evaporative light-scattering (ELSD) and MS.

Method B, LCMS. Alternatively, an Agilent 1100 analytical HPLC system with an LC/MS was used and operated at 1 mL/min and a linear gradient 5% A to 100% B in 2.2 min with a 0.4 min hold. The mobile phase was composed of 100% ($H_2O$ 0.02% TFA) in vessel A and 100% ($CH_3CN$ 0.018% TFA) in vessel B. The stationary phase was Zobax (C8) with a 3.5 um partical size and the column dimensions were 2.1 mm×50 mm. Detection was by UV at 214 nm, evaporative light-scattering (ELSD) and MS.

Method B, LCMS. Alternatively, an MDSSCIEX API 2000 equipped with a capillary column of (50×4.6 mm, 5 μm) was used. HPLC was done on Agilent-1200 series UPLC system equipped with column Zorbax SB-C18 (50×4.6 mm, 1.8 μm)

eluting with CH₃CN: ammonium acetate buffer. The reactions were performed in the microwave (CEM, Discover).

1H-NMR (hereinafter "NMR") spectra were recorded at 400 MHz using a Bruker AVANCE 400 MHz instrument, with ACD Spect manager ver 10 using for reprocessing. Multiplicities indicated are: s=singlet, d=doublet, t=triplet, q=quartet, m=multiplet, dd=doublet of doublets, dt=doublet of triplets etc. and br indicates a broad signal.

Analytical HPLC: Products were analyzed by Agilent 1100 Analytical Chromatography system, with 4.5×75 mm Zorbax XDB-C18 column (3.5 um) at 2 mL/min with a 4 min gradient from 5% CH₃CN (0.1% formic acid) to 95% CH₃CN (0.1% formic acid) in H₂O (0.1% formic acid) and a 1 min hold.

Preparative HPLC: Products were purified using a Gilson preparative chromatography system with a 75×30 mm I. D. YMC CombiPrep ODS-A column (5 um) (www.waters.com) at 50 mL/min with a 10 min gradient from 5% CH₃CN (0.1% formic acid) to 95% CH₃CN (0.1% formic acid) in H₂O (0.1% formic acid) and a 2 min hold; alternatively, products were purified using an Agilent 1100 Preparative Chromatography system, with 100×30 mm Gemini C18 column (5 um) at 60 mL/min with a 10 min gradient from 5% CH₃CN (0.1% formic acid) to 95% CH₃CN (0.1% formic acid) in H₂O (0.1% formic acid) and a 2 min hold.

Preparative normal phase chromatography was carried out using an Analogix IntelliFlash 280 or 310 System with Super-Flash Sepra Si 50 columns. Alternatively an ISCO Companion system was used. Alternatively, reverse-phase HPLC was performed on Agilent using Zorbax SB-C18 column (21.2× 250 mm, 7 μm) eluting with CH₃CN: ammonium acetate buffer (10 μM) at pH 6.8.

Example 1

1,1-Dimethylethyl 4-({[trans-2-phenylcyclopropyl]amino}methyl)-1-piperidinecarboxylate

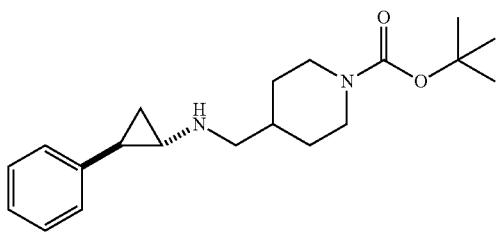

To the solution of 1,1-dimethylethyl-4-formyl-1-piperidinecarboxylate (1.2 g, 5.63 mmol) in 1,2-dichloroethane (DCE) (20 mL) and acetic acid (0.322 mL, 5.63 mmol) was added [trans-2-phenylcyclopropyl]amine (1.499 g, 11.25 mmol). The reaction mixture was stirred for 2 hour at room temperature then sodium triacetoxyborohydride (4.77 g, 22.51 mmol) was added and the reaction mixture was stirred 3 hours at room temperature. The reaction mixture was quenched with saturated solution of NH₄Cl. Water (10 mL) followed by dichlomethane (20 mL) were added. The layers were separated and the organic layer was washed with brine, dried over MgSO₄, filtered and evaporated. The solid was suspended in the mixture of acetonitrile/diethyl ether 1:1, sonicated, stirred for 1 hour at room temperature and filtered. 1,1-Dimethylethyl 4-({[trans-2-phenylcyclopropyl]amino}methyl)-1-piperidinecarboxylate (1.1 g, 3.16 mmol, 56.2% yield) was isolated as white solid. ¹H NMR (400 MHz, METHANOL-d₄) δ 7.29-7.38 (m, 2H), 7.23-7.29 (m, 1H), 7.15-7.22 (m, 2H), 4.14 (d, J=12.38 Hz, 2H), 3.14 (d, J=7.07 Hz, 2H), 3.01 (dt, J=4.14, 7.64 Hz, 1H), 2.81 (t, J=2.02 Hz, 2H), 2.54 (ddd, J=3.54, 6.63, 10.29 Hz, 1H), 1.88-2.08 (m, J=3.54, 7.41, 7.41, 11.29, 11.29 Hz, 1H), 1.81 (d, J=12.38 Hz, 2H), 1.56 (ddd, 1H), 1.47 (s, 9H), 1.41 (q, J=6.82 Hz, 1H), 1.23 (qd, J=4.29, 12.46 Hz, 2H); LC-MS Rt=0.76 min; MS (ESI): 331.2 [M+H]⁺.

Example 2

1,1-Dimethylethyl 4-({[(1R,2S)-2-phenylcyclopropyl]amino}methyl)-1-piperidinecarboxylate

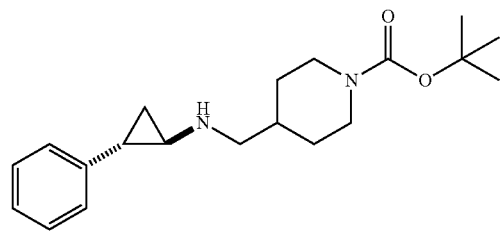

Following a procedure analogous to the procedure described in Example 1 using [(1R,2S)-2-phenylcyclopropyl]amine ((−) isomer) (94 mg, 0.703 mmol) afforded 1,1-dimethylethyl 4-({[(1R,2S)-2-phenylcyclopropyl]amino}methyl)-1-piperidinecarboxylate (92 mg, 0.264 mmol, 56.4% yield) as white solid. ¹H NMR (400 MHz, METHANOL-d₄) δ 7.29-7.37 (m, 2H), 7.23-7.28 (m, 1H), 7.17-7.22 (m, 2H), 4.14 (d, J=12.63 Hz, 2H), 3.14 (d, J=7.07 Hz, 2H), 3.01 (dt, J=4.14, 7.64 Hz, 1H), 2.81 (br. s., 2H), 2.53 (ddd, J=3.54, 6.63, 10.29 Hz, 1H), 1.97 (ddd, 1H), 1.80 (d, J=12.13 Hz, 2H), 1.55 (ddd, J=4.29, 6.63, 10.55 Hz, 1H), 1.47 (s, 9H), 1.36-1.45 (m, 1H), 1.23 (qd, J=4.29, 12.38 Hz, 2H); LC-MS Rt=0.78 min; MS (ESI): 331.3 [M+H]⁺.

Example 3

1,1-Dimethylethyl 4-({[(1S,2R)-2-phenylcyclopropyl]amino}methyl)-1-piperidinecarboxylate

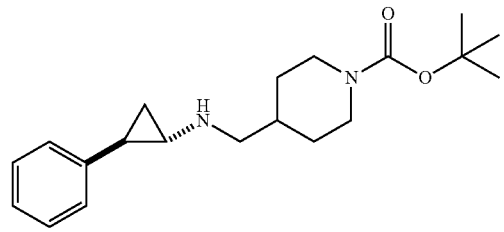

Following a procedure analogous to the procedure described in Example 1 using [(1S,2R)-2-phenylcyclopropyl]amine ((+) isomer) (94 mg, 0.703 mmol) afforded 1,1-dimethylethyl 4-({[(1S,2R)-2-phenylcyclopropyl]amino}methyl)-1-piperidinecarboxylate (85 mg, 0.244 mmol, 52.1% yield) as white solid. ¹H NMR (400 MHz, METHANOL-d₄) δ 7.29-7.38 (m, 2H), 7.23-7.28 (m, 1H), 7.20 (d, J=7.07 Hz, 2H), 4.14 (d, J=12.88 Hz, 2H), 3.14 (d, J=7.07 Hz, 2H), 3.01 (dt, J=4.07, 7.77 Hz, 1H), 2.81 (br. s., 2H), 2.52 (ddd, J=3.54, 6.63, 10.29 Hz, 1H), 1.96 (ddd, J=3.92, 7.52, 11.31 Hz, 1H), 1.80 (d, J=12.13 Hz, 2H), 1.54

(ddd, J=4.29, 6.63, 10.55 Hz, 1H), 1.47 (s, 9H), 1.42 (q, J=6.82 Hz, 1H), 1.23 (qd, J=4.42, 12.42 Hz, 2H); LC-MS Rt=0.78 min; MS (ESI): 331.3 [M+H]+.

Example 4

[trans-2-Phenylcyclopropyl](4-piperidinylmethyl)amine

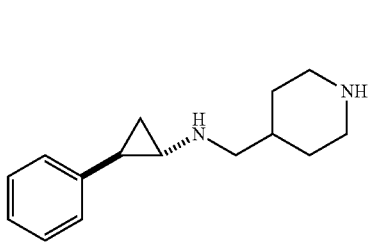

To the solution of 1,1-dimethylethyl 4-({[trans-2-phenylcyclopropyl]amino}methyl)-1-piperidinecarboxylate (Example 1) (50 mg, 0.151 mmol) in 1,4-dioxane (1 mL) was added 1 M HCl (1 ml, 32.9 mmol) and the reaction mixture was heated to reflux for 10 minutes. The reaction mixture was then evaporated. [trans-2-phenylcyclopropyl](4-piperidinylmethyl)amine (25 mg, 0.089 mmol, 58.8% yield) was isolated as white solid. ¹H NMR (400 MHz, METHANOL-d₄) δ 7.29-7.45 (m, 2H), 7.16-7.29 (m, 3H), 3.47 (d, J=13.39 Hz, 2H), 3.22 (d, J=7.07 Hz, 2H), 2.96-3.14 (m, 3H), 2.63 (ddd, J=3.66, 6.63, 10.42 Hz, 1H), 2.04-2.26 (m, 3H), 1.49-1.70 (m, 3H), 1.35-1.46 (m, 1H); LC-MS Rt=0.39 min; MS (ESI): 231.2 [M+H]+.

Example 5

[(1S,2R)-2-Phenylcyclopropyl](4-piperidinylmethyl)amine

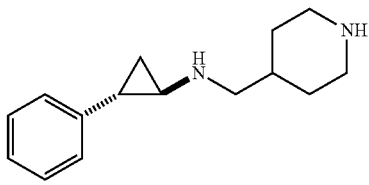

Following a procedure analogous to the procedure described in Example 4 using 1,1-dimethylethyl 4-({[(1S,2R)-2-phenylcyclopropyl]amino}methyl)-1-piperidinecarboxylate (Example 3, 50 mg, 0.151 mmol) afforded [(1S,2R)-2-phenylcyclopropyl](4-piperidinylmethyl)amine (32 mg, 0.114 mmol, 75% yield) as white solid. ¹H NMR (400 MHz, METHANOL-d₄) δ 7.29-7.39 (m, 2H), 7.24-7.29 (m, 2H), 7.18-7.24 (m, 2H), 3.47 (d, J=13.14 Hz, 2H), 3.22 (d, J=7.07 Hz, 2H), 3.00-3.13 (m, 3H), 2.62 (ddd, J=3.54, 6.63, 10.29 Hz, 1H), 2.14-2.28 (m, J=3.95, 3.95, 7.45, 11.18 Hz, 1H), 2.09 (d, J=14.15 Hz, 2H), 1.49-1.69 (m, 3H), 1.42 (q, J=6.82 Hz, 1H); LC-MS Rt=0.44 min; MS (ESI): 231.2 [M++H]+.

Example 6

[(1R,2S)-2-Phenylcyclopropyl](4-piperidinylmethyl)amine

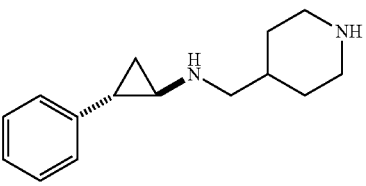

Following a procedure analogous to the procedure described in Example 4 using 1,1-dimethylethyl 4-({[(1R,2S)-2-phenylcyclopropyl]amino}methyl)-1-piperidinecarboxylate (Example 2, 60 mg, 0.182 mmol) afforded [(1R,2S)-2-phenylcyclopropyl](4-piperidinylmethyl)amine (41 mg, 0.146 mmol, 80% yield) as white solid. ¹H NMR (400 MHz, METHANOL-d₄) δ 7.29-7.38 (m, 2H), 7.23-7.29 (m, 1H), 7.18-7.23 (m, 2H), 3.47 (d, J=13.39 Hz, 2H), 3.21 (d, 2H), 2.89-3.13 (m, 3H), 2.60 (ddd, J=3.79, 6.57, 10.36 Hz, 1H), 2.13-2.28 (m, J=3.85, 3.85, 7.61, 11.21 Hz, 1H), 1.99-2.13 (m, 2H), 1.49-1.71 (m, 3H), 1.35-1.48 (m, 1H); LC-MS Rt=0.44 min; MS (ESI): 231.2 [M+H]+.

Example 7 trans-N-(Cyclohexylmethyl)-2-phenylcyclopropanamine

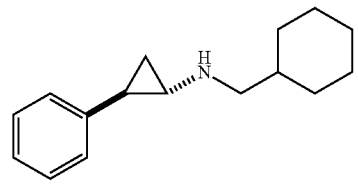

To the solution of cyclohexanecarbaldehyde (59.5 mg, 0.530 mmol) in tetrahydrofuran (THF) (10 mL) and acetic acid (0.061 mL, 1.061 mmol) was added trans-2-phenylcyclopropyl]amine hydrochloride (180 mg, 1.061 mmol). The reaction mixture was stirred for 1 hour, then sodium triacetoxyborohydride (450 mg, 2.122 mmol) was added and the reaction mixture stirred for 2 hours. The reaction mixture was quenched with saturated solution of NH₄Cl. Water (10 mL) followed by ethyl acetate (30 mL) were added. The layers were separated and the organic layer was washed with brine, dried over MgSO₄, filtered and evaporated. The oil was purified on preparative HPLC (5 to 70% AcCN:H₂O gradient with 0.1% formic acid modifier). The fractions were collected. The combined fractions were neutralized with aq. NH₄OH, concentrated and extracted with ethyl acetate. Organic layer was washed with brine, dried over MgSO₄ and evaporated. trans-N-(Cyclohexylmethyl)-2-phenylcyclopropanamine (40 mg, 0.166 mmol, 31.2% yield) was isolated as colorless liquid. ¹H NMR (400 MHz, METHANOL-d₄) δ 7.19-7.28 (m, 2H), 7.09-7.17 (m, 1H), 7.02-7.09 (m, 2H), 2.55 (dd, J=1.52, 6.82 Hz, 2H), 2.24-2.34 (m, 1H), 1.92 (ddd, J=3.28, 6.00, 9.41 Hz, 1H), 1.61-1.86 (m, 5H), 1.44-1.58 (m, J=3.41, 3.41, 7.23, 10.97, 14.64 Hz, 1H), 1.14-1.40 (m, 3H), 1.07 (dt, J=4.86, 9.47 Hz, 1H), 0.83-1.04 (m, 3H); LC-MS Rt=0.71 min; MS (ESI): 230.4 [M++H]$^+$.

Example 8

[trans-2-Phenylcyclopropyl]{[1-(phenylmethyl)-4-piperidinyl]methyl}amine

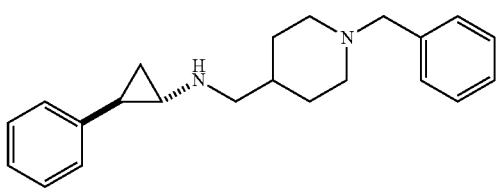

Following a procedure analogous to the procedure described in Example 7 using 1-(phenylmethyl)-4-piperidinecarbaldehyde (108 mg, 0.530 mmol) afforded [trans-2-phenylcyclopropyl]{[1-(phenylmethyl)-4-piperidinyl]methyl}amine (110 mg, 0.326 mmol, 61.5% yield) as white solid. $^1$H NMR (400 MHz, METHANOL-d$_4$) δ 7.56-7.65 (m, 2H), 7.47-7.55 (m, 3H), 7.29-7.39 (m, 2H), 7.12-7.28 (m, 3H), 4.36 (br. s., 2H), 3.54 (d, J=9.85 Hz, 2H), 3.20 (d, 2H), 3.04-3.16 (m, 2H), 3.03 (dt, J=3.88, 7.64 Hz, 1H), 2.61 (ddd, J=3.66, 6.44, 10.11 Hz, 1H), 2.03-2.28 (m, 3H), 1.53-1.80 (m, 3H), 1.40 (q, J=6.82 Hz, 1H); LC-MS Rt=0.52 min; MS (ESI): 321.2 [M+H]$^+$.

Example 9

1,1-Dimethylethyl [trans-4-({[trans-2-phenylcyclopropyl]amino}methyl)cyclohexyl]carbamate

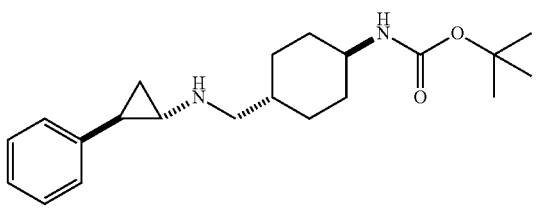

Following a procedure analogous to the procedure described in Example 7 using 1,1-dimethylethyl (trans-4-formylcyclohexyl)carbamate (121 mg, 0.530 mmol) afforded 1,1-dimethylethyl [trans-4-({[trans-2-phenylcyclopropyl]amino}methyl)cyclohexyl]carbamate (62 mg, 0.171 mmol, 32.2% yield) as white solid. $^1$H NMR (400 MHz, METHANOL-d$_4$) δ 7.29-7.38 (m, 2H), 7.22-7.28 (m, 1H), 7.16-7.21 (m, 2H), 3.08 (d, J=7.07 Hz, 2H), 2.97 (dt, J=4.14, 7.64 Hz, 1H), 2.47 (ddd, J=3.66, 6.51, 10.29 Hz, 1H), 1.94-2.04 (m, 2H), 1.83-1.93 (m, 2H), 1.70 (ddd, J=3.41, 7.33, 10.99 Hz, 1H), 1.35-1.56 (m, 11H), 1.04-1.32 (m, 4H); LC-MS Rt=0.81 min; MS (ESI): 345.2 [M++H]$^+$.

Example 10 trans-4-({[[trans-2-Phenylcyclopropyl]amino}methyl)cyclohexanamine

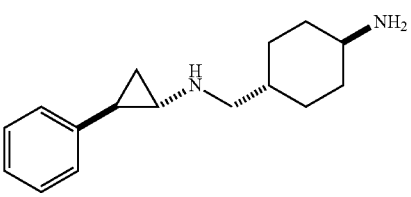

Following a procedure analogous to the procedure described in Example 4 using 1,1-dimethylethyl [trans-4-({[trans-2-phenylcyclopropyl]amino}methyl)cyclohexyl]carbamate (50 mg, 0.145 mmol) afforded trans-4-({[trans-2-phenylcyclopropyl]amino}methyl)cyclohexanamine (42 mg, 0.142 mmol, 98% yield) as white solid. $^1$H NMR (400 MHz, METHANOL-d$_4$) δ 7.30-7.37 (m, 2H), 7.23-7.28 (m, 1H), 7.14-7.22 (m, 2H), 3.06-3.18 (m, 3H), 3.00 (dt, J=4.14, 7.64 Hz, 1H), 2.57 (ddd, J=3.79, 6.57, 10.36 Hz, 1H), 2.07-2.20 (m, 2H), 2.01 (dd, J=3.03, 13.64 Hz, 2H), 1.71-1.92 (m, 1H), 1.58 (ddd, J=4.55, 6.57, 10.61 Hz, 1H), 1.34-1.54 (m, 3H), 1.14-1.33 (m, 2H); LC-MS Rt=0.51 min; MS (ESI): 245.3 [M+H]$^+$.

Example 11

2-(4-(((trans-2-Phenylcyclopropyl)amino)methyl)piperidin-1-yl)ethanol

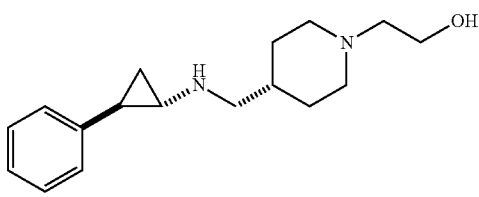

a) tert-butyl 4-((2,2,2-Trifluoro-N-(trans-2-phenylcyclopropyl)acetamido)methyl)piperidine-1-carboxylate To the solution of tert-butyl 4-(((trans-2-phenylcyclopropyl)amino)methyl)piperidine-1-carboxylate (Example 1, 600 mg, 1.816 mmol) in chloroform (5 ml) was added triethylamine (0.759 ml, 5.45 mmol) and trifluoroacetic anhydride (0.282 ml, 1.997 mmol) slowly. The reaction mixture was stirred at the room temperature for 30 min. 1 M Na$_2$CO$_3$ (2 mL) was added followed by 2 mL of dichloromethane. Organic layer was separated, washer with brine, dried over MgSO$_4$, filtered and evaporated. tert-butyl 44(2,2,2-trifluoro-N-(trans-2-phenylcyclopropyl)acetamido)methyl)piperidine-1-carboxylate (700 mg, 1.559 mmol, 86% yield) was isolated as yellow oil. $^1$H NMR (400 MHz, CHLOROFORM-d) δ 7.29-7.37 (m, 2H), 7.27 (d, J=7.33 Hz, 1H), 7.07 (d, J=7.07 Hz, 2H), 4.13 (d, J=1.26 Hz, 2H), 3.21-3.63 (m, 2H), 3.09-3.18 (m, 1H), 3.00-3.08 (m, 1H), 2.68 (t, J=12.25 Hz, 2H), 2.29-2.43 (m, 1H), 1.84-2.03 (m, J=3.66, 7.47, 7.47, 11.21 Hz, 1H), 1.57-1.72 (m, 2H), 1.48-1.56 (m, 1H), 1.45-1.49 (m, 9H), 1.19 (td, J=3.66, 12.06 Hz, 2H); LC-MS Rt=1.27 min; MS (ESI): 426.7 [M++H]$^+$.

b) 2,2,2-trifluoro-N-(trans-2-Phenylcyclopropyl)-N-(piperidin-4-ylmethyl)acetamide To the solution of tert-butyl 4-((2,2,2-trifluoro-N-(trans-2-phenylcyclopropyl)acetamido)methyl)piperidine-1-carboxylate (700 mg, 1.641 mmol) in chloroform (2 mL) was added trifluoroacetic acid (2 ml, 26.0 mmol). The reaction mixture was stirred at the room temperature for 1 hr. The reaction was evaporated, and then 2 ml of 1 M Na$_2$CO$_3$ (2 mL) were added followed by 10 mL of ethyl acetate. The organic layer was separated, washer with brine, dried over MgSO$_4$, filtered and evaporated. 2,2,2-trifluoro-N-(trans-2-phenylcyclopropyl)-N-(piperidin-4-ylmethyl)acetamide (450 mg, 1.310 mmol, 80% yield) was isolated as yellow oil. $^1$H NMR (400 MHz, CHLOROFORM-d) δ 7.30-7.38 (m, 2H), 7.27 (d, J=7.33 Hz, 1.5H), 7.08 (d, J=7.33 Hz, 1.5H), 3.35-3.49 (m, 1.7H), 3.10-3.22 (m, 2H), 2.97-3.09 (m, 0.8H), 2.52-2.67 (m, 2H), 2.30-2.44 (m, 0.8H), 1.75-2.10 (m, 2.3H), 1.59-1.75 (m, 2.4H), 1.39-1.58 (m, 2H), 1.13-1.38 (m, 2.5H); LC-MS Rt=0.70 min; MS (ESI): 327.2 [M+H]$^+$.

c) 2,2,2-Trifluoro-N-((1-(2-hydroxyethyl)piperidin-4-yl)methyl)-N-(trans-2-phenylcyclopropyl)acetamide To the solution of 2,2,2-trifluoro-N-(trans-2-phenylcyclopropyl)-N-(piperidin-4-ylmethyl)acetamide (60 mg, 0.184 mmol) in acetonitrile (10 mL) was added potassium carbonate (76 mg, 0.552 mmol) followed by 2-bromoethanol (29.9 mg, 0.239 mmol). The reaction mixture was heated in the seal tube at 80° C. for 4 hours. The reaction mixture was then filtered and evaporated. 2,2,2-Trifluoro-N-((1-(2-hydroxyethyl)piperidin-4-yl)methyl)-N-(trans-2-phenylcyclopropyl)acetamide (40 mg, 0.103 mmol, 55.8% yield) was isolated as yellow oil. $^1$H NMR (400 MHz, METHANOL-d$_4$) δ 7.07-7.37 (m, 5H), 3.75-3.87 (m, 2H), 3.57-3.66 (m, 1H), 3.49-3.57 (m, 1H), 3.46 (t, J=6.06 Hz, 1H), 3.36-3.41 (m, 3H), 3.19 (t, J=3.79 Hz, 1H), 2.78-3.04 (m, 2H), 2.56-2.76 (m, 1H), 2.48 (ddd, J=3.54, 6.51, 10.17 Hz, 1H), 1.96-2.15 (m, 1H), 1.87 (td, J=2.91, 10.80 Hz, 2H), 1.63 (dt, J=5.24, 10.23 Hz, 1H), 1.39-1.57 (m, 3H); LC-MS Rt=0.76 min; MS (ESI): 371.2 [M++H]$^+$.

d) 2-(4-(((trans-2-Phenylcyclopropyl)amino)methyl)piperidin-1-yl)ethanol

To the solution of 2,2,2-trifluoro-N-((1-(2-hydroxyethyl)piperidin-4-yl)methyl)-N-(trans-2-phenylcyclopropyl)acetamide (40 mg, 0.108 mmol) in ethanol (2 mL) was added 1 M NaOH (1 mL, 1.000 mmol). The reaction was heated to 80° C. for 1 hr. Then 10 ml of ethyl acetate was added. Layers were separated, organic layer was washed with brine, dried over MgSO$_4$, filtered and evaporated. The oil was purified on preparative HPLC (5 to 70% AcCN: H$_2$O gradient with 0.1% formic acid modifier). The fractions were collected. The combined fractions were neutralized with aq. NH$_4$OH, concentrated and extracted with ethyl acetate. Organic layer was washed with brine, dried over MgSO$_4$ and evaporated. 2-(4-(((trans-2-Phenylcyclopropyl)amino)methyl)piperidin-1-yl) ethanol (10 mg, 0.035 mmol, 32.1% yield) was isolated as colorless oil. $^1$H NMR (400 MHz, METHANOL-d$_4$) δ 7.19-7.28 (m, 2H), 7.10-7.16 (m, 1H), 7.03-7.09 (m, 2H), 3.70 (t, J=6.32 Hz, 2H), 2.95-3.08 (m, 2H), 2.61 (d, J=6.82 Hz, 2H), 2.54 (t, J=6.19 Hz, 2H), 2.25-2.37 (m, 1H), 2.02-2.16 (m, 2H), 1.92 (ddd, J=3.28, 5.87, 9.28 Hz, 1H), 1.69-1.85 (m, 2H), 1.49-1.64 (m, J=3.54, 7.48, 7.48, 14.84 Hz, 1H), 1.20-1.36 (m, 2H), 1.08 (dt, J=4.77, 9.41 Hz, 1H), 1.01 (dt, J=5.59, 7.26 Hz, 1H); LC-MS Rt=0.48 min; MS (ESI): 275.2 [M+H]$^+$.

Example 12

N-Phenyl-4-(((trans-2-phenylcyclopropyl)amino) methyl)piperidine-1-carboxamide

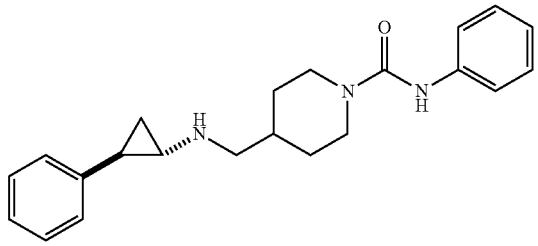

To the solution of 2,2,2-trifluoro-N-(trans-2-phenylcyclopropyl)-N-(piperidin-4-ylmethyl)acetamide (60 mg, 0.184 mmol) (Example 11b) in chloroform (2 mL) was added isocyanatobenzene (0.030 mL, 0.276 mmol) The reaction mixture was stirred at room temperature for 1 hr. The saturated solution of NH$_4$Cl was added, and layers were separated. The organic layer was evaporated and the oil dissolved in ethanol (2 mL) and 0.5 mL of 1 M NaOH was added. The reaction mixture was stirred for 1 hour at room temperature and then it was evaporated. The oil was purified on preparative HPLC (5 to 70% AcCN: H$_2$O gradient with 0.1% formic acid modifier). The fractions were collected. The combined fractions were neutralized with aq. NH$_4$OH, concentrated and extracted with ethyl acetate. The organic layer was washed with brine, dried over MgSO$_4$ and evaporated. N-phenyl-4-(((trans-2-phenylcyclopropyl)amino)methyl)piperidine-1-carboxamide (54 mg, 0.147 mmol, 80% yield) was isolated as yellow oil. $^1$H NMR (400 MHz, METHANOL-d$_4$) δ 7.32-7.38 (m, 2H), 7.20-7.31 (m, 4H), 7.10-7.17 (m, 1H), 7.05-7.10 (m, 2H), 6.98-7.05 (m, 1H), 4.20 (d, J=12.63 Hz, 2H), 2.79-3.01 (m, 2H), 2.65 (d, J=6.57 Hz, 2H), 2.28-2.45 (m, 1H), 1.95 (ddd, J=3.16, 5.94, 9.35 Hz, 1H), 1.70-1.90 (m, 3H), 1.14-1.31 (m, 2H), 1.10 (dt, J=4.86, 9.47 Hz, 1H), 1.03 (dt, 1H); LC-MS Rt=0.56 min; MS (ESI): 350.3 [M++H]$^+$.

Example 13 trans-2-Phenyl-N-((1-(phenylsulfonyl)piperidin-4-yl) methyl)cyclopropanamine

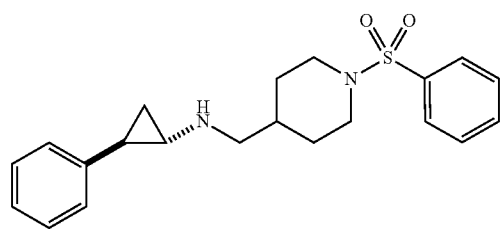

To the solution of 2,2,2-trifluoro-N-(trans-2-phenylcyclopropyl)-N-(piperidin-4-ylmethyl)acetamide (100 mg, 0.306 mmol) (Example 11b) in chloroform (2 mL) was added pyridine (0.099 mL, 1.226 mmol) followed by benzenesulfonyl chloride (0.059 mL, 0.460 mmol). The reaction mixture was stirred at room temperature for 1 hr. The saturated solution of NH$_4$Cl was added, and layers were separated. Organic layer was evaporated and the oil dissolved in ethanol (2 mL) and 0.5 mL of 1 M NaOH was added. The reaction mixture was stirred for 1 hour at the room temperature and then it was evaporated. The oil was purified on preparative HPLC (5 to 70% AcCN: H$_2$O gradient with 0.1% formic acid modifier). The fractions were collected. The combined fractions were neutralized with aq. NH$_4$OH, concentrated and extracted with ethyl acetate. The organic layer was washed with brine, dried over MgSO$_4$ and evaporated. trans-2-phenyl-N-((1-(phenylsulfonyl)piperidin-4-yl)methyl)cyclopropanamine (10 mg, 0.026 mmol, 8.37% yield) was isolated as yellow oil. $^1$H NMR (400 MHz, METHANOL-d$_4$) δ 7.76-7.85 (m, 2H), 7.65-7.73 (m, 1H), 7.52-7.66 (m, 2H), 7.15-7.28 (m, 2H), 7.06-7.16 (m, 1H), 6.97-7.05 (m, 2H), 3.77 (d, J=12.13 Hz, 2H), 2.57 (dd, J=1.26, 6.82 Hz, 2H), 2.13-2.35 (m, 3H), 1.72-1.97 (m, 3H), 1.36-1.54 (m, J=3.73, 3.73, 7.33, 7.33, 14.78 Hz, 1H), 1.14-1.35 (m, 2H), 0.90-1.10 (m, 2H); LC-MS Rt=0.76 min; MS (ESI): 370.9 [M+H]$^+$.

Example 14

Phenyl(4-(((trans-2-phenylcyclopropyl)amino)methyl)piperidin-1-yl)methanone

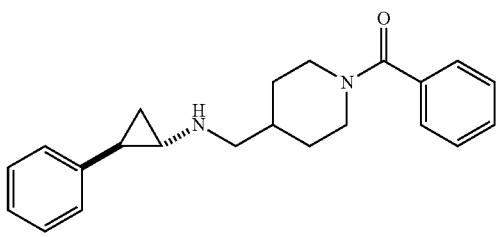

To the solution of 2,2,2-trifluoro-N-(trans-2-phenylcyclopropyl)-N-(piperidin-4-ylmethyl)acetamide (90 mg, 0.276 mmol) (Example 11b) in chloroform (2 mL) was added triethylamine (0.115 mL, 0.827 mmol) followed by benzoyl chloride (0.053 mL, 0.414 mmol). The reaction mixture was stirred at room temperature for 1 hr. A saturated solution of NH$_4$Cl was added, and layers were separated. The organic layer was evaporated and the oil dissolved in ethanol (2 mL) and 0.5 mL of 1 M NaOH was added. The reaction mixture was stirred for 1 hour at the room temperature and then it was evaporated. The oil was purified on preparative HPLC (5 to 70% AcCN: H$_2$O gradient with 0.1% formic acid modifier). The fractions were collected. The combined fractions were neutralized with aq. NH$_4$OH, concentrated and extracted with ethyl acetate. The organic layer was washed with brine, dried over MgSO$_4$ and evaporated. Phenyl(4-(((trans-2-phenylcyclopropyl)amino)methyl)piperidin-1-yl)methanone (45 mg, 0.128 mmol, 46.3% yield) was isolated as yellow oil. $^1$H NMR (400 MHz, METHANOL-d$_4$) δ 7.44-7.50 (m, 3H), 7.36-7.43 (m, 2H), 7.20-7.28 (m, 2H), 7.10-7.17 (m, 1H), 7.03-7.09 (m, 2H), 4.66 (d, J=12.88 Hz, 1H), 3.74 (d, J=12.63 Hz, 1H), 3.03-3.22 (m, 1H), 2.87 (t, J=12.51 Hz, 1H), 2.66 (dd, J=3.03, 6.32 Hz, 2H), 2.22-2.37 (m, 1H), 1.80-2.05 (m, 3H), 1.74 (d, J=13.14 Hz, 1H), 1.12-1.40 (m, 2H), 1.09 (dt, J=4.86, 9.47 Hz, 1H), 0.98-1.05 (m, 1H); LC-MS Rt=0.81 min; MS (ESI): 335.3 [M++H]$^+$.

Example 15

1-(4-(((trans-2-Phenylcyclopropyl)amino)methyl)piperidin-1-yl)ethanone

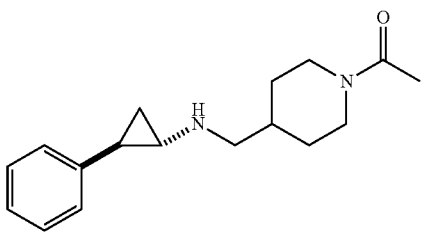

Following a procedure analogous to the procedure described in Example 14 using acetyl chloride (0.030 mL, 0.414 mmol) afforded 1-(4-(((trans-2-phenylcyclopropyl)amino)methyl)piperidin-1-yl)ethanone (28 mg, 0.098 mmol, 35.4% yield) as yellow oil. $^1$H NMR (400 MHz, METHANOL-d$_4$) δ 7.18-7.28 (m, 2H), 7.10-7.17 (m, 1H), 7.03-7.09 (m, 2H), 4.53 (dd, J=2.02, 13.14 Hz, 1H), 3.93 (dd, J=1.64, 13.52 Hz, 1H), 3.02-3.20 (m, 1H), 2.48-2.73 (m, 3H), 2.27-2.42 (m, 1H), 2.10 (s, 3H), 1.93 (ddd, J=3.41, 5.94, 9.35 Hz, 1H), 1.72-1.88 (m, 3H), 1.12-1.27 (m, 1H), 1.09 (dt, J=4.86, 9.47 Hz, 2H), 0.98-1.06 (m, 1H); LC-MS Rt=0.55 min; MS (ESI): 273.2 [M+H]$^+$.

Example 16

[trans-2-Phenylcyclopropyl](3-piperidinylmethyl)amine

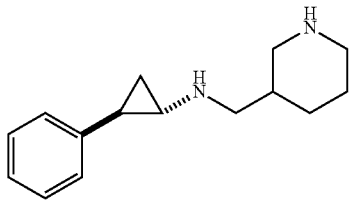

Following a procedure analogous to the procedure described in Example 4 using 1,1-dimethylethyl 3-({[trans-2-phenylcyclopropyl]amino}methyl)-1-piperidinecarboxylate (84 mg, 0.254 mmol) afforded [trans-2-phenylcyclopropyl](3-piperidinylmethyl)amine (68 mg, 0.242 mmol, 95% yield) as yellow oil. $^1$H NMR (400 MHz, METHANOL-d$_4$) δ 7.29-7.39 (m, 2H), 7.16-7.29 (m, 3H), 3.54 (d, J=11.37 Hz, 1H), 3.40 (d, J=13.64 Hz, 1H), 3.11-3.31 (m, 2H), 3.04 (dd, J=3.66, 8.21 Hz, 1H), 2.97 (td, J=3.54, 13.14 Hz, 1H), 2.86 (t, J=12.13 Hz, 1H), 2.57-2.71 (m, 1H), 2.36 (ddd, J=4.29, 7.39, 11.05 Hz, 1H), 1.95-2.17 (m, 2H), 1.73-1.93 (m, 1H), 1.65

(dddd, J=2.15, 4.48, 6.54, 10.58 Hz, 1H), 1.24-1.53 (m, 2H); LC-MS Rt=0.49 min; MS (ESI): 231.2 [M+H]+.

Example 17

N-(trans-2-Phenylcyclopropyl)-N-(piperidin-4-ylmethyl)acetamide

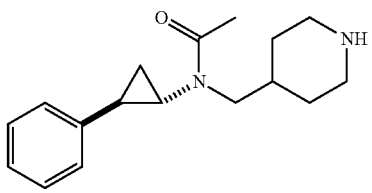

a) tert-Butyl 4-((N-(trans-2-phenylcyclopropyl)acetamido)methyl)piperidine-1-carboxylate To a solution of tert-butyl 4-((trans-2-phenylcyclopropyl)amino)methyl)piperidine-1-carboxylate (Example 1, 80 mg, 0.242 mmol) in chloroform (5 mL) was added triethylamine (0.067 mL, 0.484 mmol) followed by acetyl chloride (0.022 mL, 0.315 mmol). The solution was stirred for 1 hour, and then water (5 mL) was added. The layers were separated and the organic layer was washed with brine, dried over MgSO$_4$ and filtered. The solution was then evaporated. tert-Butyl 4-((N-(trans-2-phenylcyclopropyl)acetamido)methyl)piperidine-1-carboxylate (80 mg, 0.198 mmol, 82% yield) was isolated as yellow oil. $^1$H NMR (400 MHz, CHLOROFORM-d) δ 7.30-7.37 (m, 2H), 7.21-7.28 (m, 1H), 7.08 (d, J=7.07 Hz, 2H), 4.03-4.25 (m, 2H), 3.53 (dd, J=7.58, 13.64 Hz, 1H), 3.06-3.25 (m, 1H), 2.78-2.87 (m, 1H), 2.61-2.77 (m, 2H), 2.22 (td, J=2.65, 4.86 Hz, 1H), 2.18 (s, 3H), 1.82-1.98 (m, 1H), 1.54-1.72 (m, 2H), 1.47 (s, 9H), 1.36-1.45 (m, 2H), 1.06-1.25 (m, 2H); LC-MS Rt=1.09 min; MS (ESI): 373.0 [M++H]+.

b) N-(trans-2-Phenylcyclopropyl)-N-(piperidin-4-ylmethyl)acetamide

A solution of tert-butyl 4-((trans-2-phenylcyclopropyl)amino)methyl)piperidine-1-carboxylate (80 mg, 0.215 mmol) in chloroform (3 mL) and trifluoroacetic acid (TFA) (1 mL) was stirred for 1 hour. The reaction mixture was evaporated and the oil was partitioned between 1 M Na$_2$CO$_3$ and dichloromethane. The organic layer was separated, washed with brine, dried over MgSO$_4$, filtered and evaporated. N-(trans-2-phenylcyclopropyl)-N-(piperidin-4-ylmethyl)acetamide (48 mg, 0.159 mmol, 73.8% yield) was isolated as yellow oil. $^1$H NMR (400 MHz, METHANOL-d$_4$) δ 7.27-7.39 (m, 2H), 7.11-7.26 (m, 3H), 3.51 (dd, J=7.71, 13.52 Hz, 1H), 3.28 (dd, J=6.95, 13.52 Hz, 1H), 3.04-3.18 (m, 2H), 2.92-3.02 (m, 1H), 2.53-2.71 (m, 2H), 2.33 (ddd, J=3.54, 6.51, 9.92 Hz, 1H), 2.18 (s, 3H), 1.84-2.00 (m, 1H), 1.63-1.82 (m, 2H), 1.37-1.60 (m, 2H), 1.02-1.38 (m, 2H); LC-MS Rt=0.60 min; MS (ESI): 273.3 [M+H]

Example 18

Benzyl 4-(((trans-2-phenylcyclopropyl)amino)methyl)piperidine-1-carboxylate

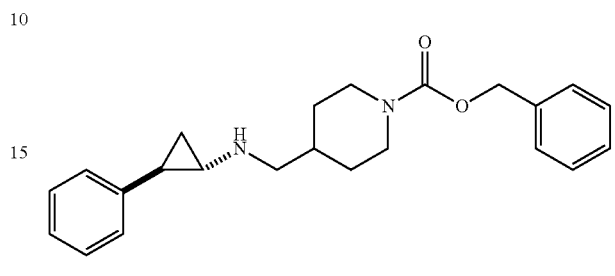

To a solution of trans-2-phenylcyclopropanamine hydrochloride (1.087 g, 6.41 mmol) in N,N-dimethylformamide (DMF) (30 mL) was added potassium carbonate (1.771 g, 12.81 mmol) followed by benzyl 4-(bromomethyl)piperidine-1-carboxylate (1 g, 3.20 mmol). The reaction mixture was refluxed overnight. Water (80 mL) was added followed by 80 mL of ethyl acetate. The organic layer was separated, washed with brine, dried over MgSO$_4$, filtered and evaporated. The oil was purified via silica gel column (DCM to 100% EtOAc). The fractions were collected and evaporated. The oil was further purified on preparative HPLC (5 to 70% AcCN: H$_2$O gradient with 0.1% formic acid modifier). The fractions were collected. The combined fractions were neutralized with aq. NH$_4$OH, concentrated and extracted with ethyl acetate. The organic layer was washed with brine, dried over MgSO$_4$ and evaporated. Benzyl 4-(((trans-2-phenylcyclopropyl)amino)methyl)piperidine-1-carboxylate (150 mg, 0.391 mmol, 12.21% yield) was isolated as yellow liquid. $^1$H NMR (400 MHz, METHANOL-d$_4$) 67.28-7.41 (m, 5H), 7.18-7.27 (m, 2H), 7.09-7.16 (m, 1H), 7.03-7.09 (m, 2H), 5.12 (s, 2H), 4.00-4.29 (m, 2H), 2.67-2.97 (m, 2H), 2.61 (d, J=6.82 Hz, 2H), 2.26-2.36 (m, 1H), 1.92 (ddd, J=3.28, 5.87, 9.28 Hz, 1H), 1.64-1.84 (m, 3H), 0.91-1.24 (m, 4H); LC-MS Rt=0.83 min; MS (ESI): 365.5 [M+H]+.

Example 19

4-(((trans-2-Phenylcyclopropyl)amino)methyl)piperidine

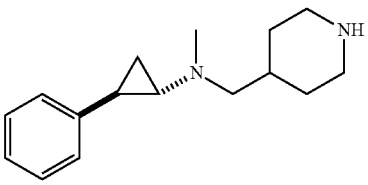

To a solution of tert-butyl 4-(((trans-2-phenylcyclopropyl)amino)methyl)piperidine-1-carboxylate (Example 1, 100 mg, 0.303 mmol) in acetonitrile (2 ml) and N,N-dimethylformamide (DMF) (0.5 ml) was added potassium carbonate (125 mg, 0.908 mmol) followed by iodomethane (0.038 ml, 0.605 mmol). The reaction mixture was stirred for 4 hours at room temperature. The reaction mixture was evaporated. The oil was purified on preparative HPLC (5 to 70% AcCN: H$_2$O gradient with 0.1% formic acid modifier). The fractions were collected. The combined fractions were neutralized with aq. NH$_4$OH, concentrated and extracted with ethyl acetate. The organic layer was washed with brine, dried over MgSO$_4$ and evaporated. The oil was dissolved in 2 mL of dioxane and 1 mL of HCl. The reaction mixture was heated under reflux for 15 min, and then evaporated to dryness. 4-(((trans-2-Phenylcyclopropyl)amino)methyl)piperidine (12 mg, 0.041 mmol, 13.41% yield) was isolated as a white solid. $^1$H NMR (400 MHz, METHANOL-d$_4$) δ 7.35 (d, J=4.29 Hz, 2H), 7.14-7.30 (m, 3H), 3.47 (d, J=13.14 Hz, 2H), 3.35-3.42 (m, 2H), 3.12-3.27 (m, 2H), 3.09 (d, J=8.34 Hz, 3H), 2.89-3.05 (m, 1H), 2.77-2.89 (m, 1H), 2.04-2.52 (m, 3H), 1.83 (d, J=5.56 Hz, 1H), 1.37-1.73 (m, 3H); LC-MS Rt=0.38 min; MS (ESI): 245.2 [M+H]$^+$.

Example 20

[(1-Methyl-4-piperidinyl)methyl][trans-2-phenylcyclopropyl]amine

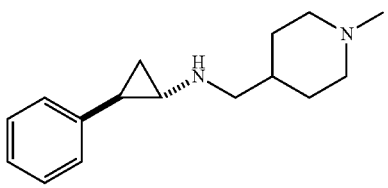

A mixture of [trans-2-phenylcyclopropyl]amine (540 mg, 4.05 mmol), 1-methyl-4-piperidinecarbaldehyde (506 mg, 3.98 mmol) and AcOH (1 µL, 0.017 mmol) in chloroform (15 mL) was stirred at room temperature for 18 hours. Sodium triacetoxyborohydride (947 mg, 4.47 mmol) was added and stirring continued for 18 hours. Upon completion, saturated NaHCO$_3$ was added to the reaction mixture and the mixture was extracted with THF—CHCl$_3$ (2×50mL). The organics were combined, dried over Na$_2$SO$_4$ and concentrated. The residue was adsorbed onto silica and purified via column chromatography on the ISCO Companion (gradient 0-100% 80:20:2 [CHCl$_3$/MeOH/NH$_4$OH]/CHCl$_3$; 40 g column) to obtain pure final compound (166 mg, 13% yield) as an off white solid: LC-MS (ES) m/z=245 (M+H)$^+$, $^1$H NMR (400 MHz, DMSO-d$_6$) δ ppm 7.17-7.27 (m, 2H), 7.06-7.15 (m, 1H), 6.97-7.06 (m, 2H), 2.64-2.77 (m, 2H), 2.41-2.49 (m, 2H), 2.27 (br. s., 1H), 2.18 (ddd, J=3.28, 4.23, 7.14 Hz, 1H), 2.08-2.15 (m, 3H), 1.70-1.83 (m, 2H), 1.57-1.70 (m, 2H), 1.30 (ddd, J=4.29, 7.26, 10.93 Hz, 1H), 1.01-1.16 (m, 2H), 0.86-0.98 (m, 2H).

Example 21

1,1-Dimethylethyl 4-({[trans-2-phenylcyclopropyl]amino}methyl)hexahydro-1H-azepine-1-carboxylate

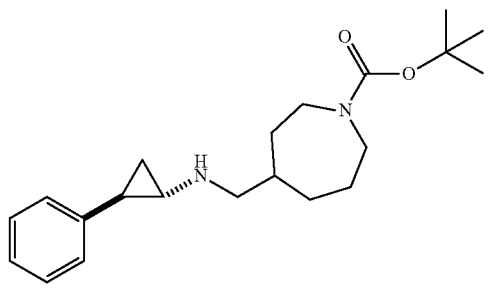

A mixture of [trans-2-phenylcyclopropyl]amine (496 mg, 3.72 mmol), 1,1-dimethylethyl 4-formylhexahydro-1H-azepine-1-carboxylate (871 mg, 3.83 mmol) and AcOH (1 µL, 0.017 mmol) in chloroform (5 mL) was stirred at room temperature for 18 hours. Sodium triacetoxyborohydride (950 mg, 4.48 mmol) was added and stirring continued for 18 hours. Upon completion, saturated NaHCO$_3$ was added to the reaction mixture and the mixture was extracted with THF—CHCl$_3$ (2×50 mL). The organics were combined, dried over Na$_2$SO$_4$ and concentrated. The residue was adsorbed onto silica and purified via column chromatography on the ISCO Companion (gradient 0-40% 80:20:2 [CHCl$_3$/MeOH/NH$_4$OH]/CHCl$_3$; 40 g column) to afford the desired product (168 mg, 12%) as a pale yellow oil LC-MS (ES) m/z=345 (M+H)$^+$.

Example 22

N-(Hexahydro-1H-azepin-4-ylmethyl)-trans-2-phenylcyclopropanamine

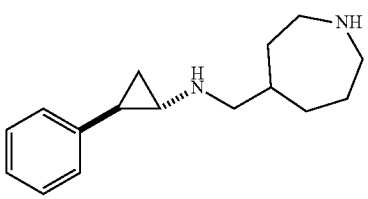

Chloroform (50 mL) was added to a 200 mL round-bottomed flask containing tert-butyl 4-(((trans-2-phenylcyclopropyl)amino)methyl)azepane-1-carboxylate (49.4 mg, 0.143 mmol) to give a suspension. HCl/1,4-Dioxane (12 mL, 48.0 mmol) was added and the mixture stirred 18 hour at room temperature. Upon completion, the residue was adsorbed directly onto silica and purified via column chromatography on the ISCO Companion (gradient 0-100% 80:20:2 [CHCl$_3$/MeOH/NH$_4$OH]/CHCl$_3$; 4 g column). Fractions were collected, solvents removed and the resulting residue was taken up in MeOH (2 mL). Excess 2M HCl in Et$_2$O and stirred for 10 minutes. The solvent was removed to yield the 2HCl salt of the desired product (28 mg, 59% yield) as a yellow solid: LC-MS (ES) m/z=245 (M+H)$^+$, $^1$H NMR (400 MHz, DMSO-d$_6$) δ ppm 1.18-1.32 (m, 1H) 1.36 (d, J=11.37 Hz, 1H) 1.54-1.79 (m, 3H) 1.80-1.96 (m, 2H) 2.06 (br. s., 2H) 2.54-2.64 (m, 1H) 2.97 (br. s., 5H) 3.06-3.27 (m, 2H) 7.14-7.26 (m, 3H) 7.27-7.35 (m, 2H) 9.03 (br. s., 2H) 9.38-9.62 (m, 2H).

Example 23

[trans-2-Phenylcyclopropyl][2-(4-piperidinyl)ethyl]amine

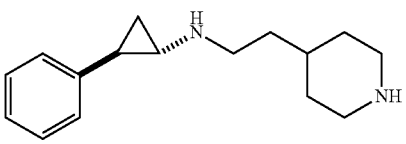

a) 1,1-dimethylethyl 4-(2-{[trans-2-phenylcyclopropyl]amino}ethyl)-1-piperidinecarboxylate A mixture of [trans-2-phenylcyclopropyl]amine (668 mg, 5.02 mmol), 1,1-dimethylethyl 4-(2-oxoethyl)-1-piperidinecarboxylate (1.04 g, 4.58 mmol) and AcOH (1 μL, 0.017 mmol) in chloroform (5 mL) was stirred at room temperature for 18 hours. Sodium triacetoxyborohydride (1.03 g, 4.86 mmol) was added and stirring continued for 18 hours. Upon completion, saturated NaHCO₃ was added to the reaction mixture and the mixture was extracted with THF—CHCl₃ (2×50 mL). The organics were combined, dried over Na₂SO₄ and concentrated. The residue was adsorbed onto silica and purified via column chromatography on the ISCO Companion (gradient 0-100% 80:20:2 [CHCl₃/MeOH/NH₄OH]/CHCl₃; 12 g column) to yield the desired product. This product was further purified via reverse phase column chromatography on Gilson ((C18 column: 0.1% Formic acid H₂O/CH₃CN, 95-5%) affording the title compound (222 mg, 13% yield) as a yellow oil: LC-MS (ES) m/z=345 (M+H)⁺.

b) [trans-2-phenylcyclopropyl][2-(4-piperidinyl)ethyl]amine

Chloroform (50 mL) was added to a 200 mL round-bottomed flask containing tert-butyl 4-(2-((trans-2-phenylcyclopropyl)amino)ethyl)piperidine-1-carboxylate (161 mg, 0.467 mmol). HCl/1,4-Dioxane (1 mL, 4.00 mmol) was added and the mixture stirred 18 hours at room temperature. Upon completion, the residue was adsorbed directly onto silica and purified via column chromatography on the ISCO Companion (gradient 0-100% 80:20:2 [CHCl₃/MeOH/NH₄OH]/CHCl₃; 4 g column). Fractions were collected, solvents removed and the resulting residue was taken up in MeOH (2 mL). Excess 2M HCl in Et₂O was added and the solution stirred for 10 minutes. The solvent was removed to yield the 2HCl of the desired product (35 mg, 22% yield) as a brown solid: LC-MS (ES) m/z=245 (M+H)⁺, ¹H NMR (400 MHz, MeOH-d₄) δ ppm 1.39 (br. s., 1H) 1.51 (br. s., 4H) 1.79 (br. s., 3H) 2.00 (br. s., 2H) 2.61 (br. s., 1H) 3.02 (br. s., 3H) 3.29 (br. s., 1H) 3.35-3.53 (m, 2H) 7.17-7.28 (m, 3H) 7.28-7.36 (m, 2H).

Example 24

[trans-2-Phenylcyclopropyl][1-(4-piperidinyl)ethyl]amine

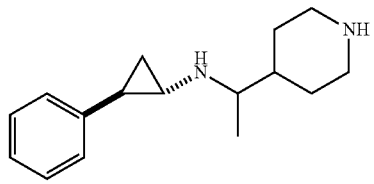

a) 1,1-dimethylethyl 4-(1-{[trans-2-phenylcyclopropyl]amino}ethyl)-1-piperidinecarboxylate

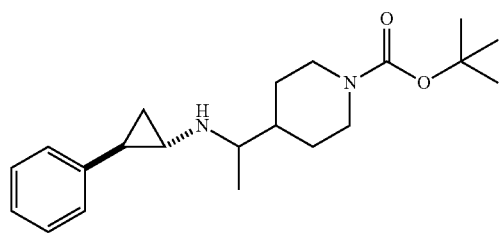

A mixture of [trans-2-phenylcyclopropyl]amine (116 mg, 0.871 mmol), 1,1-dimethylethyl 4-acetyl-1-piperidinecarboxylate (110 mg, 0.484 mmol) and AcOH (1 μL, 0.017 mmol) in Chloroform (10 mL) was stirred at room temperature for 18 hours. Sodium triacetoxyborohydride (196 mg, 0.925 mmol) was added and stirring continued for 18 hours. Upon completion, saturated NaHCO₃ was added to the reaction mixture and the mixture was extracted with CHCl₃ (2×50 mL). The organics were combined, dried over Na₂SO₄ and concentrated. The residue was adsorbed onto silica and purified via column chromatography on the Isco Companion (gradient 0-100% 80:20:2 [CHCl₃/MeOH/NH₄OH]/CHCl₃; 12 g column) to yield the desired product. This was further purified via reverse phase column chromatography on Gilson (C18 column: 0.1% Formic acid H₂O/CH₃CN, 95-5%) to obtain pure the pure title compound (67 mg, 22% yield) as a colorless oil: LC-MS (ES) m/z=345 (M+H)⁺.

b) [trans-2-phenylcyclopropyl][1-(4-piperidinyl)ethyl]amine

Chloroform (5 mL) was added to a 200 mL round-bottomed flask containing 1,1-dimethylethyl 4-(1-{[trans-2-phenylcyclopropyl]amino}ethyl)-1-piperidinecarboxylate (67 mg, 0.194 mmol) to give a suspension. HCl/1,4-Dioxane (1.5 mL, 6.00 mmol) was added and the mixture stirred 18 hours at room temperature. The Upon completion, the solvents were removed, MeOH (1 mL) added and the mixture purified via reverse phase column chromatography on Gilson ((C18 column: 0.1% Formic acid H₂O/CH₃CN, 95-5%) affording the title compound as a white solid LC-MS (ES) m/z=245 (M+H)⁺, ¹H NMR (400 MHz, MeOD-d₄) δ ppm ¹H NMR (400 MHz, MeOD) d 7.93 (s, 1H), 7.31-7.39 (m, 2H), 7.17-7.30 (m, 3H), 3.46-3.59 (m, 3H), 2.95-3.14 (m, 3H), 2.50-2.63 (m, 1H), 2.17-2.28 (m, 1H), 1.94-2.05 (m, 3H), 1.59-1.76 (m, 3H), 1.48 (t, J=7.71 Hz, 1H), 1.39 (d, J=6.82 Hz, 3H).

Example 25

N-(2-Morpholinylmethyl)-trans-2-phenylcyclopropanamine

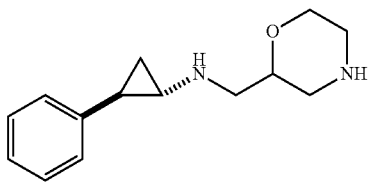

a) 1,1-Dimethylethyl-2-({[trans-2-phenylcyclopropyl]amino}methyl)-4-morpholinecarboxylate

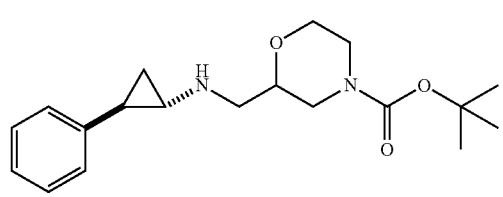

A mixture of [trans-2-phenylcyclopropyl]amine (125 mg, 0.939 mmol), 1,1-dimethylethyl 2-formyl-4-morpholinecarboxylate (211 mg, 0.980 mmol) and AcOH (1 μL, 0.017 mmol) in chloroform (10 mL) was stirred at room temperature for 18 hours. Sodium triacetoxyborohydride (201 mg, 0.948 mmol) was added and stirring continued for 18 hours. Upon completion, saturated NaHCO$_3$ was added and the mixture was extracted with CHCl$_3$ (2×50 mL). The organics were combined, dried over Na$_2$SO$_4$ and concentrated. The residue was adsorbed onto silica and purified via column chromatography on the ISCO Companion (gradient 0-80% 80:20:2 [CHCl$_3$/MeOH/NH$_4$OH]/CHCl$_3$; 12 g column) to yield the desired product as a yellow oil LC-MS (ES) m/z=333 (M+H)$^+$.

b) N-(2-morpholinylmethyl)-trans-2-phenylcyclopropanamine

Chloroform (5 mL) was added to a 200 mL round-bottomed flask containing 1,1-dimethylethyl 2-({[trans-2-phenylcyclopropyl]amino}methyl)-4-morpholinecarboxylate (330 mg, 0.993 mmol) to give a suspension. HCl/1,4-Dioxane (6.20 mL, 24.82 mmol) was added and the mixture stirred 18 hours at room temperature. Upon completion, saturated NaHCO$_3$ was added to the reaction mixture and the mixture was extracted with THF—CHCl$_3$ (2×50 mL). The organics were combined, dried over Na$_2$SO$_4$ and concentrated. The residue was adsorbed onto silica and purified via column chromatography on the ISCO Companion (gradient 0-100% 80:20:2 [CHCl$_3$/MeOH/NH$_4$OH]/CHCl$_3$; 12 g column). The compound was further purified via reverse phase column chromatography on Gilson ((C18 column: 0.1% Formic acid H$_2$O/CH$_3$CN, 95-5%) affording the title compound as an amber oil LC-MS (ES) m/z=233 (M+H)$^+$, $^1$H NMR (400 MHz, DMSO-d$_6$) δ ppm $^1$H NMR (400 MHz, DMSO-d$_6$) d 7.22 (t, J=7.58 Hz, 2H), 7.11 (t, J=7.33 Hz, 1H), 7.03 (d, J=8.08 Hz, 2H), 3.63-3.73 (m, 1H), 3.35-3.43 (m, 2H), 2.73-2.81 (m, 1H), 2.52-2.70 (m, 4H), 2.25-2.35 (m, 2H), 2.22 (qd, J=2.40, 4.59 Hz, 1H), 1.76 (ddd, J=2.91, 5.94, 9.09 Hz, 1H), 0.86-1.01 (m, 2H).

Example 26

4-((4-(((trans-2-phenylcyclopropyl)amino)methyl)piperidin-1-yl)methyl)benzoic acid

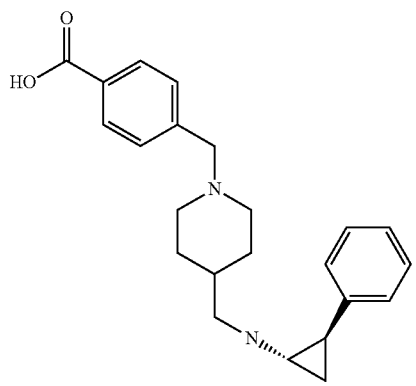 [SMILES: O=C(O)c1ccc(CN2CCC(CN[C@H]3C[C@@H]3c3ccccc3)CC2)cc1]

To the solution of 2,2,2-trifluoro-N-(trans-2-phenylcyclopropyl)-N-(piperidin-4-ylmethyl)acetamide (200 mg, 0.613 mmol, Example 11b) and 4-(bromomethyl)benzoic acid (198 mg, 0.919 mmol) in acetonitrile (6 mL) was added potassium carbonate (254 mg, 1.838 mmol). The reaction mixture was stirred for 3 hours at the 90° C. The reaction mixture was then filtered and evaporated. The crude oil was mixed with 10 mL of 10% acetic acid and 10 mL of ethyl acetate. Layers were separated, and the organic layer was discharged. Aqueous layer was neutralized with 1 M Na$_2$CO$_3$, and the product was extracted into 10 mL of ethyl acetate. The organic layer was washed with brine, dried over MgSO$_4$, filtered and evaporated. The oil was dissolved in 6 ml of EtOH and 3 ml of 1 M NaOH. The reaction mixture was stirred for 20 min, and then it was concentrated. The solution was then pardoned between 2 ml of water and 5 mL of ethyl acetate. The organic layer was separated and evaporated. The oil was purified on preparatory HPLC (2 to 10% AcCN: H$_2$O with 0.1% formic acid modifier). The fractions were collected. To each fraction was added 1 ml of 1 M HCl, and the fractions were evaporated to dryness. 4-((4-(((trans-2-phenylcyclopropyl)amino)methyl)piperidin-1-yl)methyl)benzoic acid (50 mg, 0.118 mmol, 19.33% yield) was isolated as a white solid. $^1$H NMR (400 MHz, METHANOL-d$_4$) δ 8.16 (d, J=8.34 Hz, 2H), 7.70 (d, J=8.34 Hz, 2H), 7.30-7.37 (m, 2H), 7.23-7.29 (m, 1H), 7.20 (d, J=7.33 Hz, 2H), 4.44 (br. s., 2H), 3.57 (d, J=11.62 Hz, 2H), 3.07-3.27 (m, 4H), 3.04 (dt, J=3.95, 7.52 Hz, 1H), 2.59 (ddd, J=3.54, 6.57, 10.11 Hz, 1H), 2.12 (d, J=13.89 Hz, 3H), 1.54-1.81 (m, 3H), 1.42 (q, 1H); LC-MS Rt=0.47 min; MS (ESI): 365.3 [M+H]$^+$.

Example 27

2-(4-(((trans-2-phenylcyclopropyl)amino)methyl)piperidin-1-yl)acetic acid

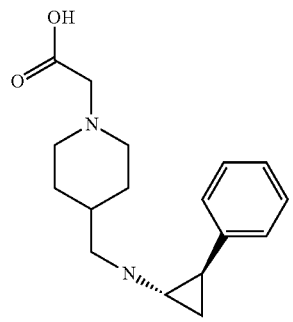 [SMILES: O=C(O)CN1CCC(CN[C@H]2C[C@@H]2c2ccccc2)CC1]

Step 1.

tert-butyl 2-(4-(((trans-2-phenylcyclopropyl)amino)methyl)piperidin-1-yl)acetate To the solution of 2,2,2-trifluoro-N-(trans-2-phenylcyclopropyl)-N-(piperidin-4-ylmethyl)acetamide (200 mg, 0.613 mmol, Example 11b) in acetonitrile (5 mL) was added potassium carbonate (254 mg, 1.838 mmol) followed by tert-butyl 2-bromoacetate (155 mg, 0.797 mmol). The reaction mixture was stirred at 80° C. for 4 hours. The suspension was filtered and evaporated. The oil was suspended in 2 mL of dioxane and 2 mL of 1 M NaOH. The solution was stirred for 1 hour, then injected on preparatory HPLC (5 to 30% AcCN: H$_2$O with 0.1% formic acid modifier). The fractions were collected. The combined fractions were neutralized with NH$_4$OH and extracted with ethyl acetate. The organic layer was separated, washed with brine, dried, filtered and evaporated till dryness. tert-butyl 2-(4-(((trans-2-phenylcyclopropyl)amino)methyl)piperidin-1-yl)acetate (55 mg, 0.152 mmol, 24.75% yield) was isolated as colorless oil. $^1$H NMR (400 MHz, METHANOL-d$_4$) δ 7.20-7.31 (m, 2H), 7.09-7.17 (m, 1H), 6.99-7.09 (m, 2H), 3.12 (s, 2H), 2.91-3.03 (m, 2H), 2.62 (d, J=7.07 Hz, 2H), 2.28-2.36 (m, 1H), 2.11-2.23 (m, 2H), 1.92 (ddd, J=3.28, 5.87, 9.28 Hz, 1H), 1.68-1.83 (m, 2H), 1.52-1.63 (m, 1H), 1.44-1.52 (m, 9H), 1.31 (qd, J=3.92, 12.34 Hz, 2H), 1.08 (dt, J=4.86, 9.47 Hz, 1H), 1.02 (dt, J=5.59, 7.26 Hz, 1H); LC-MS Rt=0.58 min; MS (ESI): 345.3 [M+H]$^+$.

Step 2.

2-(4-(((trans-2-phenylcyclopropyl)amino)methyl)piperidin-1-yl)acetic acid

The solution of tert-butyl 2-(4-(((trans-2-phenylcyclopropyl)amino)methyl)piperidin-1-yl)acetate (40 mg, 0.116 mmol) in HCl-1 M (5 ml, 165 mmol) was stirred at the 50° C. for 24 hours. The solution was evaporated. The oil was suspended in acetonitrile, sonicated and filtered. 2-(4-(((trans-2-phenylcyclopropyl)amino)methyl)piperidin-1-yl)acetic acid (25 mg, 0.073 mmol, 63.0% yield) was isolated as a white solid. $^1$H NMR (400 MHz, METHANOL-d$_4$) δ 7.30-7.38 (m, 2H), 7.17-7.29 (m, 3H), 4.13 (s, 2H), 3.74 (dd, J=1.52, 3.79 Hz, 2H), 3.11-3.29 (m, 4H), 3.05 (dt, J=4.14, 7.64 Hz, 1H), 2.61 (ddd, J=3.54, 6.63, 10.29 Hz, 1H), 2.15 (d, J=14.91 Hz, 3H), 1.73 (d, 2H), 1.62 (ddd, J=4.29, 6.63, 10.55 Hz, 1H), 1.37-1.49 (m, 1H); LC-MS Rt=0.39 min; MS (ESI): 289.3 [M+H]$^+$.

Example 28A

4-{[(3R)-3-({[(1R,2S)-2-Phenylcyclopropyl]amino}methyl)-1-pyrrolidinyl]methyl}benzoic acid Di HCL salt

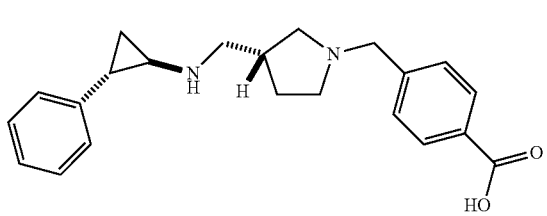

Example 28B

4-{[(3S)-3-({[(1R,2S)-2-Phenylcyclopropyl]amino}methyl)-1-pyrrolidinyl]methyl}benzoic acid Di HCL salt

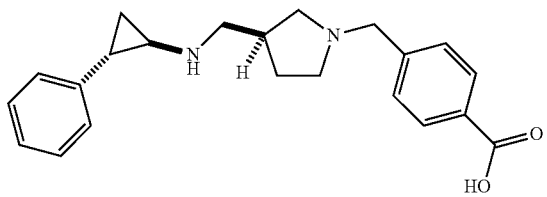

Methyl 4-[(3-formyl-1-pyrrolidinyl)methyl]benzoate

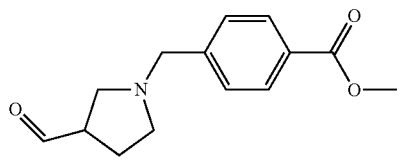 [SMILES: COC(=O)c1ccc(CN2CCC(C=O)C2)cc1]

Tert-Butyl 3-formylpyrrolidine-1-carboxylate (4.75 g, 23.84 mmol) was dissolved in dichloromethane (DCM) (20 mL). Trifluoroacetic acid (15 mL, 195 mmol) was added and the reaction mixture was stirred at room temperature for 1 hour. After concentrating acetonitrile (100 mL) was added followed by methyl 4-(bromomethyl)benzoate (6.55 g, 28.6 mmol) and potassium carbonate (16.47 g, 119 mmol). The reaction was heated to reflux for 16 hours. The mixture was filtered and concentrated. Dichloromethane (75 ml) was added and the solution was washed with water, dried over MgSO4, filtered and concentrated. The residue was purified via silica gel chromatography (0% to 100% EtOAc:Hex; 50 g-HP-silica gel column). Obtained 2.00 g $^1$H NMR (400 MHz, CHLOROFORM-d) δ ppm 1.99-2.23 (m, 2H), 2.46-2.57 (m, 1H), 2.60-2.79 (m, 2H), 2.88-2.99 (m, 2H), 3.68 (d, J=4.29 Hz, 2H), 3.92 (s, 3H), 7.40 (d, J=8.59 Hz, 2H), 7.93-8.09 (m, 2H), 9.66 (d, J=2.02 Hz, 1H);

Methyl 4-{[3-({[(1R,2S)-2-phenylcyclopropyl]amino}methyl)-1-pyrrolidinyl]methyl}benzoate

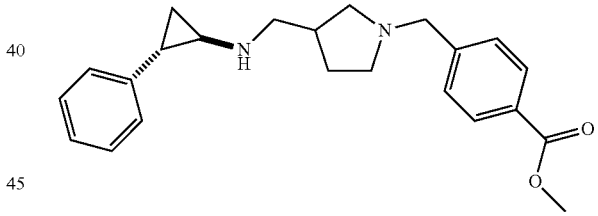

A solution of (1R,2S)-2-phenylcyclopropanamine (300 mg, 2.252 mmol) and methyl 4-((3-formylpyrrolidin-1-yl)methyl)benzoate (501 mg, 2.027 mmol) in methanol (50 mL) was heated to reflux for 5 minutes. The reaction mixture was cooled to room temperature and sodium cyanoborohydride (212 mg, 3.38 mmol) was added. The reaction was stirred at room temperature for 16 hours. After concentrating, dichloromethane was added and the solution was washed with water, dried over MgSO4, filtered and concentrated. HPLC purification (reverse phase) was performed with a Gemini NX 5u C18 110A, AXIA. 100×30.00 mm 5 micron column. A 7 minute gradient run (0% AcCN/H$_2$O, 0.1% Formic Acid to 55% ACN/H$_2$O, 0.1% Formic Acid) with UV detection at 214 nm was utilized. Added 1 ml of 1N HCl to fractions containing product and concentrated. Only the desired ester was seen by LC/MS of fractions before concentrating. Obtained 300 mg of a mixture of diastereomers.

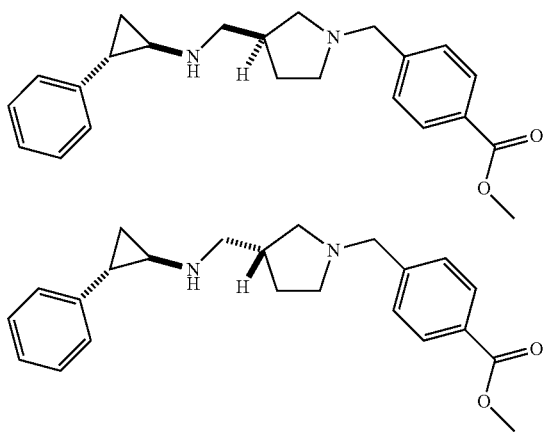

Preparative Chiral HPLC Method for separation of diastereomers:

Chiralpak AS-H, 5 microns
(30 mm×250 mm)
240 nm UV
45 ml/min. 20 deg C.
95:5:0.1 acetonitrile:IPA:isopropylamine (isocratic)

The mixture (160 mg) was dissolved the mixture in 8 mLs of mobile phase with a few drops of isopropylamine. 4 injections at about 40 mg per run were made. Observed clean, baseline resolution of the two diastereomers.

4-{[(3R)-3-({[(1R,2S)-2-Phenylcyclopropyl]amino}methyl)-1-pyrrolidinyl]methyl}benzoic acid Di HCL salt

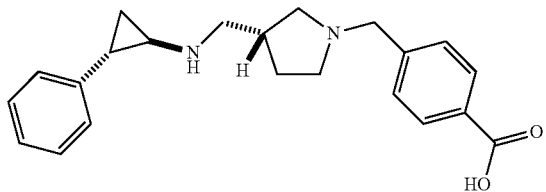

Added 1N sodium hydroxide (1 mL, 1.000 mmol) to a solution of methyl 4-((3-((((1R,2S)-2-phenylcyclopropyl)amino)methyl)pyrrolidin-1-yl)methyl)benzoate (71 mg, 0.195 mmol) in methanol (2 mL) and let stir at room temperature for 4 hours. The reaction mixture was concentrated and purified by HPLC (reverse phase) with a Gemini NX 5u C18 110A, AXIA column (100×30.00 mm 5 micron). A 7 minute gradient run (0% AcCN/H$_2$O, 0.1% Formic Acid to 25% ACN/H$_2$O, 0.1% Formic Acid) with UV detection at 214 nm was utilized. Added 1 ml of concentrated HCl to each fraction containing product and concentrated fractions. Obtained 44 mg of the di HCl salt $^1$H NMR (400 MHz, MeOD) δ ppm 1.42 (q, J=6.82 Hz, 1H), 1.60 (ddd, J=10.55, 6.63, 4.29 Hz, 1H), 2.00 (d, J=10.86 Hz, 1H), 2.43 (br. s., 1H), 2.58 (ddd, J=10.29, 6.63, 3.54 Hz, 1H), 2.81-3.00 (m, 1H), 3.04 (ddd, J=7.64, 4.29, 3.98 Hz, 1H), 3.42 (d, J=7.33 Hz, 2H), 3.48-3.80 (m, 2H), 4.54 (s, 2H), 7.17-7.29 (m, 3H), 7.30-7.38 (m, 2H), 7.72 (d, J=8.08 Hz, 2H), 8.15 (d, J=8.34 Hz, 2H); MS (ES) [M+H]$^+$ 351.2; Chiral HPLC>99% ee 4-{[(3S)-3-({[(1R,2S)-2-Phenylcyclopropyl]amino}methyl)-1-pyrrolidinyl]methyl}benzoic acid Di HCL salt

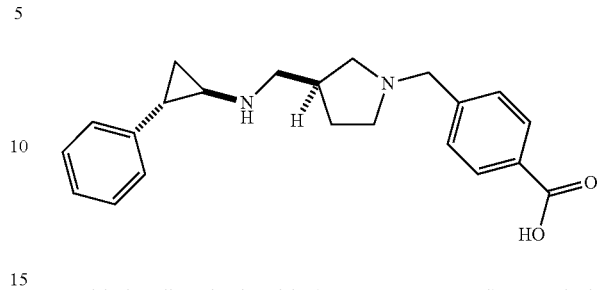

Added sodium hydroxide (1 mL, 0.195 mmol) to a solution of methyl 4-((3-((((1R,2S)-2-phenylcyclopropyl)amino)methyl)pyrrolidin-1-yl)methyl)benzoate (71 mg, 0.195 mmol) in methanol (2 mL) and let stir at room temperature over the weekend. The reaction mixture was concentrated and HPLC purification (reverse phase) was performed with a Gemini NX 5u C18 110A, AXIA column (100×30.00 mm 5 micron). A 7 minute gradient run (0% AcCN/H$_2$O, 0.1% Formic Acid to 25% ACN/H$_2$O, 0.1% Formic Acid) with UV detection at 214 nm was utilized. Added 1 ml of concentrated HCl to each fraction containing product and concentrated fractions. Obtained 42 mg of the di HCl salt. MS (ES) [M+H]$^+$ 351.3

Chiral HPLC>99% ee

Example 29

4-((4-((((1R,2S)-2-phenylcyclopropyl)amino)methyl)piperidin-1-yl)methyl)benzoic acid

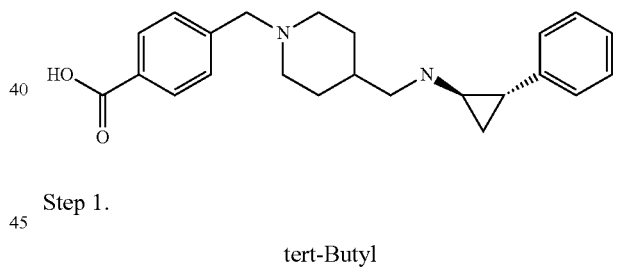

Step 1.

tert-Butyl 4-(4-(hydroxymethyl)piperidin-1-yl)methyl)benzoate tert-Butyl 4-(bromomethyl)benzoate (1 g, 3.13 mmol) and piperidin-4-ylmethanol (0.361 g, 3.13 mmol) were dissolved in acetonitrile (25 mL). K$_2$CO$_3$ (1.300 g, 9.40 mmol) was added and the reaction mixture was heated to reflux for 20 min. The reaction mixture was cooled down to room temperature, filtered and evaporated. The resulting solid was partitioned between ethyl acetate (50 mL) and 1 M HCl (50 mL). The layers were separated and the aqueous layer was washed with ethyl acetate and the organic layers were discarded. The aqueous layer was basified with 8 M NaOH to pH~10 and extracted 2 times with 50 mL of ethyl acetate. The organic layers were combined, washed with brine and dried over MgSO$_4$, filtered and evaporated. tert-Butyl 4-((4-(hydroxymethyl)piperidin-1-yl)methyl)benzoate (0.95 g, 2.99 mmol, 95% yield) was isolated as yellow oil. $^1$H NMR (400 MHz, CHLOROFORM-d) δ 7.95 (d, J=8.34 Hz, 2H), 7.39 (d, J=8.08 Hz, 2H), 3.56 (s, 2H), 3.51 (d, J=6.57 Hz, 2H), 2.90 (d, J=11.37 Hz, 2H), 1.94-2.04 (m, 2H), 1.73 (d, J=14.15 Hz, 2H), 1.61 (s, 9H), 1.40-1.56 (m, 2H), 1.30-1.37 (m, 2H); LC-MS Rt=0.67 min; MS (ESI): 306.2 [M+H]⁺.

Step 2.

tert-Butyl 4-((4-formylpiperidin-1-yl)methyl)benzoate

To a solution of oxalyl chloride (0.408 mL, 4.67 mmol) in dichloromethane (5 mL) at −60° C. was added a solution of DMSO (0.508 mL, 7.15 mmol) in 15 mL of dichloromethane over 30 minutes. The reaction was stirred for 30 minutes at −60° C. A solution of tert-butyl 4((4-(hydroxymethyl)piperidin-1-yl)methyl)benzoate (950 mg, 3.11 mmol) in 5 mL of dichloromethane was added over 10 minutes at −60° C. The reaction mixture was stirred for 3 hours at −60° C., then triethylamine (2.168 mL, 15.55 mmol) was added and after 10 minutes 10 mL of water was added. The reaction mixture was allowed to warm up to the room temperature. The layers were separated. The pH of the water layer was adjusted to ~7 with 1 M HCl and then extracted with 20 mL of dichloromethane. The combined organic layers were washed with water and brine, then dried over MgSO, filtered and evaporated. The resulting oil was purified on a silica column eluting with EtOAc to yield tert-butyl 4-((4-formylpiperidin-1-yl)methyl)benzoate (550 mg, 1.722 mmol, 55.4% yield) as a yellow oil. ¹H NMR (400 MHz, CHLOROFORM-d) δ 9.67 (d, J=1.26 Hz, 1H), 7.96 (d, J=8.34 Hz, 2H), 7.38 (d, J=8.34 Hz, 2H), 3.56 (s, 2H), 2.75-2.92 (m, 2H), 2.21-2.35 (m, 1H), 2.14 (t, J=10.48 Hz, 2H), 1.91 (dd, J=2.78, 13.14 Hz, 2H), 1.65-1.81 (m, 2H), 1.58-1.64 (m, 9H); LC-MS Rt=0.69 min; MS (ESI): 304.2 [M+H]⁺, 322.2 [M+H₂O]⁺, 336.6 [M+Na]⁺

Step 3.

tert-Butyl 4-((4-((((1R,2S)-2-phenylcyclopropyl)amino)methyl)piperidin-1-yl)methyl)benzoate To a solution of tert-butyl 4-((4-formylpiperidin-1-yl)methyl)benzoate (6.7 g, 22.08 mmol) in methanol (50 mL) was added (1R,2S)-2-phenylcyclopropanamine (3.53 g, 26.5 mmol). The reaction mixture was refluxed for 5 minutes then cooled down to the room temperature. Sodium cyanotrihydroborate (2.082 g, 33.1 mmol) was added. The reaction mixture was stirred 1 hour at room temperature. Water (50 mL) was added. The reaction was concentrated and 50 mL of dichloromethane was added. The layers were separated. The organics were washed with 10% acetic acid (50 mL). The layers were separated and 50 mL of brine was added slowly as a solid crashed out. The solid was filtered and suspended in isopropanol. The suspension was sonicated and filtered. tert-Butyl 4-((4-((((1R,2S)-2-phenylcyclopropyl)amino)methyl)piperidin-1-yl)methyl)benzoate (5.8 g, 13.65 mmol, 61.8% yield) was isolated as a white solid. ¹H NMR (400 MHz, METHANOL-d₄) δ 8.07 (d, J=8.34 Hz, 2H), 7.70 (d, J=8.08 Hz, 2H), 7.28-7.37 (m, 2H), 7.10-7.28 (m, 3H), 4.43 (br. s., 2H), 3.54 (d, J=10.86 Hz, 2H), 3.08-3.26 (m, 4H), 3.03 (dt, J=3.76, 7.39 Hz, 1H), 2.54-2.71 (m, 1H), 2.03-2.29 (m, 3H), 1.67-1.84 (m, 2H), 1.58-1.67 (m, 10H), 1.40 (q, J=6.82 Hz, 1H); LC-MS Rt=0.76 min; MS (ESI): 421.4 [M+H]⁺.

Step 4.

4-((4-((((1R,2S)-2-phenylcyclopropyl)amino)methyl)piperidin-1-yl)methyl)benzoic acid A suspension of tert-butyl 4-((4-((((1R,2S)-2-phenylcyclopropyl)amino)methyl)piperidin-1-yl)methyl)benzoate (5.8 g, 13.79 mmol) in HCL-1 M (80 ml, 80 mmol) was heated to 89° C. (internal temperature) for 2 hr. The solution was cooled down to the room temperature and held in an ice-bath for 1 hour and then filtered. 4-((4-((((1R,2S)-2-phenylcyclopropyl)amino)methyl)piperidin-1-yl)methyl)benzoic acid (3.8 g, 8.25 mmol, 59.8% yield) was isolated as white solid. ¹H NMR (400 MHz, METHANOL-d₄) δ 8.15 (d, J=8.34 Hz, 2H), 7.72 (d, J=8.59 Hz, 2H), 7.29-7.37 (m, 2H), 7.14-7.28 (m, 3H), 4.45 (br. s., 2H), 3.55 (d, J=10.36 Hz, 2H), 3.07-3.29 (m, 4H), 3.04 (dt, J=3.98, 7.71 Hz, 1H), 2.61 (ddd, J=3.66, 6.57, 10.23 Hz, 1H), 1.98-2.31 (m, 3H), 1.72 (br. s., 2H), 1.62 (ddd, J=4.42, 6.51, 10.55 Hz, 1H), 1.41 (q, J=6.82 Hz, 1H); LC-MS Rt=0.49 min; MS (ESI): 365.3 [M+H]⁺.

Example 30

4-{3-[4-({[(1R,2S)-2-Phenylcyclopropyl]amino}methyl)-1-piperidinyl]propyl}benzoic acid 2HCl

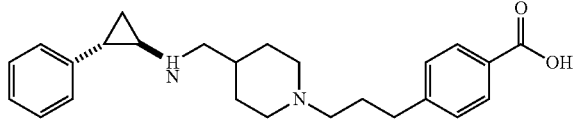

Ethyl 4-{3-[4-(hydroxymethyl)-1-piperidinyl]propyl}benzoate

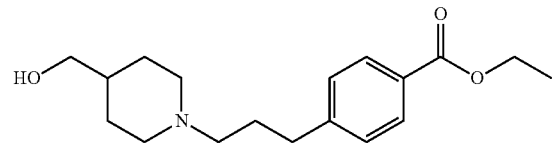 [SMILES: CCOC(=O)c1ccc(CCCN2CCC(CO)CC2)cc1]

Ethyl 4-(3-oxopropyl)benzoate (1000 mg, 4.85 mmol) and piperidin-4-ylmethanol (726 mg, 6.30 mmol), in methanol (25 mL) was heated to reflux for 5 minutes. The mixture was cooled to room temperature. Sodium cyanoborohydride (457 mg, 7.27 mmol) was added and the reaction was stirred at room temperature for 3 hours. After concentrating dichloromethane was added and the solution washed with water and brine. The organic layer was dried over MgSO4, filtered and concentrated. The residue was purified via Biotage (0% to 100% EtOAc:Hex to get off impurities then 0% to 20% MeOH:DCM; 50 g-HP-silica gel column) to yield 800 mg. ¹H NMR (400 MHz, CHLOROFORM-d) δ ppm 1.40 (t, 5H), 1.48-1.64 (m, 1H), 1.78 (d, J=11.87 Hz, 2H), 1.91 (quin, J=7.71 Hz, 2H), 2.04 (t, J=11.12 Hz, 2H), 2.38-2.53 (m, 2H), 2.71 (t, J=7.58 Hz, 2H), 3.03 (d, J=11.62 Hz, 2H), 3.51 (d, J=6.32 Hz, 2H), 4.38 (q, J=7.24 Hz, 2H), 7.11-7.40 (m, 2H), 7.97 (d, J=8.08 Hz, 2H); MS (ES) [M+H]⁺ 306.2

Ethyl 4-[3-(4-formyl-1-piperidinyl)propyl]benzoate

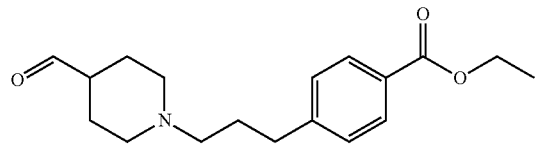 [SMILES: CCOC(=O)c1ccc(CCCN2CCC(C=O)CC2)cc1]

A solution of oxalyl chloride (2.66 mL, 30.4 mmol) in dichloromethane (150 mL) was cooled in a dry ice/acetone bath. DMSO (3.29 mL, 46.3 mmol) was added dropwise. After 10 minutes ethyl 4-(3-(4-(hydroxymethyl)piperidin-1-yl)propyl)benzoate (4.88 g, 15.98 mmol) dissolved in dichloromethane was added dropwise. After 15 minutes triethylamine (13.36 mL, 96 mmol) was added dropwise. The reaction mixture was stirred in a dry ice/acetone bath with gradual warming to room temperature over 2 hours. The reaction mixture was washed with water, brine, dried over MgSO4, filtered and rotovapped off DCM. The residue was purified via Biotage (0% to 100% EtOAc:Hex; then 0% to 20% MeOH:EtOAC; 50 g-HP-silica gel column) to yield 4.25 g $^1$H NMR (400 MHz, CHLOROFORM-d) δ ppm 1.40 (t, J=7.20 Hz, 3H), 1.64-1.78 (m, 2H), 1.78-2.01 (m, 4H), 2.02-2.17 (m, 2H), 2.19-2.31 (m, 1H), 2.31-2.40 (m, 2H), 2.69 (t, J=7.58 Hz, 2H), 2.79-2.91 (m, 2H), 4.37 (q, J=7.07 Hz, 2H), 7.06-7.38 (m, 2H), 7.87-8.07 (m, 2H), 9.66 (d, 1H); MS (ES) [M+H]$^+$ 304.2

Ethyl 4-{3-[4-({[(1R,2S)-2-phenylcyclopropyl]amino}methyl)-1-piperidinyl]propyl}benzoate

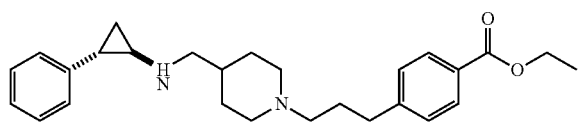

A solution of (1R,2S)-2-phenylcyclopropanamine (1.051 g, 7.89 mmol) and ethyl 4-(3-(4-formylpiperidin-1-yl)propyl)benzoate (1.9 g, 6.26 mmol) in methanol (50 mL) was heated to reflux for 5 minutes. The reaction was cooled to room temperature and sodium cyanoborohydride (0.590 g, 9.39 mmol) was added. The reaction was stirred at room temperature for 16 hours. After concentrating, dichloromethane was added and the solution was washed with water followed by brine and dried over MgSO4, filtered and concentrated. The residue was purified via Biotage (0% to 100% EtOAc:Hex; to get off impurity then 0% to 20% MeOH:DCM to get off product 50 g-HP-silica gel column) to yield 1.18 g $^1$H NMR (400 MHz, CHLOROFORM-d) δ ppm 0.90-1.18 (m, 2H), 1.20-1.36 (m, 2H), 1.40 (t, J=7.07 Hz, 4H), 1.66-1.80 (m, 2H), 1.81-2.02 (m, 5H), 2.24-2.45 (m, 3H), 2.56-2.79 (m, 4H), 2.95 (d, J=10.86 Hz, 2H), 4.38 (q, J=7.24 Hz, 2H), 6.99-7.10 (m, 2H), 7.10-7.20 (m, 1H), 7.21-7.38 (m, 5H), 7.97 (d, 2H) MS (ES); [M+H]$^+$ 421.3

4-{3-[4-({[(1R,2S)-2-Phenylcyclopropyl]amino}methyl)-1-piperidinyl]propyl}benzoic acid 2HCl

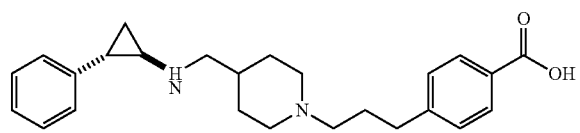

1M sodium hydroxide (14.03 mL, 14.03 mmol) was added to a solution of ethyl 4-(3-(4-((((1R,2S)-2-phenylcyclopropyl)amino)methyl)piperidin-1-yl)propyl)benzoate (1.18 g, 2.81 mmol) in methanol (60 mL) and stirred at RT for 7 hours. The reaction mixture was concentrated and purified via HPLC (reverse phase) with a Gemini NX 5u C18 110A, AXIA column, 100×30.00 mm 5 micron. A 7 minute gradient was run (0% AcCN/H$_2$O, 0.1% TFA to 40% ACN/H$_2$O, 0.1% TFA) with UV detection at 214 nm. Added 1 ml of 1N HCl to fractions containing product and concentrated to dryness. Obtained 800 mg of the di HCl salt $^1$H NMR (400 MHz, MeOD) δ ppm 1.41 (q, J=6.82 Hz, 1H), 1.61 (ddd, J=10.55, 6.51, 4.42 Hz, 3H), 2.01-2.26 (m, 5H), 2.60 (ddd, J=10.23, 6.57, 3.66 Hz, 1H), 2.82 (t, J=7.58 Hz, 2H), 2.97-3.11 (m, 3H), 3.11-3.27 (m, 4H), 3.66 (d, J=12.13 Hz, 2H), 7.16-7.29 (m, 3H), 7.32 (d, J=7.58 Hz, 2H), 7.40 (d, J=8.08 Hz, 2H), 7.90-8.07 (m, 2H); [M+H]$^+$ 393.3

Example 31 trans-N-((1-Isopropylpiperidin-4-yl)methyl)-2-phenylcyclopropanamine

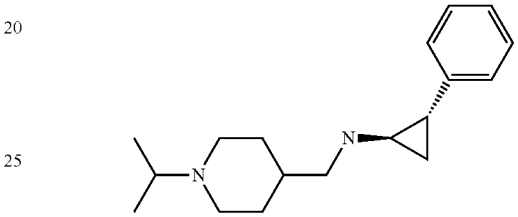

To a solution of 2,2,2-trifluoro-N-(trans-2-phenylcyclopropyl)-N-(piperidin-4-ylmethyl)acetamide (200 mg, 0.613 mmol) in acetonitrile (10 mL) was added potassium carbonate (254 mg, 1.838 mmol) followed by 2-bromopropane (98 mg, 0.797 mmol). The reaction mixture was heated in a sealed tube at 80° C. for 4 hours. The reaction mixture was filtered and evaporated. The resulting oil was purified by preparatory HPLC (5 to 40% AcCN: H$_2$O with 0.1% formic acid modifier). The fractions were collected. The solution was neutralized with 1 M NaOH, concentrated and extracted with ethyl acetate. The organic layer was separated, dried over MgSO$_4$, filtered and evaporated. The oil was dissolved in 6 ml of EtOH and 3 ml of 1 M NaOH. The reaction mixture was stirred for 20 min, and then it was concentrated. The concentrated solution was then partitioned between 2 ml of water and 5 mL of EtOAc. The organic layer was separated and evaporated. The resulting oil was dissolved in 3 mL of acetonitrile. 0.5 mL of 4 M HCl in dioxane was added. 3 mL of diethylether was added and the formed solid product was filtered. trans-N-((1-Isopropylpiperidin-4-yl)methyl)-2-phenylcyclopropanamine (80 mg, 0.246 mmol, 40.1% yield) was isolated as white solid. $^1$H NMR (400 MHz, METHANOL-d$_4$) δ 7.29-7.40 (m, 2H), 7.13-7.28 (m, 3H), 3.43-3.63 (m, 3H), 3.21 (d, J=6.57 Hz, 2H), 3.11 (t, 2H), 3.04 (dt, J=3.98, 7.71 Hz, 1H), 2.49-2.69 (m, 1H), 2.17 (d, J=12.63 Hz, 3H), 1.56-1.86 (m, 3H), 1.34-1.48 (m, 7H); LC-MS Rt=0.42 min; MS (ESI): 273.3 [M+H]$^+$.

Example 32 trans-N-((1-(2-Methoxyethyl)piperidin-4-yl)methyl)-2-phenylcyclopropanamine

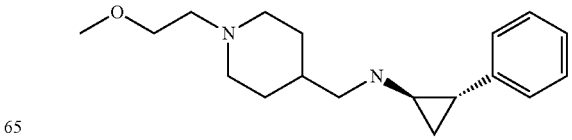

Following a procedure analogous to the procedure described in Example 31 using 2-methoxybromoethane (116 mg, 0.837 mmol) afforded trans-N-((1-(2-methoxyethyl)piperidin-4-yl)methyl)-2-phenylcyclopropanamine (87 mg, 0.254 mmol, 39.5% yield) as white solid. $^1$H NMR (400 MHz, METHANOL-d$_4$) δ 7.30-7.43 (m, 2H), 7.14-7.30 (m, 3H), 3.74-3.84 (m, 2H), 3.69 (d, J=12.13 Hz, 2H), 3.44 (s, 3H), 3.34-3.40 (m, 2H), 3.21 (d, J=6.57 Hz, 2H), 2.99-3.16 (m, 3H), 2.60 (ddd, J=3.54, 6.51, 10.17 Hz, 1H), 2.13 (d, J=13.89 Hz, 3H), 1.53-1.79 (m, 3H), 1.42 (q, J=6.82 Hz, 1H); LC-MS Rt=0.41 min; MS (ESI): 289.3 [M+H]$^+$.

Example 33 trans-2-Phenyl-N-((1-(pyridin-4-ylmethyl)piperidin-4-yl)methyl)cyclopropanamine

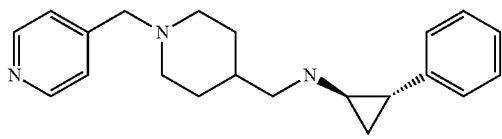 [SMILES: c1ccc([C@@H]2C[C@H]2NCC2CCN(Cc3ccncc3)CC2)cc1]

Following a procedure analogous to the procedure described in Example 31 using 4-(bromomethyl)pyridine (144 mg, 0.837 mmol) afforded trans-2-phenyl-N-((1-(pyridin-4-ylmethyl)piperidin-4-yl)methyl)cyclopropanamine (92 mg, 0.244 mmol, 37.9% yield) as white solid. $^1$H NMR (400 MHz, METHANOL-d$_4$) δ 9.01 (d, J=6.57 Hz, 2H), 8.39 (d, J=6.57 Hz, 2H), 7.29-7.41 (m, 2H), 7.10-7.29 (m, 3H), 4.71 (br. s., 2H), 3.63 (d, 2H), 3.15-3.31 (m, 4H), 3.05 (dt, J=3.88, 7.64 Hz, 1H), 2.59 (ddd, J=3.79, 6.38, 10.04 Hz, 1H), 2.07-2.33 (m, 3H), 1.71-1.95 (m, 2H), 1.60 (ddd, J=4.55, 6.44, 10.48 Hz, 1H), 1.42 (q, J=6.82 Hz, 1H); LC-MS Rt=0.40 min; MS (ESI): 322.3 [M++H]$^+$.

Example 34 trans-N-((1-(2-Fluorobenzyl)piperidin-4-yl)methyl)-2-phenylcyclopropanamine

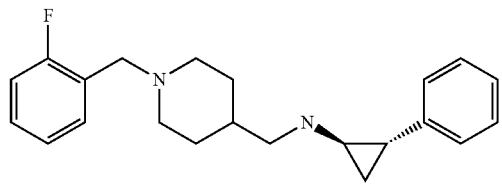 [SMILES: Fc1ccccc1CN1CCC(CN[C@@H]2C[C@H]2c2ccccc2)CC1]

Following a procedure analogous to the procedure described in Example 31 using 1-(bromomethyl)-2-fluorobenzene (87 mg, 0.460 mmol) afforded trans-N-((1-(2-fluorobenzyl)piperidin-4-yl)methyl)-2-phenylcyclopropanamine (28 mg, 0.071 mmol, 23.15% yield) as white solid. $^1$H NMR (400 MHz, DMSO-d$_6$) δ 9.48 (d, 2H), 7.76 (t, J=7.58 Hz, 1H), 7.55 (q, J=6.32 Hz, 1H), 7.27-7.40 (m, 4H), 7.14-7.27 (m, 3H), 4.21-4.47 (m, 2H), 3.41 (d, J=1.52 Hz, 1H), 3.12-3.28 (m, 1H), 2.78-3.09 (m, 5H), 2.54-2.65 (m, 1H), 2.00 (d, J=11.87 Hz, 3H), 1.42-1.70 (m, 3H), 1.17-1.36 (m, 1H); LC-MS Rt=0.56 min; MS (ESI): 339.3 [M+H]$^+$.

Example 35

1,1-Bis(2-fluorobenzyl)-4-(((trans-2-phenylcyclopropyl)amino)methyl)piperidin-1-ium chloride

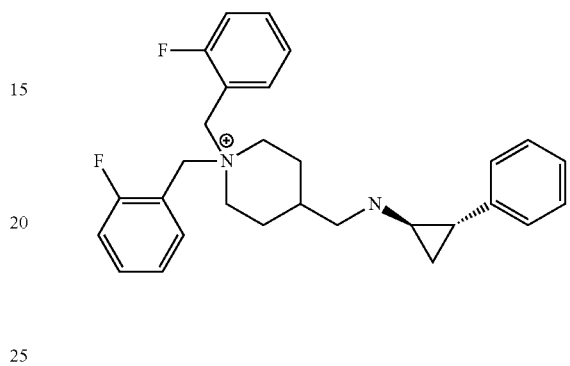

Following a procedure analogous to the procedure described in Example 31 using 1-(bromomethyl)-2-fluorobenzene (87 mg, 0.460 mmol) afforded 1,1-bis(2-fluorobenzyl)-4-(((trans-2-phenylcyclopropyl)amino)methyl)piperidin-1-ium chloride (45 mg, 0.088 mmol, 28.8% yield) as a white foam. $^1$H NMR (400 MHz, DMSO-d$_6$) δ 9.72 (br. s., 2H), 7.57-7.85 (m, 4H), 7.38-7.52 (m, 2H), 7.25-7.38 (m, 3H), 7.18-7.25 (m, 1H), 7.11-7.18 (m, 2H), 4.44 (s, 2H), 3.40-3.77 (m, 5H), 2.85-3.12 (m, 5H), 2.59 (ddd, J=3.54, 6.25, 9.92 Hz, 1H), 1.87-2.24 (m, 5H), 1.52-1.66 (m, 1H), 1.16-1.30 (m, 1H); LC-MS Rt=0.70 min; MS (ESI): 447.3 [M+H]$^+$.

Example 36 trans-N-((1-(3-Fluorobenzyl)piperidin-4-yl)methyl)-2-phenylcyclopropanamine

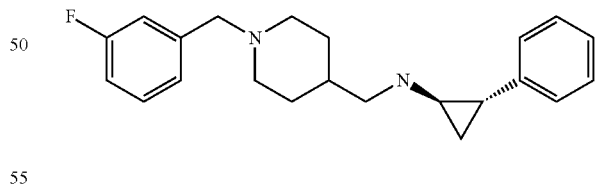

Following a procedure analogous to the procedure described in Example 31 using 1-(bromomethyl)-3-fluorobenzene (87 mg, 0.460 mmol) afforded trans-N-((1-(3-fluorobenzyl)piperidin-4-yl)methyl)-2-phenylcyclopropanamine (25 mg, 0.063 mmol, 20.67% yield) as a white solid. $^1$H NMR (400 MHz, METHANOL-d$_4$) δ 7.55 (td, J=5.94, 8.02 Hz, 1H), 7.37-7.45 (m, 2H), 7.17-7.36 (m, 6H), 4.37 (s, 2H), 3.56 (d, J=11.87 Hz, 2H), 3.20 (d, J=6.06 Hz, 2H), 3.06-3.17 (m, 2H), 3.03 (dt, J=3.88, 7.64 Hz, 1H), 2.58 (ddd, J=3.66, 6.32, 9.98 Hz, 1H), 2.12 (d, J=13.39 Hz, 3H), 1.49-1.78 (m, 3H), 1.41 (q, J=6.82 Hz, 1H); LC-MS Rt=0.56 min; MS (ESI): 339.3 [M+H]$^+$.

Example 37

1,1-Bis(3-fluorobenzyl)-4-(((trans-2-phenylcyclopropyl)amino)methyl)piperidin-1-ium chloride

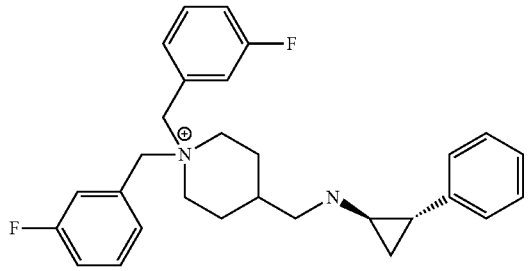 [SMILES: Fc1cccc(C[N+]2(Cc3cccc(F)c3)CCC(CN[C@@H]3C[C@H]3c3ccccc3)CC2)c1]

Following a procedure analogous to the procedure described in Example 31 using 1-(bromomethyl)-3-fluorobenzene (87 mg, 0.460 mmol) afforded 1,1-bis(3-fluorobenzyl)-4-(((trans-2-phenylcyclopropyl)amino)methyl)piperidin-1-ium chloride (36 mg, 0.071 mmol, 23.06% yield) as a white foam. $^1$H NMR (400 MHz, METHANOL-d$_4$) δ 7.65 (td, J=5.81, 7.96 Hz, 1H), 7.51-7.60 (m, 2H), 7.49 (dd, J=2.15, 9.47 Hz, 1H), 7.41 (td, J=2.27, 8.46 Hz, 1H), 7.29-7.38 (m, 6H), 7.22-7.29 (m, 1H), 7.13-7.21 (m, 2H), 4.94 (s, 2H), 4.49 (s, 2H), 3.73-3.81 (m, 1H), 3.66-3.72 (m, 2H), 3.64 (br. s., 1H), 3.58-3.63 (m, 2H), 3.20-3.31 (m, 2H), 3.02 (dt, J=4.07, 7.77 Hz, 1H), 2.58 (ddd, J=3.54, 6.63, 10.29 Hz, 1H), 2.16-2.36 (m, 2H), 2.03-2.15 (m, 2H), 1.87-2.00 (m, 1H), 1.60 (ddd, J=4.29, 6.57, 10.61 Hz, 1H), 1.42 (q, J=6.82 Hz, 1H); LC-MS Rt=0.71 min; MS (ESI): 447.3 [M+H]$^+$.

Example 38 trans-N-((1-(4-Fluorobenzyl)piperidin-4-yl)methyl)-2-phenylcyclopropanamine

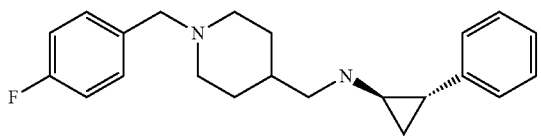 [SMILES: Fc1ccc(CN2CCC(CN[C@@H]3C[C@H]3c3ccccc3)CC2)cc1]

Following a procedure analogous to the procedure described in Example 31 using 1-(bromomethyl)-4-fluorobenzene (60.8 mg, 0.322 mmol) afforded trans-N-((1-(4-fluorobenzyl)piperidin-4-yl)methyl)-2-phenylcyclopropanamine (53 mg, 0.134 mmol, 43.8% yield) as a white solid. $^1$H NMR (400 MHz, METHANOL-d$_4$) δ 7.54-7.66 (m, 2H), 7.30-7.38 (m, 2H), 7.22-7.30 (m, 3H), 7.20 (d, 2H), 4.35 (s, 2H), 3.55 (d, J=12.13 Hz, 2H), 3.20 (d, J=6.32 Hz, 2H), 2.98-3.14 (m, 3H), 2.58 (ddd, J=3.54, 6.51, 10.17 Hz, 1H), 2.12 (d, J=13.39 Hz, 3H), 1.51-1.82 (m, 3H), 1.41 (q, J=6.82 Hz, 1H); LC-MS Rt=0.58 min; MS (ESI): 339.3 [M+H]$^+$.

Example 39

1,1-bis(4-Fluorobenzyl)-4-(((trans-2-phenylcyclopropyl)amino)methyl)piperidin-1-ium chloride

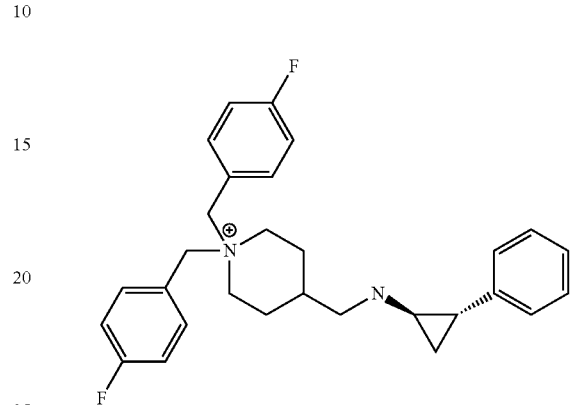

Following a procedure analogous to the procedure described in Example 31 using 1-(bromomethyl)-4-fluorobenzene (60.8 mg, 0.322 mmol) afforded 1,1-bis(4-fluorobenzyl)-4-(((trans-2-phenylcyclopropyl)amino)methyl)piperidin-1-ium chloride (28 mg, 0.055 mmol, 17.93% yield) (36 mg, 0.071 mmol, 23.06% yield) as a white foam. $^1$H NMR (400 MHz, METHANOL-d$_4$) δ 7.70 (dd, J=5.05, 8.59 Hz, 2H), 7.52 (dd, J=5.18, 8.72 Hz, 2H), 7.34 (t, J=8.59 Hz, 2H), 7.16-7.30 (m, 4H), 7.06-7.16 (m, 1H), 7.01 (d, J=7.07 Hz, 2H), 4.83 (s, 2H), 4.40 (s, 2H), 3.42-3.61 (m, 2H), 3.04-3.26 (m, 2H), 2.74 (d, J=6.82 Hz, 2H), 2.29 (dt, J=3.82, 7.26 Hz, 1H), 1.94-2.12 (m, 4H), 1.88 (ddd, J=3.28, 5.94, 9.22 Hz, 1H), 1.51-1.72 (m, 1H), 1.05-1.11 (m, 1H), 0.99-1.05 (m, 1H); LC-MS Rt=0.72 min; MS (ESI): 447.3 [M+H]$^+$.

Example 40 trans-N-((1-(2,4-Difluorobenzyl)piperidin-4-yl)methyl)-2-phenylcyclopropanamine

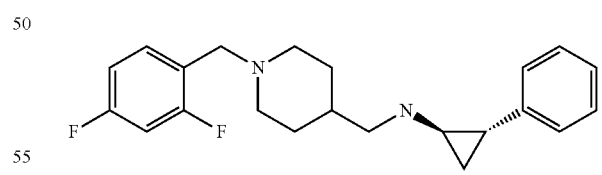

Following a procedure analogous to the procedure described in Example 31 using 1-(bromomethyl)-2,4-difluorobenzene (57.7 mg, 0.279 mmol) afforded trans-N-((1-(2,4-difluorobenzyl)piperidin-4-yl)methyl)-2-phenylcyclopropanamine (50 mg, 0.121 mmol, 56.4% yield) as a white solid. $^1$H NMR (400 MHz, METHANOL-d$_4$) δ 7.53-7.63 (m, 1H), 7.35-7.53 (m, 5H), 7.29-7.35 (m, 2H), 7.22-7.28 (m, 1H), 7.11-7.22 (m, 2H), 5.06 (s, 2H), 4.51 (s, 2H), 3.66-3.74 (m, 4H), 3.29 (d, J=6.57 Hz, 2H), 3.02 (dt, J=4.14, 7.64 Hz, 1H), 2.62 (ddd, J=3.66, 6.63, 10.42 Hz, 1H), 2.19-2.37 (m, 2H), 1.98-2.18 (m, 3H), 1.62 (ddd, J=4.29, 6.57, 10.61 Hz, 1H), 1.40 (q, J=6.82 Hz, 1H); LC-MS Rt=0.57 min; MS (ESI): 357.3 [M++H]⁺.

Example 41

1,1-Bis(2,4-difluorobenzyl)-4-(((trans-2-phenylcyclopropyl)amino)methyl)piperidin-1-ium bromide

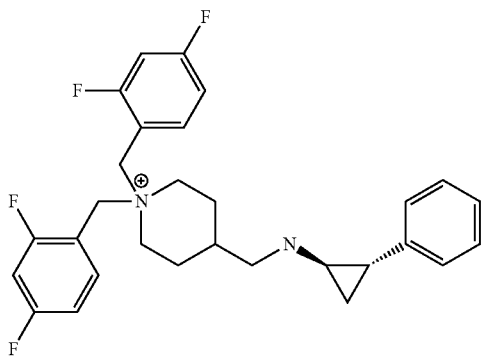 [SMILES: Fc1ccc(C[N+]2(Cc3ccc(F)cc3F)CCC(CN[C@@H]3C[C@H]3c3ccccc3)CC2)c(F)c1]

Following a procedure analogous to the procedure described in Example 31 using 1-(bromomethyl)-2,4-difluorobenzene (57.7 mg, 0.279 mmol) afforded 1,1-bis(2,4-difluorobenzyl)-4-(((trans-2-phenylcyclopropyl)amino)methyl)piperidin-1-ium bromide (20 mg, 0.034 mmol, 15.72% yield) as a white foam. ¹H NMR (400 MHz, METHANOL-$d_4$) δ 7.53-7.63 (m, 1H), 7.35-7.53 (m, 5H), 7.29-7.35 (m, 2H), 7.22-7.28 (m, 1H), 7.11-7.22 (m, 2H), 5.06 (s, 2H), 4.51 (s, 2H), 3.66-3.74 (m, 4H), 3.29 (d, J=6.57 Hz, 2H), 3.02 (dt, J=4.14, 7.64 Hz, 1H), 2.62 (ddd, J=3.66, 6.63, 10.42 Hz, 1H), 2.19-2.37 (m, 2H), 1.98-2.18 (m, 3H), 1.62 (ddd, J=4.29, 6.57, 10.61 Hz, 1H), 1.40 (q, J=6.82 Hz, 1H); LC-MS Rt=0.71 min; MS (ESI): 483.3 [M+H]⁺.

Example 42

Ethyl 4-((4-(((trans-2-phenylcyclopropyl)amino)methyl)piperidin-1-yl)methyl)benzoate

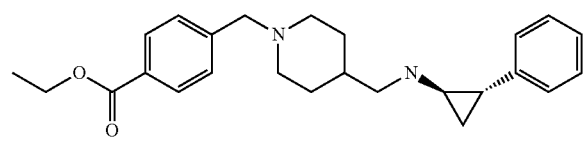 [SMILES: CCOC(=O)c1ccc(CN2CCC(CN[C@@H]3C[C@H]3c3ccccc3)CC2)cc1]

Following a procedure analogous to the procedure described in Example 31 using methyl 4-(bromomethyl)benzoate (73.7 mg, 0.322 mmol) afforded ethyl 4-((4-(((trans-2-phenylcyclopropyl)amino)methyl)piperidin-1-yl)methyl)benzoate (25 mg, 0.055 mmol, 18.07% yield) as a white solid. ¹H NMR (400 MHz, METHANOL-$d_4$) δ 8.15 (d, J=8.34 Hz, 2H), 7.71 (d, J=8.34 Hz, 2H), 7.29-7.39 (m, 2H), 7.12-7.29 (m, 3H), 4.43 (br. s., 2H), 4.41 (q, J=7.07 Hz, 2H), 3.57 (d, J=11.87 Hz, 2H), 3.20 (d, J=6.32 Hz, 2H), 3.07-3.17 (m, 2H), 3.00-3.07 (m, 1H), 2.50-2.65 (m, 1H), 2.12 (d, J=13.64 Hz, 3H), 1.52-1.77 (m, 3H), 1.42 (t, J=7.20 Hz, 4H); LC-MS Rt=0.66 min; MS (ESI): 393.3 [M+H]⁺.

Example 43 trans-N-((1-(4-(Methylsulfonyl)benzyl)piperidin-4-yl)methyl)-2-phenylcyclopropanamine

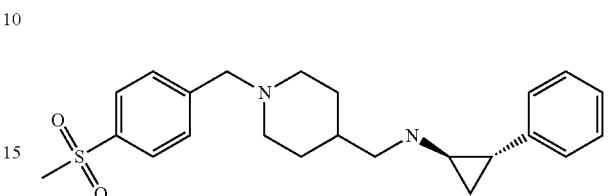

Following a procedure analogous to the procedure described in Example 31 using 1-(bromomethyl)-4-(methylsulfonyl)benzene (80 mg, 0.322 mmol) afforded trans-N-((1-(4-(methylsulfonyl)benzyl)piperidin-4-yl)methyl)-2-phenylcyclopropanamine (65 mg, 0.155 mmol, 50.6% yield) as a white solid. ¹H NMR (400 MHz, METHANOL-$d_4$) δ 7.93 (d, J=8.59 Hz, 2H), 7.63 (d, J=8.34 Hz, 2H), 7.18-7.31 (m, 2H), 7.09-7.17 (m, 1H), 6.96-7.08 (m, 2H), 3.63 (s, 2H), 3.13 (s, 3H), 2.91 (d, J=11.37 Hz, 2H), 2.61 (dd, J=1.01, 6.82 Hz, 2H), 2.24-2.35 (m, 1H), 2.06 (tt, J=2.40, 11.75 Hz, 2H), 1.91 (ddd, J=3.28, 6.06, 9.35 Hz, 1H), 1.77 (ddd, J=2.27, 6.44, 9.22 Hz, 2H), 1.47-1.64 (m, 1H), 1.28 (qd, J=3.92, 12.25 Hz, 2H), 1.07 (dt, J=4.86, 9.47 Hz, 1H), 1.01 (dt, J=5.59, 7.26 Hz, 1H); LC-MS Rt=0.51 min; MS (ESI): 399.3 [M+H]⁺.

Example 44

1-(4-(((trans-2-Phenylcyclopropyl)amino)methyl)piperidin-1-yl)butan-2-ol

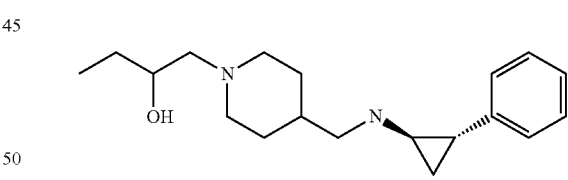

Following a procedure analogous to the procedure described in Example 31 using 1-bromobutan-2-ol (42.7 mg, 0.279 mmol) afforded 1-(4-(((trans-2-phenylcyclopropyl)amino)methyl)piperidin-1-yl)butan-2-ol (42 mg, 0.118 mmol, 54.9% yield) as a white solid. ¹H NMR (400 MHz, METHANOL-$d_4$) δ 7.30-7.38 (m, 2H), 7.24-7.29 (m, 1H), 7.21 (d, J=7.33 Hz, 2H), 3.90-4.04 (m, 1H), 3.73-3.83 (m, 1H), 3.62-3.73 (m, 1H), 3.37-3.52 (m, 1H), 3.21 (d, J=6.32 Hz, 2H), 3.08-3.18 (m, 2H), 2.96-3.08 (m, 3H), 2.42-2.70 (m, 1H), 2.00-2.28 (m, 3H), 1.64-1.81 (m, 1H), 1.55-1.64 (m, 2H), 1.48-1.55 (m, 1H), 1.42 (q, J=7.07 Hz, 1H), 1.02 (t, J=7.45 Hz, 3H); LC-MS Rt=0.46 min; MS (ESI): 303.3 [M+H]⁺.

Example 45

2-((4-(((trans-2-Phenylcyclopropyl)amino)methyl)piperidin-1-yl)methyl)benzonitrile

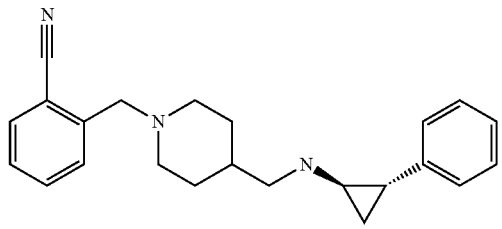 [SMILES: N#Cc1ccccc1CN1CCC(CN[C@@H]2C[C@H]2c2ccccc2)CC1]

Following a procedure analogous to the procedure described in Example 31 using 2-(bromomethyl)benzonitrile (54.7 mg, 0.279 mmol) afforded 2-((4-(((trans-2-phenylcyclopropyl)amino)methyl)piperidin-1-yl)methyl)benzonitrile (56 mg, 0.127 mmol, 59.3% yield) as a white solid. $^1$H NMR (400 MHz, DMSO-d$_6$) δ 11.25 (d, J=1.26 Hz, 1H), 8.16 (d, J=7.83 Hz, 1H), 7.97 (d, J=7.58 Hz, 1H), 7.84 (t, J=7.71 Hz, 1H), 7.63-7.75 (m, 1H), 7.27-7.38 (m, 2H), 7.14-7.27 (m, 3H), 4.29-4.58 (m, 2H), 3.32-3.54 (m, 1H), 3.17-3.33 (m, 1H), 3.09 (q, J=10.78 Hz, 2H), 2.97 (d, J=5.56 Hz, 3H), 2.62 (ddd, J=3.54, 6.32, 9.85 Hz, 1H), 1.97-2.24 (m, 3H), 1.54-1.80 (m, 3H), 1.03-1.38 (m, 1H); LC-MS Rt=0.53 min; MS (ESI): 346.3 [M+H]$^+$.

Example 46 trans-2-Phenyl-N-((1-(2-(trifluoromethyl)benzyl)piperidin-4-yl)methyl)cyclopropanamine

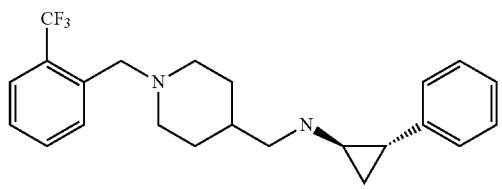 [SMILES: FC(F)(F)c1ccccc1CN1CCC(CN[C@@H]2C[C@H]2c2ccccc2)CC1]

Following a procedure analogous to the procedure described in Example 31 1-(bromomethyl)-2-(trifluoromethyl)benzene (66.7 mg, 0.279 mmol) afforded trans-2-phenyl-N-((1-(2-(trifluoromethyl)benzyl)piperidin-4-yl)methyl)cyclopropanamine (45 mg, 0.088 mmol, 40.9% yield) as a white solid. $^1$H NMR (400 MHz, METHANOL-d$_4$) δ 8.01-8.12 (m, 1H), 7.90 (d, J=7.83 Hz, 1H), 7.84 (t, J=7.58 Hz, 1H), 7.66-7.78 (m, 1H), 7.29-7.38 (m, 2H), 7.14-7.28 (m, 3H), 4.57 (s, 2H), 3.65-3.73 (m, 1H), 3.61 (dd, J=3.66, 9.22 Hz, 2H), 3.16-3.30 (m, 3H), 3.04 (dt, J=3.98, 7.71 Hz, 1H), 2.62 (ddd, J=3.41, 6.57, 10.23 Hz, 1H), 2.17-2.33 (m, 1H), 2.06-2.16 (m, 2H), 1.69-1.87 (m, 2H), 1.63 (ddd, J=4.67, 6.51, 10.55 Hz, 1H), 1.41 (q, J=6.82 Hz, 1H); LC-MS Rt=0.64 min; MS (ESI): 389.3 [M+H]$^+$.

Example 47 trans-N-((1-((5-Methylisoxazol-3-yl)methyl)piperidin-4-yl)methyl)-2-phenylcyclopropanamine

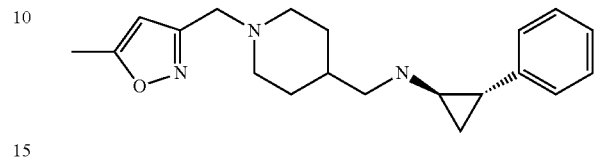

Following a procedure analogous to the procedure described in Example 31 3-(bromomethyl)-5-methylisoxazole (49.1 mg, 0.279 mmol) afforded trans-N-((1-((5-methylisoxazol-3-yl)methyl)piperidin-4-yl)methyl)-2-phenylcyclopropanamine (35 mg, 0.083 mmol, 38.9% yield) as a white solid. $^1$H NMR (400 MHz, METHANOL-d$_4$) δ 7.29-7.38 (m, 2H), 7.15-7.29 (m, 4H), 6.45 (s, 1H), 4.46 (s, 2H), 3.56-3.81 (m, 3H), 3.09-3.26 (m, 3H), 3.04 (dt, J=3.95, 7.52 Hz, 1H), 2.62 (ddd, J=3.54, 6.63, 10.29 Hz, 1H), 2.43 (s, 3H), 2.15 (d, J=14.40 Hz, 3H), 1.66-1.82 (m, 2H), 1.62 (ddd, J=4.42, 6.51, 10.55 Hz, 1H), 1.41 (q, J=6.82 Hz, 1H); LC-MS Rt=0.50 min; MS (ESI): 326.3 [M+H]$^+$.

Example 48 trans-N-((1-((1H-Pyrazol-4-yl)methyl)piperidin-4-yl)methyl)-2-phenylcyclopropanamine

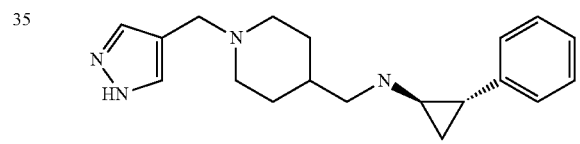

Following a procedure analogous to the procedure described in Example 31 tert-butyl 3-(bromomethyl)-1H-pyrazole-1-carboxylate (72.8 mg, 0.279 mmol) afforded trans-N-((1-((1H-pyrazol-4-yl)methyl)piperidin-4-yl)methyl)-2-phenylcyclopropanamine (15 mg, 0.035 mmol, 16.42% yield) as a white solid. $^1$H NMR (400 MHz, METHANOL-d$_4$) δ 7.81 (d, J=2.27 Hz, 1H), 7.29-7.40 (m, 2H), 7.10-7.29 (m, 3H), 6.61 (d, J=2.27 Hz, 1H), 4.39 (s, 1H), 3.73-3.79 (m, 2H), 3.66-3.71 (m, 2H), 3.57-3.66 (m, 2H), 3.16-3.26 (m, 2H), 2.96-3.16 (m, 3H), 2.52-2.70 (m, 1H), 2.06-2.20 (m, 2H), 1.55-1.78 (m, 2H), 1.35-1.46 (m, 1H); LC-MS Rt=0.46 min; MS (ESI): 311.3 [M+H]$^+$.

Example 49 trans-N-((1-Ethylpiperidin-4-yl)methyl)-2-phenylcyclopropanamine

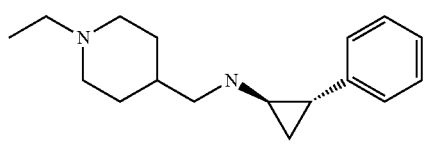 [SMILES: CCN1CCC(CN[C@@H]2C[C@H]2c2ccccc2)CC1]

Following a procedure analogous to the procedure described in Example 31 using bromoethane (30.4 mg, 0.279 mmol) afforded trans-N-((1-ethylpiperidin-4-yl)methyl)-2-phenylcyclopropanamine (56 mg, 0.161 mmol, 74.9% yield) as white solid. $^1$H NMR (400 MHz, METHANOL-d$_4$) δ 7.30-7.38 (m, 2H), 7.16-7.29 (m, 3H), 3.62-3.72 (m, 2H), 3.16-3.25 (m, 4H), 2.92-3.10 (m, 3H), 2.61 (ddd, J=3.54, 6.63, 10.29 Hz, 1H), 2.05-2.26 (m, 3H), 1.56-1.77 (m, 3H), 1.40-1.46 (m, 1H), 1.39 (t, J=7.33 Hz, 3H); LC-MS Rt=0.43 min; MS (ESI): 259.3 [M++H]$^+$.

Example 50

Diethyl (3-(4-(((trans-2-phenylcyclopropyl)amino)methyl)piperidin-1-yl)propyl)phosphonate

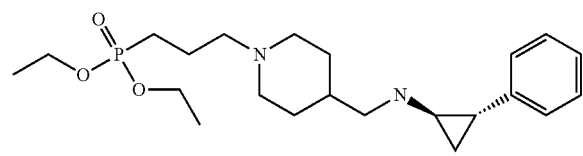 [SMILES: CCOP(=O)(CCCN1CCC(CN[C@@H]2C[C@H]2c2ccccc2)CC1)OCC]

Following a procedure analogous to the procedure described in Example 31 using diethyl (3-bromopropyl)phosphonate (175 mg, 0.674 mmol) afforded diethyl (3-(4-(((trans-2-phenylcyclopropyl)amino)methyl)piperidin-1-yl)propyl)phosphonate (45 mg, 0.084 mmol, 13.73% yield) as white solid. $^1$H NMR (400 MHz, METHANOL-d$_4$) δ 7.29-7.39 (m, 2H), 7.14-7.29 (m, 3H), 4.15 (td, J=3.28, 7.45 Hz, 4H), 3.67 (d, J=12.38 Hz, 2H), 3.17-3.27 (m, 4H), 2.95-3.16 (m, 3H), 2.62 (ddd, J=3.54, 6.63, 10.29 Hz, 1H), 2.01-2.24 (m, 5H), 1.89-2.01 (m, 2H), 1.70 (d, J=13.14 Hz, 2H), 1.63 (ddd, J=4.42, 6.51, 10.55 Hz, 1H), 1.40-1.46 (m, 1H), 1.37 (t, 6H); LC-MS Rt=0.56 min; MS (ESI): 409.3 [M+H]$^+$.

Example 51

Diethyl ((4-(((trans-2-phenylcyclopropyl)amino)methyl)piperidin-1-yl)methyl)phosphonate

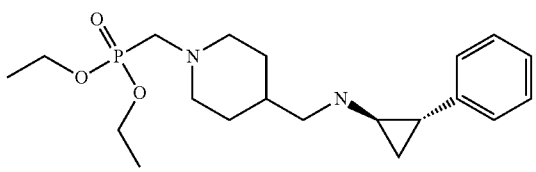 [SMILES: CCOP(=O)(CN1CCC(CN[C@@H]2C[C@H]2c2ccccc2)CC1)OCC]

Following a procedure analogous to the procedure described in Example 31 using diethyl diethyl (iodomethyl)phosphonate (78 mg, 0.279 mmol) afforded diethyl ((4-(((trans-2-phenylcyclopropyl)amino)methyl)piperidin-1-yl)methyl)phosphonate (23 mg, 0.048 mmol, 22.47% yield) as white solid. $^1$H NMR (400 MHz, METHANOL-d$_4$) δ 7.30-7.39 (m, 2H), 7.15-7.29 (m, 3H), 4.20-4.39 (m, 4H), 3.82 (d, J=12.88 Hz, 4H), 3.19-3.31 (m, 4H), 3.05 (dt, J=3.98, 7.71 Hz, 1H), 2.61 (ddd, J=3.66, 6.57, 10.23 Hz, 1H), 2.15 (d, J=13.64 Hz, 3H), 1.67-1.85 (m, 2H), 1.62 (ddd, J=4.29, 6.57, 10.61 Hz, 1H), 1.42 (t, J=7.07 Hz, 7H); LC-MS Rt=0.51 min; MS (ESI): 381.3 [M+H]$^+$.

Example 52

3-(4-(((trans-2-Phenylcyclopropyl)amino)methyl)piperidin-1-yl)propanoic acid

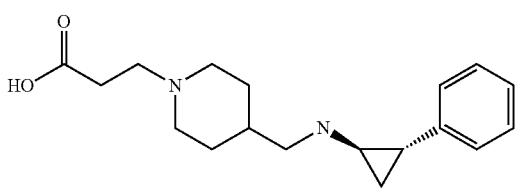 [SMILES: O=C(O)CCN1CCC(CN[C@@H]2C[C@H]2c2ccccc2)CC1]

To a solution of 2,2,2-trifluoro-N-(trans-2-phenylcyclopropyl)-N-(piperidin-4-ylmethyl)acetamide (300 mg, 0.919 mmol) in acetonitrile (10 mL) was added potassium carbonate (381 mg, 2.76 mmol) followed by tert-butyl 3-bromopropanoate (211 mg, 1.011 mmol) was heated in a seal tube at 80° C. for 4 hours. The reaction mixture was filtered, and the filtrate evaporated to dryness. The resulting oil was dissolved in 2 ml of EtOH and 2 ml of 1 M NaOH. The reaction mixture was stirred for 20 min. The solution injected on a preperatory HPLC (2 to 10% AcCN: H$_2$O with 0.1% formic acid modifier). The fractions were collected. To each fraction was added 0.1 ml of 6 M HCl, and the fractions were evaporated to dryness. Acid was formed by deprotection of t-butyl during evaporation. 3-(4-(((trans-2-phenylcyclopropyl)amino)methyl)piperidin-1-yl)propanoic acid (140 mg, 0.354 mmol, 38.5% yield) was isolated as yellow oil. $^1$H NMR (400 MHz, METHANOL-d$_4$) δ 7.29-7.37 (m, 2H), 7.11-7.29 (m, 3H), 3.65 (br. s., 2H), 3.45 (t, J=7.07 Hz, 2H), 3.23 (d, J=5.81 Hz, 2H), 3.11 (br. s., 2H), 3.04 (dt, J=4.01, 7.89 Hz, 1H), 2.90 (t, J=7.07 Hz, 2H), 2.62 (ddd, J=3.54, 6.63, 10.29 Hz, 1H), 2.04-2.29 (m, 3H), 1.70 (dd, 2H), 1.62 (ddd, J=4.42, 6.51, 10.55 Hz, 1H), 1.42 (q, J=6.91 Hz, 1H); LC-MS Rt=0.42 min; MS (ESI): 303.3 [M+H]$^+$.

Example 53

4-(4-(((trans-2-Phenylcyclopropyl)amino)methyl)piperidin-1-yl)butanoic acid

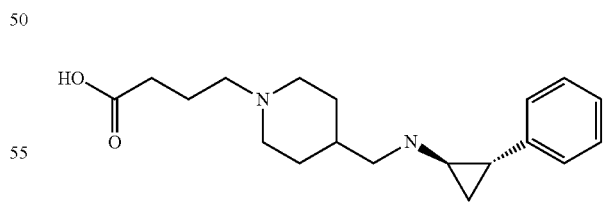

Following a procedure analogous to the procedure described in Example 52 using tert-butyl 4-bromobutanoate (226 mg, 1.011 mmol) afforded 4-(4-(((trans-2-phenylcyclopropyl)amino)methyl)piperidin-1-yl)butanoic acid (125 mg, 0.305 mmol, 33.2% yield) as white solid. $^1$H NMR (400 MHz, METHANOL-d$_4$) δ 7.30-7.37 (m, 2H), 7.17-7.29 (m, 3H), 3.69 (d, J=10.86 Hz, 2H), 3.14-3.27 (m, 4H), 2.98-3.14 (m, 3H), 2.62 (ddd, J=3.54, 6.63, 10.29 Hz, 1H), 2.49 (t, J=6.95 Hz, 2H), 2.15 (d, J=13.89 Hz, 3H), 2.06 (quin, J=7.52

Hz, 2H), 1.57-1.80 (m, 3H), 1.34-1.50 (m, 1H); LC-MS Rt=0.43 min; MS (ESI): 317.4 [M++H]⁺.

Example 54

N-(4-((4-(((trans-2-Phenylcyclopropyl)amino)methyl)piperidin-1-yl)methyl)phenyl)acetamide

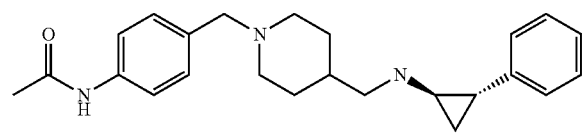 [SMILES: CC(=O)Nc1ccc(CN2CCC(CN[C@@H]3C[C@H]3c3ccccc3)CC2)cc1]

To a solution of 2,2,2-trifluoro-N-(trans-2-phenylcyclopropyl)-N-(piperidin-4-ylmethyl)acetamide (100 mg, 0.306 mmol) in methanol (2 mL) was added N-(4-formylphenyl)acetamide (50.0 mg, 0.306 mmol). The reaction mixture was refluxed for 2 minutes, then cooled down to room temperature. Sodium cyanotrihydroborate (38.5 mg, 0.613 mmol) was added. The reaction mixture was stirred for 1 hour at room temperature. The reaction mixture was injected on preperatory HPLC (5 to 40% AcCN: H₂O with 0.1% formic acid modifier). The fractions were collected and evaporated. The resulting oil was dissolved in 6 ml of EtOH and 3 ml of 1 M NaOH. The reaction mixture was stirred for 20 min, and then it was concentrated. The solution was then partitioned between 2 ml of water and 5 mL of EtOAc. Organic layer was separated and evaporated. Resulting oil was dissolved in 3 mL of acetonitrile. 0.5 mL of 4 M HCl/dioxane was added. The reaction mixture was evaporated until dryness. N-(4-((4-(((trans-2-phenylcyclopropyl)amino)methyl)piperidin-1-yl)methyl)phenyl)acetamide (28 mg, 0.059 mmol, 19.27% yield) was isolated as a white solid. ¹H NMR (400 MHz, DMSO-d₆) δ 10.61 (br. s., 1H), 10.20 (s, 1H), 9.60 (br. s., 2H), 7.66 (d, J=8.59 Hz, 2H), 7.48-7.56 (m, 2H), 7.27-7.34 (m, 2H), 7.14-7.26 (m, 3H), 4.10-4.33 (m, 2H), 3.15-3.37 (m, 2H), 2.76-3.14 (m, 5H), 2.59 (ddd, J=3.54, 6.38, 10.04 Hz, 1H), 1.84-2.12 (m, 6H), 1.48-1.68 (m, 3H), 1.17-1.32 (m, 1H); LC-MS Rt=0.53 min; MS (ESI): 378.4 [M+H]⁺.

Example 55

4-((4-(((trans-2-Phenylcyclopropyl)amino)methyl)piperidin-1-yl)methyl)benzo[c][1,2]oxaborol-1(3H)-ol

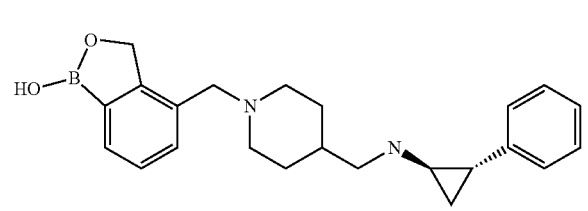 [SMILES: OB1OCc2c(CN3CCC(CN[C@@H]4C[C@H]4c4ccccc4)CC3)cccc21]

Following a procedure analogous to the procedure described in Example 54 using 1-hydroxy-1,3-dihydrobenzo[c][1,2]oxaborole-4-carbaldehyde (49.6 mg, 0.306 mmol) afforded 4-((4-(((trans-2-phenylcyclopropyl)amino)methyl)piperidin-1-yl)methyl)benzo[c][1,2]oxaborol-1(3H)-ol (28 mg, 0.059 mmol, 19.32% yield) as white solid. ¹H NMR (400 MHz, DMSO-d₆) δ 10.60 (br. s., 1H), 9.53 (d, J=1.01 Hz, 2H), 9.33 (br. s., 1H), 7.83 (dd, J=3.54, 7.33 Hz, 2H), 7.47 (t, J=7.33 Hz, 1H), 7.27-7.37 (m, 2H), 7.04-7.26 (m, 3H), 5.14-5.27 (m, 2H), 4.17-4.31 (m, 2H), 3.44-3.77 (m, 1H), 3.37 (d, J=11.37 Hz, 2H), 2.90-3.09 (m, 4H), 2.58 (ddd, J=3.66, 6.32, 9.98 Hz, 1H), 1.91-2.12 (m, 3H), 1.50-1.74 (m, 3H), 1.12-1.38 (m, 2H); LC-MS Rt=0.53 min; MS (ESI): 377.4 [M++H]⁺.

Example 56

5-((4-(((trans-2-Phenylcyclopropyl)amino)methyl)piperidin-1-yl)methyl)benzo[c][1,2]oxaborol-1(3H)-ol

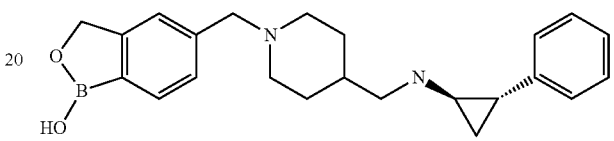

Following a procedure analogous to the procedure described in Example 54 using 1-hydroxy-1,3-dihydrobenzo[c][1,2]oxaborole-5-carbaldehyde (49.6 mg, 0.306 mmol) afforded 5-((4-(((trans-2-phenylcyclopropyl)amino)methyl)piperidin-1-yl)methyl)benzo[c][1,2]oxaborol-1(3H)-ol (35 mg, 0.074 mmol, 24.16% yield) as white solid. ¹H NMR (400 MHz, DMSO-d₆) δ 10.77 (d, J=1.77 Hz, 1H), 9.61 (br. s., 2H), 9.35 (br. s., 1H), 7.82 (d, J=7.33 Hz, 1H), 7.52-7.66 (m, 2H), 7.27-7.36 (m, 2H), 7.10-7.27 (m, 3H), 5.03 (s, 2H), 4.31 (d, J=5.05 Hz, 2H), 3.42-3.76 (m, 1H), 3.35 (d, J=11.12 Hz, 2H), 3.05-3.27 (m, 1H), 2.81-3.04 (m, 4H), 2.59 (ddd, J=3.54, 6.38, 10.04 Hz, 1H), 2.00 (d, J=13.14 Hz, 3H), 1.48-1.69 (m, 3H), 1.12-1.35 (m, 2H); LC-MS Rt=0.52 min; MS (ESI): 377.4 [M+H]⁺.

Example 57

(4-((4-(((trans-2-phenylcyclopropyl)amino)methyl)piperidin-1-yl)methyl)phenyl)boronic acid

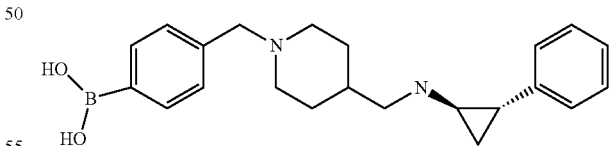

Following a procedure analogous to the procedure described in Example 54 using (4-formylphenyl)boronic acid (45.9 mg, 0.306 mmol) afforded (4-((4-(((trans-2-phenylcyclopropyl)amino)methyl)piperidin-1-yl)methyl)phenyl)boronic acid (55 mg, 0.120 mmol, 39.0% yield) as white solid. ¹H NMR (400 MHz, METHANOL-d₄) δ 7.76 (d, J=7.07 Hz, 2H), 7.57 (d, J=7.83 Hz, 2H), 7.29-7.38 (m, 2H), 7.16-7.29 (m, 3H), 4.36 (s, 2H), 3.52-3.59 (m, 2H), 3.20 (d, J=6.57 Hz, 2H), 3.05-3.16 (m, 2H), 3.03 (dt, J=4.14, 7.64 Hz, 1H), 2.59 (ddd, J=3.66, 6.69, 10.36 Hz, 1H), 2.07-2.25 (m, 3H), 1.63-

1.79 (m, 2H), 1.60 (td, J=3.54, 6.95 Hz, 1H), 1.41 (q, J=6.82 Hz, 1H); LC-MS Rt=0.53 min; MS (ESI): 365.4 [M+H]⁺.

Example 58

2-((4-(((trans-2-Phenylcyclopropyl)amino)methyl)piperidin-1-yl)methyl)benzoic acid

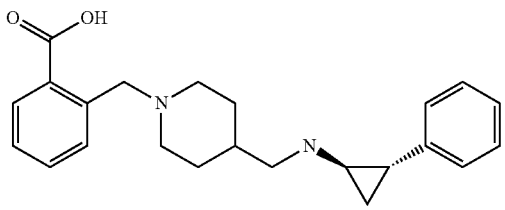 [SMILES: O=C(O)c1ccccc1CN1CCC(CN[C@@H]2C[C@H]2c2ccccc2)CC1]

Following a procedure analogous to the procedure described in Example 54 using 2-formylbenzoic acid (66.2 mg, 0.441 mmol) afforded 2-((4-(((trans-2-phenylcyclopropyl)amino)methyl)piperidin-1-yl)methyl)benzoic acid (52 mg, 0.113 mmol, 30.7% yield) as white solid. ¹H NMR (400 MHz, METHANOL-d₄) δ 8.22-8.34 (m, 1H), 7.61-7.79 (m, 3H), 7.30-7.41 (m, 2H), 7.14-7.30 (m, 3H), 4.61 (s, 2H), 3.67 (d, J=12.63 Hz, 2H), 3.40 (d, J=7.33 Hz, 1H), 3.28 (td, J=2.65, 13.07 Hz, 2H), 3.19 (d, J=6.82 Hz, 2H), 3.04 (dt, J=4.14, 7.64 Hz, 1H), 2.62 (ddd, J=3.66, 6.63, 10.42 Hz, 1H), 2.22 (ddd, J=4.29, 7.96, 15.03 Hz, 1H), 2.15 (d, J=14.91 Hz, 2H), 1.53-1.77 (m, 2H), 1.26-1.49 (m, 1H); LC-MS Rt=0.55 min; MS (ESI): 365.4 [M+H]⁺.

Example 59

3-((4-(((trans-2-Phenylcyclopropyl)amino)methyl)piperidin-1-yl)methyl)benzoic acid

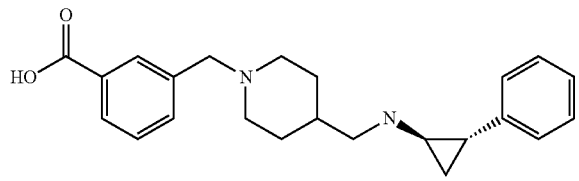 [SMILES: O=C(O)c1cccc(CN2CCC(CN[C@@H]3C[C@H]3c3ccccc3)CC2)c1]

Following a procedure analogous to the procedure described in Example 54 using 3-formylbenzoic acid (66.2 mg, 0.441 mmol) afforded 3-((4-(((trans-2-phenylcyclopropyl)amino)methyl)piperidin-1-yl)methyl)benzoic acid (35 mg, 0.076 mmol, 20.67% yield) as white solid. ¹H NMR (400 MHz, METHANOL-d₄) δ 8.24 (s, 1H), 8.18 (dt, J=1.26, 7.83 Hz, 1H), 7.83 (d, J=7.83 Hz, 1H), 7.61-7.71 (m, 1H), 7.29-7.37 (m, 2H), 7.17-7.29 (m, 3H), 4.44 (s, 2H), 3.57 (d, J=12.38 Hz, 2H), 3.07-3.25 (m, 4H), 3.03 (dt, J=3.76, 7.39 Hz, 1H), 2.60 (ddd, J=3.54, 6.32, 9.85 Hz, 1H), 2.13 (d, J=13.64 Hz, 3H), 1.53-1.81 (m, 3H), 1.41 (q, J=6.82 Hz, 1H); LC-MS Rt=0.52 min; MS (ESI): 365.4 [M++H]⁺.

Example 60

4-((4-(((trans-2-(4-Bromophenyl)cyclopropyl)amino)methyl)piperidin-1-yl)methyl)benzoic acid

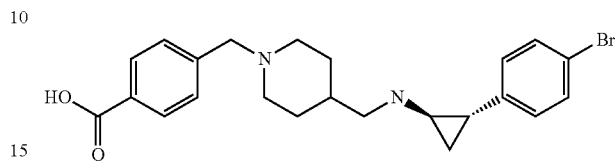

To a solution of tert-butyl 4-((4-formylpiperidin-1-yl)methyl)benzoate (250 mg, 0.824 mmol) in methanol (50 mL) was added trans-2-(4-bromophenyl)cyclopropylamine (210 mg, 0.989 mmol). The reaction mixture was refluxed for 2 minutes then cooled down to room temperature. Sodium cyanotrihydroborate (78 mg, 1.236 mmol) was added. The reaction mixture was stirred 1 hour at room temperature. Water (50 mL) was added. The reaction was concentrated and 50 mL of dichloromethane was added. The layers were separated. The organic was washed with 10% acetic acid (50 mL). The layers were separated and 50 mL of brine was added and the formed solid was filtered. The solid was refluxed in 1 M HCl for 30 min, then cooled to 0° C. and after 1 hour the solid was filtered. 4-((4-(((trans-2-(4-bromophenyl)cyclopropyl)amino)methyl)piperidin-1-yl)methyl)benzoic acid (120 mg, 0.221 mmol, 26.8% yield) was isolated as white solid. ¹H NMR (400 MHz, METHANOL-d₄) δ 8.14 (d, J=8.34 Hz, 2H), 7.71 (d, J=8.34 Hz, 2H), 7.48 (d, J=8.59 Hz, 2H), 7.15 (d, J=8.34 Hz, 2H), 4.44 (br. s., 2H), 3.55 (d, J=10.36 Hz, 2H), 3.06-3.25 (m, 4H), 3.01 (dt, J=3.98, 7.71 Hz, 1H), 2.59 (ddd, J=3.54, 6.63, 10.29 Hz, 1H), 2.02-2.29 (m, 3H), 1.53-1.80 (m, 3H), 1.41 (q, 1H); LC-MS Rt=0.61 min; MS (ESI): 445.2 [M+H]⁺.

Example 61

4-((4-(((trans-2-(4-Chlorophenyl)cyclopropyl)amino)methyl)piperidin-1-yl)methyl)benzoic acid

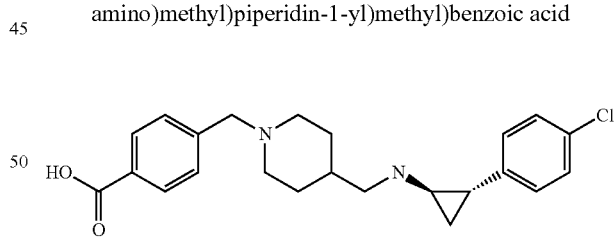

Following a procedure analogous to the procedure described in Example 60 using trans-2-(4-chlorophenyl)cyclopropylamine (172 mg, 1.028 mmol) afforded 4-((4-(((trans-2-(4-chlorophenyl)cyclopropyl)amino)methyl)piperidin-1-yl)methyl)benzoic acid (120 mg, 0.242 mmol, 28.2% yield) as white solid. ¹H NMR (400 MHz, METHANOL-d₄) δ 8.14 (d, J=8.34 Hz, 2H), 7.72 (d, J=8.34 Hz, 2H), 7.33 (d, J=8.59 Hz, 2H), 7.21 (d, J=8.59 Hz, 2H), 4.45 (s, 2H), 3.55 (d, J=10.86 Hz, 2H), 3.09-3.28 (m, 4H), 3.05 (dt, J=4.07, 7.77 Hz, 1H), 2.63 (ddd, J=3.54, 6.63, 10.29 Hz, 1H), 1.99-2.33 (m, 3H), 1.68-1.81 (m, 2H), 1.65 (ddd, J=4.29, 6.63, 10.55 Hz, 1H), 1.41 (q, J=6.82 Hz, 1H); LC-MS Rt=0.59 min; MS (ESI): 399.3 [M+H]⁺.

Example 62

4-((4-(((trans-2-(3,4-Dichlorophenyl)cyclopropyl)amino)methyl)piperidin-1-yl)methyl)benzoic acid

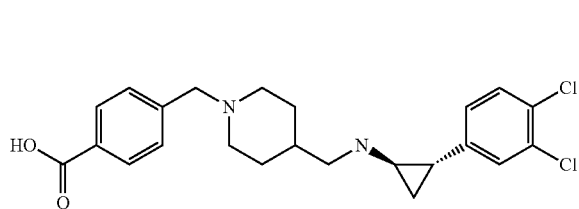 [SMILES: O=C(O)c1ccc(CN2CCC(CN[C@@H]3C[C@H]3c3ccc(Cl)c(Cl)c3)CC2)cc1]

Following a procedure analogous to the procedure described in Example 60 using trans-2-(3,4-dichlorophenyl)cyclopropylamine (160 mg, 0.791 mmol) afforded 4-((4-(((trans-2-(3,4-dichlorophenyl)cyclopropyl)amino)methyl)piperidin-1-yl)methyl)benzoic acid (70 mg, 0.131 mmol, 19.93% yield) as white solid. $^1$H NMR (400 MHz, METHANOL-$d_4$) δ 8.15 (d, J=8.34 Hz, 2H), 7.70 (d, J=8.34 Hz, 2H), 7.48 (d, J=8.34 Hz, 1H), 7.43 (d, J=2.02 Hz, 1H), 7.17 (dd, J=2.02, 8.34 Hz, 1H), 4.44 (br. s., 2H), 3.55 (br. s., 2H), 2.89-3.27 (m, 5H), 2.62 (ddd, J=3.66, 6.32, 9.98 Hz, 1H), 1.96-2.30 (m, 3H), 1.66 (ddd, J=4.67, 6.51, 10.55 Hz, 3H), 1.45 (q, 1H); LC-MS Rt=0.65 min; MS (ESI): 433.2 [M+H]$^+$.

Example 63

4-((4-(((trans-2-(4-(Trifluoromethyl)phenyl)cyclopropyl)amino)methyl)piperidin-1-yl)methyl)benzoic acid

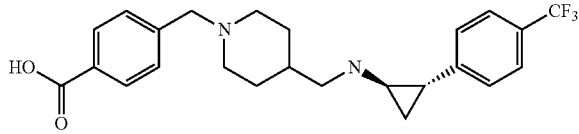 [SMILES: O=C(O)c1ccc(CN2CCC(CN[C@@H]3C[C@H]3c3ccc(C(F)(F)F)cc3)CC2)cc1]

Following a procedure analogous to the procedure described in Example 60 using trans-2-(4-(trifluoromethyl)phenyl)cyclopropylamine (223 mg, 1.107 mmol) afforded 4-((4-(((trans-2-(4-(trifluoromethyl)phenyl)cyclopropyl)amino)methyl)piperidin-1-yl)methyl)benzoic acid (62 mg, 0.117 mmol, 12.63% yield) as white solid. $^1$H NMR (400 MHz, METHANOL-$d_4$) δ 8.15 (d, J=8.34 Hz, 2H), 7.70 (d, J=8.34 Hz, 2H), 7.64 (d, J=8.08 Hz, 2H), 7.41 (d, J=8.08 Hz, 2H), 4.44 (s, 2H), 3.50-3.72 (m, 2H), 3.04-3.27 (m, 5H), 2.70 (ddd, J=3.54, 6.44, 10.23 Hz, 1H), 2.00-2.31 (m, 3H), 1.70 (ddd, J=4.55, 6.63, 10.55 Hz, 3H), 1.51 (q, 1H); LC-MS Rt=0.66 min; MS (ESI): 433.3 [M++H]$^+$.

Example 64

4-((4-(((trans-2-(3,4-Dimethoxyphenyl)cyclopropyl)amino)methyl)piperidin-1-yl)methyl)benzoic acid

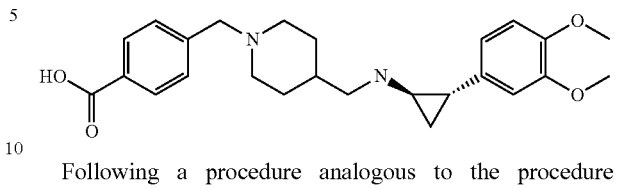

Following a procedure analogous to the procedure described in Example 60 using trans-2-(3,4-dimethoxyphenyl)cyclopropylamine (199 mg, 1.028 mmol) afforded 4-((4-(((trans-2-(3,4-dimethoxyphenyl)cyclopropyl)amino)methyl)piperidin-1-yl)methyl)benzoic acid (110 mg, 0.210 mmol, 24.51% yield) as white solid. $^1$H NMR (400 MHz, METHANOL-$d_4$) δ 8.15 (d, J=8.34 Hz, 2H), 7.70 (d, J=8.34 Hz, 2H), 6.90 (d, J=8.34 Hz, 1H), 6.82 (d, J=2.02 Hz, 1H), 6.76 (dd, J=2.02, 8.08 Hz, 1H), 4.45 (s, 2H), 3.85 (s, 3H), 3.81 (s, 3H), 3.56 (d, J=10.61 Hz, 2H), 3.05-3.27 (m, 4H), 2.99 (dt, J=3.98, 7.71 Hz, 1H), 2.55 (ddd, J=3.79, 6.57, 10.36 Hz, 1H), 2.02-2.26 (m, 3H), 1.71 (d, J=1.77 Hz, 2H), 1.55 (ddd, J=4.42, 6.51, 10.55 Hz, 1H), 1.38 (q, J=6.82 Hz, 1H); LC-MS Rt=0.48 min; MS (ESI): 425.3 [M+H]$^+$.

Example 65

4-((4-(((trans-2-(4-Acetamidophenyl)cyclopropyl)amino)methyl)piperidin-1-yl)methyl)benzoic acid

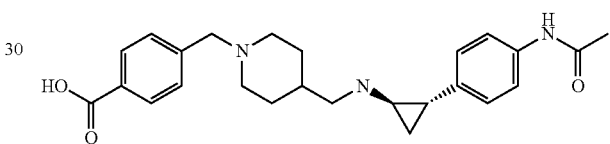

Following a procedure analogous to the procedure described in Example 60 using N-(4-(trans-2-aminocyclopropyl)phenyl)acetamide (JACS 2010, 132, 6827) (115 mg of Boc protected material, 0.396 mmol, used after deprotection) afforded 4-((4-(((trans-2-(4-acetamidophenyl)cyclopropyl)amino)methyl)piperidin-1-yl)methyl)benzoic acid (30 mg, 0.058 mmol, 14.57% yield) as white solid. $^1$H NMR (400 MHz, METHANOL-$d_4$) δ 8.15 (d, J=8.34 Hz, 2H), 7.71 (d, J=8.08 Hz, 2H), 7.52 (d, J=8.34 Hz, 2H), 7.16 (d, J=8.59 Hz, 2H), 4.44 (s, 2H), 3.57 (d, J=12.38 Hz, 2H), 3.20 (d, J=6.57 Hz, 2H), 3.14 (t, J=12.00 Hz, 2H), 3.00 (dt, J=3.98, 7.71 Hz, 1H), 2.57 (ddd, J=3.54, 6.63, 10.29 Hz, 1H), 2.03-2.23 (m, 6H), 1.62-1.77 (m, 2H), 1.58 (ddd, J=4.29, 6.63, 10.55 Hz, 1H), 1.38 (q, J=6.82 Hz, 1H); LC-MS Rt=0.40 min; MS (ESI): 422.3 [M++H]$^+$.

Example 66

4-((4-(((trans-2-(4-Benzamidophenyl)cyclopropyl)amino)methyl)piperidin-1-yl)methyl)benzoic acid

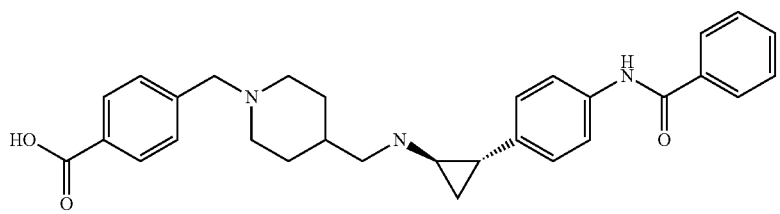 [SMILES: O=C(O)c1ccc(CN2CCC(CN[C@@H]3C[C@H]3c3ccc(NC(=O)c4ccccc4)cc3)CC2)cc1]

Following a procedure analogous to the procedure described in Example 60 using N-(4-(trans-2-aminocyclopropyl)phenyl)benzamide (JACS 2010, 132, 6827) (139 mg of Boc protected material, 0.396 mmol, used after deprotection) afforded 4-((4-(((trans-2-(4-benzamidophenyl)cyclopropyl)amino)methyl)piperidin-1-yl)methyl)benzoic acid (18 mg, 0.031 mmol, 9.32% yield) as white solid. $^1$H NMR (400 MHz, METHANOL-$d_4$) δ 8.16 (d, J=8.34 Hz, 2H), 7.86-7.98 (m, 2H), 7.65-7.75 (m, 4H), 7.57-7.64 (m, 1H), 7.49-7.57 (m, 2H), 7.23 (d, J=8.59 Hz, 2H), 4.44 (br. s., 2H), 3.54-3.62 (m, 2H), 3.08-3.25 (m, 3H), 3.04 (dt, J=3.88, 7.64 Hz, 1H), 2.45-2.66 (m, 1H), 2.04-2.26 (m, 3H), 1.52-1.78 (m, 2H), 1.43 (q, J=7.07 Hz, 1H), 1.17 (d, J=6.06 Hz, 2H); LC-MS Rt=0.59 min; MS (ESI): 484.4 [M+H]$^+$.

Example 67

1,1-Dimethyl-4-(((trans-2-phenylcyclopropyl)amino)methyl)piperidin-1-ium Iodide

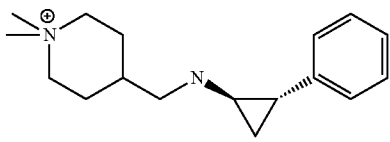 [SMILES: C[N+]1(C)CCC(CN[C@@H]2C[C@H]2c2ccccc2)CC1]

To a solution of 2,2,2-trifluoro-N-(trans-2-phenylcyclopropyl)-N-(piperidin-4-ylmethyl)acetamide (100 mg, 0.306 mmol) in acetonitrile (5 mL) was added potassium carbonate (242 mg, 1.226 mmol) followed by iodomethane (0.077 mL, 1.226 mmol). The reaction mixture was heated to 50° C. for 3 hr. The reaction mixture was filtered and evaporated.

The resulting oil was purified by preperatory HPLC (5 to 70% AcCN:Water, with 0.1% formic acid). Fractions were combined and evaporated. The resulting oil was dissolved in 2 mL of ethanol and 1 mL of 1 M NaOH was added. The reaction mixture was stirred for 30 minutes and then evaporated. The solid was suspended in acetonitrile and filtered through a syringe filter. The mother liquor was evaporated. 1,1-Dimethyl-4-(((trans-2-phenylcyclopropyl)amino)methyl)piperidin-1-ium Iodide (28 mg, 0.065 mmol, 21.29% yield) was isolated as a colorless oil. $^1$H NMR (400 MHz, METHANOL-$d_4$) δ 7.30-7.40 (m, 2H), 7.18-7.29 (m, 3H), 3.64-3.72 (m, 1H), 3.64-3.81 (m, OH), 3.53-3.64 (m, 2H), 3.46 (td, J=3.28, 12.88 Hz, 2H), 3.29 (d, J=6.82 Hz, 2H), 3.23 (s, 3H), 3.18 (s, 3H), 3.05 (dt, J=4.07, 7.77 Hz, 1H), 2.63 (ddd, J=3.54, 6.63, 10.29 Hz, 1H), 2.14-2.29 (m, J=3.73, 3.73, 3.73, 7.63, 15.30 Hz, 1H), 2.02-2.11 (m, 2H), 1.80-1.97 (m, 2H), 1.64 (ddd, J=4.55, 6.57, 10.61 Hz, 1H), 1.43 (q, J=6.82 Hz, 1H); LC-MS Rt=0.41 min; MS (ESI): 259.3 [M++H]$^+$.

Example 68 trans-2-Phenyl-N-((1-phenylpiperidin-4-yl)methyl)cyclopropanamine

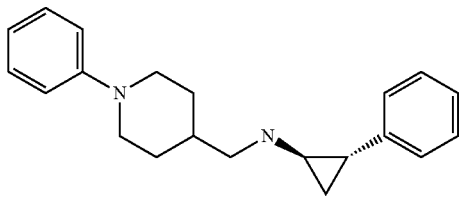 [SMILES: c1ccc([C@@H]2C[C@H]2NCC2CCN(c3ccccc3)CC2)cc1]

To a solution of 2,2,2-trifluoro-N-(trans-2-phenylcyclopropyl)-N-(piperidin-4-ylmethyl)acetamide (200 mg, 0.429 mmol) in toluene (10 mL) was added bromobenzene (0.045 mL, 0.429 mmol) followed by sodium tert-butoxide (82 mg, 0.858 mmol), Pd$_2$(dba)$_3$ (7.86 mg, 8.58 μmol) and Q_Phos (12.18 mg, 0.017 mmol). The reaction mixture was heated in a sealable tube to 80° C. for 4 hours. Water (5 mL) was added and the layers were separated. The organic layer was washed with brine and dried over MgSO$_4$, filtered and evaporated. The resulting oil was purified by preperatory HPLC (5 to 40% AcCN: H$_2$O with 0.1% formic acid modifier). The fractions were collected and evaporated. The isolated oil was dissolved in 6 ml of EtOH and 3 ml of 1 M NaOH. The reaction mixture was stirred for 20 minutes and then concentrated. The resulting solution was then partitioned between 2 ml of water and 5 mL of EtOAc. The organic layer was separated and evaporated. The resulting oil was dissolved in 3 mL of acetonitrile. 0.5 mL of 4 M HCl/dioxane was added. After 5 minutes, 10 mL of diethyl ether was added dropwise. The white solid was filtered. trans-2-Phenyl-N-((1-phenylpiperidin-4-yl)methyl)cyclopropanamine (20 mg, 0.050 mmol, 11.68% yield) was isolated as white solid. $^1$H NMR (400 MHz, METHANOL-$d_4$) δ 7.75 (d, J=7.58 Hz, 2H), 7.51-7.69 (m, 3H), 7.31-7.40 (m, 2H), 7.12-7.31 (m, 3H), 3.65-3.88 (m, 4H), 3.31 (s, 1H), 3.08 (dt, J=4.07, 7.77 Hz, 1H), 2.62 (ddd, J=3.66, 6.63, 10.42 Hz, 1H), 2.36 (ddd, J=4.29, 7.45, 11.24 Hz, 1H), 2.26 (dd, J=2.53, 14.65 Hz, 2H), 1.88-2.06 (m, 2H), 1.63 (ddd, J=4.29, 6.63, 10.55 Hz, 1H), 1.37-1.52 (m, 1H); LC-MS Rt=0.59 min; MS (ESI): 307.3 [M+H]$^+$.

Example 69

Ethyl 4-(((trans-2-phenylcyclopropyl)amino)methyl)piperidine-1-carboxylate

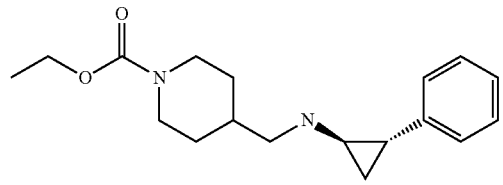 [SMILES: CCOC(=O)N1CCC(CN[C@@H]2C[C@H]2c2ccccc2)CC1]

To a solution of 2,2,2-trifluoro-N-(trans-2-phenylcyclopropyl)-N-(piperidin-4-ylmethyl)acetamide (170 mg, 0.521 mmol) in chloroform (10 mL) was added triethylamine (0.145 mL, 1.042 mmol) followed by ethyl chloroformate (0.055 mL, 0.573 mmol). The reaction mixture was stirred for 1 hour at room temperature and then it was evaporated to dryness. The oil was partitioned between 3 mL of ethanol and 3 M of 1 M NaOH. After 1 hour, the reaction mixture was concentrated, and 10 mL of ethyl acetate followed by 4 mL of brine were added. The organic layer was separated, dried over MgSO$_4$, filtered and evaporated. The resulting oil was dissolved in 5 mL of 10% AcCN:Et$_2$O and 0.5 mL of 4 M HCl/dioxane was added. The suspension was stirred for 30 min, and then it was filtered. Ethyl 4-(((trans-2-phenylcyclopropyl)amino)methyl)piperidine-1-carboxylate (120 mg, 0.336 mmol, 64.6% yield) was isolated as white solid. $^1$H NMR (400 MHz, METHANOL-$d_4$) δ 7.30-7.39 (m, 2H), 7.22-7.29 (m, 1H), 7.11-7.22 (m, 2H), 4.19 (dd, J=1.26, 13.64 Hz, 2H), 4.13 (q, J=7.16 Hz, 3H), 3.15 (d, J=7.07 Hz, 2H), 3.02 (dt, J=4.14, 7.64 Hz, 1H), 2.86 (d, J=3.28 Hz, 2H), 2.54 (ddd, J=3.66, 6.69, 10.36 Hz, 1H), 1.99 (ddd, J=4.04, 7.52, 11.18 Hz, 1H), 1.82 (d, J=12.13 Hz, 2H), 1.56 (ddd, J=4.29, 6.63, 10.55 Hz, 1H), 1.42 (q, J=6.82 Hz, 1H), 1.27 (t, J=7.07 Hz, 3H), 1.17-1.33 (m, 1H); LC-MS Rt=0.76 min; MS (ESI): 303.3 [M++H]+.

Example 70 trans-4-((4-(((trans-2-Phenylcyclopropyl)amino) methyl)piperidin-1-yl)methyl)cyclohexanecarboxylic acid

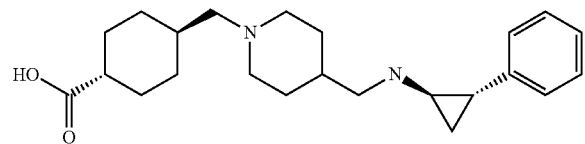 [SMILES: O=C(O)[C@H]1CC[C@H](CN2CCC(CN[C@@H]3C[C@H]3c3ccccc3)CC2)CC1]

To a solution of 2,2,2-trifluoro-N-(trans-2-phenylcyclopropyl)-N-(piperidin-4-ylmethyl)acetamide (250 mg, 0.766 mmol) in methanol (20 mL) was added trans-methyl 4-formylcyclohexanecarboxylate (130 mg, 0.766 mmol) and the reaction mixture was heated for 2 minutes to reflux. After cooling to room temperature, sodium cyanoborohydride (96 mg, 1.532 mmol) was added and the reaction mixture was stirred for 1 hour. Water (40 mL) was added. The reaction mixture was concentrated. 50 mL of ethyl acetate was added. The layers were separated. The organic layer was washed with water, brine, dried over MgSO4, filtered and evaporated. The oil was purified by preperatory HPLC (10 to 60% AcCN:water with 0.1% formic acid as modifier. Fractions were combined and evaporated. The resulting oil was dissolved in 10 ml of methanol and 5 mL of 1 M NaOH was added portion wise. The solution was stirred for 1 hour until no protected product was visible by LC-MS. The solution was concentrated, and injected on preperatory HPLC (2 to 20% AcCN:water with 0.1% formic acid as modifier. Fractions were combined 6 M HCl was added (12 mL) and evaporated. trans-4-((4-(((trans-2-phenylcyclopropyl)amino)methyl)piperidin-1-yl)methyl)cyclohexanecarboxylic acid (50 mg, 0.107 mmol, 13.98% yield) was isolated as white solid. 1H NMR (400 MHz, METHANOL-d4) δ 7.29-7.39 (m, 2H), 7.07-7.29 (m, 3H), 3.67 (d, J=12.63 Hz, 2H), 3.36 (d, J=6.82 Hz, 1H), 3.22 (d, J=6.82 Hz, 2H), 2.98-3.10 (m, 4H), 2.63 (ddd, J=3.54, 6.63, 10.29 Hz, 1H), 2.29 (tt, J=3.54, 12.25 Hz, 1H), 2.01-2.24 (m, 5H), 1.92-2.03 (m, 2H), 1.90 (dt, 1H), 1.69-1.85 (m, 2H), 1.64 (ddd, J=4.29, 6.57, 10.61 Hz, 1H), 1.51 (qd, J=3.16, 13.01 Hz, 2H), 1.33-1.45 (m, 1H), 1.03-1.25 (m, 2H); LC-MS Rt=0.50 min; MS (ESI): 371.3 [M+H]+.

Example 71

3-(4-((((1R,2S)-2-Phenylcyclopropyl)amino)methyl) piperidin-1-yl)propanoic acid

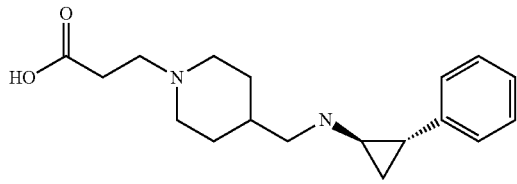 [SMILES: O=C(O)CCN1CCC(CN[C@@H]2C[C@H]2c2ccccc2)CC1]

To a solution of tert-butyl 3-(4-formylpiperidin-1-yl)propanoate (2.3 g, 9.53 mmol) in methanol (50 mL) was added (1R,2S)-2-phenylcyclopropanamine (1.523 g, 11.44 mmol). The reaction mixture was refluxed for 2 minutes, then cooled down to the room temperature. Sodium cyanotrihydroborate (0.898 g, 14.30 mmol) was added. The reaction mixture was stirred 1 hour at room temperature. Water (50 mL) was added. The reaction was concentrated. 50 mL of dichloromethane was added. The layers were separated. The organic layer was extracted 1× with 50 mL of 10% acetic acid, brine, and was separated and dried over MgSO4. The solution was filtered, evaporated. 50 mL of ethyl acetate was added, and the formed solid was filtered.

The solid was suspended in 1 M HCl, heated to reflux for 10 minutes and evaporated. The solid was suspended in ethyl acetate and filtered. 3-(4((((1R,2S)-2-phenylcyclopropyl)amino)methyl)piperidin-1-yl)propanoic acid (500 mg, 1.319 mmol, 13.84% yield) was isolated as white solid. 1H NMR (400 MHz, METHANOL-d4) δ 7.29-7.38 (m, 2H), 7.14-7.29 (m, 3H), 3.68 (d, J=12.13 Hz, 2H), 3.44 (t, J=7.07 Hz, 2H), 3.22 (d, J=6.57 Hz, 2H), 3.00-3.16 (m, 3H), 2.90 (t, J=7.20 Hz, 2H), 2.63 (ddd, J=3.66, 6.57, 10.23 Hz, 1H), 2.02-2.30 (m, 3H), 1.54-1.79 (m, 3H), 1.41 (q, J=6.82 Hz, 1H); LC-MS Rt=0.42 min; MS (ESI): 303.3 [M+H]

Example 72 trans-N,N-Dimethyl-4-(((trans-2-phenylcyclopropyl) amino)methyl)cyclohexanamine

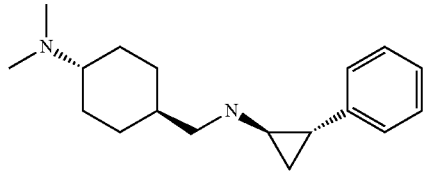 [SMILES: CN(C)[C@H]1CC[C@H](CN[C@@H]2C[C@H]2c2ccccc2)CC1]

Step 1

1,1-Dimethylethyl[trans-4-({[trans-2-phenylcyclopropyl]amino}methyl)cyclohexyl]carbamate To a solution of 1,1-dimethylethyl (trans-4-formylcyclohexyl)carbamate (500 mg, 2.200 mmol) in 1,2-dichloroethane (DCE) (20 mL) and acetic acid (0.151 mL, 2.64 mmol) was added trans-2-phenylcyclopropyl]amine (448 mg, 2.64 mmol) at room temperature. The reaction mixture was stirred for 1 hour, then sodium triacetoxyborohydride (1399 mg, 6.60 mmol) was added and the reaction mixture was stirred 2 hours at room temperature. The reaction mixture was quenched with sat NH4Cl. Water (10 mL) followed by dichloromethane (30 mL) were added. The layers were separated, organic washed with brine, dried over MgSO4, filtered and evaporated. The formed solid was suspended in diethyl ether, sonicated and filtered. 1,1-dimethylethyl [trans-4-({[trans-2-phenylcyclopropyl]amino}methyl)cyclohexyl]carbamate (400 mg, 1.103 mmol, 50.1% yield) was isolated as white solid. 1H NMR (400 MHz, CHLOROFORM-d) δ 9.88 (br. s., 2H), 7.29-7.34 (m, 2H), 7.25 (d, J=7.07 Hz, 1H), 7.16-7.22 (m, 2H), 3.21-3.48 (m, 1H), 2.81-3.07 (m, 3H), 2.58-2.80 (m, 1H), 2.12 (dd, J=2.15, 12.76 Hz, 2H), 1.97-2.07 (m, 2H), 1.93 (ddd, J=4.55, 6.25, 10.42 Hz, 2H), 1.31-1.51 (m, 9H), 1.20-1.34 (m, 1H), 0.94-1.20 (m, 4H); LC-MS Rt=0.88 min; MS (ESI): 345.3 [M+H]

Step 2

N-((trans-4-Aminocyclohexyl)methyl)-2,2,2-trifluoro-N-(trans-2-phenylcyclopropyl)acetamide To a solution of tert-butyl (trans-4-(((trans-2-phenylcyclopropyl)amino)methyl)cyclohexyl)carbamate (400 mg, 1.161 mmol) in chloroform (15 ml) was added triethylamine (0.486 ml, 3.48 mmol) followed by the slow addition of trifluoroacetic anhydride (0.180 ml, 1.277 mmol). The reaction mixture was stirred at room temperature for 30 minutes. 1 M $Na_2CO_3$ (20 mL) was added followed by 20 mL of dichloromethane. The organic layer was separated, washed with brine, dried over $MgSO_4$, filtered and evaporated. The resulting oil was dissolved in 10 mL of chloroform and 5 ml of TFA was added. The reaction mixture was stirred for 3 hours. The solution was evaporated. 1 M $Na_2CO_3$ (20 mL) were added followed by 20 mL of DCM. The organic layer was separated, washed with brine, dried over $MgSO_4$, filtered and evaporated. N-((trans-4-aminocyclohexyl)methyl)-2,2,2-trifluoro-N-(trans-2-phenylcyclopropyl)acetamide (310 mg, 0.911 mmol, 78% yield) was isolated as yellow oil. $^1$H NMR (400 MHz, METHANOL-$d_4$) δ 7.27-7.34 (m, 2H), 7.09-7.27 (m, 3H), 3.48 (t, J=6.44 Hz, 1H), 3.06-3.19 (m, 1H), 2.52-2.64 (m, 1H), 2.38-2.50 (m, 1H), 1.85-1.97 (m, 2H), 1.66-1.83 (m, 3H), 1.55-1.65 (m, 1H), 1.43-1.55 (m, 1H), 1.33 (s, 1H), 0.95-1.23 (m, 4H); LC-MS Rt=0.86 min; MS (ESI): 341.2 [M+H]$^+$.

Step 3 trans-N,N-Dimethyl-4-(((trans-2-phenylcyclopropyl)amino)methyl)cyclohexanamine To a suspension of N-((trans-4-aminocyclohexyl)methyl)-2,2,2-trifluoro-N-(trans-2-phenylcyclopropyl)acetamide (100 mg, 0.294 mmol) in tetrahydrofuran (THF) (4 mL) was added formaldehyde (0.044 mL, 0.588 mmol). The reaction mixture was stirred for 30 minutes, then sodium triacetoxyborohydride (187 mg, 0.881 mmol) was added and the solution was stirred for 1 hour. The reaction mixture was evaporated, and the resulting oil was dissolved in 10 mL of dichloromethane. The organic layer was extracted with 1 M $Na_2CO_3$, washed with brine, dried over $MgSO_4$, filtered and evaporated. Produced oil was purified by preperatory HPLC (5 to 40% AcCN:water with 0.1% formic acid as modifier). Fractions were combined and evaporated. The resulting oil was dissolved in 6 ml of EtOH and 3 ml of 1 M NaOH. The reaction mixture was stirred for 20 minutes, then concentrated. The resulting solution was then partitioned between 2 ml of water and 5 mL of EtOAc. The organic layer was separated, washed with brine, dried over $MgSO_4$, filtered and evaporated. The resulting oil was dissolved in 2 ml of acetonitrile, and 0.5 mL of 4 M HCl/dioxane was added. The suspension was stirred for 30 minutes, then 5 mL of diethyl ether was added and solid was filtered. trans-N,N-Dimethyl-4-(((trans-2-phenylcyclopropyl)amino)methyl)cyclohexanamine (28 mg, 0.086 mmol, 29.3% yield) was isolated as white solid. $^1$H NMR (400 MHz, METHANOL-$d_4$) δ 7.29-7.39 (m, 2H), 7.09-7.30 (m, 3H), 3.20-3.30 (m, 1H), 3.12 (d, J=6.82 Hz, 2H), 3.01 (dt, J=3.98, 7.71 Hz, 1H), 2.87 (s, 6H), 2.59 (ddd, J=3.54, 6.63, 10.29 Hz, 1H), 2.19 (dd, J=2.78, 12.63 Hz, 2H), 2.09 (d, J=13.39 Hz, 2H), 1.78-1.93 (m, 1H), 1.55-1.68 (m, 3H), 1.40 (q, J=6.82 Hz, 1H), 1.27 (qd, J=3.03, 12.80 Hz, 2H); LC-MS Rt=0.48 min; MS (ESI): 273.3 [M++H]$^+$.

Example 73

N-(trans-4-(((trans-2-Phenylcyclopropyl)amino)methyl)cyclohexyl)acetamide

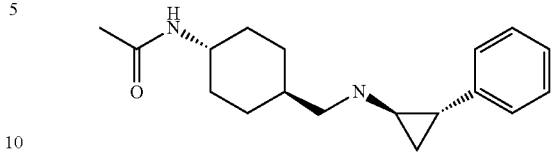

Following a procedure analogous to the procedure described in Example 72 step 3 using acetyl chloride (0.025 mL, 0.353 mmol) afforded N-(trans-4-(((trans-2-phenylcyclopropyl)amino)methyl)cyclohexyl)acetamide (52 mg, 0.153 mmol, 52.1% yield) as white solid. $^1$H NMR (400 MHz, METHANOL-$d_4$) δ 7.29-7.38 (m, 2H), 7.23-7.30 (m, 1H), 7.05-7.23 (m, 2H), 3.59-3.72 (m, 1H), 3.10 (d, J=7.07 Hz, 2H), 3.00 (dt, J=4.07, 7.77 Hz, 1H), 2.45-2.60 (m, 1H), 1.96-2.03 (m, 5H), 1.92 (dd, J=2.15, 12.76 Hz, 2H), 1.76 (ddd, J=3.28, 7.45, 10.99 Hz, 1H), 1.50-1.65 (m, 1H), 1.37-1.46 (m, 1H), 1.10-1.37 (m, 4H); LC-MS Rt=0.59 min; MS (ESI): 287.3 [M+H]$^+$.

Example 74

N-(trans-4-(((trans-2-Phenylcyclopropyl)amino)methyl)cyclohexyl)benzamide

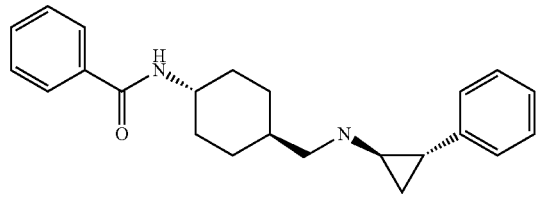 [SMILES: O=C(N[C@H]1CC[C@H](CN[C@@H]2C[C@H]2c2ccccc2)CC1)c1ccccc1]

Following a procedure analogous to the procedure described in Example 72 step 3 using benzoyl chloride (0.041 mL, 0.353 mmol) afforded N-(trans-4-(((trans-2-phenylcyclopropyl)amino)methyl)cyclohexyl)benzamide (20 mg, 0.049 mmol, 27.2% yield) as white solid. $^1$H NMR (400 MHz, METHANOL-$d_4$) δ 7.76-7.88 (m, 2H), 7.51-7.59 (m, 1H), 7.41-7.51 (m, 2H), 7.30-7.39 (m, 2H), 7.23-7.30 (m, 1H), 7.11-7.23 (m, 2H), 3.89 (tt, J=3.98, 11.68 Hz, 1H), 3.14 (d, J=7.07 Hz, 2H), 3.02 (dt, J=4.07, 7.77 Hz, 1H), 2.53 (ddd, J=3.41, 6.57, 10.23 Hz, 1H), 2.09 (dd, J=3.28, 12.88 Hz, 2H), 1.97 (dd, J=2.65, 13.26 Hz, 2H), 1.70-1.88 (m, J=3.88, 3.88, 7.74, 15.06 Hz, 1H), 1.51-1.61 (m, 1H), 1.44-1.51 (m, 2H), 1.38-1.44 (m, 1H), 1.22-1.35 (m, 2H); LC-MS Rt=0.78 min; MS (ESI): 349.3 [M+H]$^+$.

Example 75

4-(((trans-4-(((trans-2-Phenylcyclopropyl)amino)methyl)cyclohexyl)amino)methyl)benzoic acid

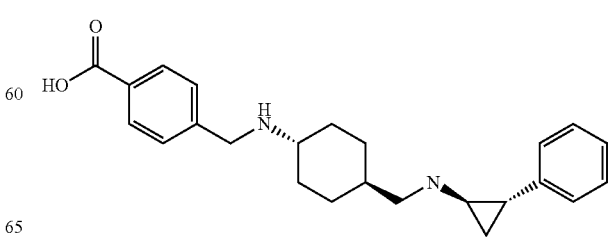

To a solution of N-((trans-4-aminocyclohexyl)methyl)-2,2,2-trifluoro-N-(trans-2-phenylcyclopropyl)acetamide (100 mg, 0.294 mmol) in 1,2-dichloroethane (3 mL) was added 4-formylbenzoic acid (48.5 mg, 0.323 mmol). The reaction mixture was refluxed for 2 minutes, then cooled down to room temperature. Sodium triacetoxyborohydride (187 mg, 0.881 mmol) was added. The reaction mixture was stirred 1 hour at room temperature. The reaction mixture was evaporated, and dissolved in 1 mL of water and 2 mL of methanol. The reaction mixture was injected on preperatory HPLC (5 to 40% AcCN: H$_2$O with 0.1% formic acid modifier). The fractions were collected and evaporated. The resulting oil was dissolved in 6 ml of EtOH and 3 ml of 1 M NaOH. The reaction mixture was stirred for 20 minutes then it was evaporated. The resulting product was injected on preperatory HPLC (2 to 20% AcCN: H$_2$O with 0.1% formic acid modifier). The fractions were collected and evaporated. 1 mL of 1 M HCl was added to each fraction and product was evaporated. 4-(((trans-4-(((trans-2-Phenylcyclopropyl)amino)methyl)cyclohexyl)amino)methyl)benzoic acid (60 mg, 0.151 mmol, 51.3% yield) was isolated as white solid. $^1$H NMR (400 MHz, DMSO-d$_6$) δ 12.68-13.69 (m, 1H), 9.23-9.66 (m, 4H), 7.99 (d, J=8.34 Hz, 2H), 7.72 (d, J=8.34 Hz, 2H), 7.28-7.35 (m, 2H), 7.11-7.26 (m, 3H), 4.24 (br. s., 2H), 2.79-3.09 (m, 4H), 2.58 (ddd, J=3.54, 6.38, 10.04 Hz, 1H), 2.20 (d, J=10.36 Hz, 2H), 1.96 (d, J=11.12 Hz, 2H), 1.65-1.85 (m, 1H), 1.54-1.66 (m, 1H), 1.46 (q, J=12.38 Hz, 2H), 1.18-1.34 (m, 1H), 1.03 (q, J=12.04 Hz, 2H); LC-MS Rt=0.56 min; MS (ESI): 379.4 [M+H]$^+$.

Example 76

4-(((trans-2-Phenylcyclopropyl)amino)methyl)piperidine

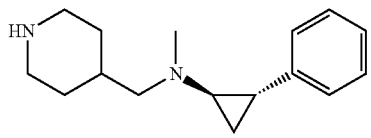 [SMILES: CN(CC1CCNCC1)[C@@H]1C[C@H]1c1ccccc1]

To a solution of tert-butyl 4-(((trans-2-phenylcyclopropyl)amino)methyl)piperidine-1-carboxylate (100 mg, 0.303 mmol) in acetonitrile (2 ml) and N,N-dimethylformamide (DMF) (0.5 ml) was added potassium carbonate (125 mg, 0.908 mmol) followed by iodomethane (0.038 ml, 0.605 mmol). The reaction mixture was stirred for 4 hours at room temperature. The reaction mixture was evaporated. The oil was purified on preperatory HPLC (5 to 70% AcCN: H$_2$O with 0.1% formic acid modifier). The fractions were collected. The solution was neutralized with NH$_4$OH, concentrated and extracted with ethyl acetate. The organic layer was dried and evaporated. The resulting oil was dissolved in 2 mL of dioxane and 1 mL of HCl. The reaction mixture was heated under reflux for 15 minutes then evaporated to dryness. 4-(((trans-2-phenylcyclopropyl)amino)methyl)piperidine (12 mg, 0.041 mmol, 13.41% yield) was isolated as a white solid. $^1$H NMR (400 MHz, METHANOL-d$_4$) δ 7.35 (d, J=4.29 Hz, 2H), 7.14-7.30 (m, 3H), 3.47 (d, J=13.14 Hz, 2H), 3.35-3.42 (m, 2H), 3.12-3.27 (m, 2H), 3.09 (d, J=8.34 Hz, 3H), 2.89-3.05 (m, 1H), 2.77-2.89 (m, 1H), 2.04-2.52 (m, 3H), 1.83 (d, J=5.56 Hz, 1H), 1.37-1.73 (m, 3H); LC-MS Rt=0.38 min; MS (ESI): 245.2 [M++H]$^+$.

Example 77 trans-N-Methyl-2-phenyl-N-(2-(piperidin-4-yl)ethyl)cyclopropanamine

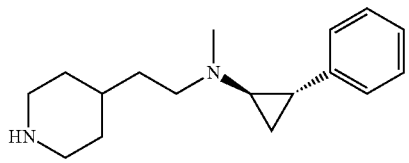 [SMILES: CN(CCC1CCNCC1)[C@@H]1C[C@H]1c1ccccc1]

Following a procedure analogous to the procedure described in Example 78 using tert-butyl 4-(2-((trans-2-phenylcyclopropyl)amino)ethyl)piperidine-1-carboxylate (85 mg, 0.247 mmol) afforded trans-N-methyl-2-phenyl-N-(2-(piperidin-4-yl)ethyl)cyclopropanamine (45 mg, 0.129 mmol, 52.3% yield) as white solid. $^1$H NMR (400 MHz, METHANOL-d$_4$) δ 7.31-7.41 (m, 2H), 7.12-7.31 (m, 3H), 3.38-3.54 (m, 4H), 3.10-3.21 (m, 1H), 3.06 (d, J=7.58 Hz, 3H), 2.87-3.03 (m, 2H), 2.57-2.81 (m, 1H), 1.71-2.12 (m, 6H), 1.67 (ddd, J=4.55, 6.63, 10.80 Hz, 1H), 1.30-1.61 (m, 3H); LC-MS Rt=0.40 min; MS (ESI): 259.2 [M+H]$^+$.

Example 78 trans-N-Methyl-N-((1-methylpiperidin-4-yl)methyl)-2-phenylcyclopropanamine

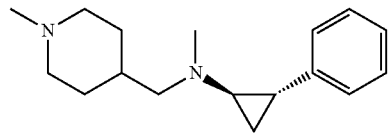 [SMILES: CN1CCC(CN(C)[C@@H]2C[C@H]2c2ccccc2)CC1]

To a suspension of tert-butyl 4-((trans-2-phenylcyclopropyl)amino)methyl)piperidine-1-carboxylate (85 mg, 0.257 mmol) in tetrahydrofuran (THF) (4 mL) was added formaldehyde—37% in water (0.038 mL, 0.514 mmol). The reaction mixture was stirred for 30 minutes and then sodium triacetoxyborohydride (109 mg, 0.514 mmol) was added. The reaction mixture was evaporated, and resulting oil was dissolved in 10 mL of dichloromethane. The organic layer was extracted with 1 M Na$_2$CO$_3$, washed with brine, dried over MgSO$_4$, filtered and evaporated.

The resulting oil was then dissolved in 2 mL of dioxane and 1 ml of 1 M HCl. The reaction mixture was heated to reflux for 15 minutes and then it was evaporated. The yellow oil was dissolved in 10 mL of dichloromethane. The organic layer was extracted with 1 M Na$_z$ CO$_3$, washed with brine, dried over MgSO$_4$, filtered and evaporated. The resulting oil was dissolved in tetrahydrofuran (THF) (4 mL), and formaldehyde—37% in water (0.038 mL, 0.514 mmol) was added and the reaction mixture stirred for 30 minutes. Sodium triacetoxyborohydride (109 mg, 0.514 mmol) was added and the reaction mixture was stirred for 1 hour at room temperature. The reaction mixture was evaporated, and produced oil was dissolved in 10 mL of dichloromethane. The organic layer was extracted with 1 M Na$_2$CO$_3$, washed with brine, dried over MgSO₄, filtered and evaporated. The resulting oil was purified on preperatory HPLC (2 to 10% AcCN:water with 0.1% formic acid as modifier. The fractions were combined and evaporated. trans-N-methyl-N-((1-methylpiperidin-4-yl)methyl)-2-phenylcyclopropanamine (18 mg, 0.056 mmol, 21.84% yield) was isolated as yellow oil. ¹H NMR (400 MHz, METHANOL-d₄) δ 7.19-7.29 (m, 2H), 7.10-7.18 (m, 1H), 7.01-7.10 (m, 2H), 3.40-3.68 (m, 2H), 2.98 (d, J=6.82 Hz, 2H), 2.86 (s, 3H), 2.43-2.55 (m, 2H), 2.39 (s, 3H), 1.99-2.13 (m, 2H), 1.77-1.99 (m, 3H), 1.28-1.49 (m, 2H), 1.09 (dt, J=4.77, 9.41 Hz, 1H), 0.96-1.05 (m, 1H); LC-MS Rt=0.39 min; MS (ESI): 259.2 [M++H]⁺.

Example 79 trans-N-(1-Cyclohexylethyl)-2-phenylcyclopropanamine

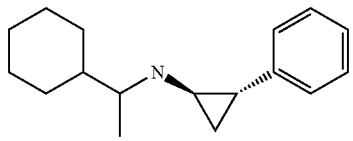 [SMILES: CC(N[C@@H]1C[C@H]1c1ccccc1)C1CCCCC1]

To a solution of 1-cyclohexylethanone (95 mg, 0.751 mmol) in 1,2-dichloroethane (DCE) (40 mL) and acetic acid (0.052 mL, 0.901 mmol) was added [(trans)-2-phenylcyclopropyl]amine (100 mg, 0.751 mmol). The reaction mixture was stirred for 2 hour at room temperature, then sodium triacetoxyborohydride (477 mg, 2.252 mmol) was added and the reaction mixture was stirred 3 hours at room temperature. The reaction mixture was quenched with saturated NH₄Cl. Water (20 mL) followed by dichloromethane (40 mL) were added. The layers were separated and the organic layer was washed with brine, dried over MgSO₄, filtered and evaporated. The solid was suspended in diethylether, sonicated and filtered. trans-N-(1-Cyclohexylethyl)-2-phenylcyclopropanamine (48 mg, 0.187 mmol, 24.95% yield) was isolated as white solid. ¹H NMR (400 MHz, DMSO-d₆) δ 9.11-9.35 (m, 1H), 8.80-9.03 (m, 1H), 7.27-7.42 (m, 2H), 7.13-7.27 (m, 3H), 3.23 (br. s., 1H), 2.91 (d, J=2.78 Hz, 1H), 2.57 (ddd, J=3.54, 6.44, 9.98 Hz, 1H), 1.68-1.87 (m, 4H), 1.57-1.68 (m, 2H), 1.46-1.57 (m, 1H), 1.26-1.42 (m, 1H), 1.18-1.24 (m, 3H), 0.95-1.18 (m, 4H); LC-MS Rt=0.83 min; MS (ESI): 244.2 [M+H]⁺.

Example 80 trans-Methyl 4-(((trans-2-phenylcyclopropyl)amino)methyl)cyclohexanecarboxylate

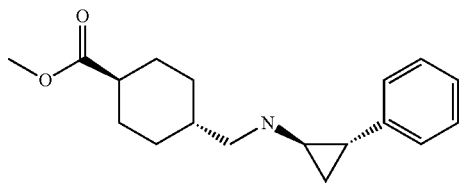 [SMILES: COC(=O)[C@H]1CC[C@H](CN[C@@H]2C[C@H]2c2ccccc2)CC1]

To a solution of trans-2-phenylcyclopropanamine (80 mg, 0.601 mmol) in methanol (10 mL) was added trans-methyl 4-formylcyclohexanecarboxylate (102 mg, 0.601 mmol) and the reaction was heated to reflux for 2 minutes. After cooling back to the room temperature, sodium cyanoborohydride (75 mg, 1.201 mmol) was added to the reaction mixture and was stirred for 1 hour. Water (20 mL) was added. The reaction was concentrated and 20 mL of ethyl acetate was added. The layers were separated. The organic layer was washed with water, brine, and dried over MgSO₄, filtered and evaporated. The resulting oil was purified on preperatory HPLC (10 to 60% AcCN:water with 0.1% formic acid as modifier). 0.5 mL of 6 M HCl was added into each fraction and the product was evaporated. trans-Methyl 4-(((trans-2-phenylcyclopropyl)amino)methyl)cyclohexanecarboxylate (95 mg, 0.250 mmol, 41.7% yield) was isolated as white solid. ¹H NMR (400 MHz, METHANOL-d₄) δ 7.29-7.38 (m, 2H), 7.22-7.29 (m, 1H), 7.11-7.22 (m, 2H), 3.68 (s, 3H), 3.09 (d, J=7.07 Hz, 2H), 2.99 (dt, J=4.11, 7.45 Hz, 1H), 2.49 (ddd, J=3.79, 6.57, 10.36 Hz, 1H), 2.35 (tt, J=3.63, 12.28 Hz, 1H), 2.07 (dd, J=3.54, 13.39 Hz, 2H), 1.93 (dd, J=3.28, 13.14 Hz, 2H), 1.66-1.83 (m, J=3.57, 3.57, 7.70, 7.70, 15.36 Hz, 1H), 1.50-1.58 (m, 1H), 1.36-1.50 (m, 3H), 1.15 (qd, J=3.54, 12.72 Hz, 2H); LC-MS Rt=0.83 min; MS (ESI): 288.2 [M++H]⁺.

Example 81 trans-4-(((trans-2-Phenylcyclopropyl)amino)methyl)cyclohexanecarboxylic acid

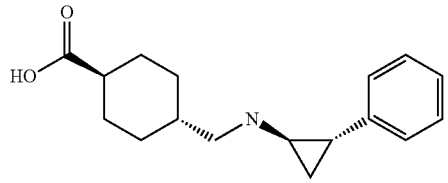 [SMILES: O=C(O)[C@H]1CC[C@H](CN[C@@H]2C[C@H]2c2ccccc2)CC1]

The trans-methyl 4-(((trans-2-phenylcyclopropyl)amino)methyl)cyclohexanecarboxylate (80 mg, 0.278 mmol) was stirred in a mixture of methanol (3 mL) and sodium hydroxide (3 ml, 3.00 mmol) for 1 hour at room temperature. The solution was then concentrated and purified by preperatory HPLC (5 to 50% AcCN:H₂O with 0.1% formic acid modifier). The fractions were combined, 0.5 mL of 6 M HCl was added into each fraction and the product was evaporated. trans-4-(((trans-2-Phenylcyclopropyl)amino)methyl)cyclohexanecarboxylic acid (30 mg, 0.082 mmol, 29.6% yield) was isolated as white solid. ¹H NMR (400 MHz, METHANOL-d₄) δ 7.29-7.38 (m, 2H), 7.22-7.28 (m, 1H), 7.08-7.22 (m, 2H), 3.09 (d, J=7.07 Hz, 2H), 3.00 (dt, J=4.07, 7.77 Hz, 1H), 2.53 (ddd, J=3.79, 6.57, 10.36 Hz, 1H), 2.29 (tt, J=3.54, 12.25 Hz, 1H), 2.08 (dd, J=3.28, 13.39 Hz, 2H), 1.94 (dd, J=3.03, 13.14 Hz, 2H), 1.76 (ddd, J=4.29, 7.71, 11.24 Hz, 1H), 1.55 (ddd, J=4.55, 6.57, 10.61 Hz, 1H), 1.43-1.52 (m, 2H), 1.35-1.42 (m, 1H), 1.15 (qd, J=3.54, 12.72 Hz, 2H); LC-MS Rt=0.62 min; MS (ESI): 274.2 [M+H]⁺.

Example 82 trans-4-((((1R,2S)-2-Phenylcyclopropyl)amino)methyl)cyclohexanecarboxylic acid

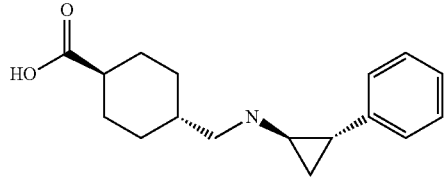 [SMILES: O=C(O)[C@H]1CC[C@H](CN[C@@H]2C[C@H]2c2ccccc2)CC1]

Following a procedure analogous to the procedure described in Example 81 using (1R,2S)-2-phenylcyclopropanamine (200 mg of tartate salt, 0.706 mmol, free based before use) afforded trans-4-((((1R,2S)-2-phenylcyclopropyl)amino)methyl)cyclohexanecarboxylic acid (82 mg, 0.251 mmol, 35.6% yield) as white solid. $^1$H NMR (400 MHz, METHANOL-d$_4$) δ 7.29-7.37 (m, 2H), 7.22-7.29 (m, 1H), 7.14-7.22 (m, 2H), 3.09 (d, J=7.07 Hz, 2H), 2.97-3.02 (m, 1H), 2.52 (ddd, J=3.54, 6.63, 10.29 Hz, 1H), 2.29 (tt, J=3.57, 12.22 Hz, 1H), 2.08 (dd, J=3.28, 13.39 Hz, 2H), 1.94 (dd, J=3.03, 13.14 Hz, 2H), 1.65-1.85 (m, 1H), 1.55 (td, J=3.54, 6.95 Hz, 1H), 1.42-1.52 (m, 2H), 1.36-1.43 (m, 1H), 1.15 (qd, J=3.54, 12.72 Hz, 2H); LC-MS Rt=0.62 min; MS (ESI): 274.2 [M+H]$^+$.

Example 83

4-(((trans-2-(4-Benzamidophenyl)cyclopropyl)amino)methyl)cyclohexanecarboxylic acid

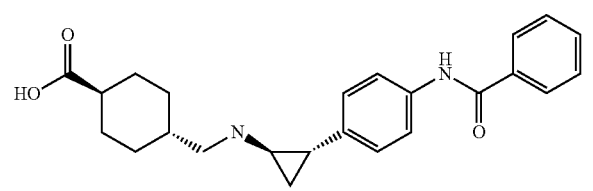 [SMILES: O=C(Nc1ccc([C@@H]2C[C@H]2NC[C@H]2CC[C@H](C(=O)O)CC2)cc1)c1ccccc1]

Following a procedure analogous to the procedure described in Example 81 using N-(4-(trans-2-aminocyclopropyl)phenyl)benzamide (400 mg of Boc protected material, 1.135 mmol, used after deprotection) afforded 4-(((trans-2-(4-benzamidophenyl)cyclopropyl)amino)methyl)cyclohexanecarboxylic acid (25 mg, 0.058 mmol, 5.14% yield). $^1$H NMR (400 MHz, METHANOL-d$_4$) δ 7.89-7.97 (m, 2H), 7.69 (d, J=8.59 Hz, 2H), 7.57-7.65 (m, 1H), 7.47-7.57 (m, 2H), 7.22 (d, J=8.59 Hz, 2H), 3.10 (d, J=7.07 Hz, 2H), 3.01 (dt, J=4.14, 7.64 Hz, 1H), 2.50 (ddd, J=3.54, 6.63, 10.29 Hz, 1H), 2.30 (tt, J=3.54, 12.25 Hz, 1H), 2.09 (dd, J=3.16, 13.52 Hz, 2H), 1.94 (dd, J=2.91, 13.26 Hz, 2H), 1.69-1.79 (m, 1H), 1.45-1.57 (m, 3H), 1.42 (q, J=6.82 Hz, 1H), 1.16 (qd, J=3.54, 12.72 Hz, 2H); LC-MS Rt=0.69 min; MS (ESI): 393.2 [M+H]$^+$.

Example 84

4-(((trans-2-(4-Acetamidophenyl)cyclopropyl)amino)methyl)cyclohexanecarboxylic acid

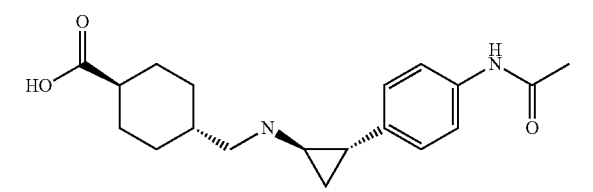 [SMILES: CC(=O)Nc1ccc([C@@H]2C[C@H]2NC[C@H]2CC[C@H](C(=O)O)CC2)cc1]

Following a procedure analogous to the procedure described in Example 81 using N-(4-((trans-2-aminocyclopropyl)phenyl)acetamide (JACS 2010, 132, 6827) (102 mg of Boc protected material, 0.353 mmol, used after deprotection) afforded 4-(((trans-2-(4-acetamidophenyl)cyclopropyl)amino)methyl)cyclohexanecarboxylic acid (30 mg, 0.074 mmol, 20.88% yield). $^1$H NMR (400 MHz, METHANOL-d$_4$) δ 7.52 (d, J=8.59 Hz, 2H), 7.16 (d, J=8.59 Hz, 2H), 3.68 (s, 1H), 3.08 (d, J=7.07 Hz, 2H), 2.97 (dt, J=3.88, 7.64 Hz, 1H), 2.51 (td, J=3.28, 6.69 Hz, 1H), 2.13 (s, 3H), 2.01-2.11 (m, 2H), 1.94 (d, J=11.87 Hz, 2H), 1.76 (ddd, J=3.66, 7.52, 11.05 Hz, 1H), 1.41-1.58 (m, 3H), 1.37 (q, J=7.24 Hz, 1H), 1.15 (qd, J=3.28, 12.72 Hz, 2H); LC-MS Rt=0.49 min; MS (ESI): 331.2 [M+H]$^+$.

Example 85 trans-2-(3-Fluoro-2-methoxyphenyl)-N-(piperidin-4-ylmethyl)cyclopropanamine, hydrochloride

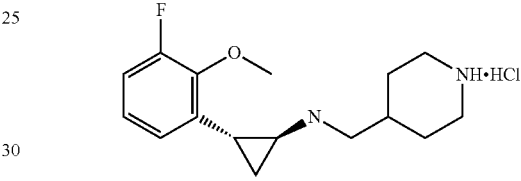

To a solution of trans-2-(3-fluoro-2-methoxyphenyl)cyclopropanamine hydrochloride (Biochemistry 2010, 49(30), 6494) (500 mg, 2.76 mmol) in a mixture of 1,2-dichloroethane (20 mL) and MeOH (5 mL) was added tert-butyl 4-formylpiperidine-1-carboxylate (588 mg, 2.76 mmol) and stirred for 3 min then Na(OAc)$_3$BH (1.75 g, 8.28 mmol) was added and stirred for 10 min at RT. The reaction mixture was diluted with DCM (100 mL) and washed with water (2×50 mL), and brine (20 mL). The organic layer was dried over anhydrous sodium sulphate and concentrated. The crude was purified by column chromatography using silica gel, eluting with 2% MeOH in DCM to afford tert-butyl 4-(((trans)-2-(3-fluoro-2-methoxyphenyl)cyclopropylamino)methyl)piperidine-1-carboxylate (250 mg, 25% yield) as yellow liquid. LCMS (ES) m/e 379.45 (M+H)$^+$. To a solution of tert-butyl 4-(((trans)-2-(3-fluoro-2-methoxyphenyl)cyclopropylamino)methyl)piperidine-1-carboxylate (200 mg, 0.529 mmol) in 1,4-dioxane (5 mL) was added 4N HCl in 1,4-dioxane (30 mL) and stirred for 8 h at RT. The reaction mixture was concentrated and the residue was triturated with diethyl ether (50 mL), EtOAc (20 mL) and dried under high vacuum to afford (trans)-2-(3-fluoro-2-methoxyphenyl)-N-(piperidin-4-ylmethyl)cyclopropanamine hydrochloride (130 mg, 88%) as off white solid. LCMS (ES) m/e 279.45 (M+H)$^+$, 95.34%, (DMSO-d6) δ ppm 9.53 (bs, 2H), 8.88 (bs, 1H), 8.69 (bs, 1H), 7.15 (t, J=8.4 Hz, 1H), 7.09-7.07 (m, 1H), 6.78 (d, J=8.0 Hz, 1H), 3.90 (s, 3H), 3.29 (d, 2H), 3.0 (bs, 3H), 2.79-2.89 (m, 3H), 2.05 (bs, 1H), 1.96 (d, J=13.6 Hz, 2H), 1.63 (m, 1H), 1.38-1.47 (m, 2H), 1.24-1.29 (m, 1H).

The following examples were synthesized starting from the appropriately substituted phenyl cyclopropyl amine (Biochemistry 2010, 49(30), 6494) in a method analogous to Example 85.

| Example | LC/MS m/e | 1HNMR (400 MHz in DMSO-d6) |
|---|---|---|
| 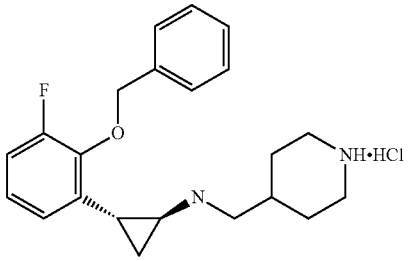 86 | 355.25 (M + H)+ | δ ppm 9.53 (bd, 2H), 8.82 (bs, 1H), 8.61 (bs, 1H), 7.56 (d, J = 6.8 Hz, 2H), 7.36-7.44 (m, 3H), 7.15-7.19 (t, J = 8.8 Hz, 1H), 7.04-7.09 (m, 1H), 6.788 (d, J = 7.6 Hz, 1H), 5.16 (d, J = 11.2 Hz, 1H), 5.061 (d, J = 11.2 Hz, 1H), 3.23 (d, J = 12.8, 2H), 2.80-2.99 (m, 6H), 1.98 (bs, 1H), 1.89 (d, J = 14.00 Hz, 1H), 1.76 (d, J = 13.2 Hz, 1H), 1.57-1.60 (m, 1H), 1.21-1.39 (m, 3H). |
| 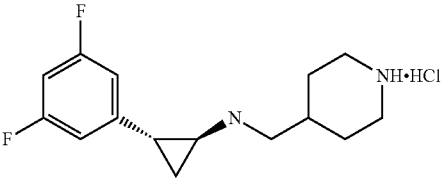 87 | 267.20 (M + H)+ | δ ppm 9.49 (bs, 2H), 8.78 (bs, 1H), 8.60 (bs, 1H), 7.06-7.11 (m, 1H), 6.99 (d, J = 6.8 Hz, 2H), 3.27 (d, J = 12.4 Hz, 2H), 3.05 (bs, 3H), 2.83-2.89 (m, 2H), 2.61 (bs, 1H), 2.01 (bs, 1H), 1.93 (d, J = 13.2 Hz, 2H), 1.62-1.67 (m, 1H), 1.36-1.44 (m, 3H). |
| 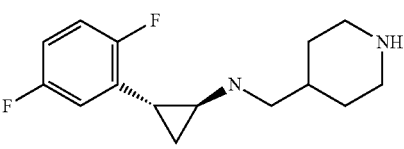 88 | 267.24 (M + H)+ | δ ppm 9.58 (bs, 2H), 8.82 (bs, 1H), 8.64 (bs, 1H), 7.25-7.28 (m, 1H), 7.09-7.15 (m, 1H), 7.01-7.04 (m, 1H), 3.27 (d, J = 13.2 Hz, 2H), 3.10 (bs, 1H), 2.99 (bs, 2H), 2.81-2.89 (m, 2H), 2.72 (bs, 1H), 2.04 (bs, 1H), 1.95 (d, J = 13.6 Hz, 2H), 1.65-1.67 (m, 1H), 1.37-1.45 (m, 3H). |

Example 89

N-(4-((trans)-2-((Piperidin-4-ylmethyl)amino)cyclopropyl)phenyl)acetamide, hydrochloride

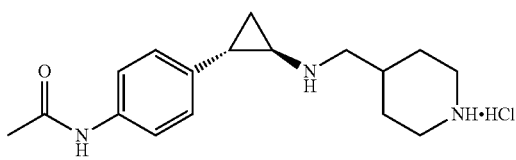

Step 1 tert-Butyl ((trans)-2-(4-acetamidophenyl)cyclopropyl)carbamate

To a cooled solution of tert-butyl ((trans)-2-(4-aminophenyl)cyclopropyl)carbamate (1 g, 4.03 mmol) in dichloromethane (5 mL) was added TEA (0.842 mL, 6.04 mmol), acetyl chloride (0.315 mL, 4.43 mmol) and stirred for 2 h at RT. The reaction mixture was diluted with ice cold water (50 mL) and extracted with DCM (2×50 mL). The combined organic layer was dried over anhydrous sodium sulphate and concentrated. The residue was purified using silica gel (100-200 mesh) column chromatography, compound eluted in 2% MeOH in DCM to afford tert-butyl ((trans)-2-(4-acetamidophenyl)cyclopropyl)carbamate (900 mg, 77% yield) as brown solid. LCMS (ES) m/e 289.26 (M−H).

Step 2

N-(4-((trans)-2-Aminocyclopropyl)phenyl)acetamide

To tert-butyl ((trans)-2-(4-acetamidophenyl)cyclopropyl) carbamate, step 1 (900 mg, 3.10 mmol) was added 4M HCl (3.444 mL, 13.78 mmol) in 1,4-dioxane and stirred for 2 h at RT. The reaction mixture was concentrated and triturated with EtOAc (10 mL) and dried under vacuum to afford N-(4-((trans)-2-aminocyclopropyl)phenyl)acetamide, hydrochloride (700 mg, 99% yield) as off white solid. LCMS (ES) m/e 190.2 (M+H).

Step 3 tert-Butyl 4-(((((trans)-2-(4-acetamidophenyl)cyclopropyl)amino)methyl)piperidine-1-carboxylate To a solution of N-(4-((trans)-2-aminocyclopropyl)phenyl)acetamide, hydrochloride (150 mg, 0.662 mmol) in a mixture of dichloromethane (10 mL) and methanol (5 mL) was added tert-butyl 4-formylpiperidine-1-carboxylate (141 mg, 0.662 mmol) and stirred for 5 min, then Na(OAc)₃BH (210 mg, 0.992 mmol) was added and stirred for 30 min. The crude was diluted with DCM (100 mL) and poured into sat NaHCO₃ solution (50 mL). The separated organic layer was washed with water (20 mL), brine solution (20 mL) and the organic layer was dried over anhy sodium sulphate and concentrated. The crude was purified using silica gel (100-200 mesh) column chromatography, eluting with MeOH in DCM. Compound eluted in 4% MeOH in DCM to afford tert-butyl 4-(((((trans)-2-(4-acetamidophenyl)cyclopropyl)amino)methyl)piperidine-1-carboxylate (150 mg, 0.387 mmol, 58.5% yield). LCMS (ES) m/e 387.96 (M+H), 95.06%

Step 4

N-(4-((trans)-2-((piperidin-4-ylmethyl)amino)cyclopropyl)phenyl)acetamide, hydrochloride To tert-butyl 4-((((trans)-2-(4-acetamidophenyl)cyclopropyl)amino)methyl)piperidine-1-carboxylate (130 mg, 0.335 mmol) in 1,4-dioxane was added 4M HCl (5 mL, 20.00 mmol) in 1,4-Dioxane and stirred for 2 hours at RT. The reaction mixture was concentrated and triturated with EtOAc (10 mL), diethyl ether (10 mL) and n-pentane (20 mL), dried under high vacuum to afford N-(4-((trans)-2-((piperidin-4-ylmethyl)amino)cyclopropyl)phenyl)acetamide, HCl salt (100 mg, 92% yield) as brown solid. LCMS (ES) m/e 288.32 (M+H). $^1$H NMR (400 MHz, D$_2$O) δ 7.40 (d, J=8.8 Hz, 2H) 7.23 (d, J=8.8 Hz, 2H), 3.68 (s, 1H), 3.51 (d, J=13.6 Hz, 2H), 3.25 (d, J=7.2 Hz, 2H), 2.99-3.09 (m, 3H), 2.55-2.60 (m, 1H), 2.18 (s, 4H), 2.06-2.09 (d, 2H), 1.43-1.61 (m, 4H).

The following examples were synthesized starting from the appropriately substituted phenyl cyclopropyl amine in a method analogous to Example 89.

Step 1

2,2,2-Trifluoro-N-((1-(methylsulfonyl)piperidin-4-yl)methyl)-N-((trans)-2-phenylcyclopropyl)acetamide To a solution of 2,2,2-trifluoro-N-((trans)-2-phenylcyclopropyl)-N-(piperidin-4-ylmethyl) acetamide, TFA salt (300 mg, 0.92 mmol) in DCM (10 mL) was added TEA (0.385 mL, 2.76 mmol) and cooled to 0° C. Then MsCl (0.106 mL, 1.38 mmol) was added and stirred for 2 h at rt. Reaction mixture quenched with ice and extracted with DCM (30 mL). The organic layer was washed with saturated sodium bicarbonate solution (2×25 mL), brine (25 mL) and dried over anhydrous Na$_2$SO$_4$ and concentrated under the reduced pressure to obtain the crude product. The crude compound was purified by column chromatography using silica gel (100-200 mesh) with 35% ethyl acetate/pet-ether as eluent and isolated desired product 2,2,2-trifluoro-N-((1-(methylsulfonyl)piperidin-4-yl)methyl)-N-((trans)-2-phenylcyclopropyl)acetamide (150 mg, 40.4%) as a colorless oil. LCMS (ES+): 405.4 [M+H]$^+$.

| Example | LCMS m/e | $^1$HNMR (400 MHz, D$_2$O) |
|---|---|---|
| 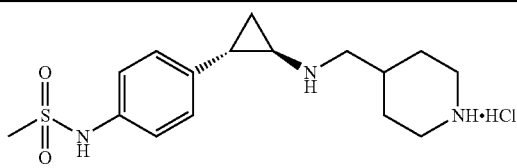<br>90 | 322.12 (M + H)$^+$ | δ 7.27 (t, J = 9.2 Hz, 4H), 3.50 (d, J = 13.2 Hz, 2 H), 3.25 (d, J = 7.2 Hz, 2 H), 3.00-3.10 (m, 6H), 2.56-2.1 (m, 1H), 2.14-2.17 (m, 1 H), 2.07 (d, J = 14.4 Hz 2H), 1.51-1.61 (d, 3H), 1.43-1.48 (m, 1H). |
| 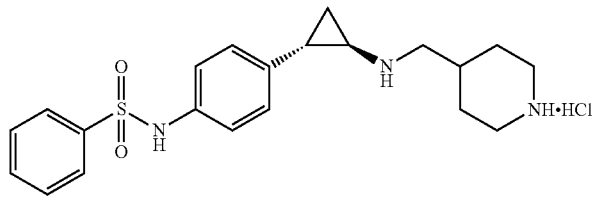<br>91 | 384.09 (M + H)$^+$ | δ 7.77 (d, J = 7.6 Hz, 2H), 7.69 (t, J = 7.6 Hz, 1H),7.56 (t, J = 7.6 Hz, 2H), 7.06-7.13 (q, 4H), 3.49 (d, J = 11.6 Hz, 2H), 3.21 (d, J = 7.2 Hz, 2 H), 3.03 (t, J = 12.8 Hz, 2H), 2.92-2.96 (m, 1H), 2.48-2.52 (m, 1 H), 2.14 (m, 1H), 2.05 (d, J = 14.8 Hz, 2H), 1.50-1.58 (m, 3H), 1.37-1.41 (m, 1H). |
| 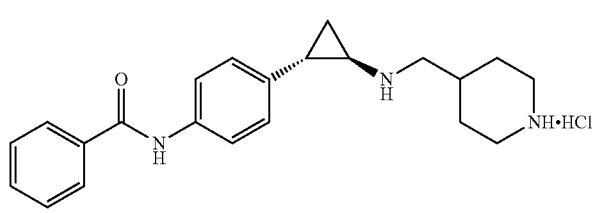<br>92 | 350.13 (M + H)$^+$ | δ 7.90 (d, J = 7.6 Hz, 2H), 7.69 (t, J = 7.6 Hz, 1H), 7.52-7.62 (m, 4H), 7.29 (d, J = 8.4 Hz, 2H), 3.51 (d, J = 12.8 Hz, 2 H), 3.26 (d, J = 7.2 Hz, 2 H), 3.02-3.09 (m, 3H), 2.58-2.63 (m, 1H), 2.07-2.22 (m, 3 H), 1.46-1.62 (m, 4H). |

Example 93

(trans)-N-((1-(Methylsulfonyl)piperidin-4-yl)methyl)-2-phenylcyclopropanamine

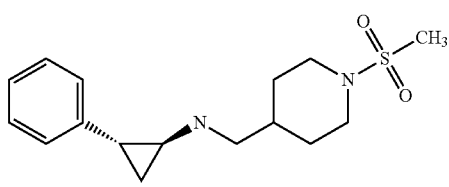 [SMILES: CS(=O)(=O)N1CCC(CN[C@H]2C[C@@H]2c2ccccc2)CC1]

Step 2

(trans)-N-((1-(Methylsulfonyl)piperidin-4-yl)methyl)-2-phenylcyclopropanamine To a solution of 2,2,2-trifluoro-N-((1-(methylsulfonyl)piperidin-4-yl)methyl)-N-((trans)-2-phenylcyclopropyl)acetamide (150 mg, 0.37 mmol) in a mixture of MeOH (6 mL) and H$_2$O (4 mL) was added KOH (62 mg, 1.11 mmol) at 0° C. stirred for 2 h rt. Reaction mixture was concentrated and the residue was dissolved in water (10 mL) and acidified with 50% HCl and washed with ethyl acetate (2×10 mL). The aqueous layer was basified with saturated sodium carbonate solution and extracted with ethyl acetate (2×25 mL). The combined organic layer was washed with water (25 mL), brine (25 mL) and dried over anhydrous $Na_2SO_4$ and concentrated under the reduced pressure to obtain the desired product (trans)-N-((1-(methylsulfonyl)piperidin-4-yl)methyl)-2-phenylcyclopropanamine (57 mg, 51.8%) as colourless gummy oil. HPLC-97.64%, m/z 309.35 (M+H)⁺. H¹NMR (CDCl₃) δ ppm 7.23-7.25 (m, 2H), 7.16-7.13 (m, 1H), 7.02 (d, J=7.2 Hz, 2H), 3.81 (d, J=11.2 Hz, 2H), 2.76 (s, 3H), 2.60-2.66 (m, 4H), 2.30-2.34 (m, 1H), 1.82-1.88 (m, 3H), 1.52-1.56 (m, 2H), 1.29-1.36 (m, 2H), 0.95-1.06 (m, 2H).

The following examples were synthesized using a method analogous to Example 89 using the appropriate sulfonyl chloride, isocyanate, or other means of synthesizing a urea.

| Example | LCMS m/e | 1HNMR (400 MHz in DMSO-d6/CDCl3) |
|---|---|---|
| 94 | 302.22 (M + H)⁺ | (CDCl3) δ ppm 7.19-7.23 (m, 2H), 7.08-7.11 (m, 1H), 7.02 (d, J = 7.2 Hz, 2H), 6.33-6.35 (t, J = 10.4 Hz, 1H), 3.90 (d, J = 16 Hz, 2H), 2.98-3.04 (m, 2H), 2.45-2.59 (m, 2H), 2.19 (br, 1H) 1.76 (br, 1H) 1.51-1.65 (m, 3H), 1.17-1.23 (m, 1H), 0.854-1.00 (m, 7H). |
| 95 | 314.10 (M + H)⁺ | (DMSO) δ ppm 7.19-7.23 (m, 2H), 7.07-7.11 (m, 1H), 7.01 (d, J = 7.2 Hz, 2H), 6.45 (br, 1H), 3.88 (d, J = 12 Hz, 2H), 2.19-2.57 (m, 5H), 1.90-2.19 (m, 1H), 1.72-1.77 (m, 1H) 1.50-1.64 (m, 3H) 0.85-0.96 (m, 4H) 0.48-0.52 (m, 2H), 0.32-0.36 (m, 2H). |
| 96 | 302.10 (M + H)⁺ | (CDCl3) δ ppm 7.23-7.24 (m, 2H), 7.14 (t, J = 7.2 Hz, 1H), 7.03 (d, J = 7.2 Hz, 2H), 3.66 (d, J = 12.4 Hz, 2H), 2.80 (s, 6H), 2.67-2.75 (m, 2H), 2.63 (d, J = 6.8 Hz, 2H) 2.30-2.34 (m, 1H) 1.84-1.89 (m, 1H), 1.69-1.78 (m, 3H), 1.59-1.64 (m, 1H), 1.27-1.21 (m, 2H), 1.02-1.07 (m, 1H), 0.95-0.99 (m, 1H). |
| 97 | 328.21 (M + H)⁺ | (CDCl3) δ ppm 7.21 (t, J = 7.6 Hz, 2H), 7.09 (t, J = 7.2 Hz, 1 H), 7.02 (d, J = 7.2 Hz, 2 H), 3.61 (d, J = 12.8 Hz, 2 H), 3.20-3.24 (m, 5 H), 2.57-2.67 (m, 3 H), 2.46 (s, 1 H), 2.17-2.20 (m, 1 H), 1.66-1.77 (m, 8 H) 0.89-1.23 (m, 4 H). |
| 98 | 335.01 (M + H)⁺ | (CDCl3) δ ppm 7.23-7.25 (m, 2H), 7.13-7.16 (m, 1H), 7.02 (d, J = 7.6 Hz, 2H), 3.81 (d, J = 12 Hz, 2H), 2.75-2.81 (m, 2H), 2.65 (d, J = 6.8 Hz, 2H), 2.21-2.34 (m, 2H), 1.80-1.89 (m, 3H), 1.57 (s, 2H), 1.25-1.35 (m, 2H), 1.14-1.17 (m, 2H), 1.02-1.06 (m, 1H), 0.93-0.99 (m, 3H). |
| 99 | 337.21 (M + H)⁺ | (CDCl3) δ ppm 7.23-7.25 (m, 2H), 7.13-7.16 (m, 1H), 7.02 (d, J = 7.2 Hz, 2H), 3.83 (d, J = 12 Hz, 2H), 3.13-3.19 (m, 1H), 2.81-2.87 (m, 2H), 2.64 (d, J = 6.8 Hz, 2H), 2.30-2.33 (m, 1H), 1.77-1.88 (m, 3H), 1.32 (d, J = 6.8 Hz, 6H), 1.21-1.27 (m, 3H), 1.02-1.06 (m, 1H), 0.95-0.99 (m, 1H). |

| Example | LCMS m/e | 1HNMR (400 MHz in DMSO-d6/CDCl3) |
|---|---|---|
| 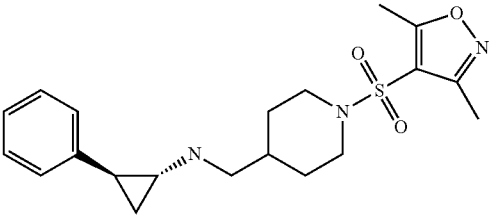 100 | 390.24 (M + H)+ | (CDCl3) δ ppm 7.22-7.24 (m, 2H), 7.14 (t, J = 7.6 Hz, 1H), 7.01 (d, J = 7.2 Hz, 2H), 3.76 (d, J = 11.2 Hz, 2H), 3.49 (s, 1H), 2.63 (d, J = 6.8 Hz, 5H), 2.47-2.52 (m, 2H), 2.40 (s, 3H), 2.28-2.32 (m, 1H), 1.82-1.85 (m, 3H), 1.47-1.50 (m, 1H), 1.23-1.33 (m, 2H), 0.94-1.04 (m, 2H). |
| 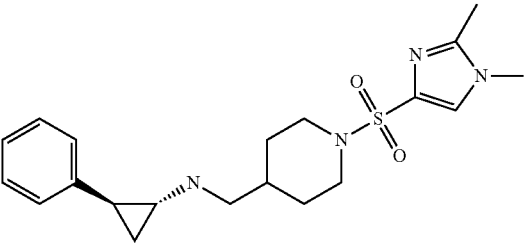 101 | 389.44 (M + H)+ | (CDCl3) δ ppm 7.68 (s, 1H), 7.18-7.22 (m, 2H), 7.07-7.11 (m, 1H), 7.00 (d, J = 7.2 Hz, 2H), 3.59 (s, 3H) 3.55 (d, J = 12 Hz, 2H), 2.36-2.50 (m, 4H), 2.30 (s, 3H) 2.15-2.19 (m, 1H), 1.71-1.76 (m, 3H), 1.34-1.35 (m, 1H), 1.06-1.15 (m, 2H), 0.87-0.94 (m, 2H). |

Example 102

(trans)-N-(2-(1-Methylpiperidin-4-yl)ethyl)-2-phenylcyclopropanamine, 2HCl

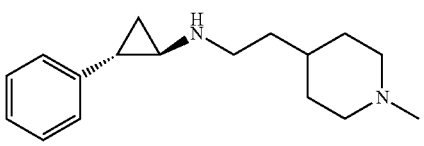 [SMILES: CN1CCC(CCN[C@@H]2C[C@H]2c2ccccc2)CC1]

Step 1 tert-Butyl 4-(2-(2,2,2-trifluoro-N-((trans)-2-phenylcyclopropyl)acetamido)ethyl)piperidine-1-carboxylate To a stirred solution of tert-butyl 4-(2-(((trans)-2-phenylcyclopropyl)amino)ethyl)piperidine-1-carboxylate (2.5 g, 7.26 mmol) in DCM (50 mL) was added TEA (3.03 mL, 21.77 mmol) followed by TFAA (1.538 mL, 10.89 mmol) 0° C. and stirred for 2 h at RT. Reaction mixture was diluted with DCM (50 mL), washed with water (3×50 mL) and brine (1×50 mL). The organic layer was dried over sodium sulphate and concentrated under reduced pressure to afford crude product. The crude product was purified by column chromatography using 100-200 mesh silica gel, eluting with 15% ethyl acetate in pet-ether to afford tert-butyl 4-(2-(2,2,2-trifluoro-N-((trans)-2-phenylcyclopropyl)acetamido)ethyl)piperidine-1-carboxylate (1.5 g, 42.2% yield) as yellow gum. LCMS (ES) m/e 441.04 (M+H)+.

Step 2

2,2,2-Trifluoro-N-((trans)-2-phenylcyclopropyl)-N-(2-(piperidin-4-yl)ethyl)acetamide, Trifluoroacetic acid salt TFA (2 mL, 26.0 mmol) was added to a stirred solution of tert-butyl 4-(2-(2,2,2-trifluoro-N-((trans)-2-phenylcyclopropyl)acetamido)ethyl)piperidine-1-carboxylate (1.8 g, 4.09 mmol) in DCM (20 mL) at 0° C. and stirred at RT for 2 h. Reaction mixture was concentrated and dried under high vacuum to afford 2,2,2-trifluoro-N-((trans)-2-phenylcyclopropyl)-N-(2-(piperidin-4-yl)ethyl)acetamide, trifluoroacetic acid salt (1.5 g, 71.8% yield) as yellow gum. LCMS (ES) m/e 341.45 (M+H)

Step 3

2,2,2-trifluoro-N-(2-(1-methylpiperidin-4-yl)ethyl)-N-((trans)-2-phenylcyclopropyl)acetamide To a stirred solution of 2,2,2-trifluoro-N-((trans)-2-phenylcyclopropyl)-N-(2-(piperidin-4-yl)ethyl)acetamide, trifluoroacetic acid salt (300 mg, 0.881 mmol) in methanol (25 mL) was added catalytic amount of acetic acid (0.505 μL, 8.81 μmol). After 10 min, formaldehyde (1.214 mL, 17.63 mmol) followed by sodium triacetoxyborohydride (560 mg, 2.64 mmol) were added at 25° C. and stirred for 4 h. Reaction mixture was concentrated, diluted with ethyl acetate (40 mL) and washed with water (10 mL). The organic layer was dried over anhydrous sodium sulphate, filtered, dried and concentrated to afford 2,2,2-trifluoro-N-(2-(1-methylpiperidin-4-yl)ethyl)-N-((trans)-2-phenylcyclopropyl)acetamide (200 mg, 64.0% yield) as colourless liquid. LCMS (ES) m/e 355.21 (M+H)+.

Step 4

(trans)-N-(2-(1-Methylpiperidin-4-yl)ethyl)-2-phenylcyclopropanamine, 2HCl

To a stirred solution of 2,2,2-trifluoro-N-(2-(1-methylpiperidin-4-yl)ethyl)-N-((trans)-2-phenylcyclopropyl)acetamide, 6 (200 mg, 0.564 mmol) in a mixture of methanol (15 mL) and water (15 mL), KOH (31.7 mg, 0.564 mmol) was added at 0° C., allowed to warm to rt. Reaction mixture was concentrated, pH was adjusted to ~1-2 using 2N HCl (15 mL) and washed with ethyl acetate (10 mL). Then the aqueous layer pH was adjusted to ~8-9 using sat NaHCO$_3$ solution (15 mL) and extracted with ethyl acetate (20 mL). The organic layer was dried over anhydrous sodium sulphate, filtered and concentrated to afford 100 mg of title compound (free base) yellow gum. The compound was not poor enough, hence converted to its corresponding HCl salt with 4M HCl in 1,4-dioxane (10 mL) and concentrated under reduced pressure. The residue was washed with ethyl acetate (5×10 mL) and dried to afford (trans)-N-(2-(1-methylpiperidin-4-yl)ethyl)-2-phenylcyclopropanamine, 2HCl (50 mg, 25.9% yield) as yellow solid. (ES) m/e 259.43 (M+H)$^+$. 1HNMR (400 MHz in D$_2$O) δ ppm 7.409-7.446 (t, J=7.2 Hz, 2H), 7.334-7.371 (t, J=7.2 Hz 1H), 7.244-7.261 (d, J=6.8 Hz, 2H), 3.458-3.537 (m, 2H), 3.29-3.31 (t, J=8 Hz, 2H), 2.818 (s, 3H) 2.944-3.018 (m, 3H) 2.541-2.58 (m, 1H), 2.046-2.080 (d, J=16 Hz, 2H), 1.747-1.778 (t, J=7.6 Hz, 3H), 1.438-1.591 (m, 4H).

Example 103

(trans)-2-Phenyl-N-(2-(1-(pyridin-2-yl)piperidin-4-yl)ethyl)cyclopropanamine

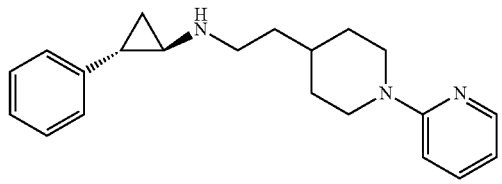 [SMILES: c1ccc([C@@H]2C[C@H]2NCCC2CCN(c3ccccn3)CC2)cc1]

Step 1

Ethyl 2-(1-(pyridin-2-yl)piperidin-4-yl)acetate

To a stirred solution of ethyl 2-(piperidin-4-yl)acetate, hydrochloride (2.0 g, 9.63 mmol) in DMF (40 mL) was added K$_2$CO$_3$ (3.99 g, 28.9 mmol) followed by 2-bromopyridine (1.521 g, 9.63 mmol) and stirred at 130° C. for 16 h. Reaction mixture was diluted with water (200 mL) and extracted with ethyl acetate (2×100 mL). The combined organic layer was washed with water (2×100 mL), brine (100 mL) and dried over Na$_2$SO$_4$ filtered and concentrated under reduced pressure. The residues was purified by column chromatography using 100-200 silica gel by eluting with 20% ethyl acetate in petroleum ether to afford ethyl 2-(1-(pyridin-2-yl)piperidin-4-yl)acetate (600 mg, 19.86% yield) as color less liquid. LCMS (ES) m/e 249.20 (M+H)$^+$.

Step 2

2-(4-(Pyridin-2-yl)piperidin-1-yl)acetaldehyde

To a stirred solution of ethyl 2-(4-(pyridin-2-yl)piperidin-1-yl)acetate (600 mg, 2.416 mmol) in toluene (20 mL) was added DIBAL-H (3.62 mL, 3.62 mmol, 1M in toluene) at −78° C. and stirred for 3 h at −78° C. The reaction mixture was quenched with methanol (0.5 mL) and then brine (10 mL) was added. The reaction mixture was filtered through celite and the filtrate was dried over sodium sulphate and concentrated under reduced pressure to afford 2-(4-(pyridin-2-yl)piperidin-1-yl)acetaldehyde (400 mg, 77% yield) as pale yellow solid. LCMS (ES) m/e 205.16 (M+H)$^+$.

Step 3

(trans)-2-Phenyl-N-(2-(1-(pyridin-2-yl)piperidin-4-yl)ethyl)cyclopropanamine

To a stirred solution of 2-(1-(pyridin-2-yl)piperidin-4-yl)acetaldehyde, 8 (500 mg, 2.448 mmol) in 1,2-dichloroethane (20 mL) was added acetic acid (0.420 mL, 7.34 mmol) followed by (trans)-2-phenylcyclopropanamine, hydrochloride (623 mg, 3.67 mmol) and stirred for 1 h at 25° C. Then sodium triacetoxyborohydride (1556 mg, 7.34 mmol) was added and stirred for 1 h at 25° C. Reaction mixture was diluted with DCM (50 mL), washed with water (2×50 mL) and brine (1×50 mL). The organic layer was dried over Na$_2$SO$_4$ and concentrated under reduced pressure to afford crude product. The crude product was purified by column chromatography using 100-200 mesh silica gel by eluting with 70% ethyl acetate in petroleum ether to afford ethyl (trans)-2-phenyl-N-(2-(1-(pyridin-2-yl)piperidin-4-yl)ethyl)cyclopropanamine (400 mg, 38.3% yield) as a pale yellow solid. Isolated compound purity was less, and hence converted to the corresponding Boc-derivative for purification purpose. LCMS (ES) m/e 322.52 (M+H)

Step 4 tert-Butyl ((trans)-2-phenylcyclopropyl)(2-(1-(pyridin-2-yl)piperidin-4-yl) ethyl)carbamate Triethyl amine (0.520 mL, 3.73 mmol) was added to a stirred solution of (Trans)-2-phenyl-N-(2-(1-(pyridin-2-yl)piperidin-4-yl)ethyl)cyclopropanamine (400 mg, 1.244 mmol) in DCM (10 mL) at 0° C. Then di-tert-butyl dicarbonate (0.318 ml, 1.369 mmol) was added at 0° C. and stirred the reaction mixture for 2 h at RT. The reaction mixture was diluted with DCM (30 mL), washed with water (3×20 mL) and brine (30 mL). The organic layer was dried over sodium sulphate and concentrated under reduced pressure to afford crude product. The crude product was purified by column chromatography using 100-200 silica gel, by eluting with 20% ethyl acetate in petroleum ether to afford tert-butyl tert-butyl ((trans)-2-phenylcyclopropyl)(2-(1-(pyridin-2-yl)piperidin-4-yl)ethyl)carbamate (400 mg, 76% yield) as yellow gum.

LCMS (ES) m/e 322.28 (M+H) 99.42%

Step 5

(trans)-2-Phenyl-N-(2-(1-(pyridin-2-yl)piperidin-4-yl)ethyl)cyclopropanamine, hydrochloride Ether-HCl (4 mL, 16.00 mmol) was added to tert-butyl ((trans)-2-phenylcyclopropyl)(2-(1-(pyridin-2-yl)piperidin-4-yl)ethyl)carbamate, 9 (350 mg, 0.830 mmol) and stirred for 4 h at 25° C. Reaction mixture was concentrated, dried and the residue was triturated with ether (2×25 mL) and ethyl acetate (2×25 mL) and dried to afford (trans)-2-phenyl-N-(2-(1-(pyridin-2-yl)piperidin-4-yl)ethyl)cyclopropanamine, hydrochloride (230 mg, 76% yield) as a pale yellow solid. LCMS (ES) m/e 322.46 (M+H)$^+$. 1HNMR (400 MHz in D$_2$O) δ ppm 7.94-7.98 (m, 1H), 7.82-7.83 (m, 1H) 7.39-7.43 (t, J=16 Hz, 2H), 7.31-7.35 (t, J=16 Hz, 1H), 7.24 (d, J=12 Hz, 2H), 6.89-6.92 (t, J=12 Hz, 1H), 4.09 (d, J=16 Hz, 2H), 3.22-3.34

(m, 4H), 2.99-3.03 (m, 1H), 2.53-2.58 (m, 1H), 1.93 (d, J=12 Hz, 2H), 1.80-1.88 (m, 1H), 1.72-1.79 (m, 2H), 1.52-1.58 (m, 1H), 1.36-1.49 (m, 3H).

Example 104

6-(4-(2-(((trans)-2-Phenylcyclopropyl)amino)ethyl)piperidin-1-yl)nicotinic acid, hydrochloride

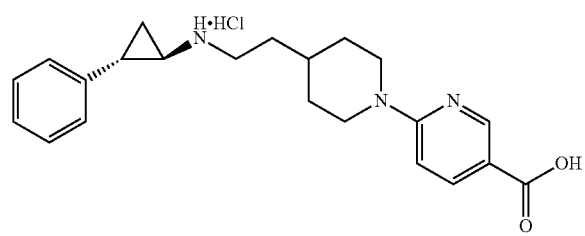

Step 1

Methyl 6-(4-(2-(2,2,2-trifluoro-N-((trans)-2-phenylcyclopropyl)acetamido)ethyl)piperidin-1-yl)nicotinate Methyl 6-bromonicotinate, 13 (0.476 g, 2.206 mmol) and CsF (2.68 g, 17.64 mmol) were added to a stirred solution of 2,2,2-trifluoro-N-((trans)-2-phenylcyclopropyl)-N-(2-(piperidin-4-yl)ethyl)acetamide, trifluoroacetate (1 g, 2.206 mmol) in N,N-dimethylacetamide (10 mL) in a Microwave vial. The reaction vessel was sealed and heated in CEM Discover to 100° C. for 45 min under microwave conditions. Reaction mixture was diluted with water (50 mL) and extracted with ethyl acetate (2×30 mL). The combined organic layer was washed with water (2×30 mL), brine (1×50 mL), filtered and dried over $Na_2SO_4$ and concentrated under reduced pressure to afford crude product The crude product was purified by column chromatography using 100-200 mesh silica gel, by eluting with 30% ethyl acetate in pet-ether to afford methyl 6-(4-(2-(2,2,2-trifluoro-N-((trans)-2-phenylcyclopropyl)acetamido)ethyl)piperidin-1-yl)nicotinate (500 mg, 27.3% yield) as yellow gum. LCMS (ES) m/e 476.14 $(M+H)^+$.

Step 2

6-(4-(2-(((trans)-2-Phenylcyclopropyl)amino)ethyl)piperidin-1-yl)nicotinic acid, hydrochloride KOH (236 mg, 4.21 mmol) was added to a stirred solution of methyl 6-(4-(2-(2,2,2-trifluoro-N-((trans)-2-phenylcyclopropyl)acetamido)ethyl)piperidin-1-yl)nicotinate (400 mg, 0.841 mmol) in a mixture of methanol (3 mL) and water (1 mL) and stirred for 4 h at 60° C. Reaction mixture was concentrated and acidified to pH ~5 with 3N HCl and the precipitated solid was filtered and dried. The residue was triturated with diethyl ether (2×25 mL), ethyl acetate (2×25 mL) and dried to afford 150 mg Product, which was again purified by Prep-HPLC. The obtained product was again treated with Ether-HCl (5 mL) for 15 min and concentrated under reduced pressure and the residue was dried to afford 6-(4-(2-(((trans)-2-phenylcyclopropyl)amino)ethyl)piperidin-1-yl)nicotinic acid, hydrochloride (31 mg, 0.075 mmol, 8.92% yield) as yellow gum. LC/MS (ES) m/e 366.24 $(M+H)^+$, 97.24%. 1HNMR (400 MHz in $D_2O$) δ ppm 8.41 (s, 1H), 8.30 (d, J=8 Hz, 1H) 7.39-7.43 (t, J=16 Hz, 2H), 7.32-7.35 (t, J=16 Hz, 1H), 7.24 (d, J=16 Hz, 2H), 4.18 (d, J=16 Hz, 2H), 3.30-3.36 (m, 4H), 2.99-3.02 (m, 1H) 2.53-2.57 (m, 1H) 1.88-2.01 (m, 3H), 1.73-1.78 (m, 2H), 1.52-1.56 (m, 1H), 1.39-1.49 (m, 3H).

The following examples were synthesized using methods analogous to examples 102, 103 and 104 and the appropriate starting materials.

| Example | LCMS (ES) | 1HNMR (400 MHz in $D_2O$) |
|---|---|---|
| 105 | 322.33 $(M+H)^+$ | δ ppm 7.99 (d, J = 7.6 Hz, 2H), 7.39-7.43 (t, J = 14.8 Hz 2H), 7.31-7.35 (m, 1H), 7.24 (d, J = 8 Hz, 2H), 7.02 (d, J = 8 Hz, 2H), 4.17 (d, J = 12 Hz, 2H), 3.36-3.29 (m, 2H), 3.21-3.02 (m, 2H), 3.00-2.57 (m, 1H) 2.08-2.55 (m, 1H), 1.75-1.92 (m, 3H), 1.70-1.74 (m, 2H), 1.53-1.56 (m, 1H), 1.43-1.51 (m, 1H), 1.28-1.37 (m, 2H). |
| 106 | 323.37 $(M+H)^+$ | δ ppm 8.57 (s, 1H), 8.03 (d, J = 8 Hz, 1H), 7.40-7.44 (t, J = 16 Hz 2H), 7.33-7.37 (t, J = 16 Hz 1H), 7.25 (d, J = 16 Hz, 2H), 7.00 (d, J = 8 Hz, 1H), 4.97 (d, J = 16 Hz, 1H), 4.17 (d, J = 12 Hz, 1H), 3.31-3.35 (m, 3H), 2.99-3.01 (m, 2H) 2.54-2.59 (m, 1H) 1.86-1.93 (m, 3H), 1.72-1.78 (m, 2H), 1.55-1.59 (m, 1H), 1.44-1.53 (m, 1H), 1.30-1.37 (m, 2H). |

| Example | LCMS (ES) | 1HNMR (400 MHz in D₂O) |
|---|---|---|
| 107 | 321.31 (M + H)⁺ | δ ppm 7.58-7.65 (m, 5H), 7.40-7.44 (t, J = 5.2 Hz, 2H), 7.33-7.36 (t, J = 7.2 Hz, 1H), 7.24-7.26 (d, J = 7.6 Hz, 2H), 3.72-3.75 (d, J = 12 Hz, 2H), 3.58-3.66 (m, 2H), 3.33-3.37 (t, J = 8.4 Hz, 2H), 3.01-3.05 (m, 1H), 2.55-2.60 (m, 1H), 2.14-2.18 (d, J = 12.8 Hz, 2H), 1.71-1.93 (m, 5H), 1.54-1.6 (m, 1H), 1.45-1.50 (m, 1H). |
| 108 | 322.50 (M + H)⁺ | δ ppm 8.25 (d, J = 4 Hz, 1H), 8.03-8.06 (m, 2H), 7.79-7.80 (m, 1 H), 7.38-7.42 (t, J = 16 Hz, 2H), 7.31-7.34 (t, J = 12 Hz, 1H), 7.24 (d, J = 8 Hz, 2H), 3.85 (d, J = 12 Hz, 2H), 3.30-3.33 (m, 2H), 2.96-3.03 (m, 3H), 2.52-2.57 (m, 1H), 1.87 (d, J = 12 Hz, 2H), 1.72-1.75 (m, 3H), 1.52-1.57 (m, 1H), 1.32-1.48 (m, 3H). |
| 109 | 323.27 (M + H)⁺ | δ ppm 8.53 (d, J = 8 Hz, 2H), 7.36-7.43 (t, J = 12 Hz 2 H), 7.32-7.36 (t, J = 16 Hz, 1H), 7.25 (d, J = 8 Hz, 2H), 6.94-6.97 (t, J = 12 Hz, 1H), 4.43 (d, J = 12 Hz, 2 H), 3.20-3.37 (m, 5H), 2.99-3.03 (m, 1H), 2.53-2.58 (m, 1H), 1.94 (d, J = 12 Hz, 2H), 1.83-1.87 (m, 1H), 1.72-1.78 (m, 2H), 1.52-1.58 (m, 1H), 1.31-1.49 (m, 3H). |
| 110 | 303.51 (M + H)⁺ | δ ppm 7.326-7.437 (m, 3H), 7.233-7.252 (t, J = 7.6 Hz, 2H), 3.792-3.768 (t, J = 4.4 Hz, 2H), 3.679-3.717 (d, J = 15.2 Hz, 2H), 3.406 (s, 3H), 3.231-3.339 (m, 4H) 2.945-3.065 (m, 3H), 2.137-2.577 (m, 1H), 2.008-2.041 (d, J = 13.2 Hz, 2H), 1.655-1.758 (t, J = 2.4 Hz, 3H), 1.430-1.576 (m, 4H). |
| 111 | 287.13 (M + H)⁺ | δ ppm 7.409-7.446 (t, J = 7.2 Hz, 2H), 7.334-7.371 (t, J = 7.2 Hz, 1H), 7.244-7.261 (d, J = 6.8 Hz, 2H), 3.458-3.537 (m, 3H), 3.29-3.31 (t, J = 8 Hz, 2H), 2.944-3.018 (m, 3H), 2.541-2.58 (m, 1H), 2.046-2.080 (d, J = 16 Hz, 2H), 1.747-1.778 (t, J = 7.6 Hz, 3H), 1.438-1.591 (m, 4H), 1.325-1.362 (t, J = 6.8 Hz, 7H). |

Example 112

3-Cyano-4-((4-((((trans)-2-phenylcyclopropyl)amino)methyl)piperidin-1-yl)methyl)benzoic acid, dihydrochloride

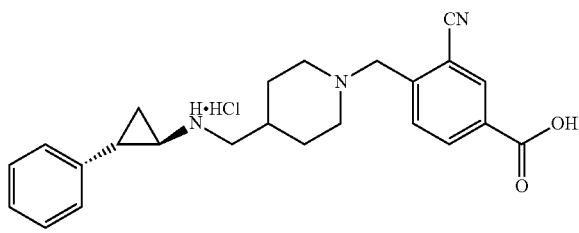

Step 1

Methyl 3-cyano-4-((4-((2,2,2-trifluoro-N-((trans)-2-phenylcyclopropyl)acetamido)methyl)piperidin-1-yl)methyl)benzoate To a stirred solution of 2,2,2-trifluoro-N-((trans)-2-phenylcyclopropyl)-N-(piperidin-4-ylmethyl)acetamide, trifluoroacetic acid salt (1 g, 2.271 mmol) and methyl 4-(bromomethyl)-3-cyanobenzoate in DMF (25 mL) was added $K_2CO_3$ (0.941 g, 6.81 mmol) at RT. Then the reaction mixture was stirred at 65° C. for 3 h, diluted with water and extracted with EtOAc (3×100 mL). The combined organic layer was washed with water (3×60 mL), brine (25 mL) dried over $Na_2SO_4$ and concentrated to afford the crude residue (1.8 g). Crude compound was purified by column chromatography using with 60-120 silica gel eluting with 0-25% EtOAc:pet-ether and isolated methyl 3-cyano-4-((4-((2,2,2-trifluoro-N-((trans)-2-phenylcyclopropyl)acetamido)methyl)piperidin-1-yl)methyl)benzoate, 13 (1.2 g, 73.0% yield). LCMS (ES) m/e 500.12 (M+H)+.

Step 2

Potassium 3-cyano-4-((4-((((trans)-2-phenylcyclopropyl)amino) methyl)piperidin-1-yl)methyl)benzoate To a stirred solution of methyl 3-cyano-4-((4-((2,2,2-trifluoro-N-((trans)-2-phenylcyclopropyl)acetamido)methyl)piperidin-1-yl)methyl)benzoate (1.2 g, 2.402 mmol) in a mixture of methanol (15 mL) and water (2 mL) was added KOH (0.404 g, 7.21 mmol) at RT. Then the reaction mixture was stirred at 65° C. for 3 h. The reaction mixture was concentrated to afford (crude) potassium 3-cyano-4-((4-((((trans)-2-phenylcyclopropyl)amino)methyl)piperidin-1-yl)methyl)benzoate (1 g, 107% yield). This was used as such in the next step.

This compound was converted to its Boc derivative to ease the purification.

Step 3

4-((4-(((tert-Butoxycarbonyl)((trans)-2-phenylcyclopropyl)amino)methyl)piperidin-1-yl)methyl)-3-cyanobenzoic acid To a stirred solution of potassium 3-cyano-4-((4-((((trans)-2-phenylcyclopropyl)amino)methyl)piperidin-1-yl)methyl)benzoate (1 g, 2.57 mmol) in a mixture of THF (20 mL) and water (4 mL) was added $Na_2CO_3$ (0.680 g, 6.42 mmol), Boc-anhydride (0.715 mL, 3.08 mmol) at RT. Then the reaction mixture was stirred at RT for 16 h. Reaction mixture was diluted with water and pH (~6) was adjusted with citric acid solution (aq) and then extracted with EtOAc (3×70 mL). The combined organic layer was washed with brine (80 mL), dried over $Na_2SO_4$ and concentrated to afford the crude residue (1.2 g). Crude was further purified by Prep HPLC and isolated 4-((4-(((tert-butoxycarbonyl)((trans)-2-phenylcyclopropyl)amino)methyl)piperidin-1-yl)methyl)-3-cyanobenzoic acid (400 mg, 0.812 mmol, 31.6% yield). LCMS (ES) m/e 490.11 (M+H)+.

Step 4

3-Cyano-4-((4-((((trans)-2-phenylcyclopropyl)amino)methyl)piperidin-1-yl)methyl)benzoic acid, dihydrochloride To a stirred solution of 4-((4-(((tert-butoxycarbonyl)((trans)-2-phenylcyclopropyl)amino) methyl)piperidin-1-yl)methyl)-3-cyanobenzoic acid (400 mg, 0.817 mmol) in DCM (5 mL) was added HCl in diethyl ether (5 mL, 0.817 mmol) at 0° C. and stirred at RT for 2 h. The reaction mixture was concentrated and the residue was triturated with diethyl ether (2×10 mL) and dried to afford 3-cyano-4-((4-((((trans)-2-phenylcyclopropyl)amino)methyl)piperidin-1-yl)methyl)benzoic acid, dihydrochloride (250 mg, 0.538 mmol, 65.9% yield) as white solid. LCMS (ES) m/z: 390.09 (M+H)+. $^1$HNMR (400 $MH_z$ in $D_2O$): δ 8.489 (bs, 1H) 8.342 (d, J=8 Hz, 1H), 7.866 (d, J=8 Hz, 1H), 7.400-7.291 (m, 3H), 7.209 (d, J=8 Hz, 2H), 4.624 (s, 2H), 3.683 (d, J=10.8 Hz, 2H), 3.269-3.214 (m, 4H), 2.979-2.997 (m, 1H), 2.526-2.577 (m, 1H), 2.107 (d, J=14.8, 3H), 1.528-1.618 (m, 3H), 1.434 (m, 1H).

The following examples were synthesized in a similar fashion to Example 112 using the appropriate benzyl bromide.

| Example | LCMS m/e | 1HNMR (400 MHz in $D_2O$) |
|---|---|---|
| 113 (structure shown) | 383.26 (M + H) | δ 7.932 (t, J = 7.8 Hz 1H), 7.364-7.395 (m, 4 H), 7.311 (t, J = 7.4 Hz 1H), 7.207 (d, J = 7.2 Hz 2H), 4.370 (bs, 2H), 3.595 (d, J = 12.4 Hz 2H), 3.21 (d, J = 6.8 Hz, 2H), 3.045-3.110 (t, J = 13.0 Hz, 2H), 2.962-2.992 (m, 1H), 2.520-2.572 (m, 1H), 2.065-2.153 (m, 3H), 1.405-1.612 (m, 4H). |

| Example | LCMS m/e | 1HNMR (400 MHz in D₂O) |
|---|---|---|
| 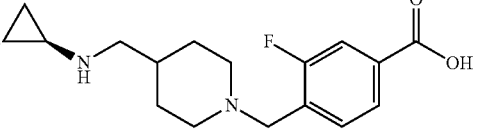 114 | 383.11 (M + H)+ | δ 7.856-7.932 (t, 2H), 7.648-7.686 (d, J = 7.6 Hz, 1 H), 7.326-7.432 (m, 3H), 7.238 (d, J = 7.2 Hz, 2H), 4.482 (bs, 2H), 3.653-3.683 (d, J = 12 Hz, 2H), 3.223-3.249 (d, J = 6.4 Hz, 2H), 3.129-3.192 (m, 2H), 3.001-3.019 (m, 1H), 2.575 (m, 1H), 2.100-2.134 (m, H), 1.544-1.646 (m, 3H), 1.437-1.491 (m, 1H). |
| 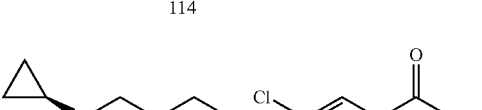 115 | 399.01 (M + H)+ | δ 8.180 (bs, 1H), 8.01 (d, J = 8 Hz. 1H), 7.726 (d, J = 8 Hz, 1H), 7.329-7.437 (m, 3H), 7.242 (d, J = 6.8 Hz, 2H), 4.585 (bs, 2H), 3.695 (d, J = 10.8 Hz, 2H), 3.237-3.276 (m, 4H), 3.104 (m, 1H), 2.580 (m, 1H), 2.095-2.182 (t, J = 17.4 Hz, 3H), 1.441-1.659 (m, 4H). |
|  116 | 395.13 (M + H)+ | δ 7.666 (d, J = 12 Hz, 2H), 7.519 (d, J = 8 Hz, 1H), 7.328-7.432 (m, 3H), 7.237 (d, J = 7.6 Hz, 2H), 3.981 (s, 3H), 3.613 (d, J = 12 Hz, 2H), 3.340-3.381 (m, 1H), 3.234 (d, J = 6.8 Hz, 2H), 3.077-3.142 (t, J = 13 Hz, 2H), 2.997-3.017 (m, 1H), 2.571 (m, 1H), 2.103 (m, 1H), 1.436-1.643 (m, 4H). |
| 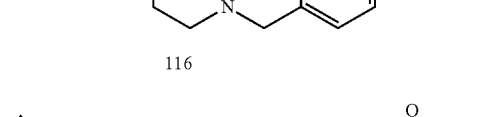 117 | 399.11 (M + H)+ | δ 7.863 (d, J = 7.6 Hz, 1H), 7.763 (s, 1H), 7.573-7.596 (m, 1H), 7.327 (t, J = 6.8 Hz, 2H), 7.244 (t, J = 7.2 Hz, 1H), 7.180 (d, J = 7.2 Hz, 2H), 4.312 (s, 2H), 3.344 (bs, 2H), 2.943-3.044 (m, 5H), 2.471-2.488 (m, 1H), 1.964 (d, J = 13.2 Hz, 3H), 1.488-1.540 (m, 3H), 1.295-1.330 (m, 1H). |

Example 30

4-{3-[4-({[(1R,2S)-2-Phenylcyclopropyl]amino}methyl)-1-piperidinyl]propyl}benzoic acid 2HCl

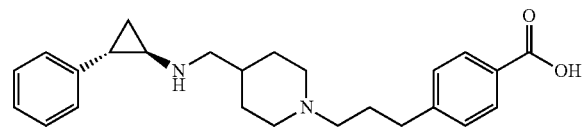 [SMILES: O=C(O)c1ccc(CCCN2CCC(CN[C@@H]3C[C@H]3c3ccccc3)CC2)cc1]

and

Example 118

4-(3-(4-(Cyano(((1R,2S)-2-phenylcyclopropyl)amino)methyl)piperidin-1-yl)propyl)benzoic acid, 2 hydrochloride

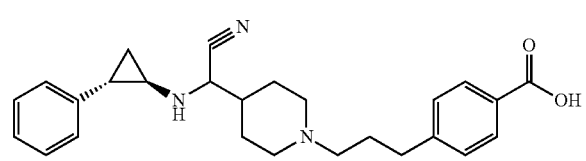 [SMILES: N#CC(N[C@@H]1C[C@H]1c1ccccc1)C1CCN(CCCc2ccc(C(=O)O)cc2)CC1]

Step 1

Ethyl 4-{3-[4-(hydroxymethyl)-1-piperidinyl]propyl}benzoate

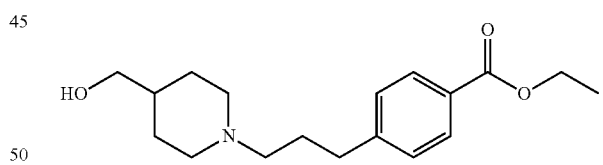

Ethyl 4-(3-oxopropyl)benzoate (1000 mg, 4.85 mmol) and piperidin-4-yl methanol (726 mg, 6.30 mmol) in methanol (25 mL) was heated to reflux for 5 minutes. The reaction was cooled to room temperature. Added sodium cyanoborohydride (457 mg, 7.27 mmol) was added and the reaction was stirred at room temperature for 3 hours. The reaction was concentrated and dichloromethane was added and washed with water, brine, dried over MgSO4, filtered and rotovapped off solvent. The residue was purified via Biotage (0% to 100% EtOAc:Hex to get off impurities then 0% to 20% MeOH:DCM; 50 g-HP-silica gel column) to yield 800 mg. ¹H NMR (400 MHz, CHLOROFORM-d) δ ppm 1.40 (t, 5H), 1.48-1.64 (m, 1H), 1.78 (d, J=11.87 Hz, 2H), 1.91 (quin, J=7.71 Hz, 2H), 2.04 (t, J=11.12 Hz, 2H), 2.38-2.53 (m, 2H), 2.71 (t, J=7.58 Hz, 2H), 3.03 (d, J=11.62 Hz, 2H), 3.51 (d, J=6.32 Hz, 2H), 4.38 (q, J=7.24 Hz, 2H), 7.11-7.40 (m, 2H), 7.97 (d, J=8.08 Hz, 2H); MS (ES) [M+H]+ 306.2

Step 2

Ethyl 4-[3-(4-formyl-1-piperidinyl)propyl]benzoate

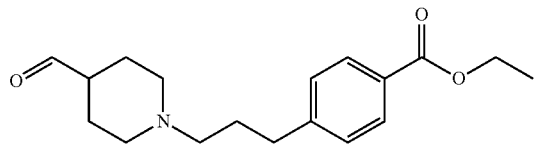 [SMILES: CCOC(=O)c1ccc(CCCN2CCC(C=O)CC2)cc1]

A solution of oxalyl chloride (2.66 mL, 30.4 mmol) in dichloromethane (150 mL) was cooled in a dry ice acetone bath. DMSO (3.29 mL, 46.3 mmol) was added dropwise. After 10 minutes ethyl 4-(3-(4-(hydroxymethyl)piperidin-1-yl)propyl)benzoate (4.88 g, 15.98 mmol) which was dissolved in DCM, was added dropwise. After 15 minutes added triethylamine (13.36 mL, 96 mmol) dropwise. Let stir in dry ice acetone bath with gradual warming to RT over 2 hours. The reaction mixture was washed with water, brine, dried over MgSO4, filtered and rotovapped off DCM. The residue was purified via Biotage (0% to 100% EtOAc:Hex; then 0% to 20% MeOH:EtOAC; 50 g-HP-silica gel column) to yield 4.25 g ¹H NMR (400 MHz, CHLOROFORM-d) δ ppm 1.40 (t, J=7.20 Hz, 3H), 1.64-1.78 (m, 2H), 1.78-2.01 (m, 4H), 2.02-2.17 (m, 2H), 2.19-2.31 (m, 1H), 2.31-2.40 (m, 2H), 2.69 (t, J=7.58 Hz, 2H), 2.79-2.91 (m, 2H), 4.37 (q, J=7.07 Hz, 2H), 7.06-7.38 (m, 2H), 7.87-8.07 (m, 2H), 9.66 (d, 1H); MS (ES) [M+H]+ 304.2

Step 3 ethyl 4-(3-(4-((((1R,2S)-2-phenylcyclopropyl)amino) methyl)piperidin-1-yl)propyl)benzoate and ethyl 4-(3-(4-(cyano(((1R,2S)-2-phenylcyclopropyl) amino)methyl)piperidin-1-yl)propyl)benzoate (1R,2S)-2-phenylcyclopropanamine (1.051 g, 7.89 mmol), ethyl 4-(3-(4-formylpiperidin-1-yl)propyl)benzoate (1.9 g, 6.26 mmol) in methanol (50 mL) were heated to reflux for 5 minutes. The reaction was cooled to room temperature and added sodium cyanoborohydride (0.590 g, 9.39 mmol). The reaction was stirred at room temperature for 16 hours. The reaction was concentrated and DCM was added and washed with water, brine, dried over MgSO4, filtered and rotovapped off solvent. The residue was purified via Biotage (0% to 100% EtOAc:Hex; to get off ethyl 4-(3-(4-(cyano(((1R,2S)-2-phenylcyclopropyl)amino)methyl)piperidin-1-yl)propyl)benzoate then 0% to 20% MeOH:DCM to get off ethyl 4-(3-(4-((((1R,2S)-phenylcyclopropyl)amino)methyl)piperidin-1-yl)propyl)benzoate 50 g-HP-silica gel column). Obtained 1.18 g of ethyl 4-(3-(4-(4(1R,2S)-2-phenylcyclopropyl) amino)methyl)piperidin-1-yl)propyl)benzoate ¹H NMR (400 MHz, CHLOROFORM-d) δ ppm 0.90-1.18 (m, 2H), 1.20-1.36 (m, 2H), 1.40 (t, J=7.07 Hz, 4H), 1.66-1.80 (m, 2H), 1.81-2.02 (m, 5H), 2.24-2.45 (m, 3H), 2.56-2.79 (m, 4H), 2.95 (d, J=10.86 Hz, 2H), 4.38 (q, J=7.24 Hz, 2H), 6.99-7.10 (m, 2H), 7.10-7.20 (m, 1H), 7.21-7.38 (m, 5H), 7.97 (d, 2H); [M+H]+ 421.3

Obtained 470 mg of ethyl 4-(3-(4-(cyano(((1R,2S)-2-phenylcyclopropyl)amino)methyl)piperidin-1-yl)propyl)benzoate ¹H NMR (400 MHz, CHLOROFORM-d) δ ppm 0.93-1.14 (m, 2H), 1.21 (ddd, J=9.09, 4.93, 4.67 Hz, 1H), 1.41 (t, J=7.20 Hz, 4H), 1.47-1.73 (m, 3H), 1.77-2.04 (m, 10H), 2.10 (ddd, J=9.28, 6.00, 2.91 Hz, 1H), 2.36 (t, J=6.82 Hz, 2H), 2.56-2.80 (m, 3H), 2.98 (br. s., 2H), 3.46 (ddd, J=10.67, 7.26, 3.28 Hz, 1H), 4.39 (q, J=7.07 Hz, 2H), 7.00-7.11 (m, 2H), 7.15-7.24 (m, 1H), 7.16-7.20 (m, 1H), 7.24-7.36 (m, 5H), 7.98 (d, J=8.34 Hz, 2H); [M+H]+ 446.3

Step 4

Example 30

4-{3-[4-({[(1R,2S)-2-Phenylcyclopropyl] amino}methyl)-1-piperidinyl]propyl}benzoic acid 2HCl

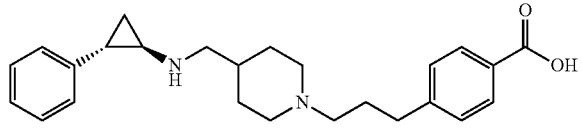

Added 1M sodium hydroxide (14.03 mL, 14.03 mmol) to a solution of ethyl 4-(3-(4-((((1R,2S)-2-phenylcyclopropyl) amino)methyl)piperidin-1-yl)propyl)benzoate (1.18 g, 2.81 mmol) in methanol (60 mL) and let stir at RT for 7 hours. Concentrated and HPLC purification (reverse phase) was performed. A 7 minute gradient run (0% AcCN/H₂O, 0.1% TFA to 40% ACN/H₂O, 0.1% TFA) with UV detection at 214 nm was utilized. Added 1 ml of 1N HCl to fractions concentrated to dryness. Obtained 800 mg of the di HCl salt ¹H NMR (400 MHz, MeOD) δ ppm 1.41 (q, J=6.82 Hz, 1H), 1.61 (ddd, J=10.55, 6.51, 4.42 Hz, 3H), 2.01-2.26 (m, 5H), 2.60 (ddd, J=10.23, 6.57, 3.66 Hz, 1H), 2.82 (t, J=7.58 Hz, 2H), 2.97-3.11 (m, 3H), 3.11-3.27 (m, 4H), 3.66 (d, J=12.13 Hz, 2H), 7.16-7.29 (m, 3H), 7.32 (d, J=7.58 Hz, 2H), 7.40 (d, J=8.08 Hz, 2H), 7.90-8.07 (m, 2H); [M+H]+ 393.3

Step 5

Example 118

4-(3-(4-(Cyano(((1R,2S)-2-phenylcyclopropyl) amino)methyl)piperidin-1-yl)propyl)benzoic acid, 2 hydrochloride Added 1N sodium hydroxide (1 mL, 1.000 mmol) to a solution of ethyl 4-(3-(4-(cyano(((1R,2S)-2-phenylcyclopropyl)amino)methyl)piperidin-1-yl)propyl)benzoate (230 mg, 0.516 mmol) and let stir at RT for 16 hours. Added and additional 1N sodium hydroxide (1 mL, 1.000 mmol) and let stir at RT for 16 hours. Concentrated and HPLC purification (reverse phase) was performed. A 7 minute gradient run (0% AcCN/H₂O, 0.1% TFA to 40% ACN/H₂O, 0.1% TFA) with UV detection at 214 nm was utilized. Added 1 ml of 1N HCl to fractions containing product and used Genevac to concentrate to dryness. Obtained 80 mg ¹H NMR (400 MHz, MeOD) δ ppm 1.30-1.43 (m, 2H), 1.47 (ddd, J=10.29, 6.25, 4.42 Hz, 1H), 1.60 (ddd, J=10.29, 6.13, 4.29 Hz, 1H), 1.68-1.95 (m, 4H), 2.03-2.31 (m, 9H), 2.32-2.50 (m, 3H), 2.56 (ddd, J=9.98, 6.57, 3.41 Hz, 1H), 2.80 (t, J=7.58 Hz, 4H), 2.90 (ddd, J=7.33, 4.04, 3.79 Hz, 1H), 2.95-3.00 (m, 1H), 3.00-3.21 (m, 4H), 3.69 (t, J=11.87 Hz, 2H), 4.58 (dd, J=5.56, 2.27 Hz, 1H), 7.12-7.24 (m, 3H), 7.25-7.33 (m, 2H), 7.37 (d, J=8.08 Hz, 2H), 7.97 (d, J=8.34 Hz, 2H); [M+H]+=418.3

The following examples were made in a fashion similar to Examples 120 and 121 using the appropriate substituted piperidine.

Example 119

4-{3-[4-({[(trans))-2-phenylcyclopropyl]amino}methyl)-1-piperidinyl]propyl}benzoic acid 2HCl

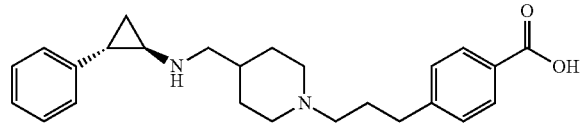 [SMILES: O=C(O)c1ccc(CCCN2CCC(CN[C@@H]3C[C@H]3c3ccccc3)CC2)cc1]

Following a procedure analogous to Example 120 using trans-phenylcyclopropyl amine afforded 4-{3-[4-({[(trans))-2-phenylcyclopropyl]amino}methyl)-1-piperidinyl]propyl}benzoic acid 2HCl. $^1$H NMR (400 MHz, MeOD) δ ppm 1.33-1.48 (m, 1H), 1.59 (ddd, J=10.67, 6.63, 4.42 Hz, 3H), 2.04-2.27 (m, 5H), 2.58 (ddd, J=10.29, 6.63, 3.54 Hz, 1H), 2.82 (t, J=7.58 Hz, 3H), 2.95-3.10 (m, 4H), 3.11-3.26 (m, 5H), 3.65 (br. s., 2H), 7.18-7.28 (m, 3H), 7.30-7.36 (m, 2H), 7.40 (d, J=8.34 Hz, 2H), 8.00 (d, J=8.34 Hz, 2H); $[M+H]^+$=393.3

Example 120

4-(4-(4-((((1R,2S)-2-Phenylcyclopropyl)amino)methyl)piperidin-1-yl)butyl)benzoic acid, 2 hydrochloride

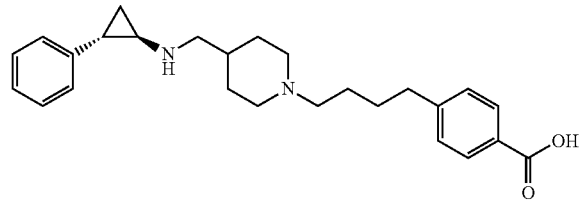 [SMILES: O=C(O)c1ccc(CCCCN2CCC(CN[C@@H]3C[C@H]3c3ccccc3)CC2)cc1]

Following a procedure analogous to Example 120 using 1R,2S-phenylcyclopropyl amine and ethyl 4-(4-oxobutyl)benzoate afforded 4-(4-(4-((((1R,2S)-2-phenylcyclopropyl)amino)methyl)piperidin-1-yl)butyl)benzoic acid, 2 hydrochloride. $^1$H NMR (400 MHz, DMSO-$d_6$) δ ppm 1.19-1.33 (m, 1H), 1.48-1.78 (m, 7H), 2.00 (d, J=13.14 Hz, 3H), 2.60 (ddd, J=9.98, 6.44, 3.54 Hz, 1H), 2.68 (t, J=7.33 Hz, 2H), 2.83 (br. s., 2H), 2.97 (d, J=7.07 Hz, 5H), 3.35 (br. s., 2H), 3.46 (d, J=11.62 Hz, 2H), 7.14-7.25 (m, 3H), 7.26-7.42 (m, 4H), 7.87 (d, J=8.34 Hz, 2H), 9.64 (br. s., 2H), 10.29 (br. s., 1H), 12.82 (br. s., 1H); $[M+H]^+$=407.3

Example 121

4-(4-(4-(Cyano(((1R,2S)-2-phenylcyclopropyl)amino)methyl)piperidin-1-yl)butyl)benzoic acid, 2 hydrochloride

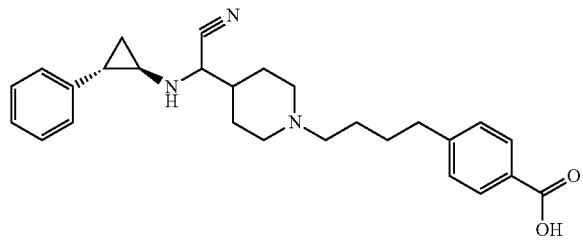 [SMILES: N#CC(N[C@@H]1C[C@H]1c1ccccc1)C1CCN(CCCCc2ccc(C(=O)O)cc2)CC1]

Following a procedure analogous to Example 120 using 1R,2S-phenylcyclopropyl amine and ethyl 4-(4-oxobutyl)benzoate afforded 4-(4-(4-(cyano(((1R,2S)-2-phenylcyclopropyl)amino)methyl)piperidin-1-yl)butyl)benzoic acid, 2 hydrochloride. $^1$H NMR (400 MHz, DMSO-$d_6$) δ ppm 1.02-1.28 (m, 2H), 1.47-1.84 (m, 8H), 1.98 (br. s., 4H), 2.69 (t, J=7.07 Hz, 3H), 2.88 (br. s., 3H), 3.03 (br. s., 3H), 3.50 (br. s., 2H), 6.95-7.50 (m, 7H), 7.88 (d, J=8.08 Hz, 2H), 8.49 (br. s., 1H), 9.81 (d, J=9.09 Hz, 1H); $[M+H]^+$=432.3

Example 122

4-(2-(4-((((trans)-2-Phenylcyclopropyl)amino)methyl)piperidin-1-yl)ethyl)benzoic acid

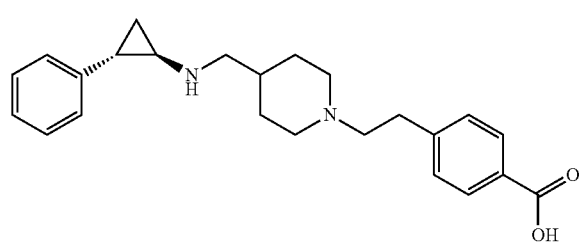 [SMILES: O=C(O)c1ccc(CCN2CCC(CN[C@@H]3C[C@H]3c3ccccc3)CC2)cc1]

Following a procedure analogous to Example 130 using trans-phenylcyclopropyl amine and methyl 4-(4-oxoethyl)benzoate afforded 4-(2-(4-((((trans)-2-phenylcyclopropyl)amino)methyl)piperidin-1-yl)ethyl)benzoic acid. $^1$H NMR (400 MHz, DMSO-$d_6$) δ ppm 1.20-1.35 (m, 1H), 1.51-1.72 (m, 3H), 2.06 (d, J=11.87 Hz, 3H), 2.61 (ddd, J=9.85, 6.19, 3.66 Hz, 1H), 2.94 (d, J=11.37 Hz, 4H), 3.09-3.42 (m, 6H), 3.60 (d, J=11.87 Hz, 2H), 7.13-7.27 (m, 3H), 7.28-7.37 (m, 2H), 7.41 (d, J=8.34 Hz, 2H), 7.92 (d, J=8.08 Hz, 2H), 9.62 (br. s., 2H), 10.69 (br. s., 1H), 12.94 (br. s., 3H); $[M+H]^+$=379.3.

Example 123

4-(2-(4-((((1R,2S)-2-phenylcyclopropyl)amino)methyl)piperidin-1-yl)ethyl)benzoic acid

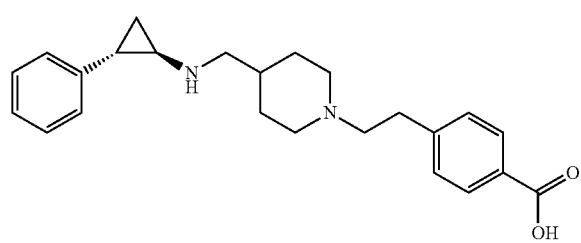 [SMILES: O=C(O)c1ccc(CCN2CCC(CN[C@@H]3C[C@H]3c3ccccc3)CC2)cc1]

Following a procedure analogous to Example 30 using 1R,2S-phenylcyclopropyl amine and methyl 4-(4-oxoethyl)benzoate afforded 4-(2-(4-((((1R,2S)-2-phenylcyclopropyl)amino)methyl)piperidin-1-yl)ethyl)benzoic acid. $^1$H NMR (400 MHz, DMSO-$d_6$) δ ppm 1.15-1.37 (m, 1H), 1.48-1.68 (m, 3H), 1.97-2.14 (m, 3H), 2.61 (ddd, J=9.92, 6.25, 3.54 Hz, 1H), 2.95 (br. s., 5H), 3.11-3.20 (m, 2H), 3.26 (br. s., 5H), 3.59 (d, J=11.37 Hz, 2H), 7.12-7.26 (m, 3H), 7.27-7.36 (m, 2H), 7.40 (d, J=8.34 Hz, 2H), 7.92 (d, J=8.08 Hz, 2H), 9.62 (br. s., 2H), 10.69 (br. s., 1H), 12.94 (br. s., 1H); [M+H]⁺=379.2.

Example 124

6-((4-((((trans)-2-Phenylcyclopropyl)amino)methyl)piperidin-1-yl)methyl)-2-naphthoic acid, 2 hydrochloride

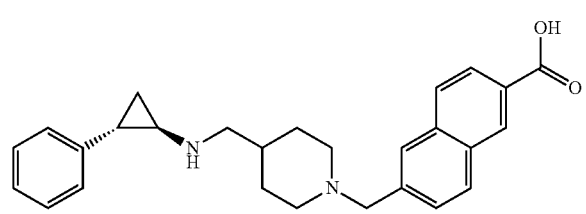 [SMILES: O=C(O)c1ccc2cc(CN3CCC(CN[C@@H]4C[C@H]4c4ccccc4)CC3)ccc2c1]

Following a procedure analogous to Example 30 using trans-phenylcyclopropyl amine and methyl 6-formyl-2-naphthoate afforded 6-((4-((((trans)-2-phenylcyclopropyl)amino)methyl)piperidin-1-yl)methyl)-2-naphthoic acid, 2 hydrochloride. ¹H NMR (400 MHz, DMSO-d₆) δ ppm 1.13-1.37 (m, 1H), 1.49-1.70 (m, 3H), 2.01 (br. s., 3H), 2.55 (dd, 1H), 2.97 (br. s., 4H), 3.17 (br. s., 1H), 4.47 (d, J=4.80 Hz, 2H), 7.07-7.41 (m, 5H), 7.86 (dd, J=8.46, 1.39 Hz, 1H), 8.04 (d, J=1.01 Hz, 2H), 8.15-8.31 (m, 2H), 8.66 (s, 1H), 9.47 (br. s., 2H), 10.71 (br. s., 1H); [M+H]⁺=415.4.

Example 125

6-((4-((((1R,2S)-2-Phenylcyclopropyl)amino)methyl)piperidin-1-yl)methyl)-2-naphthoic acid, 2 hydrochloride

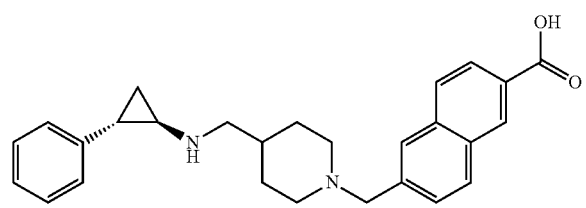 [SMILES: O=C(O)c1ccc2cc(CN3CCC(CN[C@@H]4C[C@H]4c4ccccc4)CC3)ccc2c1]

Following a procedure analogous to Example 30 using 1R,2S-phenylcyclopropyl amine and methyl 6-formyl-2-naphthoate afforded 6-((4-((((1R,2S)-2-phenylcyclopropyl)amino)methyl)piperidin-1-yl)methyl)-2-naphthoic acid, 2 hydrochloride. ¹H NMR (400 MHz, DMSO-d₆) δ ppm 1.24 (q, 1H), 1.45-1.75 (m, 3H), 1.81-2.16 (m, 3H), 2.55-2.75 (m, 1H), 2.97 (br. s., 5H), 3.38 (br. s., 5H), 4.46 (br. s., 2H), 7.07-7.25 (m, 3H), 7.26-7.48 (m, 2H), 7.89 (d, J=8.59 Hz, 1H), 8.05 (s, 2H), 8.15-8.32 (m, 2H), 8.67 (s, 1H), 9.58 (br. s., 2H), 10.93 (br. s., 1H), 13.21 (br. s., 1H); [M+H]⁺=415.3.

Example 126

(trans)-N-((1-(4-(1H-Tetrazol-5-yl)benzyl)piperidin-4-yl)methyl)-2-phenylcyclopropanamine, 2 hydrochloride

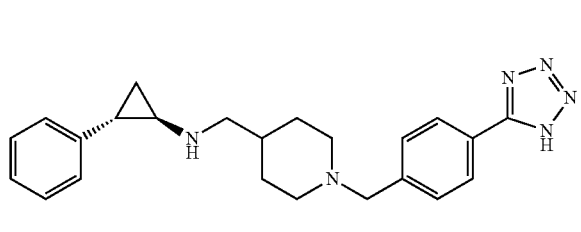 [SMILES: c1ccc([C@@H]2C[C@H]2NCC2CCN(Cc3ccc(-c4nnn[nH]4)cc3)CC2)cc1]

A solution of 2,2,2-trifluoro-N-((trans)-2-phenylcyclopropyl)-N-(piperidin-4-ylmethyl)acetamide (150 mg, 0.460 mmol), 4-(1H-tetrazol-5-yl)benzaldehyde (61.6 mg, 0.354 mmol), acetic acid (10 μL, 0.175 mmol) in methanol (50 mL) was stirred at RT for 1 hour. Added sodium cyanoborohydride (33.3 mg, 0.530 mmol) and let stir at RT for 16 hours. Added 15 mg of 4-(1H-tetrazol-5-yl)benzaldehyde followed 10 minutes later with addition of 10 mg of sodium cyanoborohydride. Let stir for 2 hours. Concentrated on a rotovap to about 5 ml of liquid remaining Added 1 ml of 1N NaOH and let stir at RT for 2 hours. Concentrated on rotovap and the residue was purified via HPLC purification (reverse phase). A 7 minute gradient was run (0% AcCN/H₂O, 0.1% Formic Acid to 40% ACN/H₂O, 0.1% Formic Acid) with UV detection at 214 nm was utilized. Added 1 ml of 1N HCl to fractions containing product and concentrated. Obtained 59 mg ¹H NMR (400 MHz, METHANOL-d₄) δ ppm 1.41 (q, J=6.82 Hz, 1H), 1.53-1.81 (m, 3H), 2.14 (d, J=14.65 Hz, 3H), 2.59 (ddd, J=10.23, 6.57, 3.66 Hz, 1H), 3.04 (ddd, J=7.71, 4.04, 3.92 Hz, 1H), 3.10-3.26 (m, 4H), 3.36-3.47 (m, 1H), 3.61 (d, J=12.38 Hz, 2H), 4.47 (s, 2H), 7.14-7.29 (m, 3H), 7.29-7.40 (m, 2H), 7.83 (d, J=8.34 Hz, 2H), 8.19 (d, J=8.34 Hz, 2H), 14.16 (none, 1H); [M+H]⁺=389.3

Example 127

2-(4-((4-((((trans)-2-Phenylcyclopropyl)amino)methyl)piperidin-1-yl)methyl)benzamido)acetic acid, 2 hydrochloride

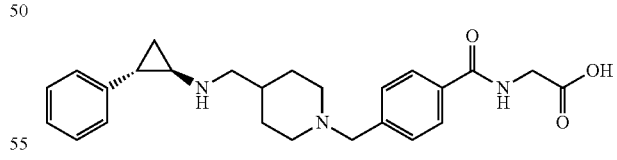

Step 1

Methyl 2-(4-formylbenzamido)acetate

Added N-methylmorpholine (2.93 mL, 26.6 mmol) to a solution of 4-formylbenzoic acid (1 g, 6.66 mmol), methyl 2-aminoacetate, hydrochloride (1.045 g, 8.33 mmol), 1-hydroxy-7-azabenzotriazole (1.813 g, 13.32 mmol), and EDC (2.55 g, 13.32 mmol) in Dimethyl Sulfoxide (DMSO) (30 mL). Let stir at RT for 16 hours. Added water and extracted with DCM. Combined DCM extracts and washed with water, brine and dried over MgSO4, filtered and rotovapped off DCM. The residue was purified via Biotage (0% to 75% gradient; EtOAc:Hex; 25 g-HP-silica gel column). Obtained 570 mg $^1$H NMR (400 MHz, CHLOROFORM-d) δ ppm 3.83 (s, 3H), 4.28 (d, J=5.05 Hz, 2H), 7.98 (s, 4H), 10.10 (s, 1H); [M+H]$^+$=222.1.

Step 2

2-(4-((4-((((trans)-2-phenylcyclopropyl)amino)methyl)piperidin-1-yl)methyl)benzamido)acetic acid, 2 hydrochloride A solution of 2,2,2-trifluoro-N-((trans)-2-phenylcyclopropyl)-N-(piperidin-4-ylmethyl)acetamide (190 mg, 0.582 mmol), methyl 2-(4-formylbenzamido)acetate (129 mg, 0.582 mmol), and 1,2-dichloroethane (DCE) (60 mL) was stirred at RT for 5 minutes. Sodium triacetoxyborohydride (247 mg, 1.164 mmol) was added. Let stir at RT for 16 hours. Added 1 g of sodium triacetoxyborohydride and let stir for 2 hours. Washed with water, dried over MgSO4, filtered and rotovapped off solvent. Dissolved residue in 3 ml of MeOH and added 1N sodium hydroxide (1 mL, 1.000 mmol) and let stir at RT for 16 hours. Concentrated and HPLC purification (reverse phase) was performed. A 7 minute gradient was run (0% AcCN/H$_2$O, 0.1% Formic Acid to 11% ACN/H$_2$O, 0.1% Formic Acid) with UV detection at 214 nm. Added 1 ml of 1N HCl to fractions containing product and concentrated. Obtained 65 mg. $^1$H NMR (400 MHz, METHANOL-d$_4$) δ ppm 1.40 (q, J=6.82 Hz, 1H), 1.57 (ddd, J=10.67, 6.63, 4.42 Hz, 3H), 2.10 (d, J=14.15 Hz, 3H), 2.56 (ddd, J=10.17, 6.63, 3.66 Hz, 1H), 3.01 (ddd, J=7.71, 4.04, 3.92 Hz, 1H), 3.05-3.25 (m, 4H), 3.43-3.63 (m, 2H), 4.07-4.19 (m, 2H), 4.42 (s, 2H), 7.13-7.27 (m, 3H), 7.27-7.35 (m, 2H), 7.68 (d, J=8.34 Hz, 2H), 7.98 (d, 2H); [M+H]$^+$=422.3.

Example 128

N-(4-((4-((((trans)-2-Phenylcyclopropyl)amino)methyl)piperidin-1-yl)methyl)phenyl)methanesulfonamide, 2 hydrochloride

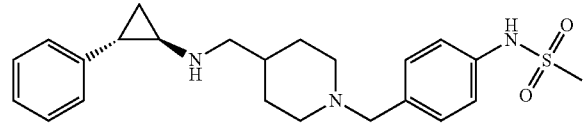 [SMILES: CS(=O)(=O)Nc1ccc(CN2CCC(CN[C@@H]3C[C@H]3c3ccccc3)CC2)cc1]

Step 1

2,2,2-trifluoro-N-((1-(4-(methylsulfonamido)benzyl) piperidin-4-yl)methyl)-N-((trans)-2-phenylcyclopropyl)acetamide, hydrochloride Added sodium triacetoxyborohydride (180 mg, 0.850 mmol) to a solution of 2,2,2-trifluoro-N-((trans)-2-phenylcyclopropyl)-N-(piperidin-4-ylmethyl)acetamide (185 mg, 0.567 mmol), N-(4-formylphenyl)methanesulfonamide (124 mg, 0.624 mmol) in 1,2-Dichloroethane (DCE) (40 mL). Let stir at RT for 16 hours. Added 100 mg of sodium triacetoxyborohydride and let stir at RT for 16 hours. Concentrated on a rotovap. Added water and extracted with DCM. Combined DCM extracts and washed with brine, dried over MgSO4, filtered and rotovapped off DCM. The residue was purified via Biotage (0% to 100% EtOAc:Hex then 0% to 20% MeOH: DCM 25 g-HP-silica gel column). Obtained 210 mg. $^1$H NMR (400 MHz, CHLOROFORM-d) δ ppm 1.47 (br. s., H), 1.90 (br. s., 4H), 2.08-2.27 (m, 3H), 2.39 (br. s., 1H), 2.65 (s, 1H), 3.04 (br. s., 4H), 3.23-3.76 (m, 3H), 4.14 (br. s., 2H), 6.99-7.15 (m, 2H), 7.2-7.3 (m, 3H), 7.46 (br. s., 23H), 7.63 (br. s., 2H), 9.05 (br. s., 1H), 11.69 (br. s., 1H)

Step 2

N-(4-((4-((((trans)-2-Phenylcyclopropyl)amino)methyl)piperidin-1-yl)methyl)phenyl)methanesulfonamide, 2 hydrochloride Added 1M sodium hydroxide (1 ml, 1.000 mmol) to a solution of 2,2,2-trifluoro-N-((1-(4-(methylsulfonamido) benzyl)piperidin-4-yl)methyl)-N-((trans)-2-phenylcyclopropyl)acetamide (170 mg, 0.334 mmol) in methanol (3 mL) and let stir at Rt for 16 hours. Concentrated and HPLC purification (reverse phase) was performed on an open-access Gilson using Trilution software, with a Gemini NX 5u C18 110A, AXIA. 100×30.00 mm 5 micron. An 7 minute gradient run (0% AcCN/H$_2$O, 0.1% Formic Acid to 40% ACN/H$_2$O, 0.1% Formic Acid) with UV detection at 214 nm was utilized. Added 1 ml of 1N HCl to fractions containing product and evaporated. Obtained 101 mg $^1$H NMR (400 MHz, METHANOL-d$_4$) δ ppm 1.39 (q, J=6.82 Hz, 1H), 1.51-1.75 (m, 3H), 1.93-2.26 (m, 4H), 2.59 (ddd, J=10.36, 6.69, 3.66 Hz, 1H), 2.95-3.12 (m, 7H), 3.18 (d, J=6.82 Hz, 2H), 3.54 (d, J=11.62 Hz, 2H), 4.30 (s, 2H), 7.14-7.27 (m, 4H), 7.27-7.39 (m, 5H), 7.49-7.57 (m, 2H); [M+H]$^+$=414.3

Example 129

(trans)-N-((1-(3-(1H-Tetrazol-5-yl)propyl)piperidin-4-yl)methyl)-2-phenylcyclopropanamine, 2 hydrochloride

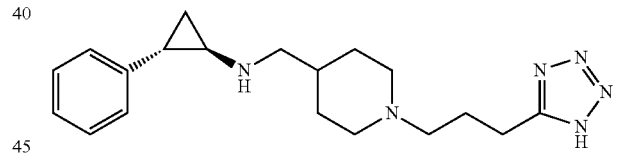

Step 1

N-((1-(3-cyanopropyl)piperidin-4-yl)methyl)-2,2,2-trifluoro-N-(2-phenylcyclopropyl)acetamide Added 4-bromobutanenitrile (100 mg, 0.674 mmol) to a solution of N,N-diisopropylethylamine (0.353 mL, 2.022 mmol), 2,2,2-trifluoro-N-(2-phenylcyclopropyl)-N-(piperidin-4-ylmethyl)acetamide (220 mg, 0.674 mmol) in acetonitrile (25 mL) and heated to reflux for 16 hours. Concentrated on rotovap and the residue was purified via Biotage (0% to 100% EtOAc:Hex; then 0% to 20% MeOH: DCM to get off more product.: 10 g-HP-silica gel column).

Obtained 260 mg (oil). $^1$H NMR (400 MHz, CHLOROFORM-d) δ ppm 1.39-1.53 (m, 5H), 1.70 (d, J=11.37 Hz, 2H), 1.83-1.99 (m, 4H), 2.17 (br. s., 1H), 2.31-2.38 (m, 1H), 2.39-2.48 (m, 2H), 2.59 (br. s., 1H), 2.94-3.08 (m, 3H), 3.35-3.45 (m, 1H), 3.46-3.55 (m, 1H), 7.05 (d, J=7.33 Hz, 2H), 7.19-7.26 (m, 5H), 7.28-7.36 (m, 7H).

Step 2

N-((1-(3-(1H-tetrazol-5-yl)propyl)piperidin-4-methyl)-2,2,2-trifluoro-N-2-phenylcyclopropyl)acetamide A mixture of N-((1-(3-cyanopropyl)piperidin-4-yl)methyl)-2,2,2-trifluoro-N-(2-phenylcyclopropyl)acetamide (260 mg, 0.661 mmol), sodium azide (129 mg, 1.982 mmol), ammonium chloride (159 mg, 2.97 mmol) in N,N-dimethylformamide (DMF) (20 mL) was heated to 110° for 16 hours. Added sodium azide (129 mg, 1.982 mmol) and ammonium chloride (159 mg, 2.97 mmol) and heated to 110° for 16 hours. Concentrated and HPLC purification (reverse phase) was performed. A 7 minute gradient was run (10% AcCN/H$_2$O, 0.1% Formic Acid to 50% ACN/H$_2$O, 0.1% Formic Acid). Obtained 36 mg N20984-94-2(oil) [M+H]$^+$=437.3

Step 3

(trans)-N-((1-(3-(1H-Tetrazol-5-yl)propyl)piperidin-4-yl)methyl)-2-phenylcyclopropanamine, 2 hydrochloride A solution of N-((1-(3-(1H-tetrazol-5-yl)propyl)piperidin-4-yl)methyl)-2,2,2-trifluoro-N-((trans)-2-phenylcyclopropyl)acetamide (36 mg, 0.082 mmol), 1N sodium hydroxide (1 mL, 1.000 mmol) in methanol (5 mL) was stirred at RT for 45 minutes. Concentrated and HPLC purification (reverse phase) was performed. A 7 minute gradient was run (0% AcCN/H$_2$O, 0.1% Formic Acid to 20% ACN/H$_2$O, 0.1% Formic Acid). Added 1 ml of 1N HCl to fractions containing product and concentrated. Obtained 25 mg $^1$H NMR (400 MHz, METHANOL-d$_4$) δ ppm 1.41 (q, J=6.82 Hz, 1H), 1.58-1.83 (m, 3H), 2.08-2.25 (m, 3H), 2.27-2.40 (m, 2H), 2.62 (ddd, J=10.11, 6.57, 3.54 Hz, 1H), 3.00-3.16 (m, 5H), 3.22 (d, J=6.57 Hz, 2H), 3.70 (d, J=11.87 Hz, 2H), 7.18-7.28 (m, 3H), 7.29-7.38 (m, 2H).

Example 130

4-((4-(2-(((trans)-2-Phenylcyclopropyl)amino)ethyl)piperidin-1-yl)methyl)benzoic acid

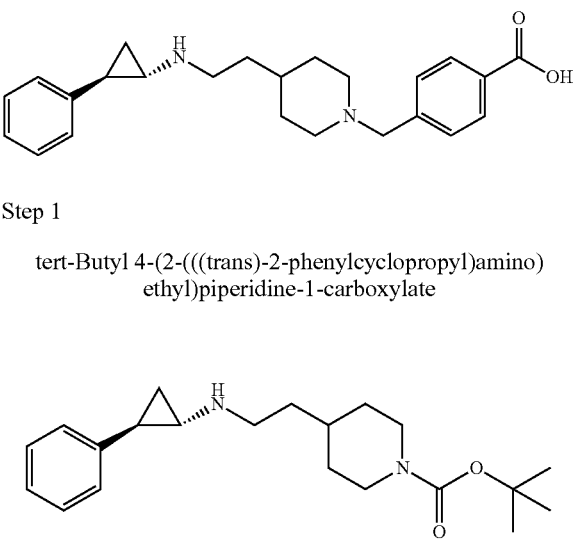

Step 1 tert-Butyl 4-(2-(((trans)-2-phenylcyclopropyl)amino)ethyl)piperidine-1-carboxylate To a solution of tert-butyl 4-(2-oxoethyl)piperidine-1-carboxylate (1 g, 4.40 mmol) in methanol (15 mL) were added (trans)-2-phenylcyclopropanamine (0.762 g, 5.72 mmol) and acetic acid (0.252 mL, 4.40 mmol), and the mixture was stirred at room temperature for 1 h. Sodium cyanoborohydride (0.415 g, 6.60 mmol) was added and the mixture was stirred at room temperature for 18 h. The reaction was quenched with water (10 mL) and the mixture was concentrated to remove methanol. The resulting aqueous layer was extracted with DCM (3×). The DCM extract was washed with 10% HOAc aqueous solution, dried (Na$_2$SO$_4$) and concentrated. The residue was purified using column chromatography (silica gel, 0 to 100% EtOAc/hexanes) to give 720 mg of product as pale yellow oil. MS: (M+H)$^+$=345.4. $^1$H NMR (400 MHz, CHLOROFORM-d) δ ppm 0.94-1.75 (m, 18H), 1.86-1.95 (m, 1H), 2.35 (dt, J=7.01, 3.69 Hz, 1H), 2.60-2.86 (m, 4H), 4.08 (br. s., 2H), 6.91-7.38 (m, 5H).

Step 2 tert-Butyl 4-(2-(2,2,2-trifluoro-N-((trans)-2-phenylcyclopropyl)acetamido)ethyl)piperidine-1-carboxylate

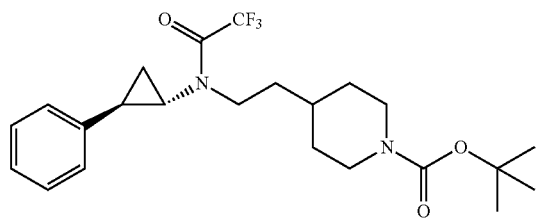 [SMILES: CC(C)(C)OC(=O)N1CCC(CCN(C(=O)C(F)(F)F)[C@H]2C[C@@H]2c2ccccc2)CC1]

To a solution of tert-butyl 4-(2-((trans-2-phenylcyclopropyl)amino)ethyl)piperidine-1-carboxylate (711 mg, 2.064 mmol) in chloroform (10 mL) were added triethylamine (0.863 mL, 6.19 mmol) and trifluoroacetic anhydride (0.379 mL, 2.68 mmol), and the mixture was stirred at room temperature for 1 h. The reaction mixture was diluted with DCM (20 mL) and washed with 10% NaHCO$_3$ aqueous solution. The organic layer was dried (Na$_2$SO$_4$) and concentrated to give 890 mg of product as oil. MS: (M+H)$^+$=441.3. $^1$H NMR (400 MHz, CHLOROFORM-d) δ ppm 1.03-1.22 (m, 2H), 1.28-1.39 (m, 3H), 1.39-1.80 (m, 13H), 2.21-2.42 (m, 1H), 2.69 (br. s., 2H), 3.01-3.23 (m, 2H), 3.33-3.66 (m, 2H), 4.09 (br. s., 2H), 7.00-7.12 (m, 1H), 7.16-7.40 (m, 4H).

Step 3

2,2,2-Trifluoro-N-((trans)-2-phenylcyclopropyl)-N-(2-(piperidin-4-yl)ethyl)acetamide

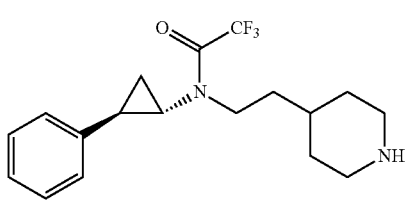 [SMILES: O=C(N(CCC1CCNCC1)[C@H]1C[C@@H]1c1ccccc1)C(F)(F)F]

To a solution of tert-butyl 4-(2-(2,2,2-trifluoro-N-(trans-2-phenylcyclopropyl)acetamido)ethyl)piperidine-1-carboxylate (650 mg, 1.476 mmol) in dichloromethane (DCM) (4 mL) was added TFA (1 mL, 12.98 mmol), and the mixture was stirred at room temperature for 1.5 h. The mixture was concentrated and the residue was dissolved in DCM (20 mL). The resulting solution was washed with 10% NaHCO$_3$ aqueous solution. The organic phase was collected and dried (Na$_2$SO$_4$) and concentrated. The residue was dried under vacuum to give 470 mg of product as oil. MS: (M+H)$^+$=341.4. $^1$H NMR (400 MHz, METHANOL-d$_4$) δ ppm 1.33-1.79 (m, 7H), 1.93-2.10 (m, 2H), 2.27-2.59 (m, 1H), 2.84-3.06 (m, 2H), 3.15-3.25 (m, 1H), 3.66 (t, J=7.20 Hz, 2H), 7.09-7.41 (m, 5H).

Step 4

4-((4-(2-(((trans)-2-phenylcyclopropyl)amino)ethyl) piperidin-1-yl)methyl)benzoic acid

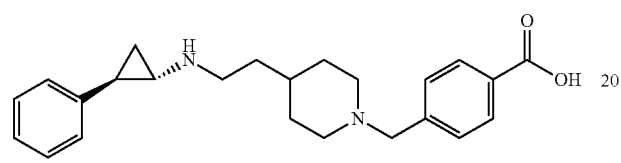

To a solution of 2,2,2-trifluoro-N-(trans-2-phenylcyclopropyl)-N-(2-(piperidin-4-yl)ethyl)acetamide (126 mg, 0.370 mmol) in 1,2-dichloroethane (DCE) (2 mL) were added 4-formylbenzoic acid (66.7 mg, 0.444 mmol) and sodium triacetoxyborohydride (157 mg, 0.740 mmol), and the mixture was stirred at room temperature for 18 h. The mixture was quenched with water (2 mL) and extracted with DCM (3×). The extract was dried (Na$_2$SO$_4$) and concentrated. The residue was dissolved into methanol (2 ml) and 1N NaOH aqueous solution (2 mL) was added. The mixture was stirred at room temperature for 1 h and concentrated. The residue was treated with MeOH (3 mL) and filtered. The filtrate was purified using reverse-phase HPLC under the acidic conditions. The resulting TFA salt of the product was treated with 1N HCl and concentrated. The residue was further dried under vacuum to give 87 mg of product as white solid (HCl salt). MS: (M+H)$^+$=379.4. $^1$H NMR (400 MHz, DMSO-d$_6$) δ ppm 1.25 (q, 1H), 1.46-1.67 (m, 5H), 1.82 (br. s., 2H), 2.87 (br. s., 3H), 3.05 (br. s., 2H), 3.30 (br. s., 2H), 4.34 (d, J=3.79 Hz, 2H), 7.10-7.40 (m, 5H), 7.74 (d, J=8.08 Hz, 2H), 8.00 (d, J=7.83 Hz, 2H), 9.53 (br. s., 2H).

Example 131

2,2-Dimethyl-3-(4-((((trans)-2-phenylcyclopropyl) amino)methyl)piperidin-1-yl)propanoic acid

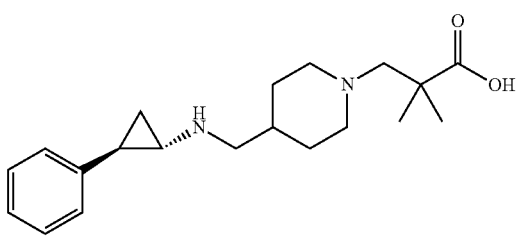 [SMILES: CC(C)(CN1CCC(CN[C@H]2C[C@@H]2c2ccccc2)CC1)C(=O)O]

To a solution of 2,2,2-trifluoro-N-(trans-2-phenylcyclopropyl)-N-(piperidin-4-ylmethyl)acetamide (130 mg, 0.398 mmol) in 1,2-dichloroethane (DCE) (2 mL) were added methyl 2,2-dimethyl-3-oxopropanoate in iodobenzene (160 mg, 0.478 mmol) and sodium triacetoxyborohydride (118 mg, 0.558 mmol), and the reaction mixture was stirred for 18 h. Additional methyl 2,2-dimethyl-3-oxopropanoate in iodobenzene (320 mg) and sodium triacetoxyborohydride (236 mg) were added and the mixture was stirred at rt for 2 h. The mixture was quenched with water (2 mL) and extracted with DCM (3×). The extract was dried (Na$_2$SO$_4$) and concentrated. The residue was dissolved in methanol (2.000 mL) and sodium hydroxide (3M, 0.664 mL, 1.992 mmol) was added. The mixture was stirred at rt for 18 h and concentrated. The residue was treated with methanol and filtered. The filtrate was purified using reverse-phase HPLC under the acidic conditions. The resulting TFA salt was treated with ACN (1 mL) and 1N HCl aqueous solution and concentrated to give 64 mg of product as off-white solid (HCl salt). MS: (M+H)$^+$=311.4. $^1$H NMR (400 MHz, DMSO-d$_6$) δ ppm 1.19-1.34 (m, 7H), 1.59-1.83 (m, 3H), 1.98 (br. s., 3H), 2.58-2.74 (m, 1H), 2.85-3.24 (m, 7H), 3.42 (br. s., 2H), 7.08-7.43 (m, 5H).

Example 132

6-((4-((((trans)-2-Phenylcyclopropyl)amino)methyl) piperidin-1-yl)methyl)nicotinic acid

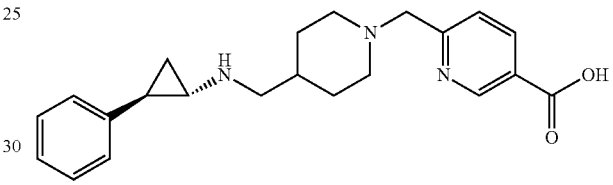

To a solution 2,2,2-trifluoro-N-(trans-2-phenylcyclopropyl)-N-(piperidin-4-ylmethyl)acetamide (130 mg, 0.398 mmol) in 1,2-dichloroethane (DCE) (2 mL) were added methyl 6-formylnicotinate (86 mg, 0.518 mmol) and sodium triacetoxyborohydride (127 mg, 0.598 mmol), and the reaction mixture was stirred at room temperature for 18 h. The mixture was quenched with water (2 mL) and extracted with DCM (3×). The extract was dried (Na$_2$SO$_4$) and concentrated to give a crude product. The product was dissolved in methanol (2.000 mL) and sodium hydroxide (3M, 0.664 mL, 1.992 mmol) was added. The mixture was stirred at room temperature for 3 h and concentrated. The residue was treated with methanol and filtered. The filtrate was purified using reverse-phase HPLC under the acidic conditions to give 110 mg of product as pale yellow solid (HCl salt). MS: (M+H)$^+$=366.4. $^1$H NMR (400 MHz, DMSO-d$_6$) δ ppm 1.24 (m, 1H),1.54-1.73 (m, 3H), 1.98-2.12 (m, 3H), 2.59-2.72 (m, 1H), 2.94 (m, 4H), 3.45 (br. s., 2H), 4.54 (br. s., 2H), 7.16-7.25 (m, 3H), 7.27-7.35 (m, 2H), 7.81 (d, J=8.08 Hz, 1H), 8.38 (dd, J=8.08, 2.27 Hz, 1H), 9.12 (d, J=1.52 Hz, 1H), 9.78 (br. s., 2H), 10.72 (br. s., 1H).

Example 133

2-(4-((4-((((trans)-2-Phenylcyclopropyl)amino)methyl)piperidin-1-yl)methyl)phenyl)acetic acid

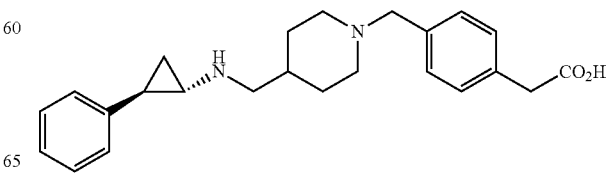

To a solution of 2,2,2-trifluoro-N-(trans-2-phenylcyclopropyl)-N-(piperidin-4-ylmethyl)acetamide (120 mg, 0.368 mmol) in 1,2-dichloroethane (DCE) (2 mL) were added 2-(4-formylphenyl)acetic acid (78 mg, 0.478 mmol) and sodium triacetoxyborohydride (117 mg, 0.552 mmol), and the reaction mixture was stirred at room temperature for 18 h. The mixture was quenched residue was dissolved in methanol (2.0 mL) and sodium hydroxide (2 mL, 2.0 mmol) was added. The mixture was stirred at room temperature for 3 h and concentrated. The residue was treated with methanol and filtered. The filtrate was purified using reverse-phase HPLC under the acidic conditions to give a TFA salt of the product. The TFA salt was then dissolved into ACN (2 mL) and treated with 1N HCl (aq.) and concentrated. The residue was further dried under vacuum to give 61 mg of product (HCl salt) as off-white solid. MS: (M+H)$^+$=379.4. $^1$H NMR (400 MHz, DMSO-d$_6$) δ ppm 1.17-1.33 (m, 1H), 1.50-1.71 (m, 3H), 1.92-2.10 (m, 3H), 2.58 (m, 1H), 2.81-3.16 (m, 4H), 3.62 (m, 2H), 4.23 (m, 2H), 7.15-7.26 (m, 3H), 7.27-7.39 (m, 4H), 7.54 (d, J=8.08 Hz, 2H), 9.59 (br. s., 2H), 10.68 (br. s., 1H).

Example 134

2-((4-(((((trans)-2-Phenylcyclopropyl)amino)methyl)piperidin-1-yl)methyl)oxazole-4-carboxylic acid

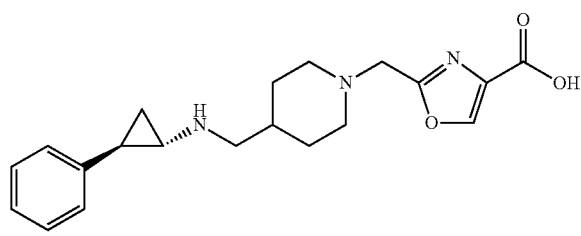 [SMILES: O=C(O)c1coc(CN2CCC(CN[C@H]3C[C@@H]3c3ccccc3)CC2)n1]

To a solution of 2,2,2-trifluoro-N-(trans-2-phenylcyclopropyl)-N-(piperidin-4-ylmethyl)acetamide (100 mg, 0.306 mmol) in 1,2-dichloroethane (DCE) (2 mL) were added ethyl 2-formyloxazole-4-carboxylate (67.4 mg, 0.398 mmol) and sodium triacetoxyborohydride (97 mg, 0.460 mmol), and the mixture was stirred at room temperature for 18 h. The mixture was quenched with water (2 mL) and extracted with DCM (3×). The extract was dried (Na$_2$SO$_4$) and concentrated. The residue was dissolved in methanol (2.0 mL) and sodium hydroxide (1 mL, 1.0 mmol) was added. The mixture was stirred at room temperature for 3 h and concentrated. The residue was treated with methanol and filtered. The filtrate was purified using reverse-phase HPLC under the acidic conditions to a TFA salt of the product. The TFA salt was treated with ACN (1 mL) and 1NHCl (0.5 mL) and concentrated. The residue was dried under vacuum to give 75 mg of product (HCl salt) as off-white solid. MS: (M+H)$^+$=356.2. $^1$H NMR (400 MHz, METHANOL-d$_4$) δ ppm 1.42 (q, 1H), 1.54-1.85 (m, 3H), 2.10-2.30 (m, 3H), 2.60 (ddd, J=10.36, 6.69, 3.66 Hz, 1H), 3.04 (dt, J=7.58, 4.04 Hz, 1H), 3.72-3.86 (m, 2H), 4.69 (s, 2H), 7.11-7.44 (m, 5H), 8.60-8.78 (m, 1H).

Example 135

2-(4-((4-(((((trans)-2-phenylcyclopropyl)amino)methyl)piperidin-1-yl)methyl)phenoxy)acetic acid

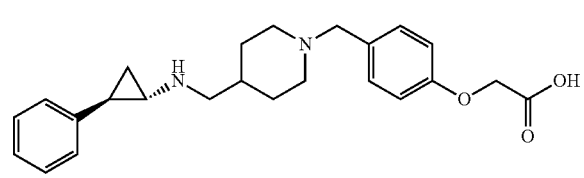 [SMILES: O=C(O)COc1ccc(CN2CCC(CN[C@H]3C[C@@H]3c3ccccc3)CC2)cc1]

Step 1

Methyl 2-(4-((4-((2,2,2-trifluoro-N-((trans)-2-phenylcyclopropyl)acetamido)methyl)piperidin-1-yl)methyl)phenoxy)acetate To a solution of 2,2,2-trifluoro-N-((trans-2-phenylcyclopropyl)-N-(piperidin-4-ylmethyl)acetamide (100 mg, 0.306 mmol) in 1,2-Dichloroethane (DCE) (2 mL) were added methyl 2-(4-formylphenoxy)acetate (71.4 mg, 0.368 mmol) and sodium triacetoxyborohydride (97 mg, 0.460 mmol), and the mixture was stirred at room temperature for 18 h. The reaction was quenched with water (3 mL) and extracted with DCM (3×). The extract was dried (Na$_2$SO$_4$) and concentrated. The residue was purified using column chromatography (silica gel, 0 to 100% EtOAc/hexanes) to give 86 mg of product as pale yellow oil. MS: (M+H)$^+$=505.3. $^1$H NMR (400 MHz, METHANOL-d$_4$) δ ppm 1.27-1.52 (m, 3H), 1.54-1.75 (m, 3H), 1.76-1.91 (m, 1H), 1.94-2.13 (m, 2H), 2.40-2.52 (m, 1H), 2.92 (br. s., 2H), 3.08-3.19 (m, 1H), 3.39-3.61 (m, 4H), 3.77-3.86 (m, 3H), 6.90 (d, J=8.59 Hz, 2H), 7.08-7.37 (m, 7H).

Step 2

2-(4-((4-(((((trans)-2-phenylcyclopropyl)amino)methyl)piperidin-1-yl)methyl)phenoxy)acetic acid To a solution of methyl 2-(4-((4-((2,2,2-trifluoro-N-(trans-2-phenylcyclopropyl)acetamido)methyl)piperidin-1-yl)methyl)phenoxy)acetate (84 mg, 0.166 mmol) in methanol (2 mL) was added sodium hydroxide (1M, 1 mL, 1.000 mmol), and the mixture was stirred at room temperature for 3 h. The mixture was then purified using reverse-phase HPLC under the acidic conditions to give a TFA salt of the product. The TFA salt was then dissolved into ACN (2 mL) and treated with 1N HCl (aq.) and concentrated. The residue was further dried under vacuum to give 56 mg of product (HCl salt) as white solid. MS: (M+H)$^+$=395.3. $^1$H NMR (400 MHz, METHANOL-d$_4$) δ ppm 1.37-1.50 (m, 1H), 1.59 (m, 3H), 2.02-2.19 (m, 3H), 2.58 (m, 1H), 2.98-3.11 (m, 3H), 3.20 (m, 2H), 3.51-3.60 (m, 2H), 4.29 (s, 2H), 4.75 (s, 2H), 7.04-7.09 (m, 2H), 7.18-7.29 (m, 3H), 7.30-7.36 (m, 2H), 7.45-7.55 (m, 2H).

Example 136

N-(Methylsulfonyl)-4-((4-(((((trans)-2-phenylcyclopropyl)amino)methyl)piperidin-1-yl)methyl)benzamide

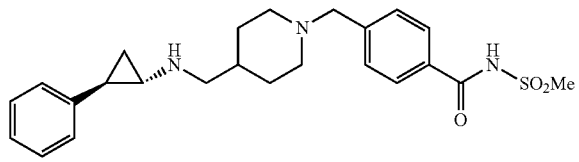 [SMILES: CS(=O)(=O)NC(=O)c1ccc(CN2CCC(CN[C@H]3C[C@@H]3c3ccccc3)CC2)cc1]

Step 1

4-((4-((2,2,2-trifluoro-N-((trans)-2-phenylcyclopropyl)acetamido)methyl)piperidin-1-yl)methyl)benzoic acid To a solution of 2,2,2-trifluoro-N-((1S,2R)-2-phenylcyclopropyl)-N-(piperidin-4-ylmethyl)acetamide (243 mg, 0.745 mmol) in 1,2-dichloroethane (DCE) (4 mL) were added 4-formylbenzoic acid (134 mg, 0.894 mmol) and sodium triacetoxyborohydride (252 mg, 1.191 mmol), and the mixture was stirred at room temperature for 18 h. The reaction was quenched with water (4 mL) and extracted with $CH_2Cl_2$ (3×). The extract was dried ($Na_2SO_4$) and concentrated. The residue was purified using column chromatography (silica gel, 0 to 5% MeOH/EtOAc) to give 180 mg of product as pale yellow solid. MS: $(M+H)^+$=461.3. $^1H$ NMR (400 MHz, DMSO-$d_6$) δ ppm 1.12-1.32 (m, 2H), 1.35-1.47 (m, 1H),1.53-1.82 (m, 3H), 1.88-2.05 (m, 2H), 2.81 (br. s., 2H), 3.09-3.22 (m, 2H), 3.26-3.41 (m, 2H), 3.27-3.43 (m, 2H), 7.09-7.35 (m, 5H), 7.39-7.50 (m, 2H), 7.86-7.94 (m, 2H).

Step 2

N-(methylsulfonyl)-4-((4-((2,2,2-trifluoro-N-((trans)-2-phenylcyclopropyl)acetamido)methyl)piperidine-1-yl)methyl)benzamide To a solution of 4-((4-((2,2,2-trifluoro-N-(trans-2-phenylcyclopropyl)acetamido)methyl)piperidin-1-yl)methyl)benzoic acid (150 mg, 0.326 mmol) in N,N-dimethylformamide (DMF) (2 mL) were added methanesulfonamide (37.2 mg, 0.391 mmol), EDC (74.9 mg, 0.391 mmol) and DMAP (39.8 mg, 0.326 mmol), and the mixture was stirred at room temperature for 18 h. The reaction was quenched with 10% $NH_4Cl$ aqueous solution and extracted with EtOAc(3×). The extract was dried ($Na_2SO_4$) and concentrated. The residue was purified using column chromatography (silica gel, 0 to 100% EtOAc/hexaens) to give 82 mg of product as off-white solid. MS: $(M+H)^+$=538.3. $^1H$ NMR (400 MHz, METHANOL-$d_4$) δ ppm 1.38-1.74 (m, 4H), 1.91-2.22 (m, 3H), 2.47 (m, 1H), 2.98-3.11 (m, 2H), 3.21 (d, J=6.82 Hz, 1H), 3.37-3.66 (m, 7H), 4.39 (s, 2H), 7.04-7.38 (m, 5H), 7.67 (d, J=8.34 Hz, 2H), 8.03 (d, J=8.08 Hz, 2H).

Step 3

N-(Methylsulfonyl)-4-((4-(((((trans)-2-phenylcyclopropyl)amino)methyl)piperidin-1-yl)methyl)benzamide To a solution of N-(methylsulfonyl)-4-((4-((2,2,2-trifluoro-N-(trans-2-phenylcyclopropyl)acetamido)methyl)piperidin-1-yl)methyl)benzamide (80 mg, 0.149 mmol) in methanol (2 mL) was added sodium hydroxide (6M, 0.5 mL, 0.500 mmol), and the mixture was stirred at room temperature for 2 h. The mixture was purified using reverse-phase HPLC under the acidic conditions and the fractions containing the product was treated with 1N HCl and concentrated. The residue was dried under vacuum to give 36 mg of product as pale yellow solid. MS: $(M+H)^+$=442.3 $^1H$ NMR (400 MHz, DMSO-$d_6$) δ ppm 1.19-1.36 (m, 1H), 1.48-1.72 (m, 3H), 1.91-2.09 (m, 2H), 1.93-2.10 (m, 3H), 2.85-3.26 (m, 5H), 4.30-4.53 (m, 2H), 7.12-7.39 (m, 5H), 7.76 (d, J=8.34 Hz, 2H), 7.71-7.82 (m, 2H), 7.98-8.09 (m, 2H).

Example 137

4-((4-(((((trans)-2-(4-Iodophenyl)cyclopropyl)amino)methyl)piperidin-1-yl)methyl)benzoic acid

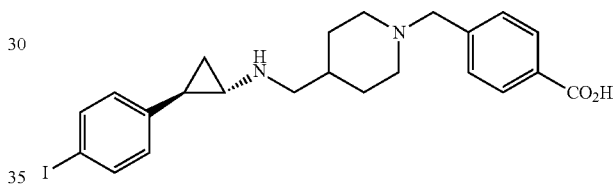

Step 1

Methyl 4-((4-(((trans-2-(4-iodophenyl)cyclopropyl)amino)methyl)piperidin-1-yl)methyl)benzoate To a solution of trans-2-(4-iodophenyl)cyclopropanamine (420 mg, 1.621 mmol) in methanol (7 mL) were added methyl 4-((4-formylpiperidin-1-yl)methyl)benzoate (466 mg, 1.783 mmol), sodium cyanoborohydride (204 mg, 3.24 mmol), and acetic acid (0.028 mL, 0.486 mmol), and the mixture was stirred at room temperature for 18 h. The mixture was then quenched with saturated $NaHCO_3$ aqueous solution (2 ml) and concentrated. The residue was treated with water (4 mL) and extracted with DCM (3×). The extract was dried ($Na_2SO_4$) and concentrated. The residue was purified using column chromatography (silica gel, 0 to 10% MeOH/EtOAc) to give 241 mg of product as pale yellow solid. MS: $(M+H)^+$=505.3 $^1H$ NMR (400 MHz, METHANOL-$d_4$) δ ppm 0.97-1.16 (m, 2H), 1.19-1.38 (m, 2H), 1.46-1.63 (m, 1H), 1.71-1.92 (m, 3H), 2.00-2.10 (m, 2H), 2.29 (ddd, J=7.45, 4.42, 3.28 Hz, 1H), 2.56-2.65 (m, 2H), 2.86-2.98 (m, 2H), 3.56-3.66 (m, 2H), 3.89-3.98 (m, 3H), 6.80-6.92 (m, 2H), 7.43-7.62 (m, 4H), 7.94-8.05 (m, 2H).

Step 2

4-((4-(((((trans)-2-(4-Iodophenyl)cyclopropyl)amino)methyl)piperidin-1-yl)methyl)benzoic acid To a solution of methyl 4-((4-(((trans-2-(4-iodophenyl)cyclopropyl)amino)methyl)piperidin-1-yl)methyl)benzoate (50 mg, 0.099 mmol) in methanol (2 mL) was added sodium hydroxide (6M, 0.5 mL, 0.500 mmol), and the mixture was stirred at room temperature for 18 h. The mixture was purified using reverse-phase HPLC. The fractions containing the product as combined, treated with 1N HCl and concentrated. The residue was dried under vacuum to give 25 mg of product (HCl salt) as yellow solid. MS: (M+H)$^+$=491.3. $^1$H NMR (400 MHz, DMSO-d$_6$) δ ppm 1.19-1.33 (m, 1H), 1.51-1.70 (m, 3H), 1.88-2.09 (m, 3H), 2.96 (br. s., 4H), 3.12 (br. s., 1H), 4.34 (br. s., 2H), 6.98-7.10 (m, 2H), 7.62-7.81 (m, 4H), 8.01 (d, J=8.34 Hz, 2H).

Example 138

4-((trans)-2-(((1-Benzylpiperidin-4-yl)methyl)amino)cyclopropyl)benzoic acid

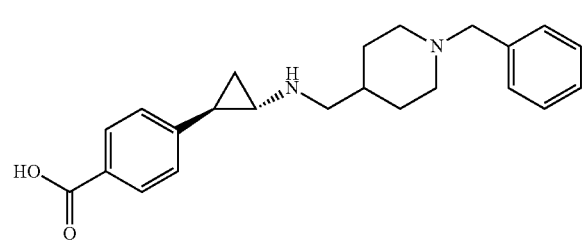 [SMILES: O=C(O)c1ccc([C@H]2C[C@@H]2NCC2CCN(Cc3ccccc3)CC2)cc1]

Step 1 tert-Butyl 4-((((trans)-2-(4-iodophenyl)cyclopropyl)amino)methyl)piperidine-1-carboxylate

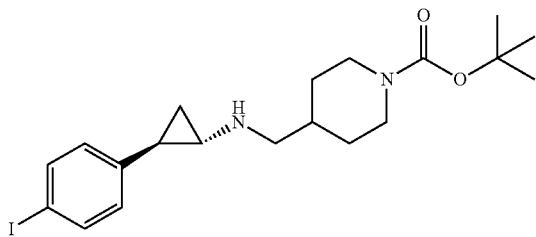 [SMILES: CC(C)(C)OC(=O)N1CCC(CN[C@H]2C[C@@H]2c2ccc(I)cc2)CC1]

To a solution of trans-2-(4-iodophenyl)cyclopropanamine (1.0 g, 3.86 mmol) in methanol (15 mL) were added tert-butyl 4-formylpiperidine-1-carboxylate (0.741 g, 3.47 mmol), acetic acid (0.066 mL, 1.158 mmol), and the mixture was stirred at rt for 1 h. Sodium cyanoborohydride (0.364 g, 5.79 mmol) was added and the mixture was stirred at room temperature for 18 h. The mixture was concentrated and the residue was treated with water (2 mL) and extracted with DCM (3×). The extract was dried (Na$_2$SO$_4$) and concentrated. The residue was purified using column chromatography (silica gel, 0 to 100% EtOAc/hexanes) to give 730 mg of product as pale yellow oil. MS: (M+H)$^+$=457.2. $^1$H NMR (400 MHz, METHANOL-d$_4$) δ ppm 0.99-1.18 (m, 3H), 1.45-1.51 (m, 9H), 1.69-1.81 (m, 3H), 1.87-1.94 (m, 1H), 2.29-2.37 (m, 1H), 2.62-2.90 (m, 3H), 4.00-4.20 (m, 2H), 6.86-6.88 (m, 2H), 7.57-7.59 (m, 2H).

Step 2 tert-Butyl 4-((2,2,2-trifluoro-N-((trans)-2-(4-iodophenyl)cyclopropyl)acetamido) methyl) piperidine-1-carboxylate

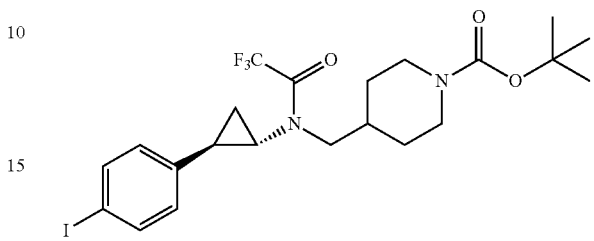

To a solution of tert-butyl 4-(((trans-2-(4-iodophenyl)cyclopropyl)amino)methyl)piperidine-1-carboxylate (730 mg, 1.600 mmol) in chloroform (7 mL) were added triethylamine (0.669 mL, 4.80 mmol) and trifluoroacetic anhydride (0.294 mL, 2.079 mmol) at 0° C., and the mixture was stirred at room temperature for 1 h. The reaction mixture was washed with 10% NaHCO$_3$ aqueous solution and the organic phase was dried (Na$_2$SO$_4$) and concentrated. The residue was purified using column chromatography (silica gel, 0 to 50% EtOAc/hexanes) to give 840 mg of product as pale yellow oil. MS: (M+H)$^+$=553.2. $^1$H NMR (400 MHz, METHANOL-d$_4$) δ ppm 1.05-1.23 (m, 3H), 1.41-1.52 (m, 9H), 1.58-1.75 (m, 3H), 1.91-2.03 (m, 2H), 2.43 (m, 1H), 3.12-3.23 (m, 1H), 3.37-3.48 (m, 1H), 3.53-3.64 (m, 1H), 4.01-4.16 (m, 2H), 6.94 (d, J=8.34 Hz, 2H), 7.59-7.69 (m, 2H).

Step 3

2,2,2-Trifluoro-N-((trans)-2-(4-iodophenyl)cyclopropyl)-N-(piperidin-4-ylmethyl)acetamide

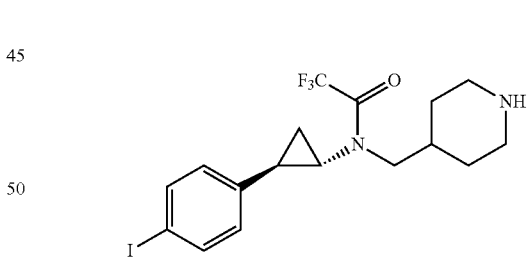

To a solution of tert-butyl 4-((2,2,2-trifluoro-N-((trans-2-(4-iodophenyl)cyclopropyl)acetamido) methyl)piperidine-1-carboxylate (820 mg, 1.485 mmol) in dichloromethane (DCM) (2 mL) was added TFA (500 μl, 6.49 mmol), and the mixture was stirred at room temperature for 2 h. The mixture was concentrated and the residue was treated with saturated NaHCO$_3$ aqueous solution and extracted with DCM (3×). The extract was dried (Na$_2$SO$_4$) and concentrated to give 586 mg of product as pale yellow oil. MS: (M+H)$^+$=453.2. $^1$H NMR (400 MHz, METHANOL-d$_4$) δ ppm 1.35-1.53 (m, 4H), 1.65 (m, 1H), 1.90 (m, 2H), 2.05-2.20 (m, 1H), 2.39-2.52 (m, 1H), 2.91 (m, 3H), 3.17-3.25 (m, 1H), 3.49 (m, 1H), 3.56-3.69 (m, 1H), 6.94 (m, 2H), 7.59-7.70 (m, 2H).

Step 4

N-((1-Benzylpiperidin-4-yl)methyl)-2,2,2-trifluoro-N-((trans)-2-(4-iodophenyl)cyclopropyl)acetamide

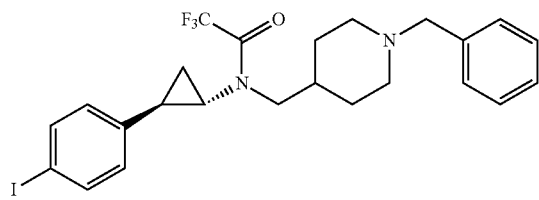 [SMILES: O=C(N(CC1CCN(Cc2ccccc2)CC1)[C@H]1C[C@@H]1c1ccc(I)cc1)C(F)(F)F]

To a solution of 2,2,2-trifluoro-N-((trans)-2-(4-iodophenyl)cyclopropyl)-N-(piperidin-4-ylmethyl)acetamide (250 mg, 0.553 mmol) in 1,2-dichloroethane (DCE) (4 mL) were added benzaldehyde (0.067 mL, 0.663 mmol) and sodium triacetoxyborohydride (176 mg, 0.829 mmol), and the mixture was stirred at room temperature for 18 h. The mixture was quenched with water (4 ml) and extracted with DCM (3×). The extract was dried ($Na_2SO_4$) and concentrated. The residue was purified using column chromatography (silica gel, 0 to 100% EtOAc/hexanes) to give 194 mg of product as pale yellow viscous oil. MS: $(M+H)^+=543.3$. $^1H$ NMR (400 MHz, METHANOL-$d_4$) δ ppm 1.29-1.52 (m, 3H), 1.57-1.93 (m, 4H), 2.04-2.25 (m, 2H), 2.37-2.51 (m, 1H), 2.91-3.22 (m, 3H), 3.40-3.66 (m, 4H), 6.89-7.07 (m, 2H), 7.27-7.40 (m, 5H), 7.64 (d, J=8.34 Hz, 2H).

Step 5

4-(trans-2-(N-((1-Benzylpiperidin-4-yl)methyl)-2,2,2-trifluoroacetamido)cyclopropyl)benzoic acid

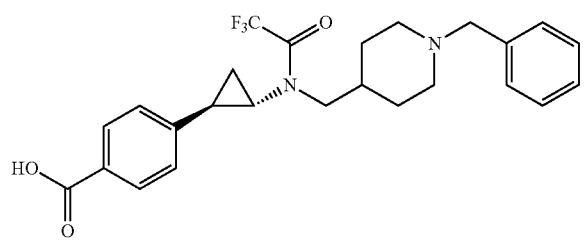 [SMILES: O=C(O)c1ccc([C@H]2C[C@@H]2N(CC2CCN(Cc3ccccc3)CC2)C(=O)C(F)(F)F)cc1]

To a 10-mL of microwave tube were added potassium formate (88 mg, 1.051 mmol), triethylamine (0.098 mL, 0.701 mmol) acetic anhydride (0.066 mL, 0.701 mmol) and DMF (1 mL), the resulting solution was stirred at room temperature for 1 h. N-((1-benzylpiperidin-4-yl)methyl)-2,2,2-trifluoro-N-((trans)-2-(4-iodophenyl)cyclopropyl)acetamide (190 mg, 0.350 mmol), $Pd_2(dba)_3$ (8.02 mg, 8.76 mmol), and lithium chloride (44.6 mg, 1.051 mmol) in DMF (1 mL) were added. The tube was sealed and the mixture was stirred at 80° C. for 4 h. The mixture was concentrated and the residue was taken up in methanol and filtered. The filtrate was purified using reverse-phase HPLC to give 20 mg of product as off-white solid. MS: $(M+H)^+=461.3$. $^1H$ NMR (400 MHz, METHANOL-$d_4$) δ ppm 1.40-1.62 (m, 3H), 1.65-1.78 (m, 1H), 1.87-2.01 (m, 2H), 2.07 (d, J=13.39 Hz, 1H), 2.51-2.62 (m, 1H), 2.80-3.00 (m, 2H), 3.20-3.71 (m, 6H), 4.23 (s, 2H), 7.21 (d, J=8.34 Hz, 2H), 7.42-7.54 (m, 5H), 7.95 (d, J=8.34 Hz, 2H).

Step 6

4-((trans)-2-(((1-Benzylpiperidin-4-yl)methyl)amino)cyclopropyl)benzoic acid

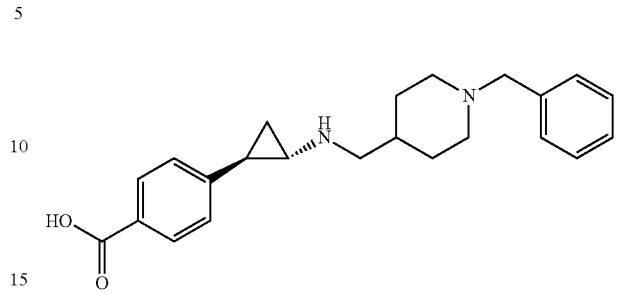

To a solution of 4-(trans-2-(N-((1-benzylpiperidin-4-yl)methyl)-2,2,2-trifluoroacetamido)cyclopropyl)benzoic acid (18 mg, 0.039 mmol) in methanol (1 mL) was added sodium hydroxide (1M, 0.5 mL, 0.500 mmol) and the mixture was stirred at room temperature for 2 h. The mixture was concentrated and the residue was purified using reverse-phase HPLC under the acidic conditions. The fractions containing the product were combined, treated with 1N HCl, and concentrated. The residue was dried under vacuum to give 9 mg of product (HCl salt) as off white solid. MS: $(M+H)^+=365.2$. $^1H$ NMR (400 MHz, METHANOL-$d_4$) δ ppm 1.50 (q, 1H), 1.59-1.77 (m, 3H), 2.14 (br. s., 3H), 2.63-2.74 (m, 1H), 3.03-3.26 (m, 5H), 3.55 (br. s., 2H), 4.36 (s, 2H), 7.32 (d, J=8.34 Hz, 2H), 7.49-7.62 (m, 5H), 7.99 (d, J=8.34 Hz, 2H).

Example 139

4-((4-((((trans)-2-(4-(1-Methyl-1H-pyrazol-4-yl)phenyl)cyclopropyl)amino)methyl)piperidin-1-yl)methyl)benzoic acid

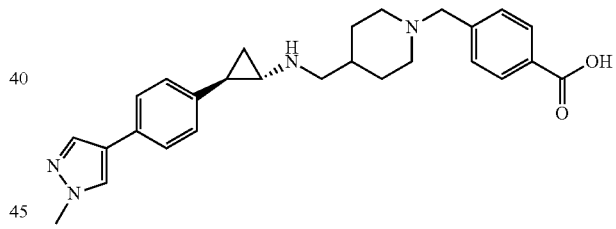

Step 1 tert-Butyl 4-((2,2,2-trifluoro-N-((trans)-2-(4-(1-methyl-1H-pyrazol-4-yl)phenyl)cyclopropyl)acetamido)methyl)piperidine-1-carboxylate

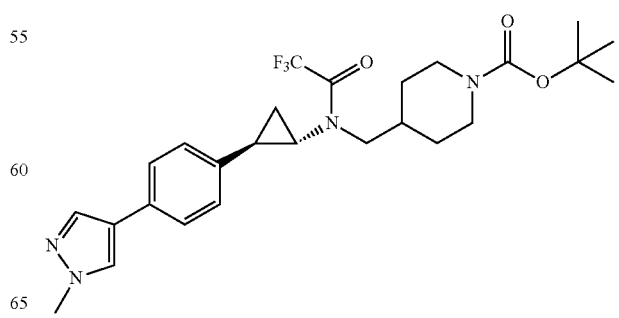

To a 10-mL microwave tube were added tert-butyl 4-((2,2,2-trifluoro-N-(trans-2-(4-iodophenyl)cyclopropyl)acetamido)methyl)piperidine-1-carboxylate (300 mg, 0.543 mmol), 1-methyl-4-(4,4,5,5-tetramethyl-1,3,2-dioxaborolan-2-yl)-1H-pyrazole (136 mg, 0.652 mmol), potassium carbonate (263 mg, 1.901 mmol), acetonitrile (2 mL) and water (0.500 mL), and the mixture was degassed by bubbling $N_2$ through. Tetrakis (31.4 mg, 0.027 mmol) was added and the tube was sealed. The mixture was stirred at 85° C. for 4 h. The mixture was cooled and concentrated. The residue was purified using column chromatography (silica gel, 0 to 100% EtOAc/hexanes) to give 120 mg of product as pale yellow solid. MS: (M+H)$^+$=507.5. $^1$H NMR (400 MHz, METHANOL-$d_4$) δ ppm 1.08-1.20 (m, 2H), 1.43-1.54 (m, 10H), 1.57-1.78 (m, 3H), 1.95-2.10 (m, 2H), 2.40-2.86 (m, 3H), 3.16 (d, J=3.54 Hz, 1H), 3.38-3.63 (m, 2H), 3.90-3.98 (m, 3H), 4.00-4.19 (m, 2H), 7.09-7.18 (m, 2H), 7.46-7.55 (m, 2H), 7.77-7.84 (m, 1H), 7.90-7.97 (m, 1H).

Step 2

2,2,2-Trifluoro-N-((trans)-2-(4-(1-methyl-1H-pyrazol-4-yl)phenyl)cyclopropyl)-N-(piperidin-4-ylmethyl)acetamide

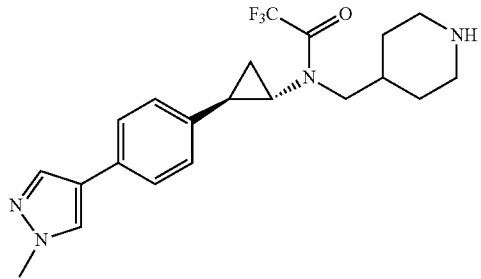 [SMILES: Cn1cc(-c2ccc([C@H]3C[C@@H]3N(CC3CCNCC3)C(=O)C(F)(F)F)cc2)cn1]

To a solution of tert-butyl 4-((2,2,2-trifluoro-N-(trans-2-(4-(1-methyl-1H-pyrazol-4-yl)phenyl)cyclopropyl)acetamido)methyl)piperidine-1-carboxylate (110 mg, 0.217 mmol) in dichloromethane (DCM) (2 mL) was added TFA (0.5 mL, 6.49 mmol), and the mixture was stirred at room temperature for 3 h. The mixture was concentrated and the residue was treated with saturated NaHCO$_3$ aqueous solution and extracted with DCM (3×). The extract was dried (Na$_2$SO$_4$) and concentrated to give 85 mg of product as pale yellow solid. MS: (M+H)$^+$=407.2. $^1$H NMR (400 MHz, METHANOL-$d_4$) δ ppm 1.41-1.54 (m, 2H), 1.58-1.81 (m, 3H), 2.40-2.52 (m, 1H), 2.56-2.69 (m, 2H), 3.06-3.20 (m, 3H), 3.44-3.62 (m, 2H), 3.92-3.97 (m, 3H), 7.13 (d, J=8.34 Hz, 2H), 7.47-7.52 (m, 2H), 7.77-7.82 (m, 1H), 7.92-7.96 (m, 1H).

Step 3

Methyl 4-((4-((2,2,2-trifluoro-N-((trans)-2-(4-(1-methyl-1H-pyrazol-4-yl)phenyl)cyclopropyl)acetamido)methyl)piperidin-1-yl)methyl)benzoate

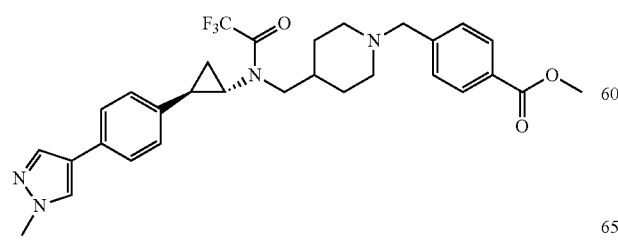

To a solution of 2,2,2-trifluoro-N-(trans-2-(4-(1-methyl-1H-pyrazol-4-yl)phenyl)cyclopropyl)-N-(piperidin-4-ylmethyl)acetamide (85 mg, 0.209 mmol) in 1,2-dichloroethane (DCE) (2 mL) were added methyl 4-formylbenzoate (41.2 mg, 0.251 mmol) and sodium triacetoxyborohydride (75 mg, 0.356 mmol), and the mixture was stirred at room temperature for 18 h. The mixture was quenched with water (3 mL) and extracted with DCM (3×). The extract was dried (Na$_2$SO$_4$) and concentrated. The residue was purified using column chromatography (silica gel, 0 to 100% EtOAc/hexanes) to give 68 mg of product as off-white solid. MS: (M+H)$^+$=555.3. $^1$H NMR (400 MHz, METHANOL-$d_4$) δ ppm 1.28-1.53 (m, 4H), 1.56-1.76 (m, 3H), 1.80-1.96 (m, 1H), 1.98-2.11 (m, 3H), 2.44 (br. s., 1H), 2.75-2.97 (m, 3H), 3.09-3.19 (m, 1H), 7.12 (d, J=8.08 Hz, 2H), 7.41-7.55 (m, 5H), 7.91-8.03 (m, 3H)

Step 4

4-((4-(((((trans)-2-(4-(1-Methyl-1H-pyrazol-4-yl)phenyl)cyclopropyl)amino)methyl)piperidin-1-yl)methyl)benzoic acid

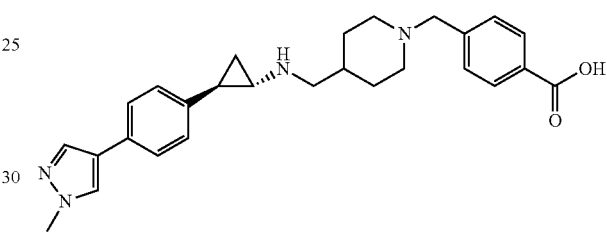

To a solution of methyl 4-((4-((2,2,2-trifluoro-N-(trans-2-(4-(1-methyl-1H-pyrazol-4-yl)phenyl)cyclopropyl)acetamido)methyl)piperidin-1-yl)methyl)benzoate (67 mg, 0.121 mmol) in methanol (2 mL) was added sodium hydroxide (1M, 0.5 mL, 0.500 mmol), and the mixture was stirred at r room temperature for 18 h. The mixture was purified using reverse-phase HPLC. The fractions containing the product as combined, treated with 1N HCl and concentrated. The residue was dried under vacuum to give 25 mg of product (HCl salt) as white solid. MS: (M+H)$^+$=445.4. $^1$H NMR (400 MHz, DMSO-$d_6$) δ ppm 1.19-1.37 (m, 1H), 1.51-1.72 (m, 3H), 1.88-2.13 (m, 3H), 2.55-2.65 (m, 1H), 2.85-3.05 (m, 4H), 3.12-3.25 (m, 1H), 3.34 (d, J=11.87 Hz, 2H), 4.34 (d, J=5.05 Hz, 2H), 7.11-7.23 (m, 2H), 7.45-7.55 (m, 2H), 7.71-7.81 (m, 2H), 7.83-7.89 (m, 1H), 7.97-8.06 (m, 2H), 8.10-8.18 (m, 1H).

Example 140

4-((4-(((((trans)-2-(4-Cyclopropylphenyl)cyclopropyl)amino)methyl)piperidin-1-yl)methyl)benzoic acid

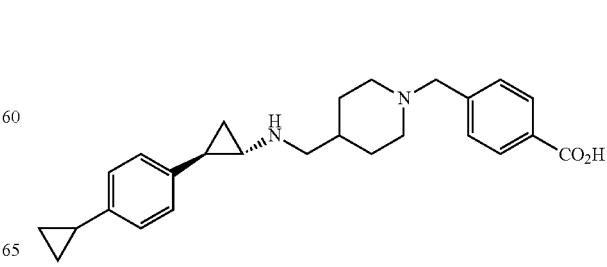

Step 1 tert-Butyl ((trans)-2-(4-cyclopropylphenyl)cyclopropyl)carbamate

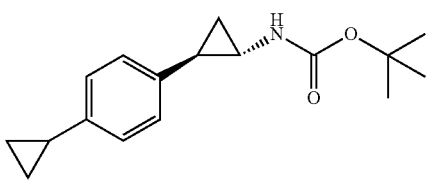 [SMILES: CC(C)(C)OC(=O)N[C@H]1C[C@@H]1c1ccc(C2CC2)cc1]

To a 30-mL microwave tube were added tert-butyl (trans-2-(4-bromophenyl)cyclopropyl)carbamate (400 mg, 1.281 mmol), cyclopropylboronic acid (143 mg, 1.666 mmol), potassium phosphate (952 mg, 4.48 mmol), tricyclohexylphosphine (35.9 mg, 0.128 mmol), toluene (4 mL) and water (0.2 mL), and the mixture was degassed by bubbling $N_2$. Palladium(II) acetate (14.38 mg, 0.064 mmol) was added and the tube was sealed. The mixture was heated at 100° C. with stirring for 4 h. The mixture was cooled and quenched with water (5 mL) and extracted with EtOAc (3×). The extract was dried ($Na_2SO_4$) and concentrated. The residue was purified using column chromatography (silica gel, 0 to 70% EtOAc/hexanes) to give 267 mg of product as pale yellow solid. MS: $(M+H)^+=274.2$. $^1$H NMR (400 MHz, CHLOROFORM-d) δ ppm 0.61-0.73 (m, 2H), 0.90-1.01 (m, 2H), 1.08-1.24 (m, 2H), 1.42-1.52 (s, 9H), 1.81-1.94 (m, 1H), 1.98-2.12 (m, 1H), 2.70 (br. s., 1H), 6.91-7.12 (m, 4H).

Step 2

(trans)-2-(4-cyclopropylphenyl)cyclopropanamine

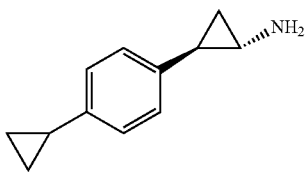 [SMILES: N[C@H]1C[C@@H]1c1ccc(C2CC2)cc1]

To a solution of tert-butyl (trans-2-(4-cyclopropylphenyl)cyclopropyl)carbamate (260 mg, 0.951 mmol) in dichloromethane (DCM) (3 mL) was added TFA (500 µL, 6.49 mmol) and the mixture was stirred at room temperature for 3 h. The mixture was concentrated and the residue was treated with saturated $NaHCO_3$ aqueous solution and extracted with DCM (3×). The extract was dried ($Na_2SO_4$) and concentrated to give 148 mg of product as pale yellow oil. MS: $(M+H)^+=174.1$. $^1$H NMR (400 MHz, METHANOL-$d_4$) δ ppm 0.57-0.70 (m, 2H), 0.86-1.04 (m, 4H), 1.78-1.93 (m, 2H), 2.37-2.48 (m, 1H), 6.86-7.00 (m, 4H).

Step 3

Methyl 4-((4-((((trans)-2-(4-cyclopropylphenyl)cyclopropyl)amino)methyl)piperidin-1-yl)methyl)benzoate

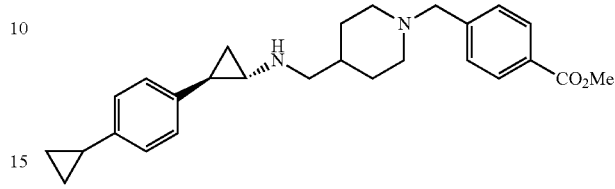

To a solution of trans-2-(4-cyclopropylphenyl)cyclopropanamine (90 mg, 0.519 mmol) in methanol (2 mL) were added methyl 4-((4-formylpiperidin-1-yl)methyl)benzoate (156 mg, 0.597 mmol) and acetic acid (8.92 µL, 0.156 mmol), and the mixture was stirred at room temperature for 1 h. Sodium cyanoborohydride (52.2 mg, 0.831 mmol) was added and the mixture was stirred at room temperature for 18 h. The reaction was quenched with 10% $NaHCO_3$ aqueous solution and extracted with DCM (3×). The extract was dried ($Na_2SO_4$) and concentrated. The residue was purified using reverse-phase HPLC to give 120 mg of product as off-white solid. MS: $(M+H)^+=419.4$. $^1$H NMR (400 MHz, METHANOL-$d_4$) δ ppm 0.56-0.71 (m, 2H), 0.89-1.07 (m, 2H), 1.32-1.43 (m, 1H), 1.51-1.77 (m, 3H), 1.83-1.94 (m, 1H), 1.97-2.25 (m, 3H), 2.53 (ddd, J=10.11, 6.44, 3.41 Hz, 1H), 2.93-3.25 (m, 5H), 3.49-3.64 (m, 2H), 3.86-4.00 (m, 3H), 4.43 (s, 2H), 6.97-7.17 (m, 4H), 7.72 (d, J=8.08 Hz, 2H), 8.14 (d, J=8.08 Hz, 2H).

Step 4

4-((4-((((trans)-2-(4-Cyclopropylphenyl)cyclopropyl)amino)methyl)piperidin-1-yl)methyl)benzoic acid

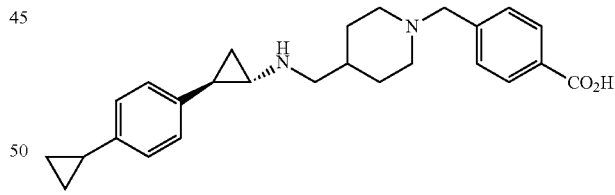

To a solution of methyl 4-((4-(((trans-2-(4-cyclopropylphenyl)cyclopropyl)amino)methyl) piperidin-1-yl)methyl)benzoate (118 mg, 0.282 mmol) in methanol (3 mL) was added sodium hydroxide (1M, 2 mL, 2 mmol), and the mixture was stirred at room temperature for 6 h. The mixture was purified using reverse-phase HPLC. The fractions containing the product were combined, treated with 1N HCl and concentrated. The residue was dried under vacuum to give 46 mg of product (HCl salt) as white solid. MS: $(M+H)^+=405.3$. $^1$H NMR (400 MHz, DMSO-$d_6$) δ ppm 0.54-0.72 (m, 2H), 0.84-1.01 (m, 2H), 1.15-1.29 (m, 1H), 1.51-1.71 (m, 3H), 1.82-2.12 (m, 4H), 2.96 (br. s., 4H), 3.12 (br. s., 1H), 4.33 (br. s., 2H), 6.94-7.14 (m, 4H), 7.74 (d, J=8.08 Hz, 2H), 8.01 (d, J=8.34 Hz, 2H).

Example 141

1-Methyl-4-((((trans)-2-phenylcyclopropyl)amino)methyl)piperidine-4-carboxylic acid

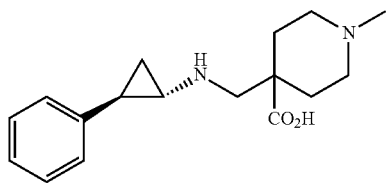 [SMILES: CN1CCC(CN[C@H]2C[C@@H]2c2ccccc2)(C(=O)O)CC1]

Step 1

1-tert-Butyl 4-methyl 4-1(2,2,2-trifluoro-N-((trans)-2-phenylcyclopropyl)acetamido)methyl)piperidine-1,4-dicarboxylate

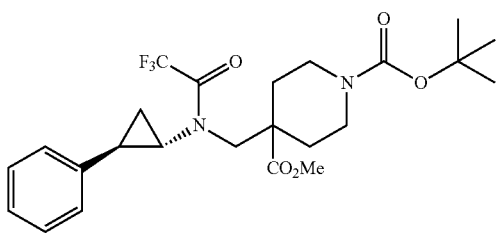 [SMILES: COC(=O)C1(CN(C(=O)C(F)(F)F)[C@H]2C[C@@H]2c2ccccc2)CCN(C(=O)OC(C)(C)C)CC1]

To a solution of trans-2-phenylcyclopropanamine (120 mg, 0.901 mmol) in methanol (3 mL) were added 1-tert-butyl 4-methyl 4-formylpiperidine-1,4-dicarboxylate (244 mg, 0.901 mmol) and acetic acid (0.015 mL, 0.270 mmol), and the mixture was stirred at room temperature for 1 h. Sodium cyanoborohydride (85 mg, 1.351 mmol) was added and the mixture was stirred at room temperature for 18 h. The reaction was quenched with 10% NaHCO$_3$ aqueous solution (3 mL) and extracted with DCM (3×). The extract was dried (Na$_2$SO$_4$) and concentrated. The residue was dried under vacuum and dissolved into dichloromethane (DCM) (3.00 mL). To this solution were added trifluoroacetic anhydride (0.191 mL, 1.351 mmol) and triethylamine (0.251 mL, 1.802 mmol), and the mixture was stirred at room temperature for 2 h. The reaction was quenched with 10% NaHCO$_3$ (2 mL) and extracted with DCM (3×). The extract was dried (Na$_2$SO$_4$) and concentrated. The residue was purified using column chromatography (silica gel, 0 to 80% EtOAc/hexanes) to give 310 mg of product as off-white solid. MS: (M+H)$^+$=485.2. $^1$H NMR (400 MHz, METHANOL-d$_4$) δ ppm 1.30-1.65 (m, 13H), 2.07-2.28 (m, 2H), 2.42 (ddd, J=10.11, 6.57, 3.54 Hz, 1H), 2.75 (br. s., 2H), 3.17 (dt, J=7.45, 3.60 Hz, 1H), 3.55 (s, 3H), 3.69-4.04 (m, 4H), 7.10 (d, J=7.07 Hz, 2H), 7.19-7.26 (m, 1H), 7.27-7.36 (m, 2H).

Step 2

Methyl 4-((2,2,2-trifluoro-N-((trans)-2-phenylcyclopropyl)acetamido)methyl)piperidine-4-carboxylate

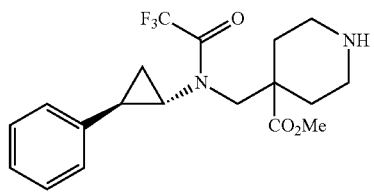 [SMILES: COC(=O)C1(CN(C(=O)C(F)(F)F)[C@H]2C[C@@H]2c2ccccc2)CCNCC1]

To a solution of 1-tert-butyl 4-methyl 4-((2,2,2-trifluoro-N-(trans-2-phenylcyclopropyl) acetamido)methyl)piperidine-1,4-dicarboxylate (150 mg, 0.310 mmol) in dichloromethane (DCM) (2 mL) was added TFA (0.5 mL, 6.49 mmol), and the mixture was stirred at room temperature for 2 h. The mixture was concentrated and the residue was treated with saturated NaHCO$_3$ aqueous solution, extracted with DCM (3×). The extract was dried (Na$_2$SO$_4$) and concentrated to give 110 mg of product as oil. MS: (M+H)$^+$=385.2. $^1$H NMR (400 MHz, METHANOL-d$_4$) δ ppm 1.37-1.67 (m, 4H), 2.11-2.32 (m, 2H), 2.42 (ddd, J=10.17, 6.51, 3.54 Hz, 1H), 2.57 (m, J=12.60, 12.60, 5.87, 2.78 Hz, 2H), 2.90-3.07 (m, 2H), 3.17 (dt, J=7.45, 3.60 Hz, 1H), 3.52-3.58 (m, 3H), 3.70-3.84 (m, 2H), 7.10 (d, J=7.07 Hz, 2H), 7.19-7.26 (m, 1H), 7.28-7.35 (m, 2H).

Step 3

Methyl 1-methyl-4-((2,2,2-trifluoro-N-((trans)-2-phenylcyclopropyl)acetamido)methyl)piperidine-4-carboxylate

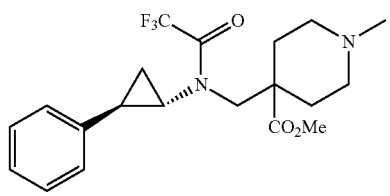 [SMILES: COC(=O)C1(CN(C(=O)C(F)(F)F)[C@H]2C[C@@H]2c2ccccc2)CCN(C)CC1]

To a solution of methyl 4-((2,2,2-trifluoro-N-((1S,2R)-2-phenylcyclopropyl)acetamido)methyl)piperidine-4-carboxylate (270 mg, 0.702 mmol) in 1,2-dichloroethane (DCE) (3 mL) and methanol (1.500 mL) were added formaldehyde (0.129 mL, 1.405 mmol) and acetic acid (0.060 mL, 1.054 mmol), and the mixture was stirred at room temperature for 1 h. Sodium triacetoxyborohydride (223 mg, 1.054 mmol) was added and the mixture was stirred at room temperature for 4 h. The mixture was quenched with 10% N NaHCO$_3$ aqueous solution and extracted with DCM (3×). The extract was dried (Na$_2$SO$_4$) and concentrated. The residue was dried under vacuum to give 265 mg of product as pale yellow oil. MS: (M+H)$^+$=399.2.

Step 4

1-Methyl-4-((((trans)-2-phenylcyclopropyl)amino)methyl)piperidine-4-carboxylic acid

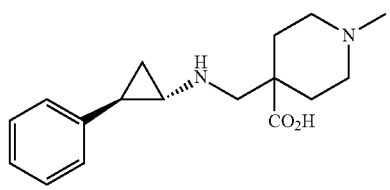 [SMILES: CN1CCC(CN[C@H]2C[C@@H]2c2ccccc2)(C(=O)O)CC1]

To a solution of methyl 1-methyl-4-((2,2,2-trifluoro-N-((trans)-2-phenylcyclopropyl)acetamido)methyl)piperidine-4-carboxylate (160 mg, 0.402 mmol) in methanol (2 mL) was added sodium hydroxide (6M, 0.3 mL, 1.800 mmol), and the mixture was stirred at room temperature for 30 h. The mixture was purified using reverse-phase HPLC. The fractions containing the product were combined, treated with 1N HCl and concentrated. The residue was dried under vacuum to give 81 mg of product (HCl salt) as white solid. MS: (M+H)$^+$=289.2. $^1$H NMR (400 MHz, DMSO-d$_6$) δ ppm 1.17-1.37 (m, 1H), 1.59-1.74 (m, 1H), 1.84-2.09 (m, 2H), 2.11-2.33 (m, 2H), 2.59-2.80 (m, 3H), 2.86-3.08 (m, 2H), 3.25 (d, J=7.58 Hz, 3H), 3.35-3.60 (m, 3H), 7.12-7.40 (m, 5H).

Example 142

4-((((trans)-2-Phenylcyclopropyl)amino)methyl)piperidine-4-carboxylic acid

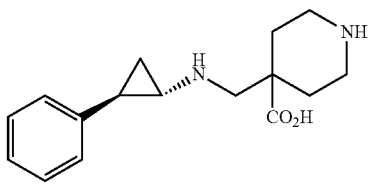 [SMILES: O=C(O)C1(CN[C@H]2C[C@@H]2c2ccccc2)CCNCC1]

To a solution of methyl 4-((2,2,2-trifluoro-N-(trans-2-phenylcyclopropyl)acetamido)methyl)piperidine-4-carboxylate (110 mg, 0.286 mmol) in methanol (2 mL) was added sodium hydroxide (6M, 0.5 mL, 3.00 mmol), and the mixture was stirred at room temperature for 30 h. The mixture was purified using reverse-phase HPLC. The fractions containing the product were combined, treated with 1N HCl and concentrated. The residue was dried under vacuum to give 51 mg of product (HCl salt) as white solid. MS: (M+H)$^+$=275.2. $^1$H NMR (400 MHz, DMSO-d$_6$) δ ppm 1.23-1.33 (m, 1H), 1.60 (br. s., 1H), 1.87 (br. s., 2H), 2.10-2.21 (m, 2H), 2.54-2.64 (m, 1H), 3.04 (br. s., 3H), 3.17-3.30 (m, 2H), 3.40-3.55 (m, 2H), 7.10-7.40 (m, 5H).

Example 143

1-Benzyl-4-((((trans)-2-phenylcyclopropyl)amino)methyl)piperidine-4-carboxylic acid

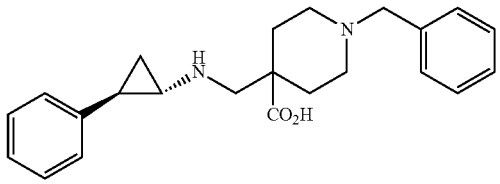 [SMILES: O=C(O)C1(CN[C@H]2C[C@@H]2c2ccccc2)CCN(Cc2ccccc2)CC1]

Step 1

Methyl 1-benzyl-4-((2,2,2-trifluoro-N-((trans)-2-phenylcyclopropyl)acetamido)methyl)piperidine-4-carboxylate

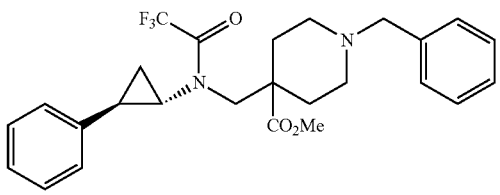 [SMILES: COC(=O)C1(CN(C(=O)C(F)(F)F)[C@H]2C[C@@H]2c2ccccc2)CCN(Cc2ccccc2)CC1]

To a solution of methyl 4-((2,2,2-trifluoro-N-(trans-2-phenylcyclopropyl)acetamido)methyl)piperidine-4-carboxylate (108 mg, 0.281 mmol) in 1,2-dichloroethane (DCE) (2 mL) were added benzaldehyde (35.8 mg, 0.337 mmol) and sodium triacetoxyborohydride (95 mg, 0.450 mmol), and the mixture was stirred at room temperature for 18 h. The reaction was quenched with water (5 mL) and extracted with DCM (3×). The extract was dried (Na$_2$SO$_4$) and concentrated. The residue was purified using column chromatography (silica gel, 0 to 100% EtOAc/hexanes) to give 78 mg or product as colorless oil. MS: (M+H)$^+$=475.3. $^1$H NMR (400 MHz, METHANOL-d$_4$) δ ppm 1.42 (q, 1H), 1.53-1.76 (m, 3H), 2.08-2.34 (m, 4H), 2.42 (ddd, J=10.11, 6.44, 3.66 Hz, 1H), 2.78-2.99 (m, 2H), 3.13-3.24 (m, 1H), 3.53-3.65 (m, 5H), 3.70-3.86 (m, 2H), 7.10 (d, J=7.07 Hz, 2H), 7.18-7.25 (m, 1H), 7.27-7.40 (m, 7H).

Step 2

1-Benzyl-4-((((trans)-2-phenylcyclopropyl)amino)methyl)piperidine-4-carboxylic acid

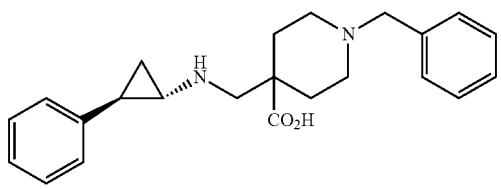 [SMILES: O=C(O)C1(CN[C@H]2C[C@@H]2c2ccccc2)CCN(Cc2ccccc2)CC1]

To a solution of methyl 1-benzyl-4-((2,2,2-trifluoro-N-(trans-2-phenylcyclopropyl)acetamido) methyl)piperidine-4-carboxylate (68 mg, 0.143 mmol) in methanol (2 mL) was added sodium hydroxide (1M, 1 mL, 6.00 mmol), and the mixture was stirred at room temperature for 30 h. The mixture was purified using reverse-phase HPLC under the acidic conditions. The fractions containing the product were combined, treated with 1N HCl and concentrated. The residue was dried under vacuum to give 29 mg of product (HCl salt) as white solid. MS: (M+H)$^+$=365.2. $^1$H NMR (400 MHz, DMSO-d$_6$) δ ppm 1.14-1.39 (m, 1H), 1.67 (br. s., 1H), 1.96-2.10 (m, 2H), 2.18-2.39 (m, 2H), 2.61-2.74 (m, 1H), 2.86-3.03 (m, 2H), 3.08-3.24 (m, 2H), 3.59 (br. s., 1H), 4.22-4.50 (m, 2H), 7.11-7.39 (m, 5H), 7.46 (br. s., 3H), 7.62 (m, 2H).

Example 144

2-Chloro-4-((4-((((1R,2S)-2-phenylcyclopropyl)amino)methyl)piperidin-1-yl)methyl)benzoic acid

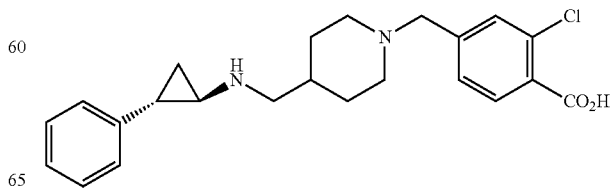

Step 1

Methyl 2-chloro-4-((4-((2,2,2-trifluoro-N-((1R,2S)-2-phenylcyclopropyl)acetamido)methyl)piperidin-1-yl)methyl)benzoate

To a solution of 2,2,2-trifluoro-N-((1R,2S)-2-phenylcyclopropyl)-N-(piperidin-4-ylmethyl)acetamide (100 mg, 0.306 mmol) in 1,2-dichloroethane (DCE) (2 mL) were added methyl 2-chloro-4-formylbenzoate (73.0 mg, 0.368 mmol) and sodium triacetoxyborohydride (104 mg, 0.490 mmol), and the reaction mixture was stirred at room temperature for 18 h. The mixture was quenched with water (4 mL) and extracted with DCM (3×). The extract was dried ($Na_2SO_4$) and concentrated. The residue was purified using column chromatography (silica gel, 0 to 100% EtOAc/hexanes, then 0 to 10% MeOH/EtOAc) to give 35 mg of product as off-white solid. MS: $(M+H)^+$=509.2. $^1$H NMR (400 MHz, METHANOL-$d_4$) δ ppm 1.28-1.78 (m, 7H), 1.81-1.94 (m, 1H), 2.09-2.21 (m, 2H), 2.39-2.54 (m, 1H), 2.89-3.01 (m, 2H), 3.10-3.22 (m, 1H), 3.41-3.67 (m, 4H), 3.90-3.95 (m, 3H), 7.12-7.42 (m, 6H), 7.53 (s, 1H), 7.81 (d, J=8.08 Hz, 1H).

Step 2

2-Chloro-4-((4-((((1R,2S)-2-phenylcyclopropyl)amino)methyl)piperidin-1-yl)methyl)benzoic acid

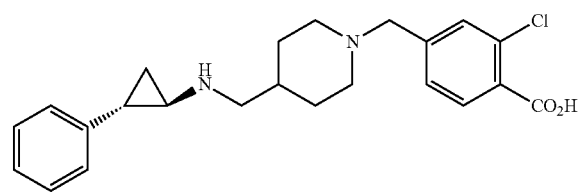 [SMILES: O=C(O)c1ccc(CN2CCC(CN[C@@H]3C[C@H]3c3ccccc3)CC2)cc1Cl]

To a solution of methyl 2-chloro-4-((4-((2,2,2-trifluoro-N-((1R,2S)-2-phenylcyclopropyl)acetamido)methyl)piperidin-1-yl)methyl)benzoate (31 mg, 0.061 mmol) in methanol (2 mL) was added sodium hydroxide (6M, 0.3 mL, 1.800 mmol), and the mixture was stirred at room temperature for 18 h. The mixture was purified using reverse-phase HPLC. The fractions containing the product as combined, treated with 1N HCl and concentrated. The residue was dried under vacuum to give 25 mg of product (HCl salt) as white solid. MS: $(M+H)^+$=399.2. $^1$H NMR (400 MHz, DMSO-$d_6$) δ ppm 1.26 (d, 1H), 1.59 (dd, J=9.98, 3.66 Hz, 3H), 1.80-2.16 (m, 3H), 2.54-2.68 (m, 1H), 2.98 (br. s., 4H), 4.31 (br. s., 2H), 7.13-7.39 (m, 5H), 7.65 (d, J=7.83 Hz, 1H), 7.81-8.01 (m, 2H).

Example 145

3-(3-(4-((((trans)-2-Phenylcyclopropyl)amino)methyl)piperidin-1-yl)propyl)benzoic acid

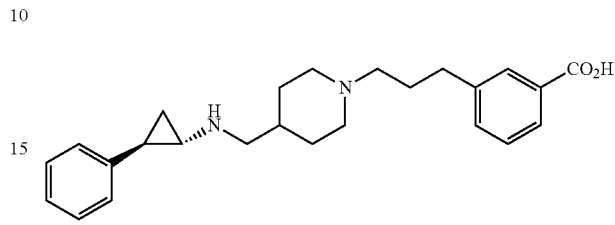

Step 1

Methyl 3-(3-(4-((2,2,2-trifluoro-N-((trans)-2-phenylcyclopropyl)acetamido)methyl)piperidin-1-yl)propyl)benzoate

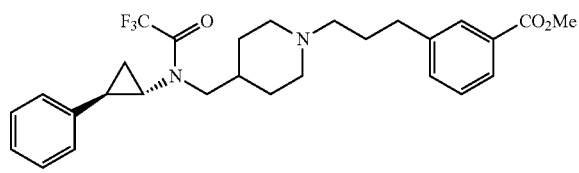 [SMILES: COC(=O)c1cccc(CCCN2CCC(CN(C(=O)C(F)(F)F)[C@H]3C[C@@H]3c3ccccc3)CC2)c1]

To a solution of 2,2,2-trifluoro-N-(trans-2-phenylcyclopropyl)-N-(piperidin-4-ylmethyl)acetamide (100 mg, 0.306 mmol) in 1,2-dichloroethane (DCE) (2 mL) were added methyl 3-(3-oxopropyl)benzoate (70.7 mg, 0.368 mmol) and sodium triacetoxyborohydride (104 mg, 0.490 mmol), and the mixture was stirred at room temperature for 18 h. The reaction was then quenched with water (5 mL) and extracted with DCM (3×). The extract was dried ($Na_2SO_4$) and concentrated. The residue was purified using column chromatography (silica gel, 0 to 100% EtOAc/hexanes then 0 to 15% MeOH/EtOAc) to give 98 mg of product as pale yellow solid. MS: $(M+H)^+$=503.1. $^1$H NMR (400 MHz, METHANOL-$d_4$) δ ppm 1.32-1.53 (m, 3H), 1.57-1.69 (m, 1H), 1.75-1.90 (m, 2H), 1.91-2.08 (m, 4H), 2.26-2.56 (m, 3H), 2.65-2.88 (m, 4H), 3.13-3.29 (m, 2H), 3.45-3.65 (m, 2H), 3.89-3.95 (m, 3H), 7.05-7.36 (m, 5H), 7.39-7.57 (m, 2H), 7.83-8.00 (m, 2H).

Step 2

3-(3-(4-((((trans)-2-Phenylcyclopropyl)amino)methyl)piperidin-1-yl)propyl)benzoic acid

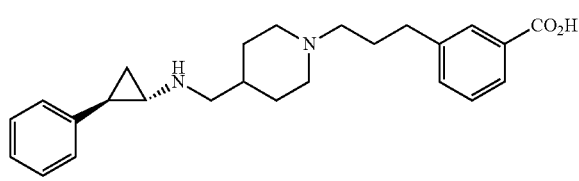 [SMILES: O=C(O)c1cccc(CCCN2CCC(CN[C@H]3C[C@@H]3c3ccccc3)CC2)c1]

To a solution of methyl 3-(3-(4-((2,2,2-trifluoro-N-(trans-2-phenylcyclopropyl)acetamido)methyl)piperidin-1-yl)propyl)benzoate (90 mg, 0.179 mmol) in methanol (2 mL) was added sodium hydroxide (6M, 0.5 mL, 3.00 mmol), and the mixture was stirred at room temperature for 18 h. The mixture was purified using reverse-phase HPLC under the acidic conditions. The fractions containing the product were combined, treated with 1N HCl and concentrated. The residue was dried under vacuum to give 42 mg of product (HCl salt) as white solid. MS: (M+H)$^+$=393.3. $^1$H NMR (400 MHz, DMSO-d$_6$) δ ppm 1.20-1.34 (m, 1H), 1.49-1.65 (m, 3H), 1.91-2.14 (m, 6H), 2.58 (br. s., 1H), 2.65-2.78 (m, 2H), 2.81-3.06 (m, 5H), 3.49 (br. s., 2H), 7.11-7.35 (m, 5H), 7.42-7.58 (m, 2H), 7.74-7.92 (m, 2H).

Example 146

4-(3-(2-((((1R,2S)-2-Phenylcyclopropyl)amino)methyl)morpholino)propyl)benzoic acid

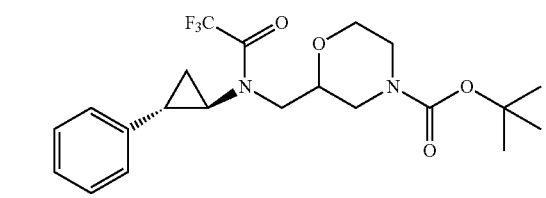 [SMILES: CC(C)(C)OC(=O)N1CCOC(CN(C(=O)C(F)(F)F)[C@@H]2C[C@H]2c2ccccc2)C1]

Step 1 tert-Butyl 2-((2,2,2-trifluoro-N-((1R,2S)-2-phenylcyclopropyl)acetamido)methyl)morpholine-4-carboxylate To a solution of (1R,2S)-2-phenylcyclopropanamine (400 mg, 3.00 mmol) in methanol (10 mL) were added tert-butyl 2-formylmorpholine-4-carboxylate (646 mg, 3.00 mmol) and acetic acid (0.052 mL, 0.901 mmol), and the mixture was stirred at room temperature for 1 h. Sodium cyanoborohydride (85 mg, 1.351 mmol) was added and the mixture was stirred at room temperature for 18 h. The reaction was quenched with 10% NaHCO$_3$ aqueous solution (3 mL) and extracted with DCM (3×). The extract was dried (Na$_2$SO$_4$) and concentrated. The residue was dried under vacuum and dissolved into dichloromethane (DCM) (10 mL). To this solution were added triethylamine (0.544 mL, 3.90 mmol) and trifluoroacetic anhydride (0.467 mL, 3.30 mmol), and the mixture was stirred at room temperature for 2 h. The reaction was quenched with 10% NaHCO$_3$ (2 mL) and extracted with DCM (3×). The extract was dried (Na$_2$SO$_4$) and concentrated. The residue was purified using column chromatography (silica gel, 0 to 60% EtOAc/hexanes) to give 830 mg of product colorless oil. MS: (M+H)$^+$=429.2. $^1$H NMR (400 MHz, METHANOL-d$_4$) δ ppm 1.38-1.82 (m, 12H), 2.39-3.28 (m, 3H), 3.38-3.53 (m, 1H), 3.57-4.03 (m, 6H), 7.07-7.37 (m, 5H).

Step 2

2,2,2-Trifluoro-N-(morpholin-2-ylmethyl)-N-((1R,2S)-2-phenylcyclopropyl)acetamide

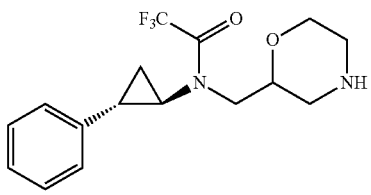 [SMILES: O=C(N(CC1CNCCO1)[C@@H]1C[C@H]1c1ccccc1)C(F)(F)F]

To a solution of tert-butyl 2-((2,2,2-trifluoro-N-((1R,2S)-2-phenylcyclopropyl)acetamido)methyl)morpholine-4-carboxylate (820 mg, 1.914 mmol) in dichloromethane (DCM) (8 mL) was added TFA (2 mL, 26.0 mmol), and the mixture was stirred at room temperature for 3 h. The mixture was concentrated and the residue was treated with saturated NaHCO$_3$ solution and extracted with DCM (3×). The extract was dried (Na$_2$SO$_4$) and concentrated. The residue was dried under vacuum to give 533 mg of product as colorless oil. MS: (M+H)$^+$=329.2. $^1$H NMR (400 MHz, METHANOL-d$_4$) δ ppm 1.28-1.83 (m, 2H), 2.40-2.98 (m, 5H), 3.45-3.95 (m, 5H), 7.06-7.39 (m, 5H).

Step 3

Ethyl 4-(3-(2-((2,2,2-trifluoro-N-((1R,2S)-2-phenylcyclopropyl)acetamido)methyl)morpholino)propyl)benzoate To a solution of 2,2,2-trifluoro-N-(morpholin-2-ylmethyl)-N-((1R,2S)-2-phenylcyclopropyl)acetamide (150 mg, 0.457 mmol) in 1,2-dichloroethane (DCE) (3 mL) were added ethyl 4-(3-oxopropyl)benzoate (113 mg, 0.548 mmol) and sodium triacetoxyborohydride (145 mg, 0.685 mmol), and the mixture was stirred at room temperature for 18 h. The reaction was quenched with water (5 mL) and extracted with DCM (3×). The extract was dried (Na$_2$SO$_4$) and concentrated. The residue was purified using column chromatography (silica gel, 20 to 100% EtOAc/hexanes) to give 200 mg or product as colorless oil. MS: (M+H)$^+$=395.2. $^1$H NMR (400 MHz, METHANOL-d$_4$) δ ppm 1.34-1.46 (m, 4H), 1.56 (br. s., 1H), 1.71-1.94 (m, 3H), 2.07-2.22 (m, 1H), 2.29-2.46 (m, 2H), 2.57 (br. s., 1H), 2.67-2.78 (m, 3H), 3.12-3.22 (m, 1H), 3.53-3.69 (m, 3H), 3.75-3.94 (m, 2H), 4.29-4.43 (m, 2H), 7.07-7.46 (m, 7H), 7.89-8.04 (m, 2H).

Step 4

4-(3-(2-((((1R,2S)-2-Phenylcyclopropyl)amino)methyl)morpholino)propyl)benzoic acid

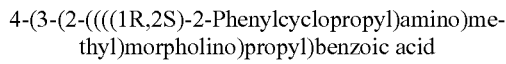
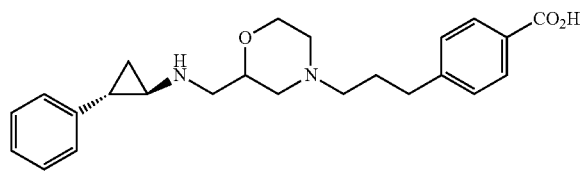 [SMILES: O=C(O)c1ccc(CCCN2CCOC(CN[C@@H]3C[C@H]3c3ccccc3)C2)cc1]

To a solution of ethyl 4-(3-(2-((2,2,2-trifluoro-N-((1R,2S)-2-phenylcyclopropyl)acetamido)methyl)morpholino)propyl)benzoate (190 mg, 0.366 mmol) in methanol (3 mL) was added sodium hydroxide (6M, 0.5 mL, 3.00 mmol), and the mixture was stirred at room temperature for 18 h. The mixture was purified using reverse-phase HPLC. The fractions containing the product were combined, treated with 1N HCl and concentrated. The residue was dried under vacuum to give 110 mg of product (HCl salt) as white solid. MS: $(M+H)^+=395.2$. $^1$H NMR (400 MHz, DMSO-$d_6$) δ ppm 1.21-1.35 (m, 1H), 1.47-1.61 (m, 1H), 2.00-2.17 (m, 2H), 2.65-3.22 (m, 9H), 3.25-3.51 (m, 3H), 3.60 (br. s., 1H), 3.88-4.15 (m, 2H), 4.38 (br. s., 1H), 7.14-7.26 (m, 3H), 7.27-7.34 (m, 2H), 7.38 (d, J=8.08 Hz, 2H), 7.90 (d, J=8.08 Hz, 2H).

Example 147

4-((2-((((1R,2S)-2-phenylcyclopropyl)amino)methyl)morpholino)methyl)benzoic acid

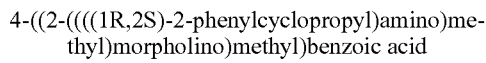
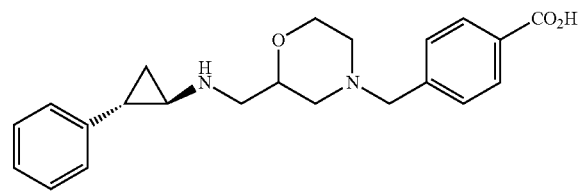 [SMILES: O=C(O)c1ccc(CN2CCOC(CN[C@@H]3C[C@H]3c3ccccc3)C2)cc1]

To a solution of 2,2,2-trifluoro-N-(morpholin-2-ylmethyl)-N-((1R,2S)-2-phenylcyclopropyl)acetamide (100 mg, 0.305 mmol) in 1,2-dichloroethane (DCE) (2 mL) were added methyl 4-formylbenzoate (60.0 mg, 0.365 mmol) and sodium triacetoxyborohydride (97 mg, 0.457 mmol), and the mixture was stirred at room temperature for 18 h. The reaction was then quenched with water (5 mL) and extracted with DCM (3×). The extract was dried (Na$_2$SO$_4$) and concentrated. The residue was dissolved into methanol (3.00 mL) and sodium hydroxide (6M, 0.5 mL, 3.00 mmol) was added. The mixture was stirred at room temperature for 18 h and purified using reverse-phase HPLC. The fractions containing the product were combined, treated with 1N HCl and concentrated. The residue was dried under vacuum to give 81 mg of product (HCl salt) as white solid. MS: $(M+H)^+=367.2$. $^1$H NMR (400 MHz, DMSO-$d_6$) δ ppm 1.16-1.36 (m, 1H), 1.50 (br. s., 1H), 2.93 (br. s., 2H), 3.10 (br. s., 2H), 3.35 (br. s., 2H), 4.05 (br. s., 2H), 4.36 (br. s., 2H), 7.10-7.39 (m, 5H), 7.74 (br. s., 2H) 8.01 (m, 2H).

Example 148

3-(3-((((1R,2S)-2-Phenylcyclopropyl)amino)methyl)pyrrolidin-1-yl)propanoic acid

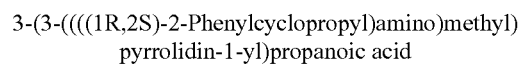
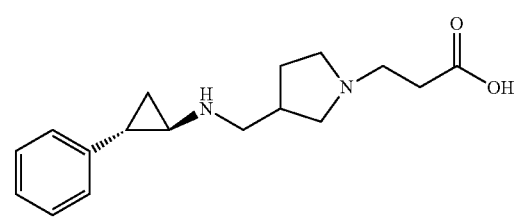 [SMILES: O=C(O)CCN1CCC(CN[C@@H]2C[C@H]2c2ccccc2)C1]

Step 1 tert-Butyl 3-(3-((2,2,2-trifluoro-N-((1R,2S)-2-phenylcyclopropyl)acetamido)methyl)pyrrolidin-1-yl)propanoate

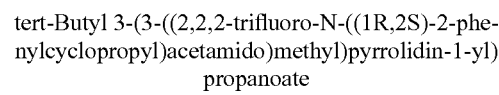
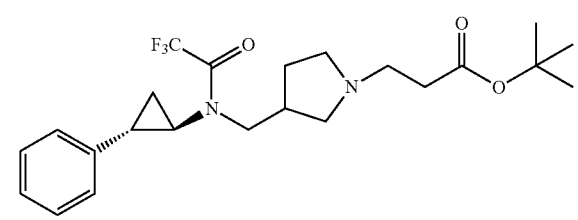 [SMILES: CC(C)(C)OC(=O)CCN1CCC(CN(C(=O)C(F)(F)F)[C@@H]2C[C@H]2c2ccccc2)C1]

To a solution of 2,2,2-trifluoro-N-((1R,2S)-2-phenylcyclopropyl)-N-(pyrrolidin-3-ylmethyl)acetamide (165 mg, 0.528 mmol) in methanol (3 mL) were added tert-butyl acrylate (0.103 mL, 0.703 mmol) and potassium carbonate (110 mg, 0.792 mmol), and the mixture was stirred at room temperature for 4 h. The mixture was quenched with saturated NH$_4$Cl aqueous solution and extracted with DCM (3×). The extract was dried (Na$_2$SO$_4$) and concentrated. The residue was purified using column chromatography (silica gel, 0 to 100% EtOAc/hexanes and then 10% MeOH/EtOAc) to give 68 mg of product as colorless oil. MS: $(M+H)^+=441.2$. $^1$H NMR (400 MHz, METHANOL-$d_4$) δ ppm 1.36-1.69 (m, 11H), 1.89-2.08 (m, 1H), 2.21-2.88 (m, 10H), 3.10-3.21 (m, 1H), 3.47-3.75 (m, 2H), 7.05-7.40 (m, 5H).

Step 2

3-(3-((((1R,2S)-2-Phenylcyclopropyl)amino)methyl)pyrrolidin-1-yl)propanoic acid

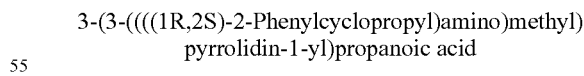
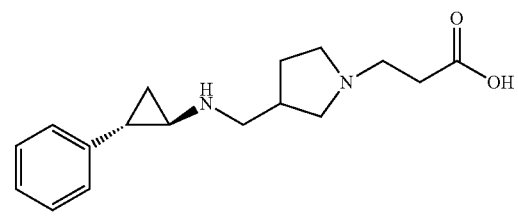 [SMILES: O=C(O)CCN1CCC(CN[C@@H]2C[C@H]2c2ccccc2)C1]

To a solution of tert-butyl 3-(3-((2,2,2-trifluoro-N-((1R,2S)-2-phenylcyclopropyl) acetamido)methyl)pyrrolidin-1-yl)propanoate (65 mg, 0.148 mmol) in methanol (2 mL) was added sodium hydroxide (6M, 0.3 mL, 1.800 mmol), and the mixture was stirred at room temperature for 18 h. The mixture was purified using reverse-phase HPLC. The fractions containing the product were combined, treated with 1N HCl and concentrated. The residue was dried under vacuum to give 28 mg of product (HCl salt) as off-white solid. MS: (M+H)$^+$=289.2. $^1$H NMR (400 MHz, METHANOL-d$_4$) δ ppm 1.43 (q, 1H), 1.58-1.74 (m, 1H), 2.01 (s, 1H), 2.38 (br. s., 1H), 2.62 (m, 1H), 2.87-3.13 (m, 4H) 3.25-3.68 (m, 8H), 7.18-7.44 (m, 5H).

Example 149

2-(4-((4-((((1R,2S)-2-Phenylcyclopropyl)amino)methyl)piperidin-1-yl)methyl)phenyl)acetic acid

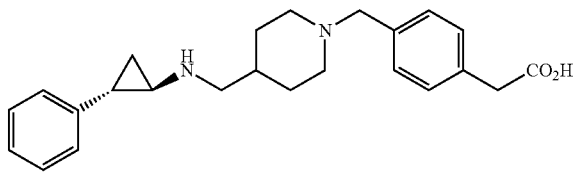 [SMILES: O=C(O)Cc1ccc(CN2CCC(CN[C@@H]3C[C@H]3c3ccccc3)CC2)cc1]

To a solution of 2,2,2-trifluoro-N-((1R,2S)-2-phenylcyclopropyl)-N-(piperidin-4-ylmethyl)acetamide (120 mg, 0.368 mmol) in 1,2-dichloroethane (DCE) (2 mL) were added 2-(4-formylphenyl)acetic acid (72.4 mg, 0.441 mmol) and sodium triacetoxyborohydride (125 mg, 0.588 mmol), and the reaction mixture was stirred at room temperature for 18 h. The mixture was quenched with water (2 mL) and extracted with DCM (3×). The extract was dried (Na$_2$SO$_4$) and concentrated. The residue was dissolved in methanol (2.000 mL) and sodium hydroxide (1M, 2 mL, 2.000 mmol) was added. The mixture was stirred at room temperature for 3 h and concentrated. The residue was treated with methanol and filtered. The filtrate was purified using reverse-phase HPLC under the acidic conditions. The fractions containing product were combined, treated and concentrated. The residue was further dried under vacuum to give 54 mg of product (HCl salt) as off-white solid. MS: (M+H)$^+$=379.3. $^1$H NMR (400 MHz, DMSO-d$_6$) δ ppm 1.20-1.34 (m, 1H), 1.51-1.70 (m, 3H), 1.87-2.13 (m, 3H), 2.56-2.66 (m, 1H), 2.83-3.15 (m, 5H), 3.32 (br. s., 2H), 4.16-4.44 (m, 2H), 7.12-7.43 (m, 7H), 7.45-7.61 (m, 2H).

Example 150

3-((R)-3-((((1R,2S)-2-Phenylcyclopropyl)amino)methyl)pyrrolidin-1-yl)propanoic acid

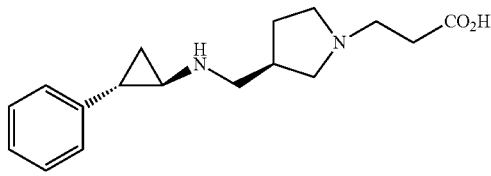 [SMILES: O=C(O)CCN1CC[C@H](CN[C@@H]2C[C@H]2c2ccccc2)C1]

Step 1:

(R)-tert-Butyl 3-((2,2,2-trifluoro-N-((1R,2S)-2-phenylcyclopropyl)acetamido)methyl) pyrrolidine-1-carboxylate

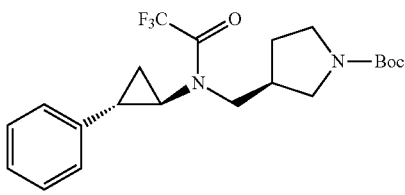 [SMILES: CC(C)(C)OC(=O)N1CC[C@H](CN(C(=O)C(F)(F)F)[C@@H]2C[C@H]2c2ccccc2)C1]

To a solution of (1R,2S)-2-phenylcyclopropanamine (700 mg, 5.26 mmol) in methanol (25 mL) were added (S)-tert-butyl 3-formylpyrrolidine-1-carboxylate (1047 mg, 5.26 mmol) and acetic acid (0.120 mL, 2.102 mmol), and the mixture was stirred at room temperature for 30 min. sodium cyanoborohydride (495 mg, 7.88 mmol) was added and the mixture was stirred at room temperature for 18 h. The reaction was quenched with 10% NaHCO$_3$ aqueous solution and concentrated. The residue was treated with water (3 mL) and extracted with DCM (3×). The extract was dried (Na$_2$SO$_4$) and concentrated. The residue was dried under vacuum and dissolved in DCM (25 mL). To this solution were added triethylamine (1.099 mL, 7.88 mmol) and trifluoroacetic anhydride (0.965 mL, 6.83 mmol) at 0° C., and the mixture was stirred at room temperature for 2 h. The mixture was quenched with 10% NaHCO$_3$ aqueous solution and extracted with DCM (3×). The extract was dried (Na$_2$SO$_4$) and concentrated. The residue was purified using column chromatography (silica gel, 0 to 70% EtOAc/hexanes) to give 1.71 g of product as colorless oil.
MS: (M+Na)$^+$=435.2
$^1$H NMR (400 MHz, METHANOL-d$_4$) δ ppm 1.39-1.54 (m, 10H), 1.55-1.85 (m, 2H), 1.96-2.13 (m, 2H), 2.20-2.54 (m, 1H), 2.65 (dt, J=14.34, 7.36 Hz, 1H), 2.99-3.23 (m, 2H), 3.40-3.83 (m, 4H), 7.09-7.37 (m, 5H).
Step 2:

2,2,2-Trifluoro-N-((1R,2S)-2-phenylcyclopropyl)-N-((S)-pyrrolidin-3-ylmethyl)acetamide

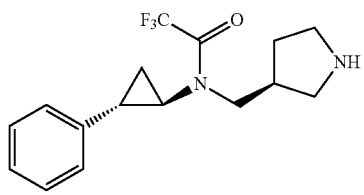 [SMILES: O=C(N(C[C@H]1CCNC1)[C@@H]1C[C@H]1c1ccccc1)C(F)(F)F]

To a solution of (R)-tert-butyl 3-((2,2,2-trifluoro-N-((1R,2S)-2-phenylcyclopropyl)acetamido) methyl)pyrrolidine-1-carboxylate (1.28 g, 3.10 mmol) in dichloromethane (DCM) (12 mL) was added TFA (3 ml, 38.9 mmol), and the mixture was stirred at room temperature for 3 h. The mixture was concentrated and the residue was treated with saturated NaHCO$_3$ solution and extracted with DCM (3×). The extract was dried (Na$_2$SO$_4$) and concentrated. The residue was dried under vacuum to give 950 mg of product as pale yellow oil.
MS: (M+H)$^+$=313.1

$^1$H NMR (400 MHz, METHANOL-$d_4$) δ ppm 1.21-1.55 (m, 2H), 1.58-1.86 (m, 2H), 2.15-2.29 (m, 1H), 2.45-2.55 (m, 1H), 2.70-3.02 (m, 2H), 3.19-3.30 (m, 2H), 3.36-3.48 (m, 2H), 3.62-3.87 (m, 2H), 7.11-7.40 (m, 5H).

Step 3:

tert-Butyl 3-((S)-3-((2,2,2-trifluoro-N-((1R,2S)-2-phenylcyclopropyl)acetamido)methyl)pyrrolidin-1-yl)propanoate

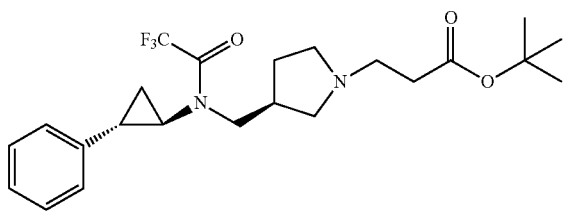 [SMILES: CC(C)(C)OC(=O)CCN1CC[C@H](CN(C(=O)C(F)(F)F)[C@@H]2C[C@H]2c2ccccc2)C1]

To a solution of 2,2,2-trifluoro-N-((1R,2S)-2-phenylcyclopropyl)-N-((S)-pyrrolidin-3-ylmethyl)acetamide (140 mg, 0.448 mmol) in tetrahydrofuran (3 mL) were added tert-butyl acrylate (0.085 mL, 0.583 mmol) and triethylamine (0.094 mL, 0.672 mmol), and the mixture was stirred at room temperature for 20 h. The mixture was concentrated and the residue was purified using column chromatography (silica gel, 0 to 100% EtOAc/hexanes) to give 110 mg of product as pale yellow oil.

MS: (M+H)$^+$=441.3
$^1$H NMR (400 MHz, METHANOL-$d_4$) δ ppm 1.38-1.68 (m, 11H), 1.91-2.08 (m, 1H), 2.22-2.51 (m, 4H), 2.55-2.91 (m, 6H), 3.45-3.85 (m, 2H), 7.06-7.37 (m, 5H).

Step 4:

3-((R)-3-((((1R,2S)-2-Phenylcyclopropyl)amino)methyl)pyrrolidin-1-yl)propanoic acid

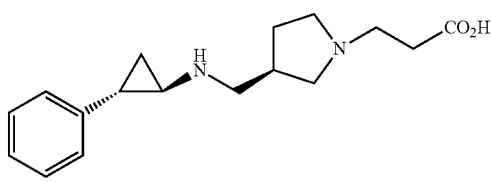 [SMILES: O=C(O)CCN1CC[C@H](CN[C@@H]2C[C@H]2c2ccccc2)C1]

To a solution of tert-butyl 3-((S)-3-((2,2,2-trifluoro-N-((1R,2S)-2-phenylcyclopropyl)acetamido)methyl)pyrrolidin-1-yl)propanoate (108 mg, 0.245 mmol) in methanol (3 mL) was added sodium hydroxide (6M, 0.5 mL, 3.00 mmol) and the mixture was stirred at r room temperature for 18 h. The mixture was purified using reverse-phase HPLC. The fractions containing the product were combined, treated with 1N HCl and concentrated. The residue was dried under vacuum to give 51 mg of product (HCl salt) as off-white solid.

MS: (M+H)$^+$=289.2
$^1$H NMR (400 MHz, METHANOL-$d_4$) δ ppm 1.43 (q, 1H), 1.59-1.71 (m, 1H), 1.92-2.09 (m, 1H), 2.42 (dq, J=13.83, 6.84 Hz, 1H), 2.58-2.71 (m, 1H), 2.82-3.01 (m, 3H), 3.06 (dt, J=7.71, 3.98 Hz, 1H), 3.38-3.63 (m, 6H), 3.72 (d, J=9.85 Hz, 1H), 7.16-7.40 (m, 5H).

Biochemical Assay for Lsd-1 Activity

The LSD-1 luminescence assay is performed in a buffer containing 25 mM Tris, pH 7.5, 50 mM potassium chloride, 0.02% heat-denatured BSA, 2 mM CHAPS and milliQ ultrapure water. An enzyme solution containing 30 nM LSD-1 (in-house prep) is prepared in this buffer, as well as a substrate solution containing 30 uM histone H3K4 dimethylated peptide (H-ART[K-Me2]QTARKSTGGKAPRKQLAGG-OH, commercial source). Two microliters of enzyme solution are added to each well of a white Greiner low volume 384 well plate (cat#784075), into which 50 mL of 100% DMSO dilution of test compound has been dispensed. The enzyme and test compound are allowed to incubate together for 30 minutes at room temperature. Two microliters of the substrate mix are then added to each well of the plate to initiate the reaction. The plates are covered, protected from light and allowed to incubate for two hours at room temperature. Then, 4 uL of HyPerBlu peroxide detection luminescence reagent (Lumigen/Beckman Coulter, cat# HPB-00005) is added to each well to quench the demethylase reaction and generate the peroxide-dependent luminescence signal. The plates are then incubated for 15-30 minutes in the dark at room temperature prior to being read for Luminescence using a Perkin Elmer Viewlux plate reader. Percent inhibition is calculated based on no compound and no enzyme controls, and inhibition curves are then plotted to determine PIC50 values.

Biochemical Assay for MAO-B Activity

The MAO-B FLINT assay is performed in a buffer containing 50 mM potassium phospate, pH 7.4, in milliQ ultrapure water. An enzyme solution containing 0.23 IU/mL MAO-B (Gentest-BD Biosciences, cat#456284) and 2 IU/mL of Type XII horseradish peroxidase (Sigma Aldrich, cat# P8415) is prepared in this buffer, as well as a substrate solution containing 200 uM benzylamine (Sigma Aldrich, cat# B-5136) and 100 uM amplex red (Molecular Probes-Invitrogen, cat# A-12222). Five microliters of enzyme solution are added to each well of a black Greiner low volume 384 well plate (cat#784076), into which 100 nL of 100% DMSO dilution of test compound has been dispensed. The enzyme and test compound are allowed to incubate together for 30 minutes at room temperature. Five microliters of the substrate mix are then added to each well of the plate to initiate the reaction. The plates are covered, protected from light and allowed to incubate for one hour at room temperature. After 60 minutes the plates are read for resorufin fluorescence (EX: 525; EM:598) using a Perkin Elmer Viewlux plate reader. Percent inhibition is calculated based on no compound and no enzyme controls, and inhibition curves are then plotted to determine PIC50 values.

Biochemistry Data

Exemplified compounds of the present invention were tested according to the above assays and were found to be inhibitors of LSD1. The PIC$_{50}$ values ranged from about 4.7 to 8.3. The PIC$_{50}$ values of the more active compounds range from about 7.5 to 8.3. The most active compounds are equal/above 8.0

The present compounds are found to be selective inhibitors of LSD1.

Each compound listed below was tested two or more times generally according to the assays described herein, and the average PIC$_{50}$ values are listed in the table below.

| | LSD1 PIC50 MEAN | MAOB PIC50 MEAN |
| --- | --- | --- |
| Example 1 | 6.8 | 5.6 |
| Example 2 | 7.4 | 6.2 |
| Example 3 | 6.2 | 5.1 |
| Example 4 | 8.2 | 4.4 |
| Example 5 | 8.3 | 4.1 |

-continued

| | LSD1 PIC50 MEAN | MAOB PIC50 MEAN |
|---|---|---|
| Example 6 | 8.2 | 4.6 |
| Example 7 | 6.8 | 6.4 |
| Example 8 | 8.2 | 4.6 |
| Example 9 | 6.8 | 6.4 |
| Example 10 | 8.1 | 5.1 |
| Example 11 | 7.9 | 4.5 |
| Example 12 | 7.1 | 5.7 |
| Example 13 | 7.3 | 5.3 |
| Example 14 | 6.9 | 4.4 |
| Example 15 | 6.5 | 4.8 |
| Example 16 | 8.1 | 4.4 |
| Example 17 | 4.7 | 4.2 |
| Example 18 | 7.5 | 6.2 |
| Example 19 | 6.4 | 4.5 |
| Example 20 | 8.2 | 4.6 |
| Example 21 | 5.7 | 4.8 |
| Example 22 | 7.1 | 4 |
| Example 23 | 8 | 4.2 |
| Example 24 | 8 | 4.2 |
| Example 25 | 7.7 | 4.9 |
| Example 26 | 6.7 | 4.3 |
| Example 27 | 6.7 | 4.2 |
| Example 28a | 6.8 | 4.5 |
| Example 28b | 7.1 | 4.6 |
| Example 29 | 6.8 | 4.6 |
| Example 30 | 7.9 | 4.5 |
| Example 33 | 7.8 | 4.3 |
| Example 35 | 7.8 | 4.5 |
| Example 43 | 8.2 | 6.3 |
| Example 47 | 7 | 4.8 |
| Example 55 | 7.6 | 5.1 |
| Example 57 | 8.1 | 4.5 |
| Example 71 | 7 | 5.1 |
| Example 77 | 6.7 | 4.5 |
| Example 91 | 8.2 | 4.8 |
| Example 100 | 7.1 | 4.8 |
| Example 123 | 7.5 | 4.7 |
| Example 150 | 7.6 | 4.1 |

The invention claimed is:

1. A compound which is 4-((4-((((1R,2S)-2-phenylcyclopropyl)amino)methyl)piperidin-1-yl)methyl)benzoic acid, represented by the formula:

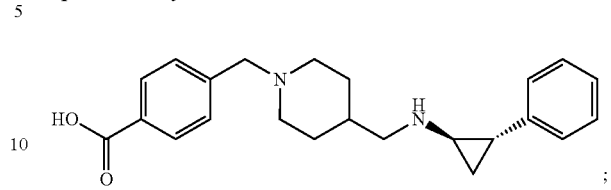

or a pharmaceutically acceptable salt thereof.

2. A compound which is 4-((4-((((1R,2S)-2-phenylcyclopropyl)amino)methyl)piperidin-1-yl)methyl)benzoic acid, represented by the formula:

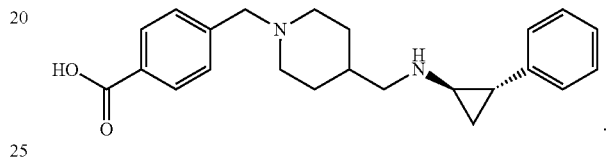

3. A pharmaceutical composition comprising the compound or pharmaceutically acceptable salt thereof according to claim 1 and a pharmaceutically acceptable excipient.

4. A pharmaceutical composition comprising the compound according to claim 2 and a pharmaceutically acceptable excipient.

* * * * *